(12) United States Patent
Marineau et al.

(10) Patent No.: US 11,311,542 B2
(45) Date of Patent: Apr. 26, 2022

(54) INHIBITORS OF CYCLIN DEPENDENT KINASE 7 (CDK7)

(71) Applicant: Syros Pharmaceuticals, Inc., Cambridge, MA (US)

(72) Inventors: Jason J. Marineau, Franklin, MA (US); Claudio Edmundo Chuaqui, Arlington, MA (US); Stephane Ciblat, Montreal (CA); Anzhelika Kabro, Montreal (CA); Henri Piras, Montreal (CA); Kenneth Matthew Whitmore, Montreal (CA); Kate-Lyn Lund, Lachine (CA)

(73) Assignee: Syros Pharmaceuticals, Inc., Cambridge, MA (US)

( * ) Notice: Subject to any disclaimer, the term of this patent is extended or adjusted under 35 U.S.C. 154(b) by 81 days.

(21) Appl. No.: 16/962,808

(22) PCT Filed: Jan. 16, 2019

(86) PCT No.: PCT/US2019/013845
§ 371 (c)(1),
(2) Date: Jul. 16, 2020

(87) PCT Pub. No.: WO2019/143719
PCT Pub. Date: Jul. 25, 2019

(65) Prior Publication Data
US 2021/0379065 A1 Dec. 9, 2021

Related U.S. Application Data

(60) Provisional application No. 62/617,884, filed on Jan. 16, 2018.

(51) Int. Cl.
| | | |
|---|---|---|
| A61K 45/06 | (2006.01) | |
| A61K 31/506 | (2006.01) | |
| C07D 401/14 | (2006.01) | |
| C07D 413/14 | (2006.01) | |
| C07D 417/14 | (2006.01) | |
| C07D 471/04 | (2006.01) | |

(52) U.S. Cl.
CPC ............ *A61K 31/506* (2013.01); *A61K 45/06* (2013.01); *C07D 401/14* (2013.01); *C07D 413/14* (2013.01); *C07D 417/14* (2013.01); *C07D 471/04* (2013.01)

(58) Field of Classification Search
None
See application file for complete search history.

(56) References Cited

U.S. PATENT DOCUMENTS

| | | |
|---|---|---|
| 7,615,562 B2 | 11/2009 | Bollbuck et al. |
| 9,012,462 B2 | 4/2015 | Wang et al. |
| 9,561,228 B2 | 2/2017 | Haq et al. |
| 2011/0160237 A1 | 6/2011 | Ali et al. |
| 2014/0031360 A1 | 1/2014 | Wang et al. |
| 2019/0276440 A1 | 9/2019 | Zhao et al. |
| 2020/0190126 A1 | 6/2020 | Marineau et al. |

FOREIGN PATENT DOCUMENTS

| | | |
|---|---|---|
| WO | 2006038001 A1 | 4/2006 |
| WO | 2006096564 A1 | 9/2006 |
| WO | 2008137105 A1 | 11/2008 |
| WO | 2012078777 A1 | 6/2012 |
| WO | 2015058126 A1 | 4/2015 |
| WO | 2015058163 A2 | 4/2015 |
| WO | 2015154039 A2 | 10/2015 |
| WO | 2015188777 A1 | 12/2015 |
| WO | 2015195228 A1 | 12/2015 |
| WO | 2018013867 A1 | 1/2018 |
| WO | 2018098473 A1 | 5/2018 |
| WO | 2019143719 A1 | 7/2019 |
| WO | 2019143730 A1 | 7/2019 |
| WO | 2019204781 A1 | 10/2019 |

(Continued)

OTHER PUBLICATIONS

Browne et al. "A Chemoproteomic Strategy for Direct and Proteome-Wide Covalent Inhibitor Target-Site Identification," Journal of the American Chemical Society, 2019, 141:191-203.
Gao et al. "Overcoming Resistance to the THZ Series of Covalent Transcriptional CDK Inhibitors," Cell Chemical Biology, 2018, 25:135-142.
Geng et al. "Targeting CDK12-mediated transcription regulation in anaplastic thyroid carcinoma," Biochemical and Biophysical Research Communications, 2019, 520:544-550.
Hu et al., "An Oral and Selective CDK7 Inhibitor Demonstrates Substantial Anti-tumor Effect in Breast and Ovarian Cancer Models," 30th EORTC-NCI-AACR Molecular Targets and Cancer Symposium, Abstract No. 96, 2018.

(Continued)

*Primary Examiner* — Heidi Reese
(74) *Attorney, Agent, or Firm* — Goodwin Procter LLP

(57) ABSTRACT

The present invention provides, inter alia, compounds having the structures of formulas described herein; pharmaceutically acceptable salts, solvates, hydrates, tautomers, and isotopic forms thereof; and compositions (e.g., pharmaceutical compositions and kits) containing one or more of the foregoing. Also provided are methods of administering and uses involving the compounds and/or pharmaceutical compositions for treating or preventing disease. The disease can be a proliferative disease, such as a cancer (e.g., a blood cancer (e.g., a leukemia or lymphoma), a brain cancer, a breast cancer, melanoma, multiple myeloma, or an ovarian cancer) a benign neoplasm, pathologic angiogenesis, or a fibrotic disease. While no aspect of the invention is limited by the biological events that may transpire, administering a compound or other composition described herein may selectively inhibit the aberrant expression or activity of cyclin-dependent kinase 7 (CDK7) and, thereby, induce cellular apoptosis and/or inhibit the transcription of disease-related genes in the patient (or in a biological sample).

20 Claims, 17 Drawing Sheets

(56) References Cited

FOREIGN PATENT DOCUMENTS

WO  2019217757 A1  11/2019

OTHER PUBLICATIONS

Hu et al., "SY-5609, an Orally Available Selective CDK7 Inhibitor, Demonstrates Broad Anti-tumor Activity In Vivo," American Association for Cancer Research (AACH) Annual Meeting, Abstract No. 4421, 2019.

Iniguez et al. "EWS/FLI Confers Tumor Cell Synthetic Lethality to CDK12 Inhibition in Ewing Sarcoma," Cancer Cell, 2018, 33:202-216.

International Search Report for PCT/US2017/042017 dated Oct. 13, 2017.

International Search Report for PCT/US2019/013845 dated Mar. 14, 2019.

International Search Report for PCT/US2019/013860 dated Mar. 22, 2019.

International Search Report for PCT/US2019/59542 dated Feb. 11, 2020.

Ito et al. "Discovery of 3-Benzyl-1-(trans-4-((5-cyanopyridin-2-yl)amino)cyclohexyl)-1-arylurea Derivatives as Novel and Selective Cyclin-Dependent Kinase 12 (CDK12) Inhibitors," Journal of Medicinal Chemistry, 2018, 61:7710-7728.

Johannes et al. "Structure-Based Design of Selective Noncovalent CDK12 Inhibitors," ChemMedChem, 2018, 13:231-235.

Johannessen et al., "Preclinical Evaluation of PK, PD, and Antitumor Activity of the Oral, Non-covalent, Potent and Highly Selective CDK7 Inhibitor, SY-5609, Provides Rationale for Clinical Development in Multiple Solid Tumor Indications," 31st EORTC-NCI-AACR Molecular Targets and Cancer Symposium, Abstract No. C091, 2019.

Krajewska et al. "CDK12 loss in cancer cells affects DNA damage response genes through premature cleavage and polyadenylation," Nature Communications, 2019, 10(1):1-16.

Olson et al. "Development of a Selective CDK7 Covalent Inhibitor Reveals Predominant Cell-Cycle Phenotype," Cell Chemical Biology, 2019, 26:792-803.

Zhang et al. "Covalent targeting of remote cysteine residues to develop CDK12 and CDK13 inhibitors," Nature Chemical Biology, 2016, 12:876-884.

| Compound | Done as | $^1$H NMR | Calcd. Mass | Found Mass (MH$^+$) |
|---|---|---|---|---|
| 100 | Example 22 | $^1$H NMR (400 MHz, MeOH-d4) δ 8.72 (s, 1 H) 8.48 (br., 1 H) 8.19 (br., 1 H) 7.55 (s, 1 H) 7.22 (br., J = 8.38 Hz, 1 H) 4.36 (br., 1 H) 3.59 (br., J = 11.69 Hz, 1 H) 3.32-3.03 (s, 1 H) 3.01-2.99 (m, 2 H) 2.46 (s, 3 H) 2.30 (s, 3 H) 2.23-2.04 (m, 2 H) 1.92-1.72 (m, 2 H) | 460.18 | 458.1 |
| 101 | Example 9 | $^1$H NMR (400 MHz, MeOD-d4) δ 9.45-8.82 (m, 1H), 8.68 (br.s., 1H), 8.41-8.18 (m, 1H), 7.80 - 7.48 (m, 1H), 4.79 -4.29 (m, 1H), 3.66 (br.d., J = 10.4 Hz, 1H), 3.44-3.33 (m, 1H), 3.28 -3.03 (m, 2H), 2.62 (br.s., 3H), 2.45 (br.s., 3H), 2.35-2.20 (m, 1H), 2.19 - 1.93 (m, 2H), 1.86 (br.d., J = 9.9 Hz, 1H) | 457.18 | 458 |
| 102 | Starting with product of Example 19 & following steps 4-6 of Example 18 | $^1$H NMR (400 MHz, MeOD-d4) δ 8.61-8.51 (m, 1H), 8.49 - 8.31 (m, 1H), 7.89 (s, 1H), 7.44-7.39 (m, 1H), 7.15-7.08 (m, 1H), 4.63-4.32 (m, 1H), 3.59 -3.37 (m, 1H), 2.95-2.77 (m, 1H), 2.70 -2.52 (m, 2H), 2.44 (s, 3H), 2.29 (s, 3H), 2.06 – 1.87 (m, 1H), 1.56-1.39 (m, 1H), 1.19 (s, 3H), 1.05 (brs, 3H) | 484.22 | 485.1 |
| 103 | Starting with product of Example 23 & following step 2 of Example 22 | $^1$H NMR (400 MHz, MeOD-d4) δ 8.75 (s, 1 H) 8.50 (br s, 1 H) 8.23 (s, 1 H) 7.95 (d, J = 3.30 Hz, 1 H) 7.89 (br d, J = 7.95 Hz, 1 H) 7.69 (d, J = 3.30 Hz, 1 H) 4.40 (br s, 1 H) 3.62 (br d, J = 10.15 Hz, 1 H) 3.35 (br d, J = 1.71 Hz, 1 H) 3.06 (br d, J = 10.03 Hz, 2 H) 2.30 -2.07 (m, 2 H) 1.98 -1.73 (m, 2H) | 445.13 | 446 |
| 104 | Example 1 | Rotamers: $^1$H NMR (500 MHz, DMSO) δ 11.88 (br s, 1H), 8.58 – 8.52 (m, 1H), 8.48 (d, J = 8.3 Hz, 0.5H), 8.29 (d, J = 8.3 Hz, 0.5H), 7.88 (d, J = 4.3 Hz, 1H), 7.75 – 7.68 (m, 1H), 7.48 (d, J = 8.2 Hz, 1H), 7.12 (d, J = 8.3 Hz, 1H), 3.95 – 3.80 (m, 1H), 2.92 - 2.86 (m, 1H), 2.74 – 2.62 (m, 1H), 2.43 (s, 3H), 2.25 (s, 3H), 1.91 – 1.63 (m, 3H), 1.51 (dt, J = 12.7, 4.3 Hz, 1H), 1.37 – 1.29 (m, 1H), 1.10 - 1.00 (m, 6H). | 484.52 | 485.2 |
| 105 | Example 18 | $^1$H NMR (400 MHz, MeOD-d4) δ 8.74 (s, 1H), 8.45-8.38 (m, 1H), 8.37 - 8.27 (m, 1H), 7.54-7.41 (m, 1H), 7.34-7.11 (m, 1H), 4.38 -4.16 (m, 1H), 3.71-3.62 (m, 1H), 3.57 - 3.44 (m, 1H), 3.34-3.32 (m, 2H), 3.28 -3.04 (m, 1H), 2.44 (s, 3H), 2.28 (s, 4H), 2.23-2.15 (m, 1H) | 472.18 | 473.1 |

FIG. 3 (Cont.)

| Compound | Done as | $^1$H NMR | Calcd. Mass | Found Mass (MH$^+$) |
|---|---|---|---|---|
| 106 | Example 2 | Rotamers: $^1$H NMR (500 MHz, DMSO): δ 12.08 (br s, 1H), 8.61 (s, 0.5H), 8.58 (s, 0.5H), 8.47 (d, J = 8.5 Hz, 0.5H), 8.35 (br s, 0.5H), 8.29 (d, J = 8.0 Hz, 0.5H), 8.10 (d, J = 9.0 Hz, 1H), 7.97 (d, J = 3.0 Hz, 1H), 7.91 (d, J = 3.3 Hz, 1H), 7.88 – 7.84 (m, 1H), 7.78 – 7.76 (m, 1H), 7.73 (d, J = 3.3 Hz, 1H), 4.14 – 4.01 (m, 1H), 3.12 – 3.05 (m, 1H), 2.89 – 2.81 (m, 1H), 1.98 – 1.82 (m, 1H), 1.79 – 1.60 (m, 2H), 1.55 – 1.46 (m, 1H), 1.20 – 1.18 (m, 6H). | 472.53 | 473.2 |
| 107 | Starting with product of Example 20 & following steps 5 and 6 of Example 18 | $^1$H NMR (MeOD-d4, 400 MHz) δ = 8.83-8.64 (m, 1H), 8.61-8.41 (m, 1H), 8.34 (br.s., 1H), 8.25 (br.s., 1H), 8.15 (br.s., 1H), 8.05-7.76 (m, 2H), 4.82 (br.s., 1H), 4.38 -4.18 (m, 1H), 3.69 -3.43 (m, 2H), 3.40 -3.33 (m, 2H), 2.34 (br.s., 1H), 2.23-1.94 (m, 1H) | 460.13 | 461.1 |
| 108 | Starting with product of Example 10 & following steps 5-7 of Example 9 | $^1$H NMR (400 MHz, MeOD-d4) δ 9.28 - 8.76 (m, 1H), 8.70 (br s, 1H), 8.38 (br d, J = 19.2 Hz, 2H), 8.20 (br s, 1H), 8.01 (br s, 1H), 4.76-4.29 (m, 1H), 3.67 (br dd, J = 3.1, 12.1 Hz, 1H), 3.40 (br d, J = 13.0 Hz, 1H), 3.27 -3.06 (m, 2H), 2.30 (br s, 1H), 2.20 - 2.11 (m, 1H), 2.00 (br s, 1H), 1.93-1.80 (m, 1H) | 445.13 | 446 |
| 109 | Starting with product of Example 17 & following step 5 of Example 15 | $^1$H NMR (400 MHz, MeOD-d4) δ 8.38 - 8.70 (m, 2H), 8.07 - 8.24 (m, 3H), 7.75-8.00 (m, 2H), 4.44-4.83 (m, 1H), 3.52-3.73 (m, 1H), 3.06-3.16 (m, 1H), 2.64-2.96 (m, 2H), 1.93-2.15 (m, 1H), 1.57 -1.70 (m, 1H), 1.25 (s, 3H), 1.14 (s, 3H) | 472.17 | 473.1 |
| 110 | Example 3 | Rotamers: $^1$H NMR (500 MHz, DMSO) δ 12.16 (br s, 1H), 8.61 (s, 0.5H), 8.56 (s, 0.5H), 8.53 – 8.48 (m, 0.5H), 8.40 – 8.34 (m, 1.5H), 8.20 (d, J = 0.7 Hz, 1H), 8.15 – 8.09 (m, 1H), 7.99 (s, 1H), 7.90 – 7.75 (m, 2H), 7.37 (s, 1H), 4.10 – 3.96 (m, 1H), 3.20 – 3.14 (m, 1H), 2.95 – 2.88 (m, 1H), 2.60 – 2.52 (m, 2H), 2.08 – 1.92 (m, 1H), 1.76 – 1.70 (m, 1H), 1.59 – 1.44 (m, 2H). | 428.41 | 429.3 |

FIG. 3 (Cont.)

| Compound | Done as | ¹H NMR | Calcd. Mass | Found Mass (MH⁺) |
|---|---|---|---|---|
| 111 | Example 3 | Rotamers: ¹H NMR (500 MHz, DMSO) δ 12.01 (br s, 1H), 8.60 (s, 0.5H), 8.55 (s, 0.5H), 8.45 (d, J = 8.0 Hz, 0.5H), 8.42 (s, 1H), 8.36 (br s, 1H), 8.32 (d, J = 8.0 Hz, 0.5H), 7.91 (br s, 1H), 7.84 – 7.80 (m, 2H), 7.67 (s, 1H), 7.57 – 7.49 (m, 1H), 4.06 – 3.93 (m, 1H), 3.17 – 3.10 (m, 1H), 2.92 – 2.84 (m, 1H), 2.61 – 2.52 (m, 2H), 2.05 – 1.92 (m, 1H), 1.71 (br s, 1H), 1.56 – 1.43 (m, 2H). | 428.41 | 429.3 |
| 112 | Example 15 | ¹H NMR (400 MHz, MeOD-d4) δ 8.77-8.55 (m, 2H), 8.43-8.23 (m, 1H), 7.61-7.13 (m, 2H), 4.58 (br s, 1H), 3.77 (br d, J = 10.09 Hz, 1H), 3.59 (br s, 1H), 3.47 (br d, J = 12.28 Hz, 1H), 3.27-3.17 (m, 2H), 3.06-2.68 (m, 6H), 2.52 (br s, 1H), 2.46 (s, 3H), 2.31 (s, 3H), 1.94-1.79 (m, 1H) | 527.23 | 528.2 |
| 113 | Starting with product of Example 16 & following step 6 of Example 15 | ¹H NMR (400 MHz, MeOD-d4) δ 8.64 (s, 1 H), 8.47 (br s, 1 H), 8.37-8.11 (m, 1 H), 7.50-7.21 (br s, 2 H), 4.49-4.79 (m, 1 H), 3.70-3.74(br s, 1 H), 3.50-3.52 (br s, 1 H), 3.50 (dd, J = 12.72,3.91 Hz, 1 H), 3.48(m, 2 H), 3.36-3.32 (m, 1 H), 2.74 (s, 3 H), 2.46 (s, 3 H), 2.30 (s, 3 H), 1.99 (br s, 1 H) | 513.21 | 514.2 |
| 114 | Example 4 | Rotamers: ¹H NMR (500 MHz, DMSO): δ 11.96 (br s, 1H), 9.13 (s, 1H), 8.60 (s, 0.5H), 8.57 (s, 0.5H), 8.47 (d, J = 8.2 Hz, 0.5H), 8.35 (br s, 1H), 8.27 (d, J = 8.2 Hz, 0.5H), 7.93 – 7.85 (m, 2H), 7.61 (d, J = 11.5 Hz, 1H), 7.33 – 7.26 (m, 1H), 4.20 – 4.04 (m, 1H), 3.27 – 3.17 (m, 1H), 3.04 – 2.89 (m, 1H), 2.73 – 2.56 (m, 2H), 2.43 (s, 3H), 2.05 – 1.92 (m, 1H), 1.84 – 1.69 (m, 1H), 1.64 – 1.47 (m, 2H). | 442.44 | 443.8 |
| 115 | Starting with product of Example 11 & following steps 6 and 7 of Example 9 | ¹H NMR (400 MHz, MeOD-d4) δ 9.29 - 8.80 (m, 1H), 8.67 (s, 1H), 8.31-8.12 (m, 1H), 7.54 (d, J = 8.2 Hz, 1H), 3.75-3.56 (m, 1H), 3.33 (br. d, J = 1.7 Hz, 1H), 3.12 (br. d, J = 13.0 Hz, 1H), 3.04-2.71 (m, 2H), 2.61 (s, 3H), 2.44 (br. s, 3H), 2.05(br. d, J = 12.3 Hz, 1H), 1.65 (br. s, 1H), 1.26 (s, 3H), 1.13 (br. s, 3H). | 485.22 | 486.2 |

FIG. 3 (Cont.)

| Compound | Done as | ¹H NMR | Calcd. Mass | Found Mass (MH⁺) |
|---|---|---|---|---|
| 116 | Product of Example 5 combined with (S)-6,6-dimethylpiperidin-3-amine (Example 1), & then following step 6 of Example 1 | Rotamers: ¹H NMR (500 MHz, DMSO): δ 12.49 (br s, 1H), 8.90 (d, J = 8.0 Hz, 0.5H), 8.63 – 8.55 (m, 1.5H), 8.38 (br s, 1H), 7.96 (s, 0.5H), 7.93 (s, 0.5H), 7.88 – 7.84 (m, 1H), 7.41 – 7.35 (m, 1H), 4.01 – 3.86 (m, 1H), 3.01 – 2.92 (m, 1H), 2.78 – 2.70 (m, 1H), 2.60 (s, 3H), 2.43 (s, 3H), 1.93 – 1.78 (m, 1H), 1.76 – 1.66 (m, 1H), 1.61 – 1.51 (m, 1H), 1.46 – 1.35 (m, 1H), 1.17 – 1.04 (m, 6H). | 485.5 | 486.9 |
| 117 | Example 6 | Rotamers: ¹H NMR (500 MHz, DMSO) δ 12.49 (br s, 1H), 8.89 (d, J = 8.2 Hz, 0.5H), 8.65 (d, J = 8.1 Hz, 0.5H), 8.58 (d, J = 9.6 Hz, 1H), 8.35 (br s, 1H), 8.01 – 7.84 (m, 2H), 7.37 (d, J = 8.2 Hz, 1H), 3.97 (br s, 1H), 3.38 – 3.32 (m, 2H), 3.29 (s, 3H), 3.19 – 3.04 (m, 1H), 3.02 – 2.83 (m, 1H), 2.67 – 2.57 (m, 3H), 2.48 – 2.37 (m, 3H), 2.17 – 1.94 (m, 1H), 1.43 – 1.25 (m, 1H). | 487.49 | 488.2 |
| 118 | Example 12 | ¹H NMR (400 MHz, MeOD-d4) δ 8.93-8.53 (m, 2H), 7.58-7.31 (m, 1H), 4.54-4.18 (m, 1H), 3.53 (br.d.., J = 10.8 Hz, 1H), 3.32-3.23 (m, 1H), 3.07-2.88 (m, 2H), 2.58 (s, 3H), 2.41 (s, 3H), 2.14 (br.s., 1H), 2.03 (br.d., J = 12.8 Hz, 1H), 1.84 (br.s., 1H), 1.78-1.65 (m, 1H) | 458.18 | 459.2 |
| 119 | Example 13 | ¹H NMR (400 MHz, MeOD-d4) δ 9.00 - 8.66 (m, 1H), 8.60 (br s, 1H), 8.51 (br s, 0.51H), 8.03 (br s, 1H), 7.44-7.30 (m, 1H), 4.35 (br s, 1H), 3.62-3.46 (m, 1H), 3.28 - 3.10 (m, 4H), 3.06-2.87 (m, 5H), 2.78 (br t, J =11.4 Hz, 1H), 2.61 (s, 3H), 2.46 (s, 3H), 2.32 (br s, 1H), 1.91-1.72 (m, 1H). | 528.22 | 529.2 |
| 120 | Starting with product of Example 14 & following step 4 of Example 13 | ¹H NMR (400 MHz, MeOD-d4) δ 8.91 (br s, 2H), 8.61-8.47 (m, 0.66H), 8.02 (br s,1H), 7.45-7.30 (m, 1H), 4.32 (br s, 1H), 3.57 -3.46 (m, 1H), 3.35 (br s, 1H), 3.00 - 2.84 (m, 1H), 2.79 -2.67 (m, 5H), 2.61 (s,3H), 2.46 (s, 3H), 2.33 (br d, J = 12.8 Hz, 1H), 1.89 -1.75 (m, 1H) | 514.21 | 515.3 |
| 121 | Example 21 | ¹H NMR (400 MHz, MeOD-d4) δ 8.60 (s, 1H), 8.54 (s, 1H), 8.26 (s, 1H), 8.03 (br. s, 1H), 7.92 (br. d, J = 8.1 Hz, 1H), 4.35 (br. s, 1H), 3.56 (br. d, J = 10.8 Hz, 1H), 3.29 - 3.24 (m, 1H), 3.08 -2.93 (m, 2H), 2.45 (s, 3H), 2.20 (br. s, 1H), 2.14-2.03 (m, 1H), 1.93-1.70 (m, 2H) | 443.17 | 444.1 |

FIG. 3 (Cont.)

| Compound | Done as | ¹H NMR | Calcd. Mass | Found Mass (MH⁺) |
|---|---|---|---|---|
| 122 | Example 24 | ¹H NMR (400 MHz, MeOH-d4) δ 8.67 (s, 2H), 8.19 (br. s, 1H), 8.01 (br. s, 1H), 7.83-7.53 (m, 1H), 4.66-4.35 (m, 1H), 4.30 (s, 3H), 3.64 (br. d, $J$ = 9.9 Hz, 1H), 3.41-3.36 (m, 1H), 3.24-2.99 (m, 2H), 2.29 (br. s, 1H), 2.17-2.08 (m, 1H), 2.01-1.70 (m, 2H) | 443.18 | 444.2 |
| 123 | Following steps 2 and 3 of Example 24 substituting 2-bromo-5-methyl-1,3,4-thiadiazole for 5-bromo-1-methyl-tetrazole in step 2 | ¹H NMR (400 MHz, MeOH-d4) δ 8.82-8.67 (m, 1H), 8.52 (br d, $J$ = 7.7 Hz, 1H), 8.41 (br s, 1H), 8.18 (br s, 1H), 8.07-7.75 (m, 1H), 4.74 (br s, 1H), 3.70 (br d, $J$ = 9.8 Hz, 1H), 3.52-3.34 (m, 2H), 3.23-3.08 (m, 1H), 2.89 (s, 3H), 2.37 (br s, 1H), 2.25-2.13 (m, 1H), 2.02 (br s, 1H), 1.96-1.81 (m, 1H) | 459.15 | 460.2 |
| 124 | Example 25 | ¹H NMR (400 MHz, MeOH-d4) δ 9.40 - 8.84 (m, 1H), 8.68 (s, 1H), 8.36-8.14 (m, 1H), 7.77 - 7.50 (m, 1H), 4.70 -4.25 (m, 1H), 3.69 (br. d, $J$ = 10.6 Hz, 1H), 3.33 (br. d, $J$ = 1.7 Hz, 1H), 3.19 -2.88 (m, 1H), 2.62 (br. d, $J$ = 13.6 Hz, 3H), 2.52-2.40 (m, 3H), 2.38 -2.19 (m, 1H), 2.10 (br. s, 1H), 1.80 (br. s, 2H), 1.40 (br. d, $J$ = 6.0 Hz, 3H) | 471.20 | 472.3 |
| 125 | Example 25 | ¹H NMR (400 MHz, MeOH-d4) δ 9.40 - 8.82 (m, 1H), 8.68 (s, 1H), 8.36-8.13 (m, 1H), 7.78 - 7.51 (m, 1H), 4.74-4.25 (m, 1H), 3.69 (br. d, $J$ = 11.5 Hz, 1H), 3.33 (br. d, $J$ = 1.7 Hz, 1H), 3.18 -2.88 (m, 1H), 2.62 (br. d, $J$ = 14.1 Hz, 3H), 2.45 (br. d, $J$ = 16.9 Hz, 3H), 2.38 -2.19 (m, 1H), 2.10 (br. s, 1H), 1.90 -1.64 (m, 2H), 1.40 (br. d, $J$ = 6.0 Hz, 3H) | 471.20 | 472.3 |
| 126 | Starting with product of Example 26 following steps 6 and 7 of Example 9 | ¹H NMR (400 MHz, MeOH-d4) δ 8.76-8.49 (m, 2H), 8.46-8.06 (m, 2H), 7.82 (br d, $J$ = 1.3 Hz, 1H), 7.67 - 7.32 (m, 1H), 4.71-4.33 (m, 1H), 4.29 (s, 3H), 3.71-3.60 (m, 1H), 3.36 (br d, $J$ = 12.8 Hz, 1H), 2.97 -3.26 (m, 2H), 2.33 (br d, $J$ = 12.8 Hz, 1H), 2.12 (dt, $J$ = 14.7, 4.2 Hz, 1H), 1.96 (br s, 1H), 1.83 (q, $J$ = 10.2 Hz, 1H) | 442.18 | 443.1 |
| 127 | Example 7 | Rotamers: ¹H NMR (500 MHz, DMSO) δ 11.87 (br s, 1H), 8.57 (d, $J$ = 11.6 Hz, 1H), 8.47 (d, $J$ = 8.1 Hz, 0.5H), 8.39 – 8.15 (m, 1.5H), 7.95 – 7.79 (m, 2H), 7.46 (s, 1H), 7.21 – 7.05 (m, 1H), 4.15 – 3.96 (m, 1H), 3.42 – 3.33 (m, 1H), 3.29 (s, 3H), 3.20 – 3.08 (m, 1H), 3.04 – 2.86 (m, 1H), 2.64 – 2.53 (m, 1H), 2.43 (s, 3H), 2.25 (s, 3H), 2.16 – 1.96 (m, 1H), 1.45 – 1.31 (m, 1H). | 486.49 | 487.1 |

FIG. 3 (Cont.)

| Compound | Done as | $^1$H NMR | Calcd. Mass | Found Mass (MH$^+$) |
|---|---|---|---|---|
| 128 | Starting with product of Example 8 & following Step 2 of Example 7 | Rotamers: $^1$H NMR (500 MHz, DMSO) δ 11.96 (br s, 1H), 8.97 (s, 1H), 8.60 (s, 0.5H), 8.57 (s, 0.5H), 8.48 (d, J = 8.2 Hz, 0.5H), 8.34 (br s, 1H), 8.30 (d, J = 8.2 Hz, 0.5H), 7.93 – 7.85 (m, 2H), 7.59 (s, 0.5H), 7.56 (s, 0.5H), 7.30 – 7.22 (m, 1H), 4.17 – 4.05 (m, 1H), 3.25 – 3.18 (m, 1H), 3.02 – 2.92 (m, 1H), 2.72 – 2.58 (m, 2H), 2.51 (s, 3H), 2.08 – 1.93 (m, 1H), 1.82 – 1.72 (m, 1H), 1.62 – 1.50 (m, 2H). | 458.5 | 459 |
| 129 | Example 27 | 1H NMR (400 MHz, MeOH-d4) δ 8.64-8.50 (m, 2H), 8.20 (s, 1H), 8.01-7.86 (m, 2H), 4.38 (br s, 1H), 3.63-3.47 (m, 1H), 3.35 (br s, 1H), 3.14-2.95 (m, 2H), 2.69 (s, 3H), 2.32-2.07 (m, 2H), 2.00-1.72 (m, 2H) | 443.17 | 444.10 |
| 130 | Steps 2-3 of Example 24, substituting 5-bromo-3-methyl-1,2,4-thiadiazole for 5-bromo-1-methyl-tetrazole in step 2 | $^1$H NMR (400 MHz, MeOH-d4) δ 8.57 (br s, 1H), 8.40 (br s, 1H), 8.31-7.95 (m, 2H), 7.88 (br s, 1H), 4.71-4.06 (m, 1H), 3.56 (br d, J = 10.0 Hz, 1H), 3.34-3.22 (m, 2H), 3.03 (br d, J = 6.0 Hz, 1H), 2.59 (s, 3H), 2.24 (br s, 1H), 2.06 (br d, J = 14.4 Hz, 1H), 1.97-1.69 (m, 2H) | 459.15 | 460.1 |
| 131 | Starting with product of Example 28 and following steps 3-6 of Example 18 | $^1$H NMR (400 MHz, MeOH-d4) δ 8.79 (s, 1H), 8.42 (d, J = 8.2 Hz, 1H), 8.35 (s, 1H), 7.52 (s, 1H), 7.38 - 7.16 (m, 1H), 4.88 -4.82 (m, 1H), 3.96 (br s, 1H), 3.75-3.62 (m, 2H), 3.57 (s, 4H), 3.26 (br s, 1H), 2.45 (s, 3H), 2.35 (br d, J = 14.1 Hz, 2H), 2.29 (s, 3H) | 486.20 | 487.1 |

FIG. 3 (Cont.)

| Compound | Done as | ¹H NMR | Calcd. Mass | Found Mass (MH⁺) |
|---|---|---|---|---|
| 132 | Following Example 9, substituting 3-methyl-4-(4,4,5,5-tetramethyl-1,3,2-dioxaborolan-2-yl)isoxazole for (3,5-dimethylisoxazol-4-yl) boronic acid in step 1 | ¹H NMR (400 MHz, MeOH-d4) δ 9.12 (s, 1H), 9.06-8.66 (m, 1H), 8.64 (s, 1H), 8.11 (br.s, 1H), 7.62 (br.s., 1H), 4.65-4.27 (m, 1H), 3.68 -3.54 (m, 1H), 3.33 (br.d., J = 1.7 Hz, 2H), 3.11-2.95 (m, 1H), 2.66 (s, 3H), 2.24 (br.s., 1H), 2.17 -2.05 (m, 1H), 1.99 - 1.75 (m, 2H) | 443.43 | 444.1 |
| 133 | Example 29 | ¹H NMR (400 MHz, DMSO-d6) δ12.27 (br s, 1H), 9.49 (br s, 1H), 9.28 (br s, 1H), 8.73 (br s, 1H), 8.63 (s, 1H), 7.95 (s, 1H), 7.78 (br s, 1H), 7.41 (br s, 1H), 4.44 (br s, 1H), 4.02 (br d, J = 4.5 Hz, 1H), 3.38 (br d, J = 10.9 Hz, 1H), 3.23 (br d, J = 10.3 Hz, 1H), 2.90 (br s, 1H), 2.67 (br s, 1H), 2.61 (s, 3H), 2.44 (s, 3H), 2.28 (br d, J = 12.6 Hz, 1H), 1.73-1.58 (m, 1H) | 473.18 | 474.2 |
| 134 | Example 56 | ¹H NMR (500 MHz, DMSO-d6) δ 12.15 (brs, 1H), 8.66 – 8.49 (m, 1H), 8.45 – 8.22 (m, 1.5H), 8.16 – 8.04 (m, 0.5H), 8.04 – 7.84 (m, 2H), 7.55 – 7.38 (m, 1H), 4.19 – 4.01 (m, 1H), 3.27 – 3.05 (m, 1H), 3.05 – 2.85 (m, 1H), 2.78 – 2.54 (m, 2H), 2.36 (s, 3H), 2.17 (s, 3H), 2.13 – 1.91 (m, 1H), 1.84 – 1.70 (m, 1H), 1.66 – 1.44 (m, 2H). Rotamers. | 474.45 | 475.0 |
| 135 | Example 64 | ¹H NMR (500 MHz, DMSO-d6) δ 11.89 (brs, 1H), 8.57 (s, 0.5H), 8.54 (s, 0.5H), 8.47 (d, J = 8.3 Hz, 0.5H), 8.36 (brs, 1H), 8.24 (d, J = 8.3 Hz, 0.5H), 7.88 (s, 0.5H), 7.85 (s, 0.5H), 7.81 – 7.73 (m, 1H), 7.48 – 7.45 (m, 1H), 7.16 – 7.11 (m, 1H), 3.77 – 3.68 (m, 1H), 3.16 – 3.08 (m, 1H), 2.99 – 2.87 (m, 1H), 2.53 – 2.49 (m, 1H), 2.43 (s, 3H), 2.42 – 2.36 (m, 1H), 2.25 (s, 3H), 1.77 – 1.58 (m, 2H), 1.29 – 1.13 (m, 1H), 0.98 - 0.93 (m, 3H). Rotamers. | 470.50 | 471.0 |
| 136 | Example 30 | ¹H NMR (400 MHz, MeOD-d4) δ 9.06 (br.s, 1H), 8.62 (s, 1H), 8.55 (br.s, 0.64H), 8.27-8.06 (m, 2H), 4.31 (br.s, 1H), 3.53 (br.s., 1H), 3.28-3.22 (m, 1H), 2.96 (br.t, J = 11.1 Hz, 2H), 2.49 (s, 3H), 2.27-2.00 (m, 2H), 1.92-1.68 (m, 2H) | 444.16 | 445.1 |

FIG. 3 (Cont.)

| Compound | Done as | ¹H NMR | Calcd. Mass | Found Mass (MH⁺) |
|---|---|---|---|---|
| 137 | Example 31 | ¹H NMR (400 MHz, MeOD-d4): δ 8.86-8.68 (m, 1H), 8.58 (s, 1H), 8.15 (br s, 1H), 8.03 (br s, 1H), 7.96 (d, J = 3.51 Hz, 1H), 7.74 (d, J = 3.07 Hz, 1H), 4.72-4.47 (m, 1H), 3.60 (br s, 1H), 3.11 (br d, J = 13.16 Hz, 1H), 2.91-2.83 (m, 2H), 1.98 (br s, 1H), 1.60 (br s, 1H), 1.23-1.11 (m, 6H) | 473.16 | 474.1 |
| 138 | Example 57 | ¹H NMR (500 MHz, DMSO-d6) δ 8.87 (d, J = 11.0 Hz, 0.6H), 8.62 (s, 0.6H), 8.59 (s, 0.4H), 8.43 (d, J = 11.0 Hz, 0.4H), 8.23 (s, 1H), 8.08 (s, 0.6H), 8.06 (s, 0.4H), 8.02 (d, J = 7.8 Hz, 0.6H), 7.94 (d, J = 7.8 Hz, 0.4H), 4.06 – 3.96 (m, 1H), 3.15 – 3.09 (m, 1H), 2.99 – 2.87 (m, 1H), 2.65 –2.54 (m, 2H), 2.44 (s, 3H), 2.28 (s, 3H), 2.10 – 1.95 (m, 1H), 1.78 – 1.71 (m, 1H), 1.59 – 1.47 (m, 2H). Rotamers. | 475.45 | 476.0 |
| 139 | Example 32 | ¹H NMR (400 MHz, MeOD-d4) δ 8.62 (s, 2H), 8.55 (br s, 1H), 8.17 (br s, 1H), 8.04 (br d, J = 7.9 Hz, 1H), 4.35 (br s, 1H), 3.57 (br d, J = 11.4 Hz, 1H), 3.33 (br d, J = 1.6 Hz, 1H), 3.08 -2.95 (m, 2H), 2.73 (s, 3H), 2.20 (br s, 1H), 2.09 (br d, J = 13.9 Hz, 1H), 1.95 -1.71 (m, 2H) | 444.16 | 445.1 |
| 140 | Example 33 | ¹H NMR (400 MHz, MeOD-d4) δ 9.09-8.88 (m, 1H), 8.57 (br s, 1H), 8.12 (s, 1H), 7.39 (br. d, J = 13.9 Hz, 1H), 4.08 (br. s, 1H), 3.25 (s, 1H), 2.95 (br. s, 1H), 2.62 (br. d, J = 9.04 Hz, 2H), 2.38 (s, 6H), 2.11 (br. s, 1H), 1.81 (br. s, 1H), 1.66-1.60 (m, 2H) | 457.2 | 458.2 |
| 141 | Example 34 | ¹H NMR (400 MHz, MeOD-d4) δ9.12-8.90 (m, 1H), 8.58 (br s, 1H), 8.11 (s, 1H), 7.85 (br d, J = 17.4 Hz, 1H), 4.10 (br d, J = 7.2 Hz, 1H), 3.26 (br s, 1H), 2.95 (s, 4H), 2.63 (br d, J = 8.4 Hz, 2H), 2.12 (br s, 1H), 1.82 (br s, 1H), 1.67-1.62 (m, 2H) | 444.17 | 445.1 |
| 142 | Example 35 | ¹H NMR (400 MHz, MeOD-d4) δ9.03 (br s, 1H), 8.63 (s, 1H), 8.22 -8.03 (m, 2H), 4.35 (br. s, 1H), 3.60 (br. d, J = 12.8 Hz, 1H), 3.39 -3.34 (m, 1H), 3.10 -2.94 (m, 2H), 2.70 (s, 3H), 2.22 (br. s, 1H), 2.16 -2.07 (m, 1H), 1.96 -1.71 (m, 1H), 1.96 -1.71 (m, 2H) | 460.14 | 461 |
| 143 | Example 63 | ¹H NMR (500 MHz, DMSO-d6) δ 12.48 (s, 1H), 8.90 (d, J = 8.2 Hz, 0.64H), 8.57 (d, J = 10.2 Hz, 1H-0.4H), 8.35 (s, 1H), 7.94 (d, J = 17.6 Hz, 1H), 7.88 (d, J = 8.5 Hz, 0.60H), 7.84 (d, J = 8.8 Hz, 0.40H), 7.40 (d, J = 8.2 Hz, 0.40H), 7.36 (d, J = 8.2 Hz, 0.60H), 3.75 – 3.66 (m, 1H), 3.19 – 3.04 (m, 1H), 3.00 – 2.88 (m, 1H), 2.62 (s, 3H), 2.43 (s, 3H), 2.41 – 2.33 (m, 1H), 1.83 – 1.54 (m, J = 34.8 Hz, 2H), 1.29 – 1.14 (m, 1H), 0.95 (d, J = 6.0 Hz, 3H). Rotamers. | 471.48 | 472.0 |
| 144 | Example 61 | ¹H NMR (500 MHz, DMSO-d6) δ 9.00 (d, J = 8.4 Hz, 0.6H), 8.74 (s, 0.5H), 8.72 (s, 0.5H), 8.67 (d, J = 8.4 Hz, 0.4H), 8.39 (brs, 1H), 8.19 (d, J = 8.0 Hz, 0.6H), 8.10 (d, J = 8.0 Hz, 0.4H), 7.54 (d, J = 8.1 Hz, 0.4H), 7.49 (d, J = 8.1 Hz, 0.6H), 4.13 – 4.00 (m, 1H), 3.12 – 3.04 (m, 1H), 2.90 – 2.76 (m, 1H), 2.64 (s, 3H), 2.46 (s, 3H), 1.95 – 1.84 (m, 1H), 1.79 – 1.57 (m, 2H), 1.54 – 1.41 (m, 1H), 1.23 – 1.14 (m, 6H). Rotamers. | 486.50 | 487.1 |

FIG. 3 (Cont.)

| Compound | Done as | $^1$H NMR | Calcd. Mass | Found Mass (MH+) |
|---|---|---|---|---|
| 145 | Example 36 | $^1$H NMR (400 MHz, DMSO-d6) δ 8.81 (br s, 1H), 8.58 (s, 1H), 8.10 (br d, J = 7.95 Hz, 1H), 7.99 (s, 1H), 7.97 (d, J = 3.18 Hz, 1H), 7.78 (d, J = 3.18 Hz, 1H), 7.69 (br d, J = 8.07 Hz, 1H), 7.50 (br s, 1H), 3.97 (br s, 1H), 3.16 (br d, J = 11.74 Hz, 1H), 2.99 (br d, J = 9.17 Hz, 1H), 2.59 (d, J = 4.65 Hz, 3H), 2.36-2.47 (m, 3H), 2.11 (br d, J = 12.47 Hz, 1H), 1.67 (q, J = 11.86 Hz, 1H) | 502.15 | 503.1 |
| 146 | Example 37 | $^1$H NMR (400 MHz, MeOD-d4) δ 9.45-8.82 (m, 1H), 8.68 (br.s., 1H), 8.41 -8.18 (m, 1H), 7.80-7.48 (m, 1H), 4.79-4.29 (m, 1H), 3.66 (br.d., J = 10.4 Hz, 1H), 3.44-3.33 (m, 1H), 3.28 -3.03 (m, 2H), 2.62 (br.s., 3H), 2.45 (br.s., 3H), 2.35-2.20 (m, 1H), 2.19-1.93 (m, 2H), 1.86 (br.d..,J = 9.9 Hz, 1H) | 474.17 | 475.1 |
| 147 | Example 62 | $^1$H NMR (400 MHz, CD3OD) δ 9.09 (s, 1H), 8.87 (brs, 1H), 8.57 (d, J = 19.1 Hz, 2H), 7.99 (brs, 1H), 7.52 (d, J = 8.0 Hz, 1H), 4.31 (brs, 1H), 3.44 (brs, 1H), 3.16 (brs, 1H), 2.66 (s, 3H), 2.20 – 2.03 (m, 1H), 2.01 – 1.86 (m, 2H), 1.85 – 1.72 (m, 1H), 1.43 (brs, 6H). | 471.48 | 471.4 |
| 148 | Example 38 | $^1$H NMR (400 MHz, MeOD-d4) δ 9.08 (s, 1H), 8.86-8.55 (m, 2H), 8.54-8.51 (m, 1H), 7.99 (s, 1H), 7.54 (br s, 1H), 4.44-4.22 (m, 1H), 3.97 (br s, 1H), 3.19 (br s, 2H), 2.87 (br s, 1H), 2.76 (br s, 1H), 2.66 (s, 3H), 2.32 (br s, 1H), 1.83-1.69 (m, 1H) | 459.16 | 460.1 |
| 149 | Example 59 | $^1$H NMR (500 MHz, DMSO-d6) δ 9.32 (s, 1H), 8.89 (d, J = 8.0 Hz, 0.5H), 8.63 (d, J = 8.0 Hz, 0.5H), 8.62 (s, 0.5H), 8.58 (s, 0.5H), 8.32 (br s, 1H), 7.97 (s, 1H), 7.96 (d, J = 7.9 Hz, 0.5H), 7.89 (d, J = 7.9 Hz, 0.5H), 7.61 (d, J = 8.1 Hz, 0.5H), 7.58 (d, J = 8.1 Hz, 0.5H), 4.07 – 3.99 (m, 1H), 3.17 (d, J = 11.0 Hz, 1H), 2.95 – 2.90 (m, 1H), 2.73 (s, 3H), 2.63 – 2.55 (m, 2H), 2.03 – 1.93 (m, 1H), 1.78 – 1.70 (m, 1H), 1.60 – 1.48 (m, 2H). Rotamers. | 459.49 | 460.0 |
| 150 | Example 39 | $^1$H NMR (400 MHz, MeOD-d4) δ 9.03 -8.59 (m, 2H), 8.38 (br. s, 1H), 8.13 (s, 1H), 7.73 (br. s, 1H), 4.56 (s, 3H), 4.35(br. d, J = 18.7 Hz, 1H), 3.68 (br. s, 1H), 3.25 (br. s, 1H), 2.90 (br. s, 1H), 2.24 (br. s, 1H), 2.12 (br. d, J = 11.4 Hz, 1H), 1.84 -1.59(m, 2H), 1.37 (d, J = 6.4 Hz, 3H) | 457.45 | 458.2 |
| 151 | Example 40 | $^1$H NMR (400 MHz, METHANOL-d4) δ 9.45-8.82 (m, 1H), 8.68 (br.s., 1H), 8.41 - 8.18 (m, 1H), 7.80 -7.48 (m, 1H), 4.79 -4.29 (m, 1H), 3.66 (br.d., J = 10.4 Hz, 1H), 3.44 -3.33 (m, 1H), 3.28 -3.03 (m, 2H), 2.62 (br.s., 3H), 2.45 (br.s., 3H), 2.35 -2.20 (m, 1H), 2.19 -1.93 (m, 2H), 1.86 (br.d., J = 9.9 Hz, 1H) | 457.45 | 458.1 |
| 152 | Example 41 | $^1$H NMR:(400MHz, DMSO)δ = 9.09-8.67 (m, 2H), 7.71-7.49 (m, 1H), 4.49-4.23 (m, 1H), 3.51 (br d, J = 11.7 Hz, 1H), 3.33-3.09 (m, 1H), 3.02-2.79 (m, 1H), 2.75-2.63 (m, 3H), 2.49 (s, 3H), 2.12 (br d, J = 12.6 Hz, 1H), 2.00 (br t, J = 14.2 Hz, 1H), 1.80-1.55 (m, 2H), 1.31 (d, J = 6.5 Hz, 3H) | 472.47 | 473.2 |

FIG. 3 (Cont.)

| Compound | Done as | $^1$H NMR | Calcd. Mass | Found Mass (MH$^+$) |
|---|---|---|---|---|
| 153 | Example 42 | $^1$H NMR:(400MHz, DMSO) δ = 8.95 (d, J = 8.4 Hz, 1H), 8.77 (s, 1H), 8.72-8.61 (m, 1H), 8.67 (br d, J = 8.7 Hz, 1H), 7.65-7.40 (m, 1H), 4.45-4.15 (m, 1H), 3.53-3.37 (m, 1H), 3.16 (br s, 1H), 2.92-2.75 (m, 1H), 2.69-2.60 (m, 3H), 2.45 (s, 3H), 2.07 (br d, J = 15.2 Hz, 1H), 1.96 (br d, J = 14.4 Hz, 1H), 1.73-1.49 (m, 2H), 1.25 (d, J = 6.5 Hz, 3H) | 472.47 | 473.2 |
| 154 | Example 43 | $^1$H NMR(400 MHz, METHANOL-d4) δ 9.12-8.60 (m, 2H), 8.42-7.90 (m, 2H), 4.72-4.23 (m, 1H), 3.71 (br d, J = 10.96 Hz, 1H), 3.20-2.92 (m, 1H), 2.87 (s, 4H), 2.34 (br s, 1H), 2.13 (br d, J = 9.21 Hz, 1H), 1.80 (br s, 2H), 1.40 (br d, J = 5.70 Hz, 3H) | 474.16 | 475.1 |
| 155 | Example 44 | $^1$H NMR (400 MHz, MeOD-d4) δ 8.67-9.18 (m, 2H) 8.49-8.04 (m, 2H), 4.77-4.27 (m, 1H), 3.69 (br s, 1H), 3.39 (br d, J = 12.72 Hz, 1H), 3.28-3.23 (m, 1H), 3.30-3.22 (m, 1H), 2.86 (s, 3H), 2.32 (br s, 1H), 2.19-1.77 (m, 3H) | 460.48 | 461.1 |
| 156 | Example 45 | $^1$H NMR (400 MHz, MeOD-d4) δ ppm 9.09 (s, 1H), 8.67-8.48 (m, 2H), 7.99 (br s, 1H), 7.53 (br s, 1H), 4.23 (br s, 1H), 3.63-3.41 (m, 1H), 3.14-2.90 (m, 1H), 2.76 (br t, J = 11.7 Hz, 1H), 2.66 (s, 3H), 2.21 (br s, 1H), 1.99 (br s, 1H), 1.80-1.44 (m, 2H), 1.27 (br s, 3H) | 457.45 | 458.1 |
| 157 | Example 46 | $^1$H NMR (400 MHz, MeOD-d4) δ 9.09 (s, 1H), 8.8844(s, 0.5H), 8.67-8.48 (m, 2H), 7.99 (br s, 1H), 7.53 (br s, 1H), 4.23 (br s, 1H), 3.63-3.41 (m, 1H), 3.14-2.90 (m, 1H), 2.76 (br t, J = 11.7 Hz, 1H), 2.66 (s, 3H), 2.21 (br s, 1H), 1.99 (br s, 1H), 1.80-1.44 (m, 2H), 1.27 (br s, 3H) | 457.18 | 458.2 |
| 158 | Example 47 | $^1$HNMR (400 MHz, MeOD-d4) δ 9.13-8.77 (m, 1H), 8.68 (br s, 1H), 8.47-8.09 (m, 2H), 4.73-4.24 (m, 1H), 3.72 (br d, J = 9.65 Hz, 1H), 3.31 (br s, 1H), 3.23-2.94(m, 1H), 2.88 (s, 3H), 2.44-2.07 (m, 2H), 1.80 (br s, 2H), 1.41 (br d, J = 5.70 Hz, 3H) | 474.16 | 475.1 |
| 159 | Example 48 | $^1$H NMR (400 MHz, MeOD-d4) δ 9.18-8.95 (m, 2H), 8.16 (br s, 2H), 4.33 (br s, 1H), 3.68 (br s, 1H), 3.29-3.21 (m, 1H), 2.88 (br d, J = 9.9 Hz, 1H), 2.71 (s, 3H), 2.35-2.07 (m, 2H), 1.86-1.61 (m, 2H), 1.37 (br d, J = 6.2 Hz, 3H) | 474.16 | 475.1 |
| 160 | Example 60 | $^1$H NMR (400 MHz, CD3OD) δ 9.26 (s, 1H), 8.83 (s, 1H), 8.72 (s, 1H), 8.54 (s, 1H), 7.64 (d, J = 8.4Hz, 1H), 4.28 (s, 1H), 3.50 – 3.36 (m, 1H), 3.17 – 3.07 (m, 1H), 2.71 (s, 3H), 2.17 – 1.65 (m, 4H), 1.40 (br s, 6H). | 472.47 | 472.9 |
| 161 | Example 49 | $^1$H NMR (400 MHz, MeOD-d4) δ 8.60 (s, 2H), 8.54 (br s, 1H), 8.21 (s, 1H), 8.02 (br s, 1H), 7.65 (br d, J = 7.2 Hz, 1H), 4.35 (br s, 1H), 3.62 -3.50 (m, 1H), 3.10 -2.92 (m, 2H), 2.67 (s, 3H), 2.30 -2.02 (m, 2H), 1.96 -1.67 (m, 2H) | 443.17 | 444.2 |
| 162 | Example 50 | $^1$H NMR (400 MHz, MeOD-d4) δ 9.08 -8.65 (m, 1H), 8.62 (s, 1H), 8.49 (s, 1.072H), 8.22 -7.98 (m, 2H), 4.32 (br s., 1H), 3.74 -3.59 (m, 1H), 3.23 (br s., 1H), 2.86 (br s.., 1H), 2.73 (s, 3H), 2.33 -2.05 (m, 2H), 1.85 -1.56 (m, 2H), 1.35 (br s., 3H) | 458.18 | 459.2 |

FIG. 3 (Cont.)

| Compound | Done as | $^1$H NMR | Calcd. Mass | Found Mass (MH$^+$) |
|---|---|---|---|---|
| 163 | Example 51 | $^1$H NMR (400 MHz, MeOD-d4) δ 8.60 (s, 2H), 8.54 (br s, 1H), 8.21 (s, 1H), 8.02 (br s, 1H), 7.65 (br d, J = 7.2 Hz, 1H), 4.35 (br s, 1H), 3.62 -3.50 (m, 1H), 3.10 -2.92 (m, 2H), 2.67 (s, 3H), 2.30 -2.02 (m, 2H), 1.96 -1.67 (m, 2H) | 458.18 | 459.1 |
| 164 | Example 52 | $^1$H NMR (400 MHz, MeOD-d4) δ 9.07 (br s, 1H), 8.70-8.66 (br s, 1H), 8.51 (m, 1H), 8.17 (br s, 2H), 4.59 (s, 3H), 4.31 (br s, 1H), 3.65 (br s, 1H), 3.22 (br s, 1H), 2.86 (br s, 1H), 2.36-2.03 (m, 2H), 1.85-1.56 (m, 2H), 1.35 (br d, J = 5.26 Hz, 3H) | 458.19 | 459.1 |
| 165 | Example 53 | $^1$H NMR (400 MHz, MeOD-d4) δ 9.09-8.67 (m, 1H), 8.61 (s, 1H), 8.52 (br s, 1H), 8.16 (br s, 2H), 4.59 (s, 3H), 4.31 (br s, 1H), 3.65 (br s, 1H), 3.22 (br s, 1H), 2.87 (br s, 1H), 2.36-2.03 (m, 2H), 1.90-1.54 (m, 2H), 1.35 (br d, J = 5.26 Hz, 3H) | 458.19 | 459.1 |
| 166 | Example 58 | $^1$H NMR (500 MHz, DMSO-d6) δ 12.53 (brs, 1H), 8.93 (d, J = 8.1 Hz, 0.5H), 8.66 (d, J = 8.1 Hz, 0.5H), 8.62 (s, 0.5H), 8.59 (s, 0.5H), 8.36 (brs, 1H), 8.00 – 7.87 (m, 2H), 7.38 - 7.30 (m, 1H), 4.02 (brs, 1H), 3.19 (brs, 1H), 2.94 (brs, 1H), 2.60 (brs, 2H), 2.52 (s, 3H), 2.42 (s, 3H), 2.06 - 1.94 (m, 1H), 1.74 (brs, 1H), 1.53 (brs, 2H). Rotamers. | 473.52 | 474.0 |
| 167 | Example 54 | $^1$H NMR (400 MHz, MeOD-d4) δ 9.05 (br s, 1H), 8.74 (s, 1H), 8.10 (br s, 1H), 4.35 (br s, 1H), 3.69 (br s, 1H), 3.29 -3.19 (m, 1H), 2.90 (br s, 1H), 2.75 (s, 3H), 2.26 (br s, 1H), 2.13 (br d, J = 14.0 Hz, 1H), 1.87 -1.55 (m, 2H), 1.37 (br s, 3H) | 459.17 | 460.1 |
| 168 | Example 55 | $^1$H NMR (400 MHz, MeOD-d4) δ 8.74 (s, 2H), 8.10 (br s, 1H), 4.38 (br s, 1H), 3.63 (br d, J = 11.4 Hz, 1H), 3.37 (br s, 1H), 3.07 (br s, 2H), 2.74 (s, 3H), 2.32 -2.05 (m, 2H), 1.99 -1.72 (m, 2H) | 445.16 | 446.1 |

INHIBITORS OF CYCLIN DEPENDENT KINASE 7 (CDK7)

CROSS-REFERENCE TO RELATED APPLICATIONS

This application is a national stage application under 35 U.S.C. 371 of International Application No. PCT/US2019/013845 filed on Jan. 16, 2019, which claims the benefit of the priority of U.S. Provisional Application 62/617,884 filed on Jan. 16, 2018, the disclosure of each of which is incorporated herein by reference in its entirety.

BACKGROUND OF THE INVENTION

Kinases that are members of the cyclin-dependent kinase (CDK) family play critical roles in cellular proliferation. Among the mammalian CDKs, CDK7 has uniquely consolidated kinase activities that help regulate both the cell cycle and gene transcription. In the cytosol, CDK7 exists within a heterotrimeric complex and is thought to function as a CDK1/2-activating kinase (CAK); phosphorylation of conserved residues in CDK1/2 by CDK7 is required for full catalytic activity and cell cycle progression. In the nucleus, CDK7 forms the kinase core of the RNA polymerase (RNAP) II general transcription factor complex and phosphorylates its C-terminal domain (CTD), a requisite step in initiating gene transcription. By both activating CDK1/2 and phosphorylating the CTD of RNAP II, CDK7 supports critical facets of cellular proliferation, cell cycling, and gene transcription.

Although some progress has been made, it is difficult to develop selective inhibitors of CDK7 because its sequence and structure are similar to the sequences and structures of other CDKs. Thus, there is still an unmet need for selective CKD7 inhibitors.

SUMMARY OF THE INVENTION

Described herein are selective CDK7 inhibitors (compounds) of Formula (I) and pharmaceutically acceptable salts, solvates (e.g., hydrates), tautomers, and isotopic forms thereof. These compounds preferably demonstrate greater specificity for CDK7 than for one or more of CDK2, CDK9, and CDK12 (e.g., at least 10-, 100-, or 1,000-fold greater specificity) when assessed in an enzymatic assay that measures the IC50 of the compound. Also described are compositions containing a compound described herein (e.g., a pharmaceutical composition or kit) and methods of using the compounds (or salts, solvates (e.g., hydrates), tautomers, and isotopic forms thereof), pharmaceutical compositions, or kits to treat or prevent a disease associated with aberrant CDK7 expression (e.g., overexpression or misexpression) or activity (e.g., overactivity). The disease can be a proliferative disease (e.g., a cancer such as a blood cancer (e.g., leukemia) breast cancer, melanoma, multiple myeloma, ovarian cancer (or any other cancer described further below), a benign neoplasm, or a condition characterized by pathologic angiogenesis, or a fibrotic disease). The fibrotic disease can be NASH (non-alcoholic steatohepatitis) or NAFLD (non-alcoholic fatty liver disease), which can progress to cirrhosis of the liver and eventual liver failure; any other disease or chronic damage to the liver that results in fibrosis (e.g., alcoholism or hepatitis); scleroderma, which can progress to systemic scleroderma (also known as systemic sclerosis (SSc)); any other disease characterized by cutaneous fibrosis or resulting in pulmonary fibrosis (e.g., cystic fibrosis, multiple sclerosis, rheumatoid arthritis, systemic lupus erythematosus (SLE), or idiopathic pulmonary fibrosis); kidney fibrosis (e.g., as occurs in connection with chronic kidney disease such as Alport Syndrome, glomerulonephritis, polycystic kidney disease, and reflux nephropathy); and cardiac (e.g., endomyocardial) fibrosis, which is a common phenomenon in heart or cardiovascular diseases such as ischemic heart disease, atherosclerosis, arteriosclerosis, and inherited cardiomyopathies, as well as in Behcet's disease, diabetes, and ageing. The disease can also be an infectious disease (e.g., a viral infection caused by an influenza virus, human immunodeficiency virus (HIV), herpes virus, or human papilloma virus (HPV)) or a disease caused by or associated with expanded repeats of simple nucleotide tracts including, but not limited to, Huntington's Disease (HD), myotonic dystrophy (e.g., DM1 and DM2), and some forms of amyotrophic lateral sclerosis (ALS). Diseases caused by or associated with an expanded repeat are also known in the art as trinucleotide repeat disorders, trinucleotide repeat expansion disorders, triplet repeat expansion disorders, and codon reiteration disorders. In these genetic diseases, trinucleotide repeats in certain genes or introns exceed the stable threshold observed in healthy patients.

In one aspect, the present invention provides compounds of formula (I)

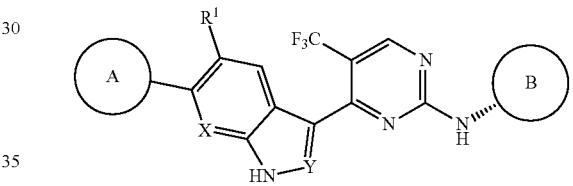

and pharmaceutically acceptable salts, solvates (e.g., hydrates), tautomers, and isotopically labeled derivatives thereof, wherein Ring A, Ring B, X, Y, $R^1$ and subvariables thereof are as defined herein. For ease of reading, we may not refer to both a compound of the invention and a pharmaceutically acceptable salt thereof when describing each and every composition, method, and use within the scope of the invention. It is to be understood that where a compound of the invention can be used, a pharmaceutically acceptable salt thereof may also be useful, and making that determination is well within the ability of one of ordinary skill in the art.

While pharmaceutical compositions within the scope of the invention are described further below, we note here that they can contain a compound of Formula (I) (or a pharmaceutically acceptable salt, solvate (e.g., hydrate), tautomer, or isotopic form thereof) and a pharmaceutically acceptable excipient. The active ingredient (e.g., a compound of Formula (I)), regardless of its precise chemical form (e.g., isomeric or isotopic forms), can be present in a therapeutically or prophylactically effective amount, and the pharmaceutical compositions described herein can be packaged in unit dosages, fractions thereof or multiples thereof.

In addition to administering a composition described herein to a patient who has been diagnosed as having a disease described herein, the compositions of the invention can be used ex vivo to alter CDK7 expression or activity in a biological sample (e.g., a cultured cell line or a blood or tissue sample obtained from a patient). In any circumstance in which a compound or composition described herein is administered to a patient, the patient may have been diagnosed with a disease that is associated with aberrant expression or activity of CDK7, and any of the methods of treatment or uses described herein can include a step of determining whether CDK7 expression or activity is aberrant in a biological sample obtained from the patient. This information may also be obtained indirectly. Thus, the methods of treatment and uses described herein can include a step of administering/using a compound or composition described herein, where, prior to the administration/use, a biological sample obtained from the patient has been determined to exhibit aberrant (e.g., elevated) CDK7 expression or activity.

The kits can include a container with a compound of Formula (I) or a pharmaceutically acceptable salt, solvate (e.g., hydrate), tautomer, or isotopic form thereof, or a pharmaceutical composition thereof. In certain embodiments, the kits described herein further include instructions (in written or other form) for administering a compound described herein (e.g., a compound of Formula (I) or a pharmaceutically acceptable salt, solvate (e.g., hydrate), tautomer, or isotopic form thereof, or the pharmaceutical composition thereof. Paraphernalia (e.g., a syringe, needles, tubing, gloves, bandages, tape, local anestheics, etc. . . . ) may also be included.

The following definitions apply to the compositions and methods described herein unless the context clearly indicates otherwise. It will be evident to one of ordinary skill in the art that the definitions apply to grammatical variants of these terms, some of which are particularly mentioned below (e.g., "administration" and "administering"). The chemical elements are identified in accordance with the Periodic Table of the Elements, CAS version, Handbook of Chemistry and Physics, $75^{th}$ Ed. Additionally, general principles of organic chemistry that may facilitate the production of the compounds described herein can be found in "Organic Chemistry," Thomas Sorrell, University Science Books, Sausalito, 1999; "March's Advanced Organic Chemistry," $5^{th}$ Ed., Ed. Smith and March, John Wiley & Sons, New York, 2001; Larock, "Comprehensive Organic Transformations," VCH Publishers, Inc., New York, 1989; and Carruthers, "Some Modern Methods of Organic Synthesis," $3^{rd}$ Edition, Cambridge University Press, Cambridge, 1987.

The term "about," when used in reference to a value, signifies any value or range of values that is plus-or-minus 10% of the stated value (e.g., within plus-or-minus 1%, 2%, 3%, 4%, 5%, 6%, 7%, 8%, 9% or 10% of the stated value). For example, a dose of about 10 mg means any dose as low as 10% less than 10 mg (9 mg), any dose as high as 10% more than 10 mg (11 mg), and any dose or dosage range therebetween (e.g., 9-11 mg; 9.1-10.9 mg; 9.2-10.8 mg; and so on). In case of any doubt, the stated value is included; about 10 mg includes 10 mg. Where a stated value cannot be exceeded (e.g., 100%), "about" means a value or range of values that is up to and including 10% less than the stated value (e.g., a purity of about 100% means 90%-100% pure (e.g., 95%-100% pure, 96%-100% pure, 97%-100% pure etc. . . . )).

The term "administration" and variants thereof, such as "administering," refer to the application of a compound described herein, a form thereof (e.g., a pharmaceutically acceptable salt or solvate) or a composition containing any such compounds or forms (e.g., a pharmaceutical composition) to a patient (e.g., a human patient) or system (e.g., a cell- or tissue-containing system maintained ex vivo (e.g., any cell, tissue, or organ culture, which may be maintained by conventional or new techniques). One of ordinary skill in the art will know a variety of routes that may, in appropriate circumstances, be utilized for administration to a patient or system. For example, the route of administration to a patient may be oral (i.e., by swallowing a pharmaceutical composition) or parenteral (a term encompassing any route of administration that is not oral; e.g., intra-arterial or intravenous, intra-articular, intracranial, intralesional, intramuscular, intraperitoneal, or intrathecal). Preferably, the compositions are administered orally, subcutaneously, intralesionally, intraperitoneally or intravenously. Any pharmaceutical composition described herein can be sterile and/or in an orally available or injectable form made using techniques and excipients known in the art (including those described further herein).

Further, the route of administration to a patient can be bronchial (e.g., by bronchial instillation), by mouth (i.e., oral), dermal (which may be or comprise topical application to the dermis or intradermal, interdermal, or transdermal administration), intragastric or enteral (i.e., directly to the stomach or intestine, respectively), intramedullary, intramuscular, intranasal, intraperitoneal, intrathecal, intravenous (or intra-arterial), intraventricular, by application to or injection into a specific organ (e.g., intrahepatic), mucosal (e.g., buccal, rectal, sublingual, or vaginal), subcutaneous, tracheal (e.g., by intratracheal instillation), or ocular (e.g., topical, subconjunctival, or intravitreal). Administration can involve continuous dosing (e.g., by oral administration or perfusion) for a selected time (e.g., over or every 1-3 hours; 3-6 hours; over a period of 12 hours; over a period of 24 hours; etc. . . . ), intermittent dosing (e.g., a plurality of doses separated in time), and/or periodic dosing (e.g., doses separated by a common period of time (e.g., every so many hours, daily, weekly, twice per week, etc.)).

The term "angiogenesis" refers to the formation and growth of new blood vessels. Normal angiogenesis occurs in healthy patients during development and in the context of wound healing. However, patients suffering from many different diseases, including cancer, diabetes (particularly the progression to blindness associated therewith), age-related macular degeneration, rheumatoid arthritis, and psoriasis, experience excessive and detrimental angiogenesis. Angiogenesis is detrimental when it produces blood vessels that support diseased cells (e.g., tumor cells), destroy normal tissues (e.g., tissue within the eye), or facilitates tumor metastases. We may refer to such unwanted angiogenesis as "pathologic angiogenesis."

Two events or entities are "associated" with one another if one or more features of the first (e.g., its presence, level, activity, and/or form) are correlated with a feature of the second. For example, a first entity (e.g., a CDK7), gene expression profile, genetic signature (i.e., a single or combined group of genes in a cell with a uniquely characteristic pattern of gene expression), metabolite, or event (e.g., loss of cell cycle control in CDK7-positive cells)) is associated with a particular disease, if its presence, level, activity, and/or form correlates with the incidence of, severity of, and/or susceptibility to the disease (e.g., a cancer disclosed herein). Associations are typically assessed across a relevant population. Two or more entities are physically "associated" with one another if they interact, directly or indirectly, so that they are and/or remain in physical proximity with one another in a given circumstance (e.g., within a cell maintained under physiological conditions (e.g., within cell culture) or within a pharmaceutical composition). Entities that are physically associated with one another can be covalently linked to one another or non-covalently associated by, for example, hydrogen bonds, van der Waals forces, hydrophobic interactions, magnetism, or combinations thereof.

The terms "binding" and variants thereof (such as "bound" and "bind(s)") refer to a covalent or non-covalent association of two or more entities (e.g., a compound and an agent within a pharmaceutical composition or a compound and its target within a cell). "Direct" binding or direct association occurs when the two entities physically contact one another (e.g., through a chemical bond) whereas indirect binding or indirect association occurs when one of the entities physically contacts one or more intermediate entities that bring the entities into physical proximity with one another (e.g., within a complex). Binding can be assessed in a variety of contexts (e.g., in full or partial isolation or in more complex, naturally occurring or model systems (e.g., in a tissue, organ, or cell in vivo or maintained in a tissue culture environment)).

The term "biologically active" describes an agent (e.g., a compound described herein) that produces an observable biological effect or result in a biological system or model thereof (e.g., in a human, other animal, or a system maintained in vitro). The "biological activity" can result from binding between the agent and a target (e.g., a CDK7), and it may result in modulation (e.g., induction, enhancement, or inhibition) of a biological pathway or event (e.g., a cellular activity (e.g., immunostimulation) or proliferation). The presence of biological activity and, optionally, its extent, can be assessed using known and/or standard methods to detect an immediate or downstream product or event associated with the biological activity, and any of the methods described herein can include a step of assessing such activity.

The term "biological sample" refers to a sample obtained or derived from a biological source of interest (e.g., a tissue or organism (e.g., an animal or human patient) or cell culture). The biological sample can contain a biological cell, tissue or fluid or any combination thereof. For example, a biological sample can be or can include ascites; blood; blood cells; bodily fluid(s), any of which may include or exclude cells; bone marrow; cerebrospinal fluid (CSF); feces; flexural fluid; free floating nucleic acids; gynecological fluids; immune infiltrates; lymph; peritoneal fluid; plasma; saliva; sputum; surgically-obtained specimens; tissue scraped or swabbed from the skin or a mucus membrane (e.g., in the nose, mouth, or vagina); tissue or fine needle biopsy samples; urine; washings or lavages such as a ductal lavage or broncheoalveolar lavage; or other body fluids, tissues, secretions, and/or excretions. A biological sample may include cancer cells or immune cells, such as NK cells and/or macrophages, which are found in many tissues and organs, including the spleen and lymph nodes. Cells (e.g., NK cells, macrophages, and cancer cells) within the sample may have been obtained from an individual for whom a treatment is intended. Samples used in the form in which they were obtained may be referred to as "primary" samples, and samples that have been further manipulated (e.g., by adding or removing one or more components to/from the sample) may be referred to as "secondary" or "processed" samples. Such processed samples can contain or be enriched for a particular cell type (e.g., a CDK7-expressing cell such as a macrophage or tumor cell), cellular component (e.g., a membrane fraction), or cellular material (e.g., one or more cellular proteins, including one or more of a CDK7, DNA, or RNA (e.g., mRNA), which may have been subjected to amplification).

The term "cancer" refers to a disease in which cells exhibit an aberrant growth phenotype characterized by loss of control of cell proliferation to an extent that will be detrimental to a patient having the disease; such cells can be referred to as a "cancer cell," a "tumor cell," or a "malignant cell." A cancer can be classified by the type of tissue in which it originated (histological type) and/or by the primary site in the body in which the cancer first developed. Based on histological type, cancers are generally grouped into six major categories: carcinomas; sarcomas; myelomas; leukemias; lymphomas; and mixed types. A cancer treated as described herein can be of any one of these types and may comprise cells that are precancerous (e.g., benign), malignant, pre-metastatic, metastatic, and/or non-metastatic. A patient who has a malignancy or malignant lesion has a cancer. The present disclosure specifically identifies certain cancers to which its teachings may be particularly relevant, and one or more of these cancers may be characterized by a solid tumor or by a hematologic tumor, which may also be known as a blood cancer (e.g., of a type described herein).

The term "comparable" refers to two or more items (e.g., agents, entities, situations, sets of conditions, etc.) that are not identical to one another but are sufficiently similar to permit comparison therebetween so that one of ordinary skill in the art will appreciate that conclusions may reasonably be drawn based on differences or similarities observed. Comparable sets of conditions, circumstances, individuals, or populations are characterized by a plurality of substantially identical features and one or a small number of varied features. One of ordinary skill in the art will understand, in context, what degree of identity is required in any given circumstance for two or more items to be considered comparable. For example, two items are comparable to one another when they have in common a sufficient number and type of substantially identical features to warrant a reasonable conclusion that any differences in results obtained or phenomena observed with the items are caused by or are indicative of the variation in those features that are varied. A comparable item can serve as a "control." For example, a "control patient/population" can be an untreated patient/population who is afflicted with the same disease as a patient/population being treated.

The term "combination therapy" refers to those situations in which a patient is exposed to two or more therapeutic regimens (e.g., two or more therapeutic agents) to treat a single disease (e.g., a cancer). The two or more regimens may be administered simultaneously or sequentially (e.g., all "doses" of a first regimen are administered prior to administration of any dose(s) of a second regimen by the same or a different route of administration). For clarity, combination therapy does not require that individual agents be administered together in a single composition (or even necessarily at the same time), although in some embodiments, two or more agents (e.g., compounds described herein) may be administered together in a single composition or even as a combination compound (e.g., associated in a single chemical complex or covalent entity). In any of the compositions or methods described herein, a compound of Formula I can be a "first" agent.

The term "compound" means a chemical compound (e.g., a compound represented by a structural Formula depicted herein, a sub-genus thereof, or a species thereof). Any given compound can be biologically, therapeutically, or prophylactically active (e.g., when contained in a pharmaceutical composition in an effective amount) and can be provided and/or utilized (e.g., used in a biological assay, administered to a patient, incorporated into a medicament, or otherwise used as described herein) in any of a variety of forms.

A "disease" is a pathologic state regardless of whether the disease is commonly referred to as a condition, disorder, syndrome, or the like (e.g., a myeloproliferative disorder is a disease).

The terms "dosage form," "formulation," and "preparation" are used to refer to compositions containing a compound or other biologically and/or therapeutically active agent that is suitable for administration to a patient. The term "unit dosage form" refers to a physically discrete unit of a compound or other biologically and/or therapeutically active agent (e.g., a therapeutic or diagnostic agent) formulated for administration to a patient. Typically, each such unit contains a predetermined quantity of the active agent, which may be the amount prescribed for a single dose (i.e., an amount expected to correlate with a desired outcome when administered as part of a therapeutic regimen) or a fraction thereof. One of ordinary skill in the art will appreciate that the total amount of a therapeutic composition or agent administered to a particular patient is determined by one or more attending physicians and may involve administration of multiple unit dosage forms.

The term "dosing regimen" refers to the unit dosage form(s) administered to, or prescribed for, a patient, and typically includes more than one dose separated by periods of time (e.g., as described elsewhere herein). The dosage form(s) administered within a dosing regimen can be of the same unit dose amount or of different amounts. For example, a dosing regimen can comprises a first dose in a first dose amount, followed by one or more additional doses in a second dose amount that is the same as or different from the first dose amount.

An "effective amount" of a compound of Formula (I) refers to an amount sufficient to elicit the desired biological response (e.g., treating or preventing the disease). As will be appreciated by one of ordinary skill in the art, the effective amount of a compound described herein may vary depending on such factors as the desired biological endpoint, the pharmacokinetics of the compound, the disease being treated, the mode of administration, and the age and health of the patient. An effective amount encompasses therapeutic and prophylactic treatment. For example, in treating cancer, an effective amount of an inventive compound may reduce the tumor burden or stop the growth or spread of a tumor.

The term "excipient" refers to an adjuvant, carrier, diluent, or other vehicle with which a compound or composition described herein is administered or otherwise used. The excipient can be a sterile or sterilizable liquid, such as a water (e.g., water for injection), an aqueous solution (e.g., an isotonic salt solution (e.g., 0.9% NaCl), Ringer's solution, or a solution comprising 1,3-butanediol), or a natural or synthetic oil (e.g., a petroleum-based or mineral oil, an animal oil, or a vegetable oil (e.g., a peanut, soybean, sesame, or canola oil)). The oil may also be a nonvolatile oil of any animal or plant origin (i.e., a "fixed" oil). Sterile, fixed oils are conventionally employed as solvents and suspending media.

The excipient can be a solid; a liquid that includes one or more solid components (e.g., a salt, for example, a "normal saline"); a mixture of solids; or a mixture of liquids. The excipient may have characteristics that make it useful as a binding agent, buffering agent, diluent, disintegrating agent, dispersing agent, emulsifier, granulating agent, lubricating agent, preservative, or surface active agent. Excipients include, but are not limited to, alumina, aluminum stearate, a buffer (e.g., a phosphate salt (e.g., disodium hydrogen phosphate or potassium hydrogen phosphate) a sodium salt (e.g., sodium chloride), a zinc salt, or other salts or electrolytes), a cellulose-based substance (e.g., sodium carboxymethylcellulose), colloidal silica, glycine, an ion exchanger, lecithin, polyethylene glycol, potassium sorbate, protamine sulfate, a serum protein (e.g., human serum albumin), sorbic acid, a partial glyceride mixture of saturated vegetable fatty acids, magnesium trisilicate, polyvinyl pyrrolidone, a polyethylene-polyoxypropylene-block polymer, a polyacrylate, water, wax, and wool fat.

The term "hydrate" refers to a compound that is bound to water. The amount of water contained in the hydrate can be expressed as a ratio of the number of water molecules to the number of compound molecules. Thus, a hydrate of a compound may be represented by a general formula such as $R.x H_2O$, where R is the compound and x is a number greater than 0. For example, where x is 1, the hydrate is a monohydrate; where x is 0.5, the hydrate is a hemihydrate; where x is 2, the hydrate is a dihydrate; and where x is 6, the hydrate is a hexahydrate. A hydrate is a type of solvate.

"Improve(s)," "increase(s)" or "reduce(s)/decrease(s)" are terms used to characterize the manner in which a value has changed relative to a reference value. For example, a measurement obtained from a patient (or a biological sample obtained therefrom) prior to treatment can be increased or reduced/decreased relative to that measurement obtained during or after treatment in the same patient, a control patient, on average in a patient population, or biological sample(s) obtained therefrom. The value may be improved in either event, depending on whether an increase or decrease is associated with a positive therapeutic outcome.

The term "inhibitor" refers to an agent, including a compound described herein, whose presence (e.g., at a certain level or in a certain form) correlates with a decrease in the expression or activity of another agent (i.e., the inhibited agent or target) or a decrease in the occurrence of an event (e.g., tumor progression or metastasis). In some embodiments, an inhibitor exerts its influence on a target by binding to the target, directly or indirectly. In other embodiments, an inhibitor exerts its influence by binding and/or otherwise altering a regulator of the target, so that the expression and/or activity of the target is reduced. Inhibition can be assessed in silico, in vitro (e.g., in a cell, tissue, or organ culture or system), or in vivo (e.g., in a patient or animal model).

An "isotopic form" of a compound described herein (e.g., a compound of Formula (I)) is a form in which one or more elements of the compound have been replaced with an isotopic variant of that element. Where a compound contains an isotopic substitution, it can be, e.g., $^2H$ or $^3H$ for H; $^{11}C$, $^{13}C$ or $^{14}C$ for $^{12}C$; $^{13}N$ or $^{15}N$ for $^{14}N$; $^{17}O$ or $^{18}O$ for $^{16}O$; $^{36}Cl$ for $^{35}C$; $^{18}F$ for $^{19}F$; $^{131}I$ for $^{127}I$; etc. Such compounds have use, for example, as analytical tools, as probes in biological assays, and/or as therapeutic or prophylactic agents for use in accordance with the present invention. In particular, an isotopic substitution of deuterium ($^2H$) for hydrogen is known to potentially slow down metabolism, shift metabolism to other sites on the compound, slow down racemization and/or have other effects on the pharmacokinetics of the compound that may be therapeutically beneficial. In particular, deuterated forms of a compound described herein (or other forms thereof, such as salts or solvates) are embodiments of the present invention; such forms include deuterium in place of one or more of the hydrogen atoms in the compound but no other isotopic variants (e.g., no isotopes of $^{12}C$, $^{14}N$, or $^{18}O$).

The terms "neoplasm" and "tumor" are used herein interchangeably and refer to an abnormal mass of tissue in which the growth of the mass surpasses and is not coordinated with the growth of a normal tissue. A neoplasm or tumor may be "benign" or "malignant" depending on the following characteristics: the degree of cellular differentiation (including morphology and functionality), rate of growth, local invasion, and metastasis. A "benign neoplasm" is generally well differentiated, has a slower growth rate than a malignant neoplasm, and remains localized to the site of origin (i.e., does not have the capacity to infiltrate, invade, or metastasize to distant sites). Benign neoplasms include, but are not limited to, acrochordons, adenomas, chondromas, intraepithelial neoplasms, lentigos, lipoma, sebaceous hyperplasias, seborrheic keratoses, and senile angiomas. The benign neoplasm can also be tuberous sclerosis, or tuberous sclerosis complex (TSC) or epiloia (derived from "epilepsy, low intelligence, adenoma sebaceum"). Benign neoplasms can later give rise to malignant neoplasms (believed to occur as a result of genetic changes in a subpopulation of the tumor's neoplastic cells), and such neoplasms are referred to as "pre-malignant neoplasms." An exemplary pre-malignant neoplasm is a teratoma. In contrast, a "malignant neoplasm" is generally poorly differentiated (anaplasia) and grows rapidly with progressive infiltration, invasion, and destruction of surrounding tissue. Malignant neoplasms also generally have the capacity to metastasize to distant sites.

A "patient" is any organism to which a compound described herein (or any variant thereof, as also described herein (e.g., a salt or solvate) is administered in accordance with the present invention e.g., for experimental, diagnostic, prophylactic, and/or therapeutic purposes. Typical patients include animals (e.g., mammals such as mice, rats, rabbits, non-human primates, and humans; birds; insects; worms; etc.). A patient can be suffering from a disease described herein (e.g., a proliferative disease, such as cancer or a benign neoplasm).

A "pharmaceutical composition" is a composition in which an active agent (e.g., an active pharmaceutical ingredient (e.g., a compound described herein)) is formulated together with one or more pharmaceutically acceptable excipients. The active agent can be present in a unit dose amount appropriate for administration in a therapeutic regimen that shows a statistically significant probability of achieving a predetermined therapeutic effect when administered to patients of a relevant population. The pharmaceutical composition may be specially formulated for administration in solid or liquid form, including forms made for oral or parenteral (e.g., intravenous) administration. For parenteral administration, the composition can be formulated, for example, as a sterile solution or suspension for subcutaneous, intramuscular, intravenous, intra-arterial, intraperitoneal, or epidural injection. Pharmaceutical compositions comprising an active agent (e.g., a compound described herein) can also be formulated as sustained-release formulations or as a cream, ointment, controlled-release patch, or spray for topical application. Creams, ointments, foams, gels, and pastes can also be applied to mucus membranes lining the nose, mouth, vagina, and rectum. Any of the compounds described herein and any pharmaceutical composition containing such a compound may also be referred to as a "medicament."

The term "pharmaceutically acceptable," when applied to an excipient used to formulate a composition disclosed herein (e.g., a pharmaceutical composition), means an excipient that is compatible with the other ingredients of the composition and not prohibitively deleterious to a patient (e.g., it is sufficiently non-toxic in the amount required and/or administered (e.g., in a unit dosage form). When applied to a salt (e.g., a salt of a compound described herein), "pharmaceutically acceptable" refers to the salt form of a compound that is, within the scope of sound medical judgment, suitable for use in contact with the tissues of humans and lower animals without prohibitive toxicity, irritation, allergic response and the like, and that is commensurate with a reasonable benefit/risk ratio. Pharmaceutically acceptable salts are well known in the art (see, e.g., Berge et al., *J. Pharmaceutical Sciences*, 66:1-19, 1977). Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as lower alkyl sulfonate, aryl sulfonate, carboxylate, halide, hydroxide, nitrate, phosphate, and sulfate.

When applied to a composition (e.g., a pharmaceutical composition), the term "pharmaceutically acceptable" indicates that the composition is suitable for administration to a patient by virtue of being non-contamiated (e.g., sterile) and non-toxic (i.e., generally safe; not expected to be poisonous).

A "prophylactically effective amount" of a compound described herein is an amount sufficient to delay the onset of a disease for a period of time that is substantially longer than expected (e.g., as evidenced by the absence of the signs and symptoms associated with the disease). A prophylactically effective amount can be an amount that improves overall prophylaxis or enhances the prophylactic efficacy of another prophylactic agent (a "second" prophylactic agent (e.g., a "second" compound)).

A "proliferative disease" is a disease that occurs due to abnormal growth or extension by the multiplication of cells (Walker, *Cambridge Dictionary of Biology*; Cambridge University Press: Cambridge, UK, 1990). A proliferative disease can be associated with the pathological proliferation of normally quiescent or normally dividing cells; the pathological migration of cells from their normal location (e.g., metastasis of neoplastic cells); the pathological expression of proteolytic enzymes such as the matrix metalloproteinases (e.g., collagenases, gelatinases, and elastases); and/or pathologic angiogenesis, as occurs in proliferative retinopathies and tumor metastases. Exemplary proliferative diseases include cancers, which may also be referred to as "malignant neoplasms," benign neoplasms, and pathologic angiogenesis.

A "sign or symptom is reduced" when one or more objective signs or subjective symptoms of a disease are reduced in magnitude (e.g., intensity, severity, etc.) and/or frequency. A delay in the onset of a particular sign or symptom is one form of reducing the frequency of that sign or symptom. Reducing a sign or symptom can be achieved by, e.g., a "therapeutically active" compound optionally administered in an effective amount, as described herein.

The term "solvate" refers to a compound bound to a solvent, usually by a solvolysis reaction. This physical association may include hydrogen bonding. Solvents that can be used in the reaction include water, methanol, ethanol, acetic acid, DMSO (dimethyl sulfoxide), THF (tetrahydrofuran), diethyl ether, and the like. A compound of Formula I or (Ia) can be prepared, e.g., in crystalline form, and then solvated. The solvate can be pharmaceutically acceptable and can be either a stoichiometric or non-stoichiometric solvate. In certain instances, the solvate will be capable of isolation, for example, when one or more solvent molecules are incorporated in the crystal lattice of a crystalline solid. "Solvate" encompasses both solution-phase and isolable solvates, and representative solvates include hydrates, ethanolates, and methanolates.

The term "specific," as used herein with reference to an agent (e.g., a compound) having an activity (e.g., inhibition of a target), means that the agent discriminates between potential target entities or states. For example, an agent binds "specifically" to its intended target (or otherwise specifically inhibits its target) if it preferentially binds or otherwise inhibits the expression or activity of that target in the presence of one or more alternative targets. Although the invention is not so limited, a specific and direct interaction can depend upon recognition of a particular structural feature of the target (e.g., an epitope, a cleft, or a binding site). Specificity need not be absolute; the degree of specificity need only be enough to result in an effective treatment without unacceptable side effects. The specificity of an agent can be evaluated by comparing the effect of the agent on an intended target or state relative to its effect on a distinct target or state. The effects on the intended and distinct targets can each be determined or the effect on the intended target can be determined and compared to a reference standard developed at an earlier time (e.g., a reference specific binding agent or a reference non-specific binding agent). In some embodiments, the agent does not detectably bind the competing alternative target under conditions in which it detectably (and, preferably, significantly) binds its intended target and/or does not detectably inhibit the expression or activity of the competing target under conditions in which it detectably (and, preferably, significantly) inhibits the expression or activity of its intended target. A compound of the invention may exhibit, with respect to its target(s), a higher on-rate, lower off-rate, increased affinity, decreased dissociation, and/or increased stability compared with the competing alternative target, and any of these parameters can be assessed in methods of the invention.

As used herein with regard to a compound, the term "stable," means the compound is not rendered inactive or substantially inactive when it is subjected to conditions that allow for its production, detection, recovery, purification, or use as described herein.

The invention encompasses "stereoisomeric forms" of a compound described herein (e.g., an optical and/or structural isomer). The stereoisomers of any referenced or depicted structure can be enantiomers and diastereomers (e.g., cis/trans isomers and conformational isomers). These include the R and S configurations for each asymmetric center, Z and E double bond isomers, and Z and E conformational isomers. Compositions containing a single type of stereochemical isomer as well as enantiomeric, diastereomeric, and geometric (or conformational) mixtures of the present compounds are within the scope of the invention. Where a particular enantiomer is preferred, it can be provided substantially free of the corresponding enantiomer, and may also be referred to as "optically enriched," meaning that the compound is made up of a significantly greater proportion of one enantiomer. For example, a plurality of the compound molecules can be made up of at least about 90% by weight of the preferred enantiomer (e.g., at least about 95%, 98%, or 99% by weight). Preferred enantiomers can be isolated from racemic mixtures by methods known in the art, including chiral high pressure liquid chromatography (HPLC) and the formation and crystallization of chiral salts. They can also be prepared by asymmetric syntheses. If needed, one could consult, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972).

The term "substantially" refers to the qualitative condition of exhibiting a characteristic or property of interest to a total or near-total extent or degree. One of ordinary skill in the art will understand that biological and chemical phenomena rarely, if ever, go to completion and/or proceed to completeness or achieve or avoid an absolute result. The term "substantially" may therefore be used to capture the potential lack of completeness inherent in many biological and chemical phenomena. For example, a chemical reaction may be characterized as substantially complete even though the yield is well below 100%. Certain features may also be deemed "substantially identical" when they are about the same and/or exhibit about the same activity. For example, two nearly identical compounds that produce about the same effect on an event (e.g., cellular proliferation) may be described as substantially similar. With regard to the purity of a compound or composition, "substantially pure" is defined below.

The term "substantially pure," when used to refer to a compound described herein, means that a preparation of the compound is more than about 85% (w/w) compound (e.g., more than about 90%, 95%, 97%, 98%, 99%, or 99.9%).

An individual who is "susceptible to" a disease (e.g., a proliferative disease, such as cancer) has a greater than average risk for developing the disease. Such an individual may not yet display any symptoms of the disease and may not have not been diagnosed with the disease. Such an individual may have been exposed to conditions associated with development of the disease (e.g., exposure to a carcinogen). Susceptibility can be assessed by one of ordinary skill in the art and can be determined relative to a population-based risk.

The term "tautomer" refers to a structural or constitutional isomer of a compound; tautomers are compounds having the same molecular formula but different atomic organization and bonding patterns. Tautomeric compounds readily interconvert and vary from one another in the displacement of hydrogen atoms and electrons. Thus, two tautomeric compounds may be in equilibrium through the movement of $\pi$ electrons and an atom (usually H). For example, enols and ketones are tautomers because they are rapidly interconverted by treatment with either acid or base. Tautomeric compounds may exhibit improved chemical reactivity and biological activity relative to the comparable non-tautomeric compound.

A "therapeutic regimen" refers to a dosing regimen that, when administered across a relevant population, is correlated with a desired therapeutic outcome.

The term "treatment," and linguistic variants thereof, such as "treat(s)" and "treating," refer to any use of a compound or pharmaceutical composition described herein to partially or substantially completely alleviate, ameliorate, relieve, inhibit, reduce the severity of, and/or reduce the incidence of one or more signs or symptoms of a particular disease (e.g., a proliferative disease such as cancer). The patient being treated (or who has been identified as a candidate for treatment) may exhibit only early signs or symptoms of the disease or may exhibit one or more established or advanced signs or symptoms of the disease. "Treatment" is distinguished from "prophylaxis," which relates to delaying the onset of one or more signs or symptoms of a disease. In that case, the patient may not exhibit signs and/or symptoms of the disease and/or may be known to have one or more susceptibility factors that are statistically correlated with increased risk of development of the relevant disease. However, once a patient exhibits signs or symptoms of a disease and has been treated, treatment may be continued to delay or prevent recurrence.

A "therapeutically effective amount" of a compound described herein is an amount sufficient to treat a disease in a population of patients. A therapeutically effective amount is an amount that provides a therapeutic benefit in the treatment of a disease (e.g., by treating one or more signs or symptoms associated with the disease). A therapeutically effective amount of a compound described herein can also be an amount that enhances the therapeutic efficacy of another therapeutic agent (a "second" therapeutic agent (e.g., a "second" compound)).

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "premalignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The details of one or more embodiments of the invention are set forth herein. Other features, objects, and advantages of the invention will be apparent from the Detailed Description, the Figures, the Examples, and the claims.

BRIEF DESCRIPTION OF THE DRAWINGS

FIG. 3 is a Table providing additional details of the synthesis of certain compounds of the invention, as well as their NMR and MS values.

DETAILED DESCRIPTION

In one aspect of the present invention, provided are compounds of formula (I):

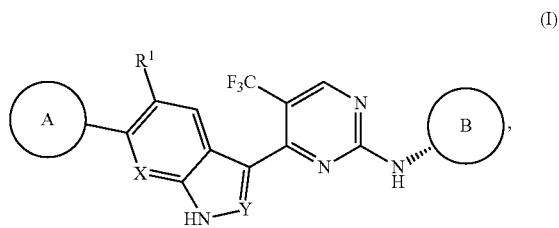

or a pharmaceutically acceptable salt, solvate (e.g., hydrate), tautomer, stereoisomer, or isotopic form thereof, wherein:
ring A is:

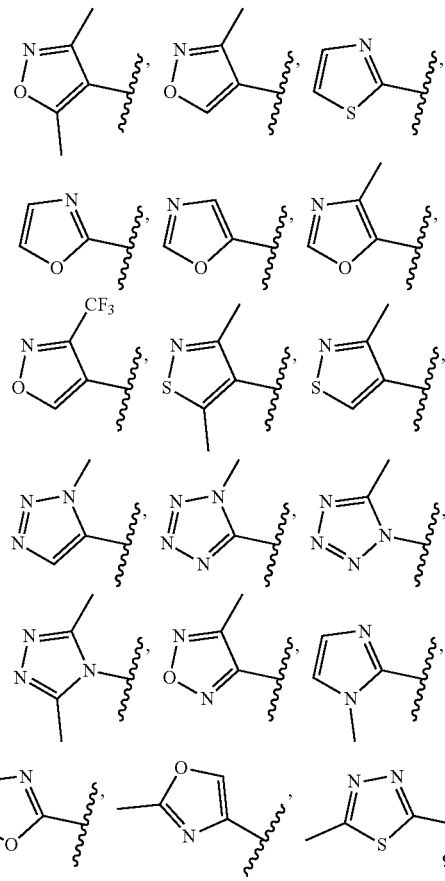

-continued
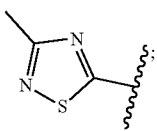
ring B is:
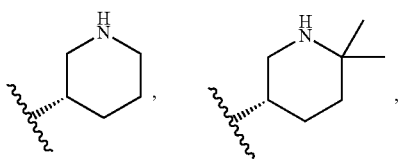
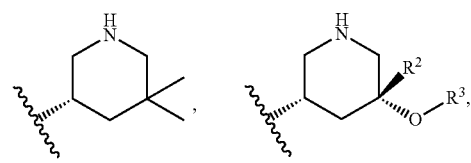
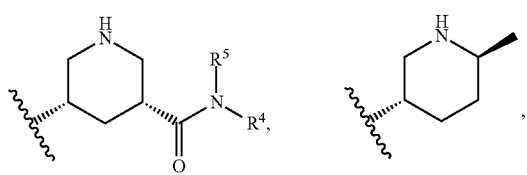
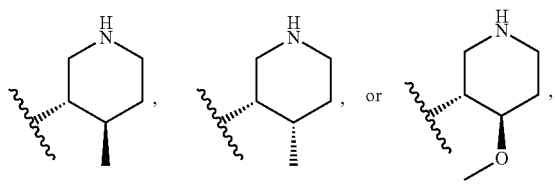
wherein each of $R^2$, $R^3$, $R^4$ and $R^5$ are, independently, hydrogen or —CH$_3$;
X and Y are, independently, N or CH;
$R^1$ is hydrogen or fluoro; and
wherein the compound is other than:
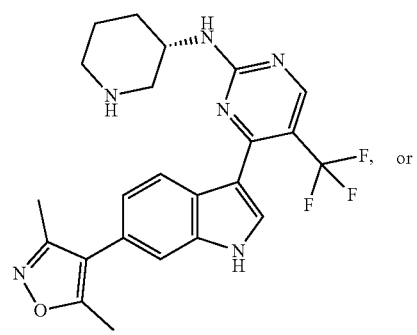
-continued
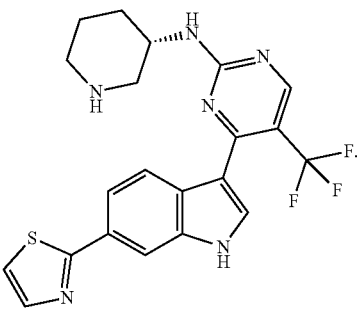
In some embodiments, ring A is:
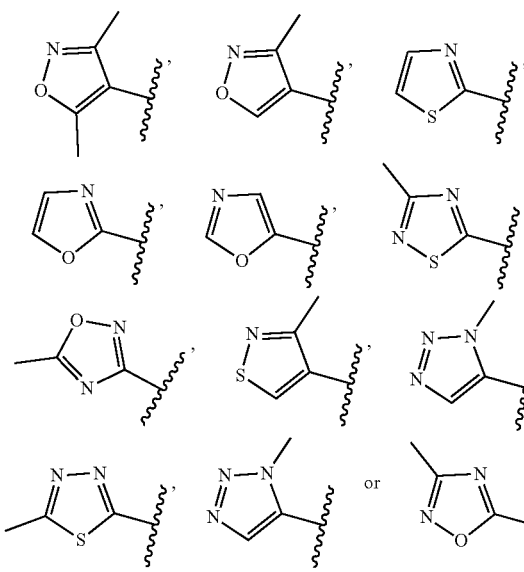
In more specific embodiments, ring A is
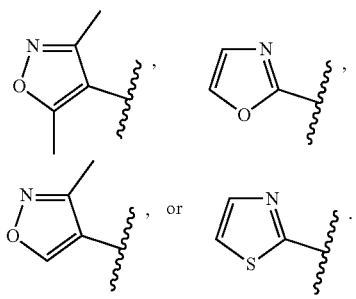
In even more specific embodiments, ring A is
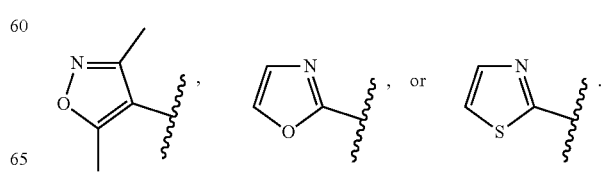

In some embodiments, ring A is

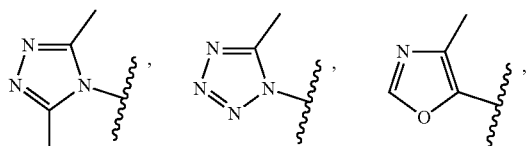

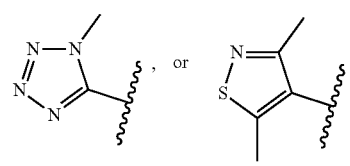

In some embodiments, ring B is:

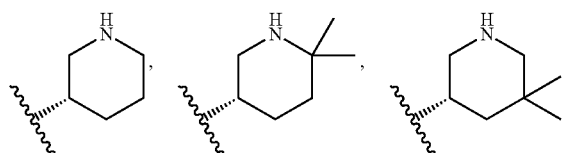

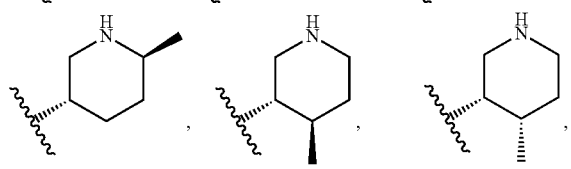

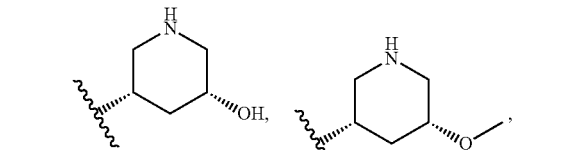

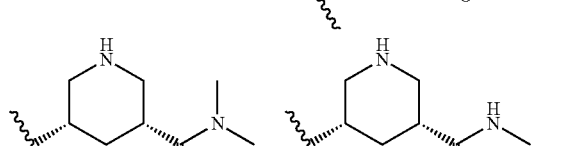

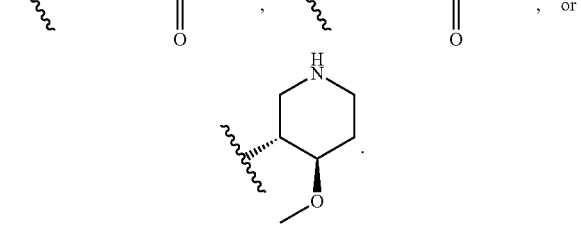

In some embodiments, ring B is:

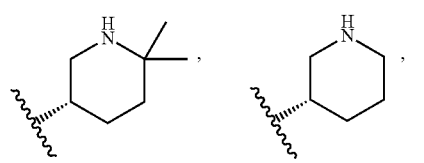

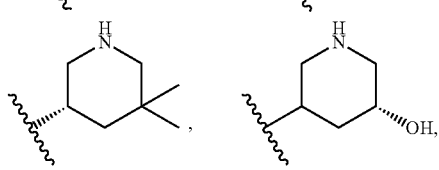

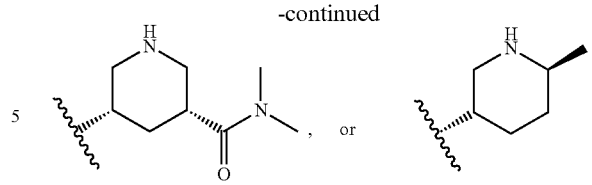

In some embodiments, ring B is:

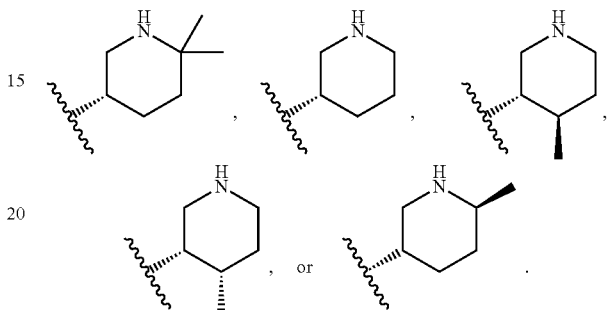

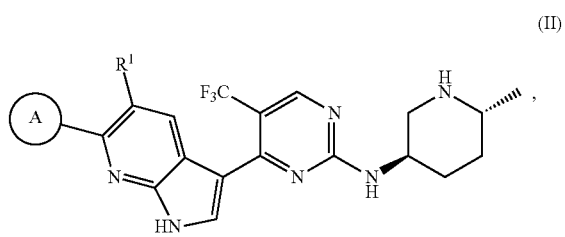

In various embodiments of Formula I: $R^1$ is hydrogen; $R^1$ is fluoro; X is CH and Y is CH; X is N and Y is CH; X is N and Y is N; $R^2$ and $R^3$ is hydrogen; each of $R^4$ and $R^5$ are —$CH_3$; $R^4$ is hydrogen and $R^5$ is —$CH_3$.

Also described herein are compounds of Formula II:

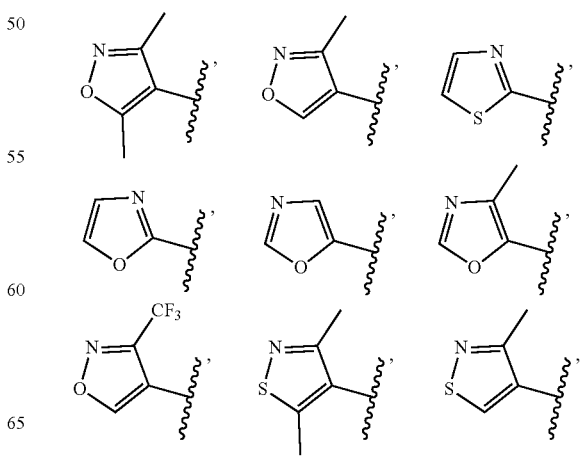

(II)

and pharmaceutically acceptable salts, solvates (e.g., hydrates), tautomers, stereoisomers, and isotopic forms thereof, wherein:

ring A is:

-continued

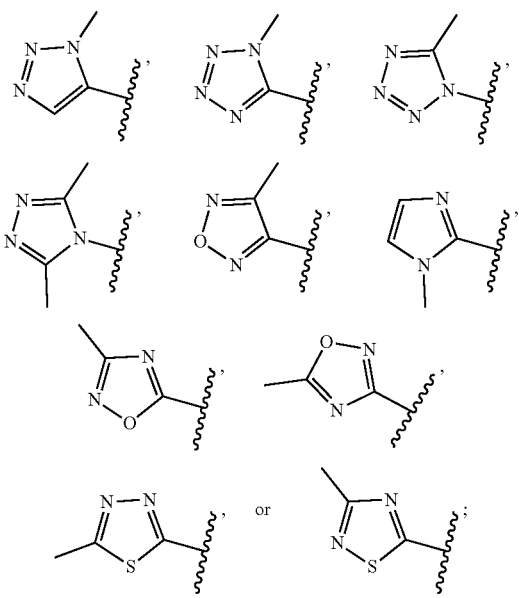

and

R¹ is selected from hydrogen and fluoro.

In some embodiments of a compound of Formula II, ring A is:

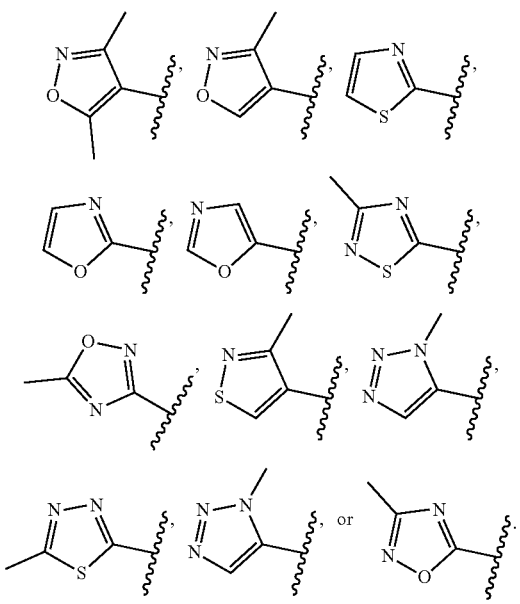

In more specific embodiments, ring A is:

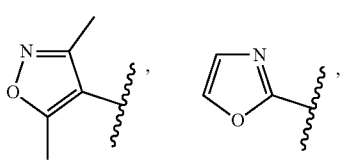

-continued

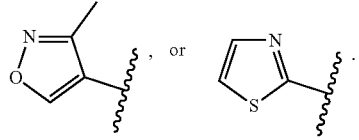

In even more specific embodiments, ring A is:

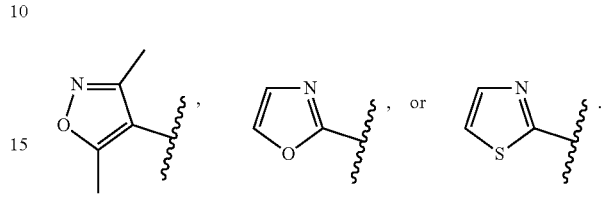

In some embodiments of Formula II, ring A is

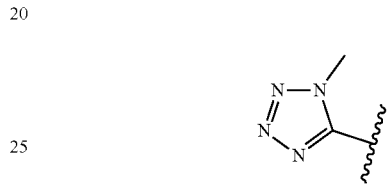

In various embodiments of Formula II: R¹ is hydrogen; R¹ is fluoro.

Figure 1:
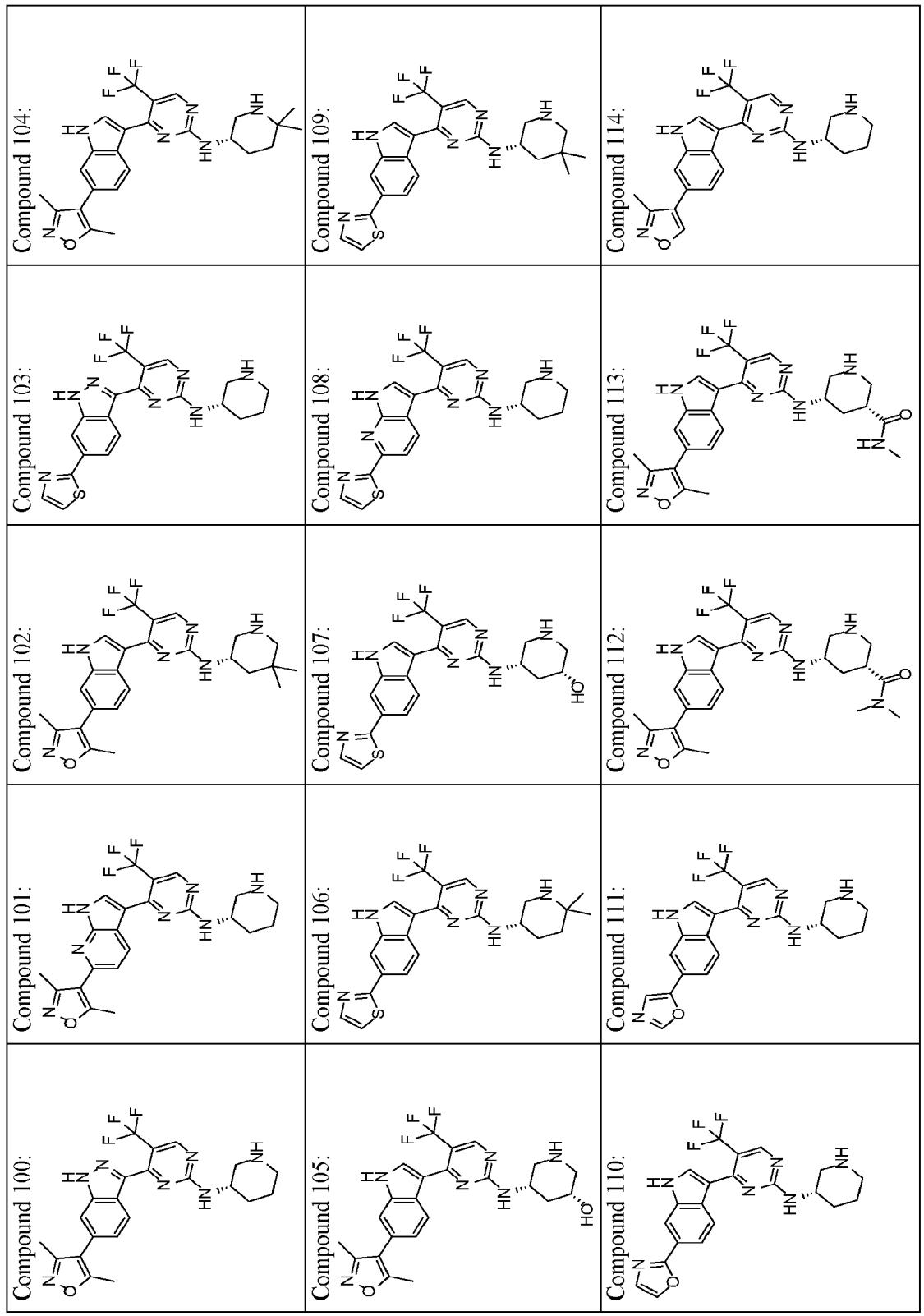
FIG. 1 is a Table disclosing exemplary compounds of the invention.
Figure 1:
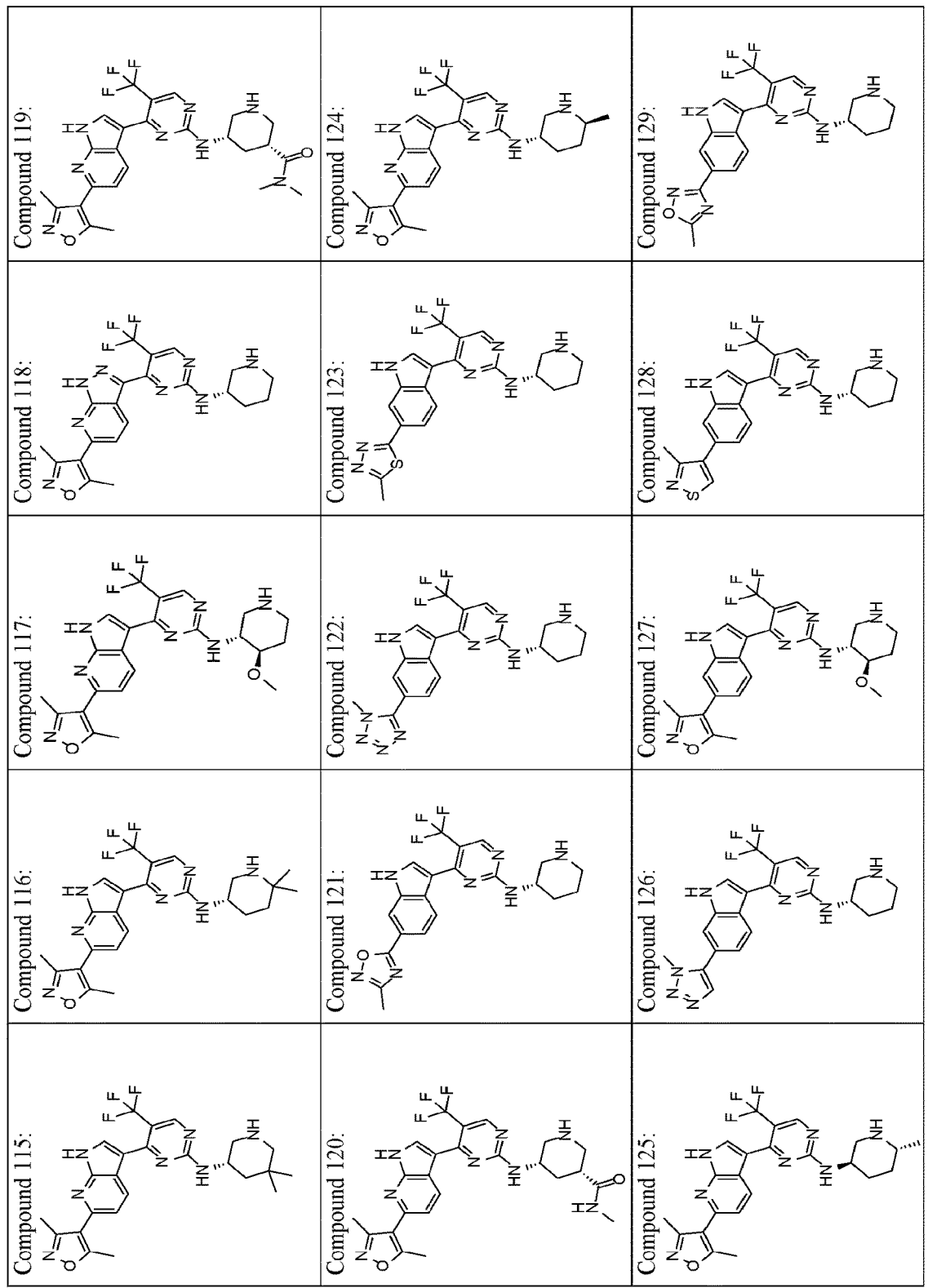
Figure 1:
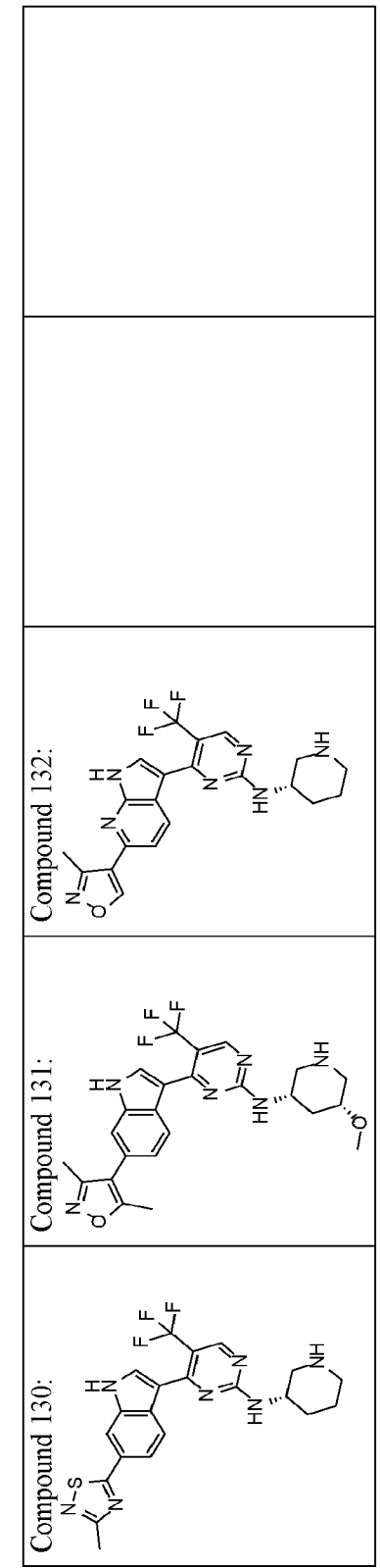
Figure 2:
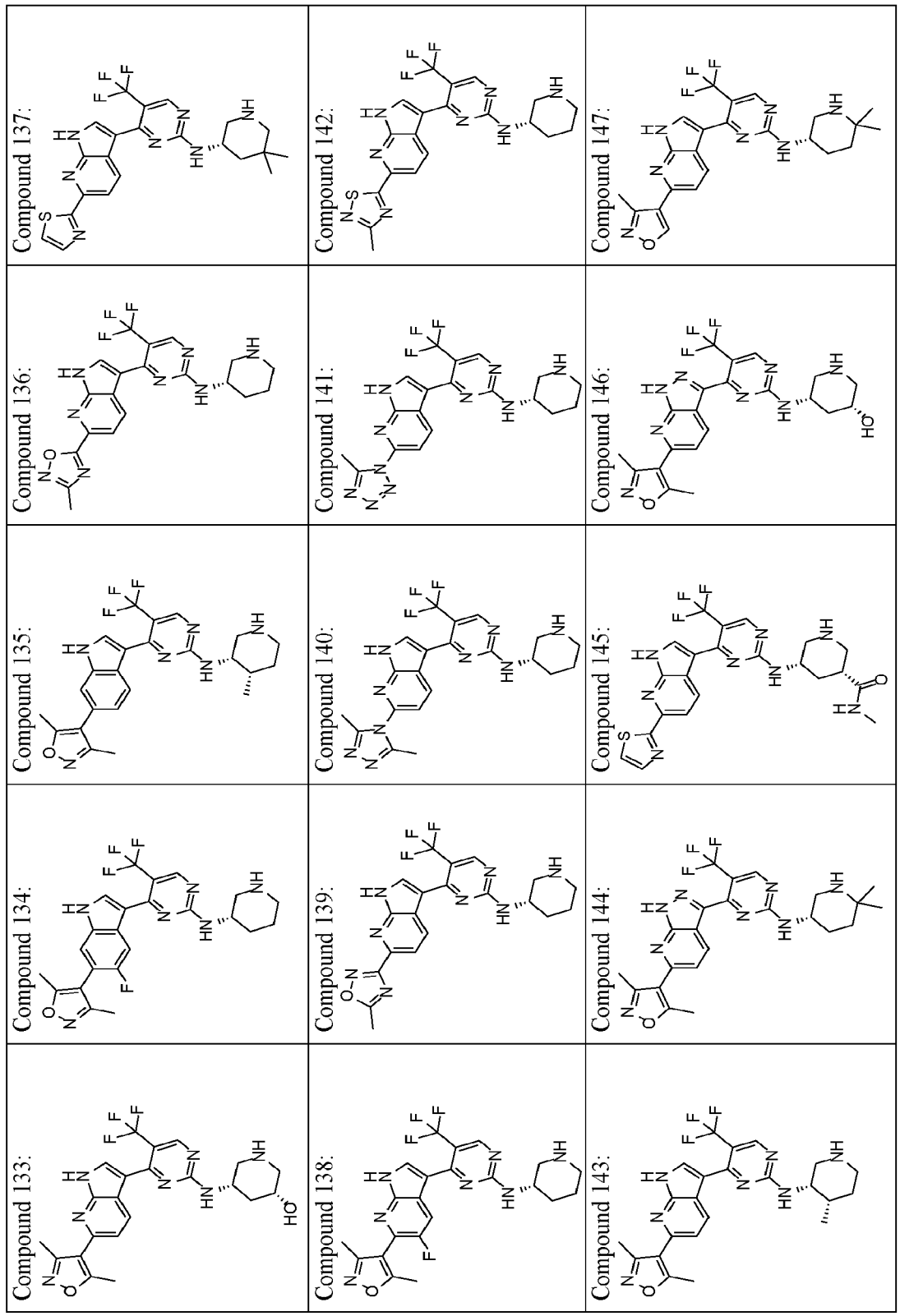
FIG. 2 is a Table disclosing further exemplary compounds of the invention.
Figure 2:
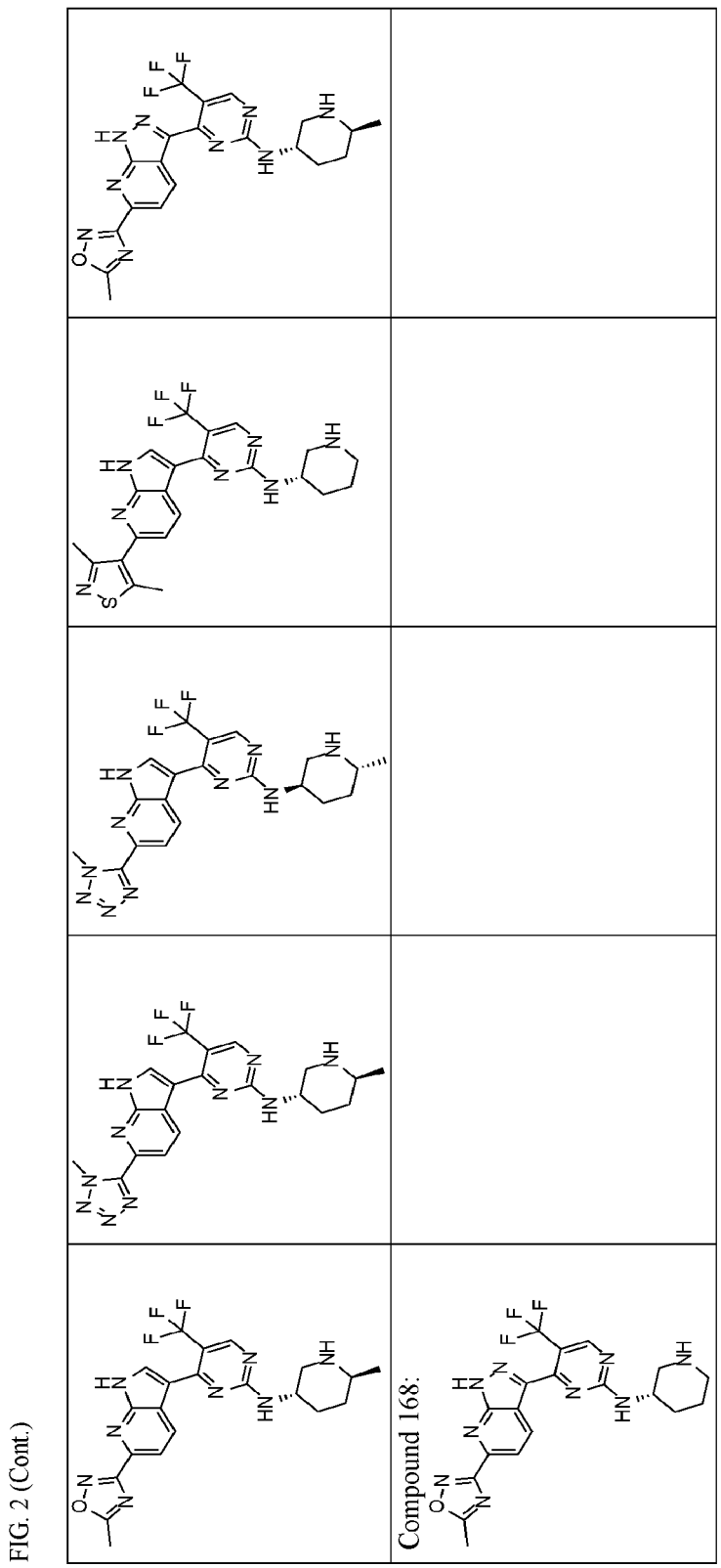

The compound can be selected from any of the compounds in the Table of FIG. 1 or the Table of FIG. 2 or can be a pharmaceutically acceptable salt, solvate (e.g., hydrate), tautomer, stereoisomer, or isotopic form thereof.

Any compound described herein can be prepared using methods described herein and/or known in the art. Techniques useful in synthesizing these compounds are accessible to one of ordinary skill in the art, and the discussion below illustrates certain of the diverse methods available for use in assembling them. The discussion is not intended to limit the scope of useful reactions or reaction sequences. Any pharmaceutical composition described herein can be prepared by methods known in the art of pharmacology. In general, such preparatory methods include the steps of bringing the compound (e.g., a compound of formula (I); the "active ingredient") into association with an excipient and/or one or more other accessory ingredients or "second" agents, and then, if necessary and/or desirable, shaping and/or packaging the product into a desired single- or multi-dose unit and/or packaging the composition within a kit.

Compounds and/or other compositions provided herein (e.g., pharmaceutical compositions) have a variety of uses, including in research and/or clinical settings (e.g., in methods of providing a diagnosis or prognosis and in prophylactic or therapeutic treatment methods).

In some embodiments, a provided compound and/or composition is considered to be specific for a given kinase or set of kinases when it shows at least or about 2-fold, 3-fold, 4-fold, 5-fold, 10-fold, 15-fold, 20-fold, 50-fold, 100-fold or more activity for the specific kinase(s) than for one or more appropriate comparator kinase(s) (e.g., for CDK7 relative to one or more of CDK2, CDK9, and/or CDK12). One of ordinary skill in the art will recognize that evaluating specificity in terms of "fold difference" is only one applicable measure. For example, specificity can be expressed as a "percent difference." For example, a provided compound and/or composition is considered to be specific for CDK7 when it shows at least 101%, 105%, 110%, 120%, 130%, 140%, 150%, 200%, 300%, 400%, 500% or more activity for CDK7 than for one or more of CDK2, CDK9, and/or CDK12.

Compounds of the present disclosure can be prepared and administered in a wide variety of oral and parenteral dosage forms. Thus, the compounds of the present disclosure can be formulated for administration by injection (e.g. intravenously, intramuscularly, intracutaneously, subcutaneously, or intraperitoneally). The compounds can also be formulated for administration by inhalation (e.g., intranasally) or by insufflation. In other embodiments, the compounds described herein can be formulated for topical or transdermal administration (i.e., they can be in a dosage form suitable for administration by the various routes just described).

For preparing pharmaceutical compositions including a compound described herein, pharmaceutically acceptable carriers can be added in either solid or liquid form or a combination thereof. Solid dosage form preparations within the scope of the present invention include powders, tablets, pills, capsules, cachets, suppositories, and dispersible granules. A solid carrier can be a substance that may also act as a diluent, flavoring agent, binder, preservative, tablet disintegrating agent, or an encapsulating material. In powders, the carrier is a finely divided solid in a mixture with the finely divided active component (e.g., a compound described herein, e.g., a compound conforming to the structure of Formula II). In tablets, the active component is mixed with the carrier having the necessary binding properties in suitable proportions and compacted in the shape and size desired. Pharmaceutical compositions, including those formulated as powders and tablets, can contain from about 5% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Tablets, powders, capsules, pills, cachets, and lozenges can be used as solid dosage forms suitable for oral administration. For preparing suppositories, a low melting wax, such as a mixture of fatty acid glycerides or cocoa butter, is melted and the active component is dispersed therein.

Liquid form preparations include solutions, suspensions, and emulsions, for example, water or water/propylene glycol solutions. For parenteral injection, liquid preparations can be formulated in solution in aqueous polyethylene glycol solution. When parenteral application is needed or desired, particularly suitable admixtures for the compounds of the invention are injectable, sterile solutions, preferably oily or aqueous solutions, as well as suspensions, emulsions, or implants, including suppositories. In some embodiments, suitable carriers for parenteral administration will be selected for human administration.

In particular, carriers for parenteral administration include aqueous solutions of dextrose, saline, pure water, ethanol, glycerol, glycerol formal, polyethylene glycol, propylene glycol, peanut oil, sesame oil, polyoxyethylene-block polymers, pyrrolidine, N-methyl pyrrolidione, and the like. Ampoules are convenient unit dosage forms. The compounds of the present disclosure can also be incorporated into liposomes or administered via transdermal pumps or patches. Pharmaceutical admixtures suitable for use in the present disclosure include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical compositions are preferably in unit dosage form. The unit dosage form can be a packaged preparation, the package containing discrete quantities of preparation, such as packeted tablets, capsules, and powders in vials or ampoules. Unit dosage forms can also be capsules, tablets, cachets, lozenges, or the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition (e.g., polysorbate 20, 60, and 80; Pluronic® F-68, F-84, and P-103; cyclodextrin; and polyoxyl 35 castor oil). Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

Compositions of the present invention may additionally include components to provide sustained release and/or comfort (e.g., high molecular weight, anionic mucomimetic polymers, gelling polysaccharides, and finely-divided drug carrier substrates). These components are discussed in detail in U.S. Pat. Nos. 4,911,920; 5,403,841; 5,212,162; and 4,861,760. The entire contents of these patents are incorporated herein by reference in their entirety for all purposes.

Pharmaceutical compositions provided by the present disclosure include compositions wherein the active ingredient is contained in a therapeutically effective amount, i.e., in an amount effective to achieve its intended purpose. The actual amount effective for a particular application will depend, inter alia, on the condition being treated. For example, when administered in methods to a subject with cancer, such compositions will contain an amount of active ingredient effective to achieve the desired result.

The dosage and frequency (single or multiple doses) of compound administered can vary depending on a variety of factors, including route of administration; the size, age, sex, health, body weight, body mass index, and diet of the recipient; nature and extent of symptoms of the disease being treated; any concurrent treatment; and complications from any disease or treatment regimen. Other therapeutic regimens or agents can be used in conjunction with the methods and compounds of the present disclosure.

For any compound, any variant form thereof (e.g., any salt or solvate), or any pharmaceutical composition described herein, the therapeutically effective amount can be initially determined from, or informed by data generated in, cell culture assays and/or animal models of disease. For example, a dose for humans can be formulated to achieve a concentration that has been found to be effective in animals. The dosage in humans can be adjusted by, for example, monitoring kinase (CDK7) inhibition, the signs an symptoms of the disease being treated, and side effects and subsequently adjusting the dosage upwards or downwards.

Dosages may be varied depending upon the requirements of the patient and the compound being employed. The dose administered to a patient should be sufficient to effect a beneficial therapeutic response in the patient over time. The size of the dose also will also be determined by the existence, nature, and extent of any adverse side effects. Generally, treatment is initiated with smaller dosages, which are less than the optimum dose of the compound. Thereafter, the dosage is increased by small increments until the optimum effect under a desired circumstance is reached. In some embodiments, the concentration of compound is about 0.001% to 10% w/v (e.g., about 0.1% to about 5% w/v). In some embodiments, the concentration range is 0.1% to 5% w/v. Concentrations, dosage amounts, and intervals can be adjusted in each individual patient to provide levels of the administered compound effective for the particular disease being treated. This will provide a therapeutic regimen commensurate with the severity of the patient's disease.

Methods of Treatment and Uses: The disease to be treated or prevented using the compounds of Formula (I), pharmaceutically acceptable salts, solvates (e.g., hydrates), tautomers, stereoisomers, isotopically labeled derivatives thereof, or compositions containing any of the foregoing will typically be associated with aberrant expression or activity of CDK7. For example, a gene encoding CDK7 can be overexpressed or misexpressed (i.e., expressed at abnormally high levels in a tissue where it is normally expressed; expressed or overexpressed in a tissue where it is not normally expressed; or expressed at a time during which it is not normally expressed). The activity of the encoded protein can also be increased, and aberrant expression or activity can be relative to the expression or activity in a comparable patient, population of patients, biological sample, or plurality of biological samples that do not manifest signs or symptoms of the disease in question. Both expression and activity may be abberant, or only activity may be abberant.

Methods of testing patients and biological samples for levels of CDK7 expression or activity are within the scope of the invention and may be performed prior to, during, or after treatment as described herein. CDK7 levels can be tested and compared between healthy patients and patients having a disease; between treated and untreated patients; between biological samples from healthy tissues and diseased tissues (whether treated or untreated); and between biological samples that represent models of a disease disclosed herein. Although no aspect of the invention is limited by the cellular mechanisms that result from contacting a cell described herein (whether in a patient or a biological sample ex vivo) with a compound or other composition described herein, this contact may cause cytotoxicity via induction of apoptosis, and assessing cytotoxicity can be a part of the methods of testing patients and biological samples prior to, during, or after treatment.

As noted, the proliferative disease to be treated or prevented using the compounds described herein or pharmaceutically acceptable salts, solvates (e.g., hydrates), tautomers, stereoisomers, isotopically labeled derivatives, and compositions thereof include the cancers described herein, particularly when a given cancer is known to be or found to be associated with aberrant CDK7 expression or activity. The proliferative disease can be a cancer associated with dependence on BCL-2 anti-apoptotic proteins (e.g., MCL-1 and/or XIAP); with overexpression of MYC; with overexpression of CDK18; with overexpression of CDK19; with overexpression of FGFR1; with overexpression of CDK6; with overexpression of CCND2; or with overexpression of CDKN2A. In certain embodiments, the proliferative disease is a cancer associated with the absence of, or suppression of, a wild-type RB1 gene.

In certain embodiments, the proliferative disease is a blood cancer, which may also be referred to as a hematopoietic or hematological cancer or malignancy. More specifically and in various embodiments, the blood cancer can be a leukemia such as acute lymphocytic leukemia (ALL; e.g., B cell ALL or T cell ALL), acute myelocytic leukemia (AML; e.g., B cell AML or T cell AML), chronic myelocytic leukemia (CML; e.g., B cell CML or T cell CML), chronic lymphocytic leukemia (CLL; e.g., B cell CLL (e.g., hairy cell leukemia) or T cell CLL), chronic neutrophilic leukemia (CNL), or chronic myelomonocytic leukemia (CMML). The blood cancer can also be a lymphoma such as Hodgkin lymphoma (HL; e.g., B cell HL or T cell HL), non-Hodgkin lymphoma (NHL; e.g., B cell NHL or T cell NHL), follicular lymphoma, chronic lymphocytic leukemia/small lymphocytic lymphoma (CLL/SLL), mantle cell lymphoma (MCL), a marginal zone B cell lymphoma (e.g., splenic marginal zone B cell lymphoma), primary mediastinal B cell lymphoma (e.g., splenic marginal zone B cell lymphoma), primary mediastinal B cell lymphoma, Burkitt lymphoma, lymphoplasmacytic lymphoma (i.e., Waldenstrom's macroglobulinemia), immunoblastic large cell lymphoma, precursor B lymphoblastic lymphoma, or primary central nervous system (CNS) lymphoma. The B cell NHL can be diffuse large cell lymphoma (DLCL; e.g., diffuse large B cell lymphoma), and the T cell NHL can be precursor T lymphoblastic lymphoma or a peripheral T cell lymphoma (PTCL). In turn, the PTCL can be a cutaneous T cell lymphoma (CTCL) such as mycosis fungoides or Sezary syndrome, angioimmunoblastic T cell lymphoma, extranodal natural killer T cell lymphoma, enteropathy type T cell lymphoma, subcutaneous anniculitis-like T cell lymphoma, or anaplastic large cell lymphoma. While the invention is not limited to treating or preventing blood cancers having any particular cause or presentation, stem cells within the bone marrow may proliferate, thereby becoming a dominant cell type within the bone marrow and a target for a compound described herein. Leukemic cells can accumulate in the blood and infiltrate organs such as the lymph nodes, spleen, liver, and kidney. In some embodiments, a compound of the present disclosure is useful in the treatment or prevention of a leukemia or lymphoma.

In other embodiments, the proliferative disease is characterized by a solid tumor considered to be either of its primary location or metastatic. Exemplary cancers include, but are not limited to, acoustic neuroma; adenocarcinoma;

adrenal gland cancer; anal cancer; angiosarcoma (e.g., lymphangiosarcoma, lymphangioendotheliosarcoma, hemangiosarcoma); appendix cancer; benign monoclonal gammopathy (also known as monoclonal gammopathy of unknown significance (MGUS); biliary cancer (e.g., cholangiocarcinoma); bladder cancer; breast cancer (e.g., adenocarcinoma of the breast, papillary carcinoma of the breast, mammary cancer, or medullary carcinoma of the breast, any of which may be present in subjects having a particular profile, such as an HR+(ER+ or PR+), HR– (having neither estrogen nor progesterone receptors), a triple negative breast cancer (TNBC; ER–/PR–/HER2–), or a triple-positive breast cancer); brain cancer (e.g., meningioma, glioblastoma, glioma (e.g., astrocytoma, oligodendroglioma), medulloblastoma, or neuroblastoma); bronchus cancer; carcinoid tumor carcinoid tumor, which may be benign; cervical cancer (e.g., cervical adenocarcinoma); choriocarcinoma; chordoma; craniopharyngioma; colorectal cancer (e.g., colon cancer, rectal cancer, or colorectal adenocarcinoma); connective tissue cancer; epithelial carcinoma; ependymoma; endotheliosarcoma (e.g., Kaposi's sarcoma or multiple idiopathic hemorrhagic sarcoma); endometrial cancer (e.g., uterine cancer or uterine sarcoma); esophageal cancer (e.g., adenocarcinoma of the esophagus or Barrett's adenocarcinoma; Ewing's sarcoma (or other pediatric sarcoma, such as embryonal rhabdomyosarcoma or alveolar rhabdomyosarcoma); eye cancer (e.g., intraocular melanoma or retinoblastoma); familial hypereosinophilia; gallbladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma)), throat cancer (e.g., laryngeal cancer, pharyngeal cancer, nasopharyngeal cancer, oropharyngeal cancer)); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer or small intestine cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The proliferative disease can be associated with pathologic angiogenesis, and the methods of the invention (and uses of the compounds and other compositions described herein) encompass inhibiting pathologic angiogenesis in the context of cancer treatment.

As noted, the patient for which administration is contemplated includes, but is not limited to, a human (i.e., a male, female or transgendered person of any age group, e.g., a pediatric patient (e.g., infant, child, adolescent) or adult patient (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). Thus, the patient may be a domesticated animal. The non-human animal may be a transgenic animal (e.g., an animal valuable in research, such as a transgenic mouse or transgenic pig).

A cell used or treated as described herein may be a healthy cell or an unhealthy or abnormal cell (e.g., a cancer cell, tumor cell, or other cell that is proliferating uncontrollably). A compound of the invention may be administered to any such cell in vitro or in vivo. In various embodiments, the cell is: a cancer cell; a tumor cell; a proliferating cell; a blood cell (e.g., a lymphocyte); an endothelial cell; or an immune cell. In various embodiments, the cancer cell is: a leukemia cell; a CLL cell; a CMML cell; an AML cell; a breast cancer or ovarian cancer cell; a melanoma cell; a multiple myeloma cell; or a cell of any other cancer or disease disclosed herein.

In certain embodiments, the methods described herein comprise the additional step of administering one or more additional pharmaceutical agents in combination with the compound of formula (I) a pharmaceutically acceptable salt thereof, or compositions comprising such compound or pharmaceutically acceptable salt thereof. Such additional pharmaceutical agents include, but are not limited to, anti-proliferative agents, anti-cancer agents, anti-diabetic agents, anti-inflammatory agents, immunosuppressant agents, and a pain-relieving agent. The additional pharmaceutical agent(s) may synergistically augment inhibition of CDK7 induced by the inventive compounds or compositions of this invention in the biological sample or subject. Thus, the combination of the inventive compounds or compositions and the additional pharmaceutical agent(s) may be useful in treating proliferative diseases resistant to a treatment using the additional pharmaceutical agent(s) without the inventive compounds or compositions.

As indicated, the present invention provides the compounds described herein (e.g., a compound of Formula (I)) and pharmaceutically acceptable salts, solvates (e.g., hydrates), tautomers, isotopic forms, and compositions thereof (e.g., pharmaceutical compositions), for use in the treatment of a proliferative disease or any other disease described herein in a patient. While the compounds, variants thereof, compositions containing them, and methods of use are not limited according to the underlying mechanism of action, we note that use may result in an inhibition of cell growth by, for example, promoting apoptosis or altering the expression or activity of disease-related genes.

EXAMPLES

The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., Protecting Groups in Organic Synthesis, Second Edition, Wiley, New York, 1991, and references cited therein.

Example 1. Synthesis of (S)-4-(6-(3,5-dimethyl-isoxazol-4-yl)-1H-indol-3-yl)-N-(6,6-dimethylpiperidin-3-yl)-5-(trifluoromethyl)pyrimidin-2-amine (Compound 104)

Step 1: 6-bromo-3-(2-chloro-5-(trifluoromethyl)pyrimidin-4-yl)-1H-indole

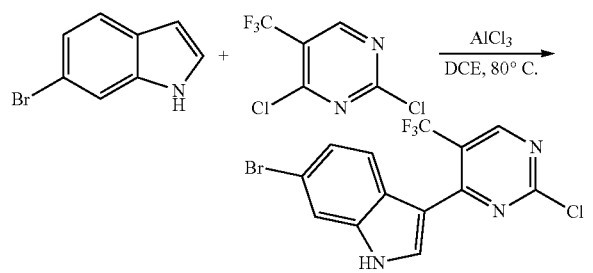

To a solution of 2,4-dichloro-5-(trifluoromethyl)pyrimidine (4.87 g, 22.44 mmol) in dichloroethane (29 mL) was added aluminum trichloride (3.26 g, 24.49 mmol). The resulting suspension was stirred at 70° C. for 15 min to provide a clear yellow solution. Reaction mixture was then slightly cooled down (to 60° C.) followed by addition of 6-bromoindole (4.0 g, 20.40 mmol). The resulting orange solution was stirred at 80° C. for 2 h. The reaction mixture was cooled down to RT (room temperature), and ice-cold water was then added followed by stirring for 30 min. The resulting slurry was further diluted with EtOAc (ethyl acetate) and water, then filtered. Aqueous layer was extracted with EtOAc (twice), the organics were combined, dried over Na$_2$SO$_4$, and concentrated under vacuum. The crude red solid was dissolved in minimal amount of MeOH (methanol) and, after stirring for 30 min at RT, was then filtered to provide the desired regioisomer as a beige solid (2.20 g, 5.85 mmol, 29% yield). The product was used in the next step without further purification.

Step 2: 6-bromo-3-(2-chloro-5-(trifluoromethyl)pyrimidin-4-yl)-1-(phenylsulfonyl)-1H-indole

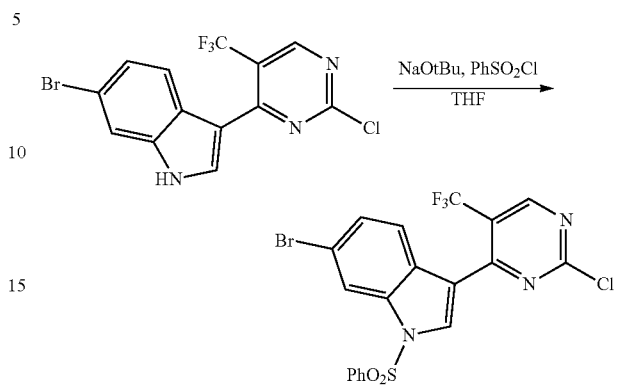

To a solution of 6-bromo-3-(2-chloro-5-(trifluoromethyl)pyrimidin-4-yl)-1H-indole (1.19 g, 3.16 mmol) in dry THF (tetrahydrofuran; 15.8 mL) was added sodium tert-butoxide, 2 M in THF (1.90 mL, 3.79 mmol), and the resulting mixture was stirred for 30 min at 0° C. Benzenesulfonyl chloride (0.48 mL, 3.79 mmol) was then added. Reaction mixture was stirred for 15 min at 0° C. and then at RT for overnight. The mixture was diluted with EtOAc and washed with water. The organic phase was separated, dried over Na$_2$SO$_4$, and concentrated under vacuum to provide the crude title compound as a beige solid (1.40 g, 2.71 mmol, 86% yield). The product was used in the next step without further purification.

Step 3: (S)-6,6-dimethylpiperidin-3-amine

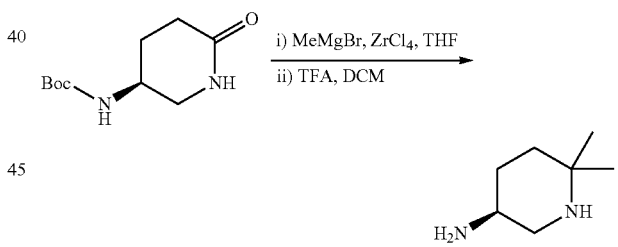

(S)-tert-Butyl (6-oxopiperidin-3-yl)carbamate (1.00 g, 4.67 mmol) (Tetrahedron Letters 36:8204, 1995) was dissolved in THF (47 mL), and the solution was cooled to −10° C. Zirconium(IV) chloride (2.61 g, 11.22 mmol) was added, and the mixture was stirred for 30 min at this temperature. Methylmagnesium bromide 3 M solution in ether (20.25 mL, 60.75 mmol) was added, and then reaction mixture was allowed to slowly warm up to RT and then stirred for overnight. The solution was quenched with 30% NaOH, diluted with EtOAc, filtered, and then extracted 3 times with EtOAc. The organics were combined, dried over Na$_2$SO$_4$, filtered, and concentrated under vacuum to provide crude product as a yellow oil that was used without further purification. The obtained oil was dissolved in DCM (dichloromethane; 47 mL) and TFA (trifluoroacetic acid; 3.58 mL, 46.73 mmol) was added. The reaction mixture was stirred at RT for 16 h. The mixture was concentrated under reduced pressure and co-evaporated for few times with DCM to provide a brown oil of crude title compound, which was used in the next step without further purification.

Step 4: (S)-4-(6-bromo-1-(phenylsulfonyl)-1H-indol-3-yl)-N-(6,6-dimethylpiperidin-3-yl)-5-(trifluoromethyl)pyrimidin-2-amine

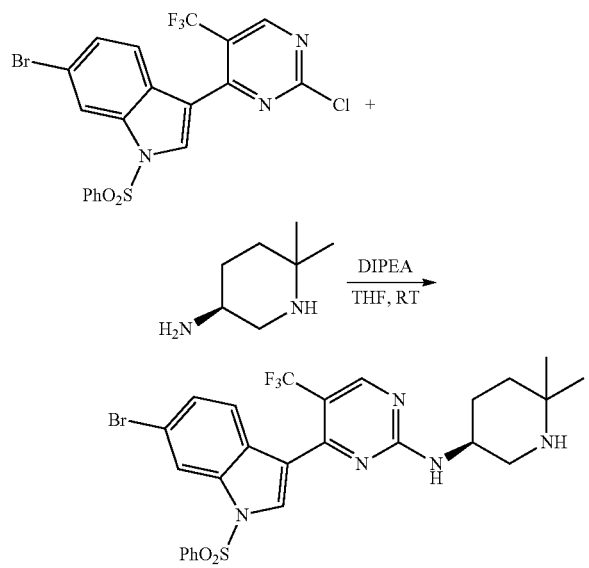

To a solution of 6-bromo-3-(2-chloro-5-(trifluoromethyl)pyrimidin-4-yl)-1-(phenylsulfonyl)-1H-indole (1.40 g, 2.71 mmol) and crude (S)-6,6-dimethylpiperidin-3-amine from the previous step (4.67 mmol) in dry THF (21 mL) was added DIPEA (N,N-diisopropyl ethylamine; 1.42 mL, 8.13 mmol). The reaction mixture was then stirred at RT for 16 h. The reaction mixture was diluted with EtOAc and washed with water. Organic phase was separated, dried over $Na_2SO_4$, filtered, and concentrated under vacuum to provide a yellow oil of crude product that was purified by reverse phase chromatography (C18, MeCN in aq. (aqueous) 10 mM ammonium bicarbonate, 30 to 100% gradient, where product was washed out from the column at 100% MeCN with 10 mL of IPA (isopropanol)). The title compound was obtained as a brown foam (330 mg, 0.54 mmol, 20% yield).

Step 5: (S)-4-(6-(3,5-dimethylisoxazol-4-yl)-1-(phenylsulfonyl)-1H-indol-3-yl)-N-(6,6-dimethylpiperidin-3-yl)-5-(trifluoromethyl)pyrimidin-2-amine

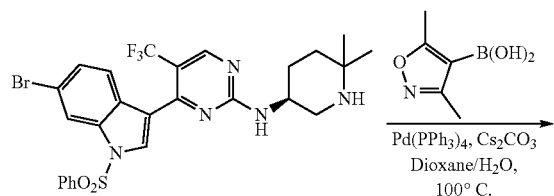

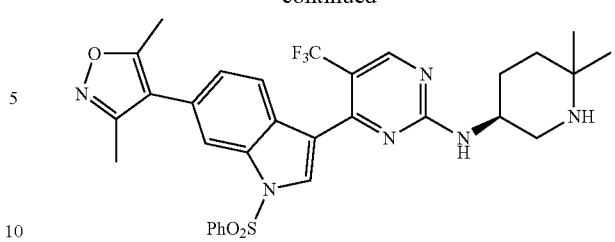

To a solution of (S)-4-(6-bromo-1-(phenylsulfonyl)-1H-indol-3-yl)-N-(6,6-dimethylpiperidin-3-yl)-5-(trifluoromethyl)pyrimidin-2-amine (100 mg, 0.164 mmol) and (3,5-dimethylisoxazol-4-yl)boronic acid (69 mg, 0.493 mmol) in previously degassed 2:1 mixture of dioxane/$H_2O$ (3 mL) was added $Cs_2CO_3$ (161 mg, 0.493 mmol), and the mixture was degassed for another 15 min. Then, $Pd(PPh_3)_4$ (19 mg, 0.016 mmol) was added, and the reaction mixture was stirred at 100° C. for 1.5 h. The mixture was allowed to cool down to RT, diluted with EtOAc and washed with water and brine. The organic phase was separated, dried over $Na_2SO_4$, filtered, and concentrated under reduced pressure. The residue was purified by silica gel column chromatography (EtOAc in hexanes, 0 to 100% gradient followed by 100% of IPA) to give the title compound as a yellowish oil (56 mg, 0.09 mmol, 55% yield).

Step 6: (S)-4-(6-(3,5-dimethylisoxazol-4-yl)-1H-indol-3-yl)-N-(6,6-dimethylpiperidin-3-yl)-5-(trifluoromethyl)pyrimidin-2-amine

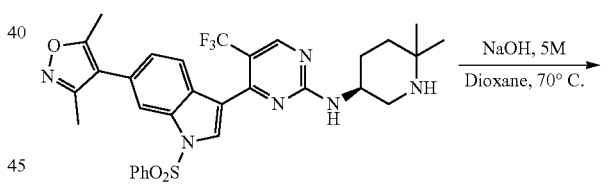

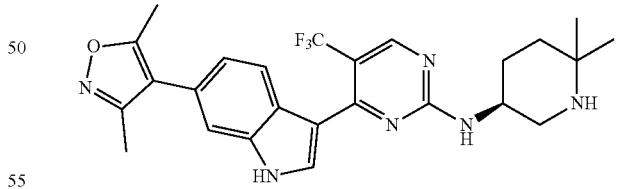

To a solution of (S)-4-(6-(3,5-dimethylisoxazol-4-yl)-1-(phenylsulfonyl)-1H-indol-3-yl)-N-(6,6-dimethylpiperidin-3-yl)-5-(trifluoromethyl)pyrimidin-2-amine (56 mg, 0.09 mmol) in dioxane (1 mL) was added 5M aq. NaOH (0.18 mL, 0.90 mmol). The reaction mixture was stirred at 70° C. for 3 h. The mixture was then concentrated, and the residue was purified by reverse phase chromatography (C18, MeCN in aq. 10 mM ammonium bicarbonate, 0 to 100% gradient) to provide the title compound as an off-white solid (26 mg, 0.052 mmol, 58% yield).

Example 2. Synthesis of (S)—N-(6,6-dimethylpiperidin-3-yl)-4-(6-(thiazol-2-yl)-1H-indol-3-yl)-5-(trifluoromethyl)pyrimidin-2-amine (Compound 106)

Step 1: (S)—N-(6,6-dimethylpiperidin-3-yl)-4-(1-(phenylsulfonyl)-6-(thiazol-2-yl)-1H-indol-3-yl)-5-(trifluoromethyl)pyrimidin-2-amine

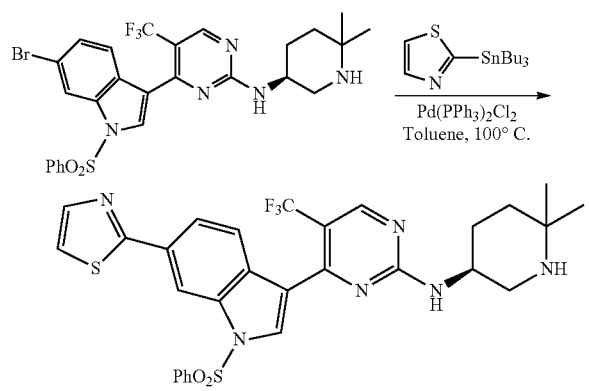

To a solution of (S)-4-(6-bromo-1-(phenylsulfonyl)-1H-indol-3-yl)-N-(6,6-dimethylpiperidin-3-yl)-5-(trifluoromethyl)pyrimidin-2-amine (Example 1; 220 mg, 0.36 mmol) in toluene (3.6 mL) was added 2-(tributylstannyl)thiazole (169 mg, 0.45 mmol), and this suspension was degassed for 20 min. Bis(triphenylphosphine)palladium(II) dichloride (13 mg, 0.02 mmol) was then added, and the reaction mixture was stirred at 100° C. for 2 h. After cooling down to RT, the mixture was filtered through Celite, then diluted with water (20 mL) and EtOAc (30 mL) and basified with sat. (saturated) aq. NaHCO₃ (5 mL). Organic phase was separated, washed with water (20 mL) and brine (2×10 mL), dried over MgSO₄, filtered, and concentrated under reduced pressure. The residue was purified by silica gel column chromatography (THF in hexanes, 0 to 100% gradient) to obtain the title compound as a yellow oil (101 mg, 0.16 mmol, 45% yield).

Step 2: (S)—N-(6,6-dimethylpiperidin-3-yl)-4-(6-(thiazol-2-yl)-1H-indol-3-yl)-5-(trifluoromethyl)pyrimidin-2-amine

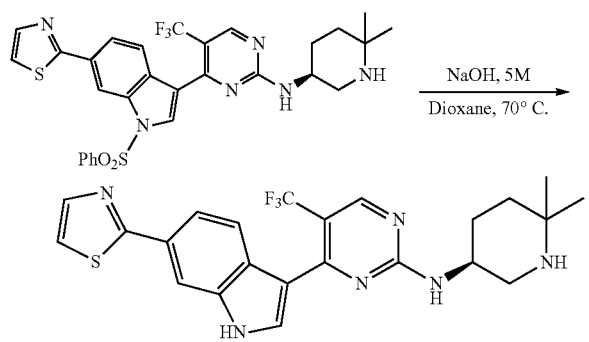

To a solution of (S)—N-(6,6-dimethylpiperidin-3-yl)-4-(1-(phenylsulfonyl)-6-(thiazol-2-yl)-1H-indol-3-yl)-5-(trifluoromethyl)pyrimidin-2-amine (101 mg, 0.16 mmol) in dioxane (1.6 mL) was added 5M aq. NaOH (0.32 mL, 1.60 mmol), and the reaction mixture was stirred at 70° C. for 2 h. The mixture was then concentrated, and the residue was purified by reverse phase chromatography (C18, MeCN in aq. 10 mM ammonium formate pH 3.8, 0 to 100% gradient) to obtain the title compound as a pale yellow solid (20.3 mg, 0.043 mmol, 27% yield).

Example 3. Synthesis of (S)-4-(6-(oxazol-2-yl)-1H-indol-3-yl)-N-(piperidin-3-yl)-5-(trifluoromethyl)pyrimidin-2-amine (Compound 110) and (S)-4-(6-(oxazol-5-yl)-1H-indol-3-yl)-N-(piperidin-3-yl)-5-(trifluoromethyl)pyrimidin-2-amine (Compound 111)

Step 1: (5)-tert-butyl 3-((4-(6-bromo-1-(phenylsulfonyl)-1H-indol-3-yl)-5-(trifluoromethyl)pyrimidin-2-yl)amino)piperidine-1-carboxylate

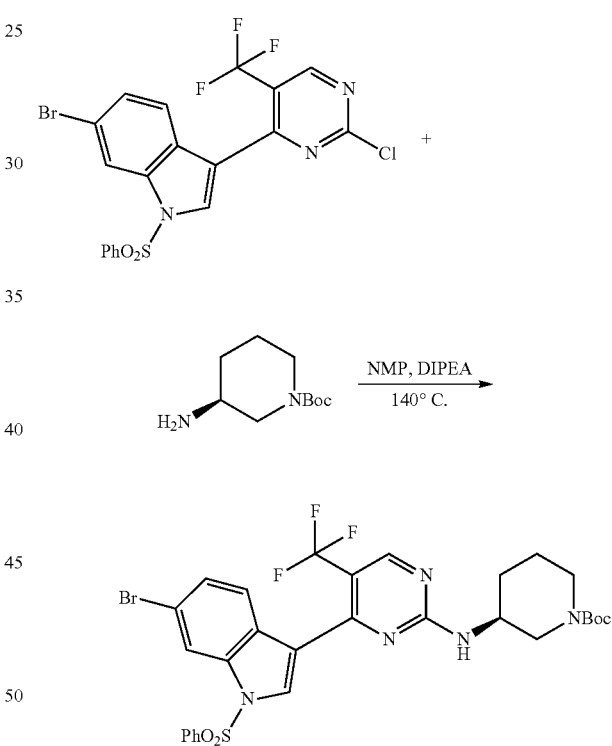

A mixture of 1-(benzenesulfonyl)-6-bromo-3-[2-chloro-5-(trifluoromethyl)pyrimidin-4-yl]indole (Example 1, step 2; 1.00 g, 1.94 mmol, 1.00 eq), (S)-tert-butyl (3S)-3-aminopiperidine-1-carboxylate (388.54 mg, 1.94 mmol, 1.00 eq) and DIEA (N,N-diisopropylethylamine; 752.18 mg, 5.82 mmol, 1.02 mL, 3.00 eq) in NMP (N-methyl-2-pyrrolidone; 10.00 mL) was stirred at 140° C. for 1 hr. The mixture was diluted with water (100 mL) and extracted with EtOAc (50 mL×2). Combined organic layers were washed with brine (100 mL×2), dried over Na₂SO₄, filtered, and concentrated under reduced pressure to a yellow oil. The residue was purified by SiO₂ chromatography (PE/EtOAc, 10:1 to 5:1) to afford the title compound (1.13 g, 86%) as a yellow solid.

Step 2: (S)-tert-butyl 3-((4-(6-(oxazol-2-yl)-1-(phenylsulfonyl)-1H-indol-3-yl)-5-(trifluoromethyl)pyrimidin-2-yl)amino)piperidine-1-carboxylate and (S)-tert-butyl 3-((4-(6-(oxazol-5-yl)-1-(phenylsulfonyl)-1H-indol-3-yl)-5-(trifluoromethyl)pyrimidin-2-yl)amino)piperidine-1-carboxylate

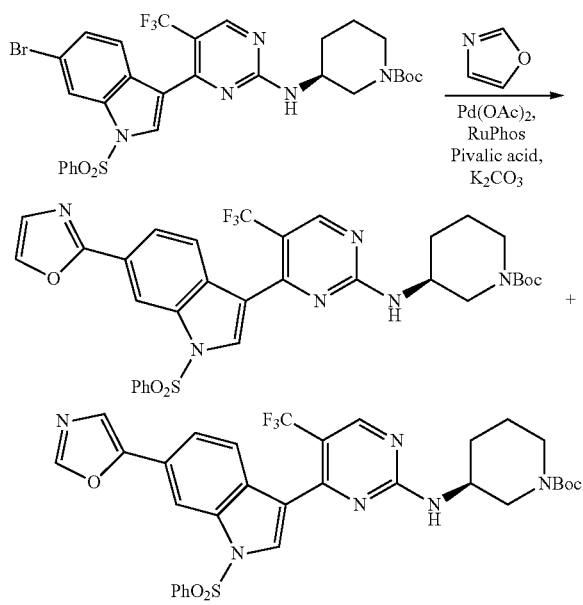

To a microwave vial, (S)-tert-butyl 3-((4-(6-bromo-1-(phenylsulfonyl)-1H-indol-3-yl)-5-(trifluoromethyl)pyrimidin-2-yl)amino)piperidine-1-carboxylate (150.0 mg, 0.220 mmol), pivalic acid (9.0 mg, 0.088 mmol), K$_2$CO$_3$ (91.4 mg, 0.661 mmol), Pd(OAc)$_2$ (2.5 mg, 0.011 mmol; 5 mol %), and RuPhos (2-dicyclohexylphosphino-2',6'-diisopropoxybiphenyl; 10.3 mg, 0.022 mmol; 10 mol %) were added. The microwave vial was sealed under nitrogen. Dry, degassed toluene (1.0 mL) was then added followed by oxazole (29 μL, 0.441 mmol). The reaction mixture was stirred at 110° C. in an oil bath for 16 h. After cooling down to RT, the reaction mixture was concentrated, and the residue was purified by silica gel column chromatography (EtOAc in hexanes, 0 to 100% gradient) to give the title compounds: 23 mg (pale oil, 0.034 mmol, 16% yield) and 46 mg (pale oil, 0.069 mmol, 31% yield), correspondingly.

Step 3: (S)-4-(6-(oxazol-2-yl)-1H-indol-3-yl)-N-(piperidin-3-yl)-5-(trifluoromethyl)pyrimidin-2-amine

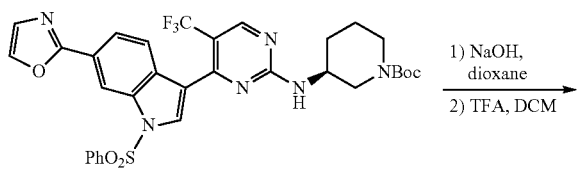

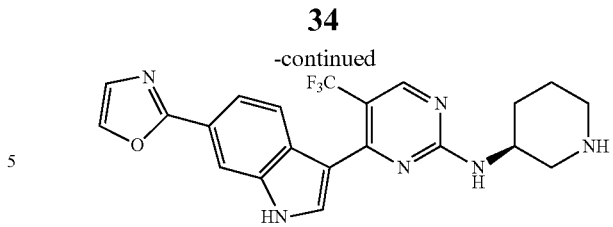

To a solution of (S)-tert-butyl 3-((4-(6-(oxazol-2-yl)-1-(phenylsulfonyl)-1H-indol-3-yl)-5-(trifluoromethyl)pyrimidin-2-yl)amino)piperidine-1-carboxylate (41 mg, 0.061 mmol) in dioxane (3 mL) was added 5M aq. NaOH (0.122 mL, 0.610 mmol), and the reaction mixture was stirred at 50° C. for 3 h. The mixture was cooled down to RT, diluted with MeTHF (2-methyltetrahydrofuran; 5 mL) and water (5 mL). Organic phase was separated, dried over Na$_2$SO$_4$, filtered, and concentrated under reduced pressure. The obtained crude was then re-dissolved in DCM (2 mL), and TFA was added (0.187 mL, 2.440 mmol). The reaction mixture was stirred at RT for 1 h. The mixture was concentrated under reduced pressure and azeotroped for few times with DCM. The basified crude product was then purified by reverse phase chromatography (C18, MeCN in aq. 10 mM ammonium formate pH 3.8, 0 to 100% gradient) to obtain the title compound as an off-white solid (7.0 mg, 0.016 mmol, 27% yield).

Example 4. Synthesis of (S)-4-(6-(3-methylisoxazol-4-yl)-1H-indol-3-yl)-N-(piperidin-3-yl)-5-(trifluoromethyl)pyrimidin-2-amine (Compound 114)

Step 1: (S)-tert-butyl 3-((4-(6-(3-methylisoxazol-4-yl)-1-(phenylsulfonyl)-1H-indol-3-yl)-5-(trifluoromethyl)pyrimidin-2-yl)amino)piperidine-1-carboxylate

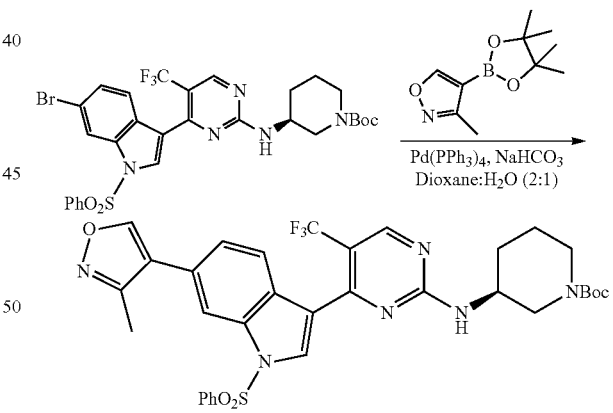

To a solution of (S)-tert-butyl 3-((4-(6-bromo-1-(phenylsulfonyl)-1H-indol-3-yl)-5-(trifluoromethyl)pyrimidin-2-yl)amino)piperidine-1-carboxylate (Example 3, step 1; 150 mg, 0.22 mmol) in degassed 2:1 mixture of dioxane/water (1.5 mL) were added NaHCO$_3$ (37 mg, 0.44 mmol) and 3-methyl-4-(4,4,5,5-tetramethyl-1,3,2-dioxaborolan-2-yl)isoxazole (81 mg, 0.39 mmol), the resulted suspension was degassed for 15 min. Tetrakis(triphenylphosphine)palladium(0) (25 mg, 0.02 mmol) was added, and the reaction mixture was stirred at 100° C. for 1 h. After cooling down to RT, the mixture was diluted with EtOAc (15 mL) and water (10 mL), the crude product was extracted with EtOAc (2×10 mL). The combined organic phase was washed with sat. aq. NaHCO₃ (5 mL), water (2×5 mL), and brine (2×10 mL), then dried over Na₂SO₄, filtered, and concentrated under reduced pressure. The residue was purified by silica gel column chromatography (EtOAc in hexanes, 0 to 100% gradient) to obtain the title compound as a yellow oil (139 mg, 0.20 mmol, 93% yield).

Step 2: (S)-tert-butyl 3-((4-(6-(3-methylisoxazol-4-yl)-1H-indol-3-yl)-5-(trifluoromethyl)pyrimidin-2-yl)amino)piperidine-1-carboxylate

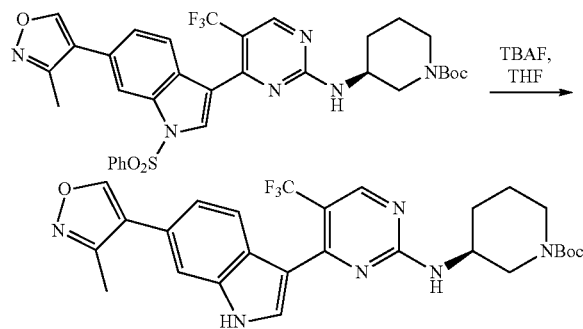

To a solution of (S)-tert-butyl 3-((4-(6-(3-methylisoxazol-4-yl)-1-(phenylsulfonyl)-1H-indol-3-yl)-5-(trifluoromethyl) pyrimidin-2-yl)amino)piperidine-1-carboxylate (139 mg, 0.20 mmol) in THF (2 mL) was added 1M TBAF (tetrabutylammonium fluoride) solution in THF (2 mL, 2.04 mmol), and the reaction mixture was stirred at 70° C. for 30 min. The mixture was then concentrated under vacuum, re-dissolved in MeTHF (5 mL) and washed with sat. aq. NH₄Cl (5×5 mL) and brine (5 mL). Organic phase was separated, dried over MgSO₄, filtered, and concentrated under reduced pressure to provide a yellow oil of crude title compound (111 mg, 0.20 mmol, quant. yield), which was used in the next step without further purification.

Step 3: (S)-4-(6-(3-methylisoxazol-4-yl)-1H-indol-3-yl)-N-(piperidin-3-yl)-5-(trifluoromethyl)pyrimidin-2-amine

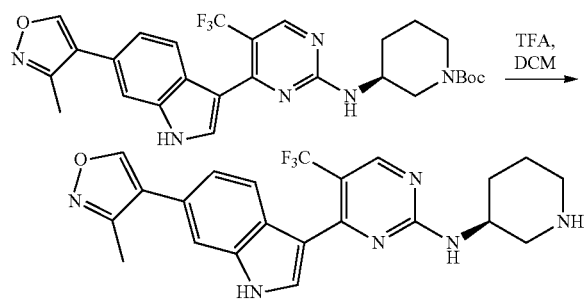

To a solution of (S)-tert-butyl 3-((4-(6-(3-methylisoxazol-4-yl)-1H-indol-3-yl)-5-(trifluoromethyl)pyrimidin-2-yl) amino)piperidine-1-carboxylate (111 mg, 0.20 mmol) in DCM (6 mL) was added TFA (0.31 mL, 4.00 mmol), and the reaction mixture was stirred at RT for 1 h. The mixture was then concentrated and azeotroped for few times with DCM. The basified residue was purified by reverse phase chromatography (C18, MeCN in aq. 10 mM ammonium formate pH 3.8, 0 to 100% gradient) to obtain the title compound as a white solid (49.6 mg, 0.11 mmol, 56% yield over 2 steps).

Example 5. Synthesis of 3,5-dimethyl-4-(3-(2-(methylsulfonyl)-5-(trifluoromethyl)-pyrimidin-4-yl)-1-(phenylsulfonyl)-1H-pyrrolo[2,3-b]pyridin-6-yl)isoxazole for Synthesis of Compound 116

Step 1: 3,5-dimethyl-4-(1H-pyrrolo[2,3-b]pyridin-6-yl)isoxazole

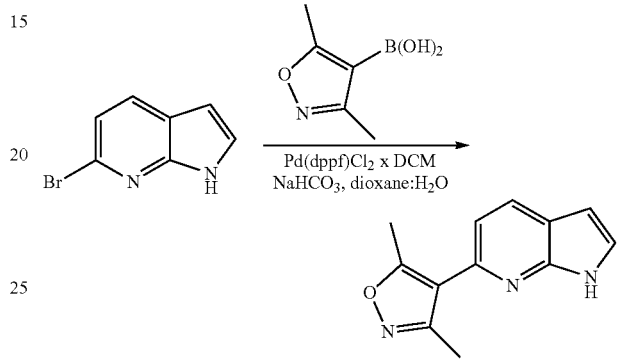

To a solution of 6-bromo-1H-pyrrolo[2,3-b]pyridine (6.00 g, 30.5 mmol) in degassed 2:1 mixture of dioxane/water (150 mL) were added (3,5-dimethylisoxazol-4-yl)boronic acid (4.72 g, 33.5 mmol) and NaHCO₃ (5.12 g, 60.9 mmol), and the resulted suspension was degassed for 30 min. Pd(dppf)Cl₂ ([1,1'-Bis(diphenyl-phosphino)ferrocene]dichloropalladium(II)) DCM complex (620 mg, 0.76 mmol) was then added, and the reaction mixture was stirred at 100° C. for 2 h. After cooling down to RT, the mixture was extracted with EtOAc (3×30 mL), the combined organic phase was then washed with sat. aq. NaHCO₃ (2×20 mL) and brine (2×20 mL), dried over Na₂SO₄, filtered, and concentrated under reduced pressure to obtain the crude title compound as a tan solid (6.5 g, 30.5 mmol, quant. yield), which was used in the next step without further purification.

Step 2: 4-(3-bromo-1H-pyrrolo[2,3-b]pyridin-6-yl)-3,5-dimethylisoxazole

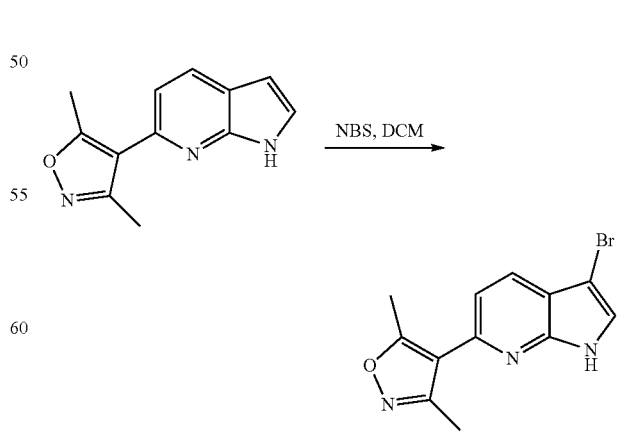

A suspension of 3,5-dimethyl-4-(1H-pyrrolo[2,3-b]pyridin-6-yl)isoxazole (6.5 g, 30.5 mmol) in DCM (150 mL)

was cooled to 0° C., and ½ amount of the required NBS (N-bromosuccinimide; 2.71 g, 15.2 mmol) was added portion wise followed by stirring for 30 min. Reaction was followed by LCMS (liquid chromatography mass spectrometry). After 30 min (where the conversion of about 40% was observed), the remaining ½ amount of NBS (2.71 g, 15.2 mmol) was added portion wise, and the reaction mixture was stirred for another 20 minutes. The reaction was then quenched by the addition of sat. aq. $Na_2S_2O_3$ and stirred vigorously for 16 h. After overnight, the mixture was concentrated under reduced pressure and re-dissolved in EtOAc (100 mL) and water (50 mL). Organic phase was separated, washed with sat. aq. $NaHCO_3$ (50 mL), water (2×50 mL), and brine (2×50 mL), then dried over $Na_2SO_4$, filtered, and concentrated under reduced pressure to provide the crude title compound as a brown solid (8.54 g, 29.2 mmol, 96% yield), which was used in the next step without further purification.

Step 3: 4-(3-bromo-1-(phenylsulfonyl)-1H-pyrrolo[2,3-b]pyridin-6-yl)-3,5-dimethylisoxazole

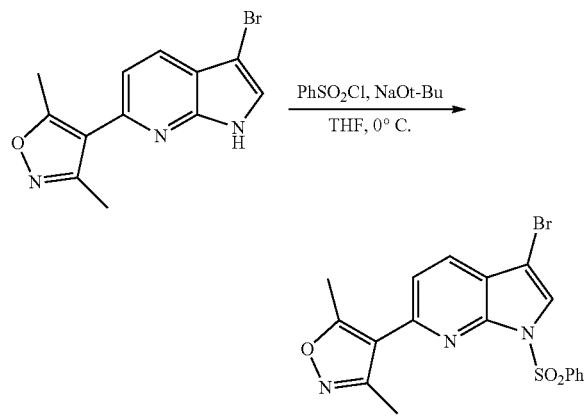

A solution of 4-(3-bromo-1H-pyrrolo[2,3-b]pyridin-6-yl)-3,5-dimethylisoxazole (8.54 g, 29.2 mmol) in dry THF (146 mL) at 0° C. was treated with NaOt-Bu (3.37 g, 35.1 mmol) and then was stirred for 30 min at this temperature before adding benzenesulfonyl chloride (3.92 mL, 30.7 mmol). The reaction mixture was then stirred for 30 min at 0° C. The mixture was concentrated to about 20 mL of THF remaining and diluted with water (70 mL). After sonication, the obtained suspension was filtered, the solid was rinsed with water and then dried for to provide the crude title compound as a red solid (12.64 g, 29.2 mmol, quant. yield), which was used in the next step without further purification.

Step 4: 3,5-dimethyl-4-(1-(phenylsulfonyl)-3-(4,4,5,5-tetramethyl-1,3,2-dioxaborolan-2-yl)-1H-pyrrolo[2,3-b]pyridin-6-yl)isoxazole

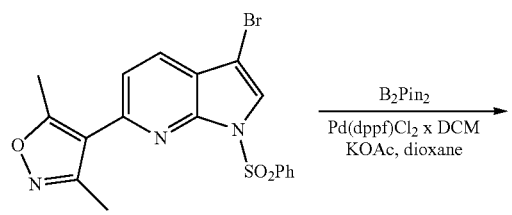

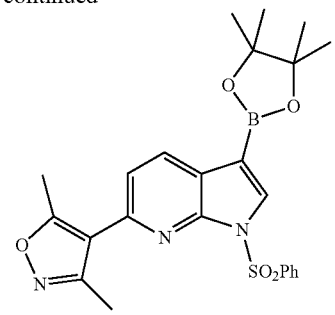

To a solution of 4-(3-bromo-1-(phenylsulfonyl)-1H-pyrrolo[2,3-b]pyridin-6-yl)-3,5-dimethylisoxazole (8.69 g, 20.1 mmol) in degassed dioxane (67 mL) were added bis(pinacolato)diboron (12.9 g, 50.7 mmol) and KOAc (9.91 g, 101.0 mmol), and the mixture was degassed for 30 min. Pd(dppf)Cl$_2$ DCM complex (1.63 g, 2.00 mmol) was added, and then the reaction mixture in the sealed tube was stirred at 100° C. for 1 h. The resulted black solution was cooled down to RT, diluted with EtOAc (100 mL), filtered through Celite and treated with sat. aq. NaHCO$_3$ (75 mL). Crude product was extracted with EtOAc (2×30 mL), combined organic phase was then washed with water (2×50 mL) and brine (2×50 mL), dried over Na$_2$SO$_4$, filtered, and concentrated under reduced pressure to a black sticky solid of crude title compound (9.61 g, 20.1 mmol, quant. yield), which was used in the next step without further purification.

Step 5: 3,5-dimethyl-4-(3-(2-(methylthio)-5-(trifluoromethyl)pyrimidin-4-yl)-1-(phenylsulfonyl)-1H-pyrrolo[2,3-b]pyridin-6-yl)isoxazole

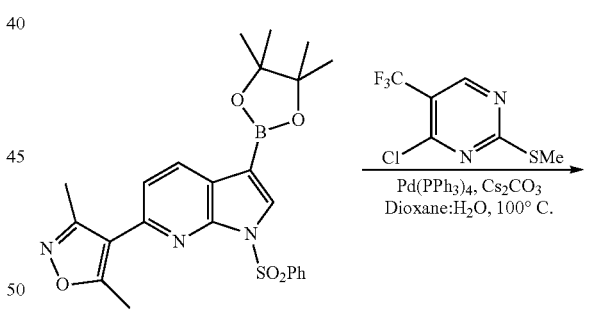

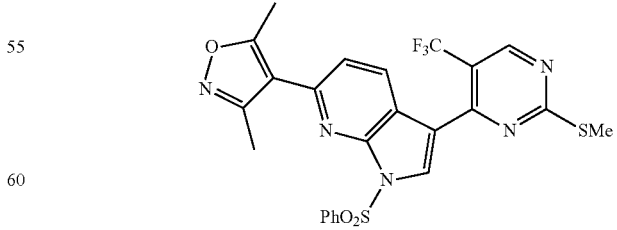

To a solution of 3,5-dimethyl-4-(1-(phenylsulfonyl)-3-(4,4,5,5-tetramethyl-1,3,2-dioxaborolan-2-yl)-1H-pyrrolo[2,3-b]pyridin-6-yl)isoxazole (9.61 g, 20.1 mmol) in degassed 2:1 mixture of dioxane/water (100 mL) was added Cs$_2$CO$_3$ (13.06 g, 40.1 mmol), and obtained suspension was degassed for 30 min. 4-Chloro-2-(methylthio)-5-(trifluoromethyl)pyrimidine (US20130017194) (5.04 g, 22.1 mmol) and tetrakis(triphenylphosphine)palladium(0) (2.32 g, 2.01 mmol) were added, and the reaction mixture was stirred at 100° C. After 2 h, another portion of 4-chloro-2-(methylthio)-5-(trifluoromethyl)pyrimidine (1.00 g, 4.38 mmol) was added, and the reaction mixture was heated for another 30 min at 100° C. After cooling down to RT, the mixture was diluted with EtOAc (100 mL) and water (75 mL), and pH was adjusted to pH 8 with sat. aq. NaHCO$_3$. Crude product was extracted with EtOAc (3×75 mL), combined organic phase was then washed with water (2×50 mL) and brine (75 mL), separated, dried over Na$_2$SO$_4$, filtered, and concentrated under reduced pressure. The residue was purified by silica gel column chromatography (EtOAc in hexanes, 0 to 100% gradient) to provide an orange paste, which was then re-purified by reverse phase chromatography (C18, MeCN in aq. 10 mM ammonium formate pH 3.8, 0 to 100% gradient) to give the title compound as a brown solid (2.05 g, 3.76 mmol, 19% yield).

Step 6: 3,5-dimethyl-4-(3-(2-(methylsulfonyl)-5-(trifluoromethyl)pyrimidin-4-yl)-1-(phenylsulfonyl)-1H-pyrrolo[2,3-b]pyridin-6-yl)isoxazole

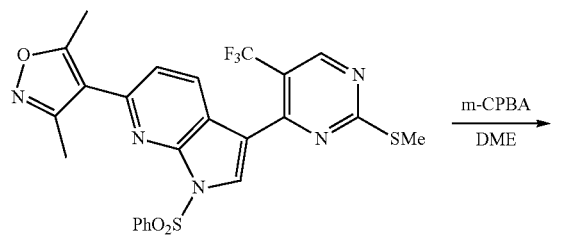

To a solution of 3,5-dimethyl-4-(3-(2-(methylthio)-5-(trifluoromethyl)pyrimidin-4-yl)-1-(phenylsulfonyl)-1H-pyrrolo[2,3-b]pyridin-6-yl)isoxazole (2.00 g, 3.67 mmol) in DME (dimethoxyethane; 37 mL) was added m-CPBA (3-chloroperbenzoic acid; 77%) (1.65 g, 7.34 mmol), and the reaction mixture was stirred at RT for 2 h. The suspension was then filtered, and the solids were washed with DCM (20 mL) and EtOAc (20 mL). The collected organic filtrate was concentrated under reduced pressure, and the residue was purified by silica gel column chromatography (EtOAc in hexanes, 0 to 100% gradient). The title compound was obtained as a pale orange solid (1.08 g, 1.87 mmol, 51% yield).

Example 6. Synthesis of 4-(6-(3,5-dimethylisoxazol-4-yl)-1H-pyrrolo[2,3-b]pyridin-3-yl)-N-((3R,4R)-4-methoxypiperidin-3-yl)-5-(trifluoromethyl)pyrimidin-2-amine (Compound 117)

Step 1: Racemic trans tert-butyl 3-azido-4-methoxypiperidine-1-carboxylate

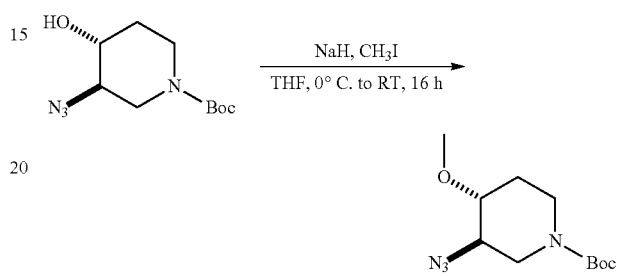

To a solution of racemic trans tert-butyl 3-azido-4-hydroxypiperidine-1-carboxylate (*Angew. Chem., Int. Ed.* 2016, 55, 11382) (504 mg, 2.08 mmol) in dry THF at 0° C. in an ice/water bath, was added sodium hydride (100 mg, 2.5 mmol) portion wise. The suspension was stirred at this temperature for 15 min. Then, iodomethane (0.144 mL, 2.29 mmol) was added. The resulting solution was allowed to reach RT and stirred for 16 h. After full conversion of starting material, the reaction mixture was quenched by addition of MeOH and then diluted with DCM. Water was added, and organic layer was separated, washed with brine (2×20 mL), dried over MgSO$_4$, filtered, and concentrated under reduced pressure. The yellowish residue was purified by silica gel chromatography (EtOAc in hexanes, 0 to 30% gradient). The title compound (511 mg, 1.99 mmol, 96% yield) was obtained as a translucent oil.

Step 2: Racemic trans tert-butyl 3-amino-4-methoxypiperidine-1-carboxylate

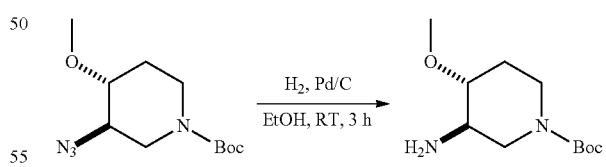

To a solution of racemic trans tert-butyl 3-azido-4-methoxypiperidine-1-carboxylate (511 mg, 1.99 mmol) in EtOH (ethanol; 10 mL) was added Pd/C, 10 wt. % (400 mg). The suspension was purged with hydrogen (three times). The resulting mixture was then stirred at RT for 3 h under atmospheric pressure of hydrogen. After full conversion of starting material, the suspension was filtered through a pad of Celite. The filtrate was concentrated under reduced pressure to provide the crude title compound as a yellowish oil, which was used in the next step without further purification.

Step 3: Racemic trans tert-butyl 3-((4-(6-(3,5-dimethylisoxazol-4-yl)-1-(phenylsulfonyl)-1H-pyrrolo[2,3-b]pyridin-3-yl)-5-(trifluoromethyl)pyrimidin-2-yl)amino)-4-methoxypiperidine-1-carboxylate

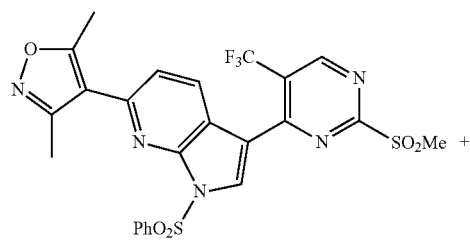

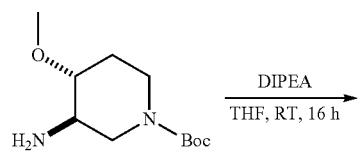

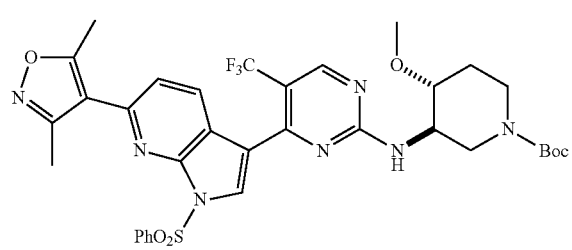

To a solution of 3,5-dimethyl-4-(3-(2-(methylsulfonyl)-5-(trifluoromethyl)pyrimidin-4-yl)-1-(phenylsulfonyl)-1H-pyrrolo[2,3-b]pyridin-6-yl)isoxazole (Example 5; 105 mg, 0.182 mmol) and racemic trans tert-butyl 3-amino-4-methoxypiperidine-1-carboxylate (63 mg, 0.273 mmol) in dry THF (0.9 mL) was added DIPEA (0.1 mL, 0.545 mmol). The reaction mixture was then stirred for 16 h at RT. The mixture was diluted with EtOAc (10 mL), washed with brine (2×10 mL). Organic phase was separated, dried over Na₂SO₄, filtered, and concentrated under reduced pressure. The obtained crude title compound (130 mg, 0.179 mmol, 98% yield) was used in the next step without further purification.

Step 4: Racemic trans tert-butyl 3-((4-(6-(3,5-dimethylisoxazol-4-yl)-1H-pyrrolo[2,3-b]pyridin-3-yl)-5-(trifluoromethyl)pyrimidin-2-yl)amino)-4-methoxypiperidine-1-carboxylate

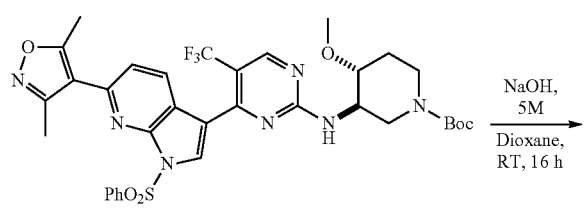

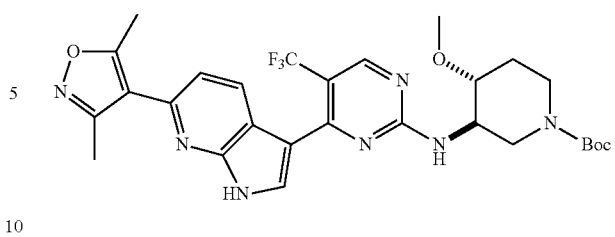

To a solution of racemic trans tert-butyl 3-((4-(6-(3,5-dimethylisoxazol-4-yl)-1-(phenylsulfonyl)-1H-pyrrolo[2,3-b]pyridin-3-yl)-5-(trifluoromethyl)pyrimidin-2-yl)amino)-4-methoxypiperidine-1-carboxylate (130 mg, 0.179 mmol) in dioxane (1.2 mL) was added 5M aq. NaOH (0.360 mL, 1.79 mmol). The reaction mixture was then stirred at room temperature for 16 h. After overnight, the mixture was concentrated under reduced pressure, and the residue was purified by reverse phase chromatography (C18, MeCN in aq. 10 mM ammonium formate pH 3.8, 0 to 100% gradient). The title compound (65 mg, 0.111 mmol, 62% yield) was obtained as a pale yellow solid.

Step 5: (3R,4R)-tert-butyl 3-((4-(6-(3,5-dimethylisoxazol-4-yl)-1H-pyrrolo[2,3-b]pyridin-3-yl)-5-(trifluoromethyl)pyrimidin-2-yl)amino)-4-methoxypiperidine-1-carboxylate (A)

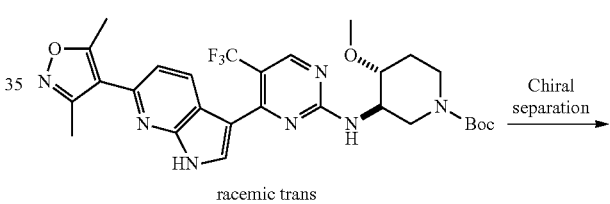

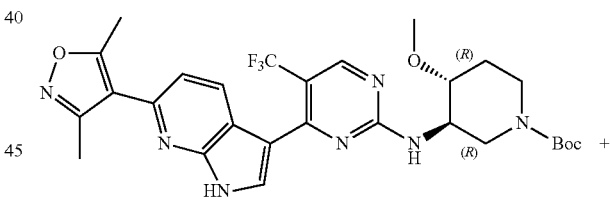

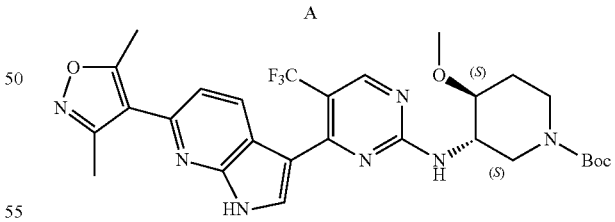

Racemic trans tert-butyl 3-((4-(6-(3,5-dimethylisoxazol-4-yl)-1H-pyrrolo[2,3-b]pyridin-3-yl)-5-(trifluoromethyl)pyrimidin-2-yl)amino)-4-methoxypiperidine-1-carboxylate (65 mg) was separated by chiral HPLC (high pressure liquid chromatography) using a ChiralPak IA column and 8:92 mixture of EtOH/Hexanes for elution. Two enantiomers were obtained: Peak 1 (A, tentatively assigned as (3R,4R), 20 mg, pale yellow solid), and Peak 2 (B, tentatively assigned as (3S,4S), 18 mg, pale yellow solid).

Step 6: 4-(6-(3,5-dimethylisoxazol-4-yl)-1H-pyrrolo[2,3-b]pyridin-3-yl)-N-((3R,4R)-4-methoxypiperidin-3-yl)-5-(trifluoromethyl)pyrimidin-2-amine

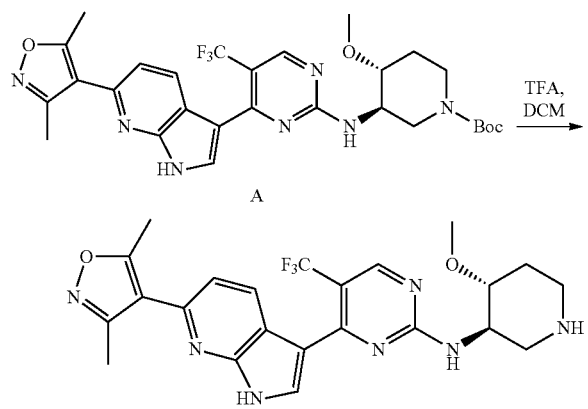

To a solution of Compound A from the previous step assigned as (3R,4R)-enantiomer (20 mg, 0.034 mmol) in DCM (1 mL) was added TFA (0.22 mL, 2.87 mmol). After 1 h of stirring at RT, reaction mixture was concentrated under reduced pressure, and the basified residue was purified by reverse phase chromatography (C18, MeCN in aq. 10 mM ammonium formate pH 3.8, 10 to 50% gradient) to afford the title compound (9.4 mg, 0.019 mmol, 57% yield) as a white solid.

Example 7. Synthesis of 4-(6-(3,5-dimethylisoxazol-4-yl)-1H-indol-3-yl)-N-((3R,4R)-4-methoxypiperidin-3-yl)-5-(trifluoromethyl)pyrimidin-2-amine (Compound 127)

Step 1: (3R,4R)-tert-butyl 3-((4-(6-(3,5-dimethylisoxazol-4-yl)-1-(phenylsulfonyl)-1H-indol-3-yl)-5-(trifluoromethyl)pyrimidin-2-yl)amino)-4-methoxypiperidine-1-carboxylate (A)

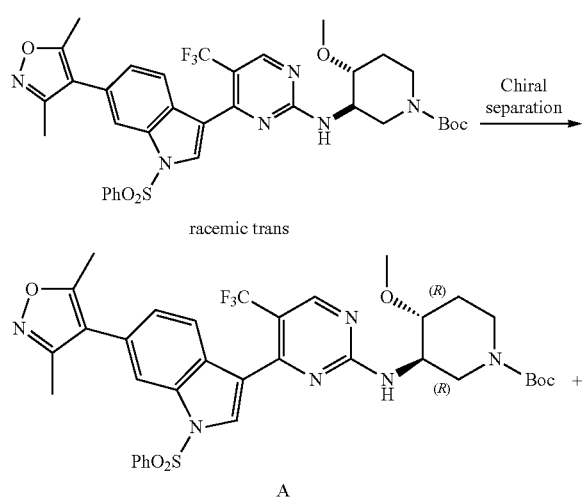

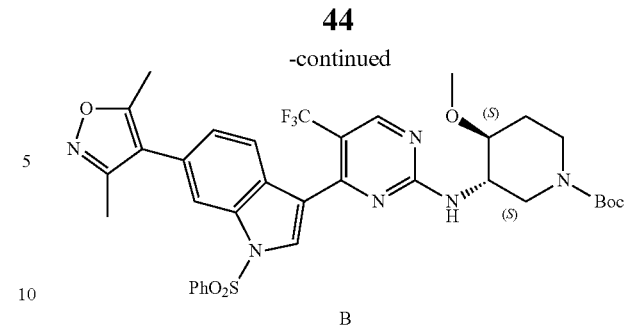

Racemic trans tert-butyl 3-((4-(6-(3,5-dimethylisoxazol-4-yl)-1-(phenylsulfonyl)-1H-indol-3-yl)-5-(trifluoromethyl)pyrimidin-2-yl)amino)-4-methoxypiperidine-1-carboxylate (Example 6; 197 mg, 0.271 mmol) was separated by chiral HPLC using a ChiralPak IA column and 8:20:72 mixture of MeOH/IPA/hexanes for elution. Two enantiomers were obtained: Peak 1 (A, tentatively assigned as (3R,4R), 84 mg, pale yellow solid), and Peak 2 (B, tentatively assigned as (3S,4S), 81 mg, pale yellow solid).

Step 2: 4-(6-(3,5-dimethylisoxazol-4-yl)-1H-indol-3-yl)-N-((3R,4R)-4-methoxypiperidin-3-yl)-5-(trifluoromethyl)pyrimidin-2-amine

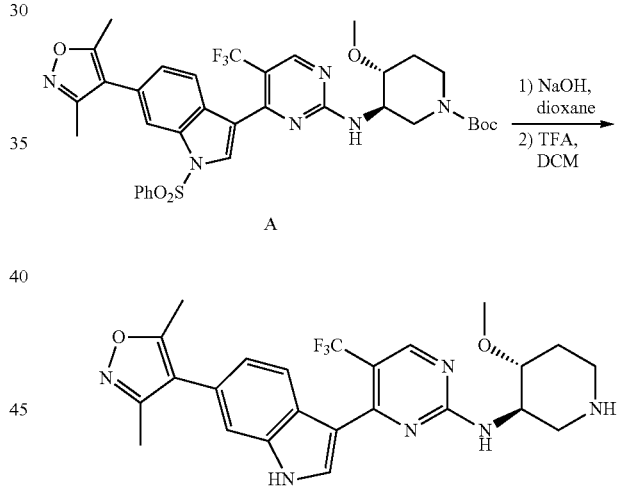

To a solution of Compound A from the previous step assigned as (3R,4R)-enantiomer (84 mg, 0.116 mmol) in dioxane (1 mL) was added 5M aq. NaOH (1.2 mL, 5.8 mmol). The reaction mixture was then stirred at 70° C. until full conversion. After 4 h, mixture was cooled down to RT and diluted in water. Aqueous layer was extracted with MeTHF (3×25 mL). Combined organic phase was washed with brine (50 mL), separated, dried over Na₂SO₄, filtered, and concentrated under reduced pressure. The obtained crude was re-dissolved in DCM (1.7 mL), and TFA (0.444 mL, 5.8 mmol) was added. After 1 h of stirring at RT, the reaction mixture was concentrated under reduced pressure, and the basified residue was purified by reverse phase chromatography (C18, MeCN in aq. 10 mM ammonium formate pH 3.8, 10 to 55% gradient) to afford the title compound (39.2 mg, 0.081 mmol, 70% yield over 2 steps) as a white solid.

Example 8. Synthesis of (S)-tert-butyl 3-((4-(6-(3-methylisothiazol-4-yl)-1-(phenylsulfonyl)-1H-indol-3-yl)-5-(trifluoromethyl)pyrimidin-2-yl)amino)piperidine-1-carboxylate useful in the synthesis of Compound 128

Step 1: (S)-tert-butyl 3-((4-(1-(phenylsulfonyl)-6-(4,4,5,5-tetramethyl-1,3,2-dioxaborolan-2-yl)-1H-indol-3-yl)-5-(trifluoromethyl)pyrimidin-2-yl)amino)piperidine-1-carboxylate

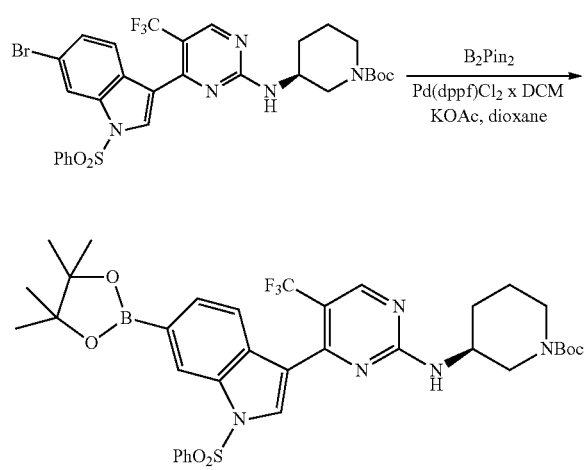

To a solution of (S)-tert-butyl 3-((4-(6-bromo-1-(phenylsulfonyl)-1H-indol-3-yl)-5-(trifluoromethyl)pyrimidin-2-yl)amino)piperidine-1-carboxylate (Example 3, step 1; 400 mg, 0.59 mmol) in degassed dioxane (4.2 mL) were added bis(pinacolato)diboron (373 mg, 1.47 mmol) and KOAc (288 mg, 2.95 mmol), and the mixture was degassed for 15 min. Pd(dppf)Cl₂ DCM complex (48 mg, 0.06 mmol) was added, and then the reaction mixture was stirred at 95° C. until full conversion (followed by LCMS). After 2 h, the mixture was cooled down to RT, diluted with EtOAc (50 mL), washed with sat. aq. NaHCO₃ (50 mL), water (50 mL), and brine (50 mL). Organic phase was separated, dried over Na₂SO₄, filtered, and concentrated under reduced pressure to provide a brown semi-solid of crude title compound, which was used in the next step without further purification.

Step 2: (S)-tert-butyl 3-((4-(6-(3-methylisothiazol-4-yl)-1-(phenylsulfonyl)-1H-indol-3-yl)-5-(trifluoromethyl)pyrimidin-2-yl)amino)piperidine-1-carboxylate To a solution of (S)-tert-butyl 3-((4-(1-(phenylsulfonyl)-6-(4,4,5,5-tetramethyl-1,3,2-dioxaborolan-2-yl)-1H-indol-3-yl)-5-(trifluoromethyl)pyrimidin-2-yl)amino)piperidine-1-carboxylate (214 mg, 0.294 mmol) and 4-bromo-3-methylisothiazole (79 mg, 0.441 mmol) in previously degassed 2:1 mixture of dioxane/H₂O (6 mL) was added Na₂CO₃ (94 mg, 0.882 mmol), and the mixture was degassed for 15 min. Pd(dppf)Cl₂ DCM complex (24 mg, 0.029 mmol) was added, and the reaction mixture was stirred at 100° C. for 2 h. The mixture was cooled down to RT, diluted with EtOAc (30 mL), washed with sat. aq. NaHCO₃ (30 mL), water (30 mL), and brine (30 mL). The organic phase was separated, dried over Na₂SO₄, filtered, and concentrated under reduced pressure. The residue was purified by silica gel column chromatography (EtOAc in 1:1 mixture of hexanes/DCM, 0 to 100% gradient) to provide the title compound as a yellowish oil (152 mg, 74% yield).

Example 9. Synthesis of 4-[6-(3,5-dimethylisoxazol-4-yl)-1H-pyrrolo-[2,3-b]-pyridin-3-yl]-N-[(3S)-3-piperidyl]-5-(trifluoromethyl)pyrimidin-2-amine (Compound 101)

Step 1: 3,5-dimethyl-4-(1H-pyrrolo-[2,3-b]-pyridin-6-yl) isoxazole

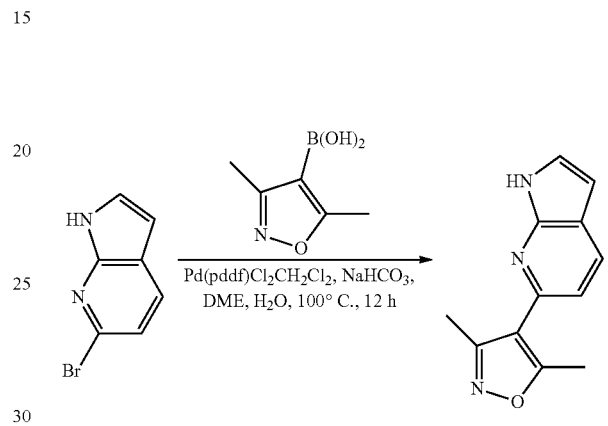

A mixture of 6-bromo-1H-pyrrolo-[2,3-b]-pyridine (1 g, 5.08 mmol, 1 eq), (3,5-dimethylisoxazol-4-yl) boronic acid (1.43 g, 10.15 mmol, 2 eq), Pd(dppf)Cl₂·CH₂Cl₂ (207.23 mg, 253.77 μmol, 0.05 eq), NaHCO₃ (1.28 g, 15.23 mmol, 592.17 μL, 3 eq) in DME (10 mL) and H₂O (3 mL) was degassed and purged with N₂ for 3 times, and then the mixture was stirred at 100° C. for 12 h under N₂ atmosphere. The reaction mixture was poured into H₂O (20 mL) and extracted with EtOAc (20 mL×3). The combined organic layers were washed with brine (20 mL×2), dried over Na₂SO₄, filtered and concentrated under reduced pressure to give a residue. The residue was purified by column chromatography (SiO₂, PE/EtOAc=10/1 to 2/1) to afford the title compound (1.1 g, 90% purity) as a white solid.

Step 2: 4-(3-bromo-1H-pyrrolo-[2,3-b]-pyridin-6-yl)-3,5-dimethyl-isoxazole

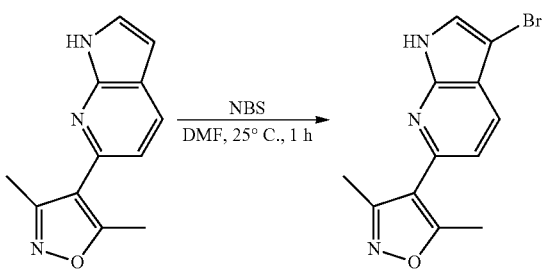

To a solution of 3,5-dimethyl-4-(1H-pyrrolo-[2,3-b]-pyridin-6-yl) isoxazole (0.9 g, 4.22 mmol, 1 eq) in DMF (dimethylformamide; 10 mL) was added NBS (676.10 mg, 3.80 mmol, 0.9 eq). The mixture was stirred at 25° C. for 1 h. The reaction mixture was poured into H₂O (20 mL), and extracted with EtOAc (20 mL×3). The combined organic layers were washed with brine (20 mL×2), dried over Na₂SO₄, filtered and concentrated under reduced pressure to give a residue. The residue was purified by column chromatography (SiO₂, PE/EtOAc=10/1 to 1/1) to afford the title compound (600 mg, crude) as pink solid which was used in the next step directly.

Step 3: 4-[1-(benzenesulfonyl)-3-bromo-pyrrolo-[2,3-b]-pyridin-6-yl]-3,5-dimethyl-isoxazole

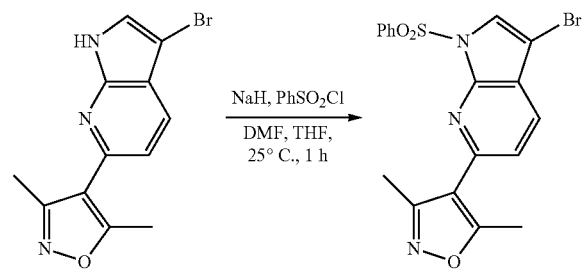

To a solution of 4-(3-bromo-1H-pyrrolo[2,3-b]-pyridin-6-yl)-3,5-dimethyl-isoxazole (0.6 g, 2.05 mmol, 1 eq) in DMF (9 mL) and THF (1 mL) was added NaH (98.58 mg, 2.46 mmol, 60% purity, 1.2 eq) and benzenesulfonyl chloride (471.58 mg, 2.67 mmol, 341.73 µL, 1.3 eq). The mixture was stirred at 25° C. for 1 h. The reaction mixture was poured into H₂O (20 mL) while white solid formed. The solid was filtered and concentrated under reduced pressure to afford the title compound (600 mg) as white solid, which used into the next step without further purification.

Step 4: 4-[1-(benzenesulfonyl) pyrrolo-[2,3-b]-pyridin-6-yl]-3,5-dimethyl-isoxazole; 4-[1-(benzenesulfonyl)-3-(4,4,5,5-tetramethyl-1,3,2-dioxaborolan-2-yl) pyrrolo-[2,3-b]-pyridin-6-yl]-3,5-dimethyl-isoxazole

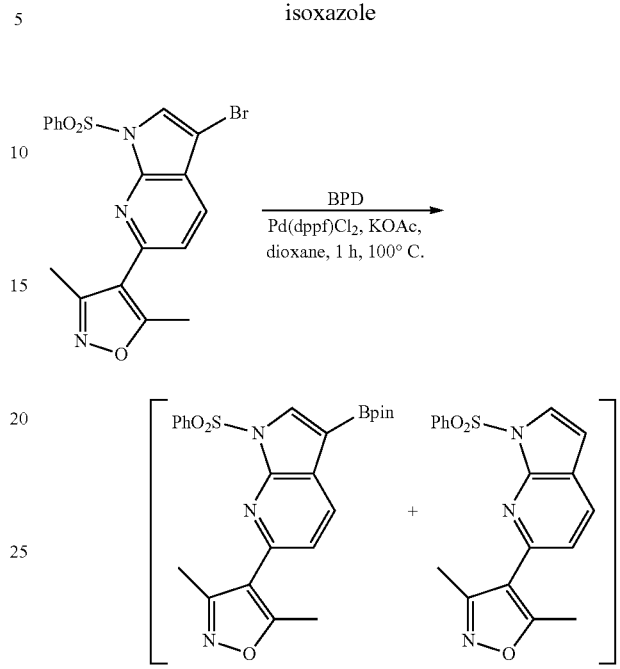

A mixture of 4-[1-(benzenesulfonyl)-3-bromo-pyrrolo-[2,3-b]-pyridin-6-yl]-3,5-dimethyl-isoxazole (0.27 g, 624.58 µmol, 1 eq), BPD (237.91 mg, 936.87 µmol, 1.5 eq), Pd(dppf)Cl₂ (45.70 mg, 62.46 µmol, 0.1 eq), KOAc (122.60 mg, 1.25 mmol, 2 eq) in dioxane (3 mL) was degassed and purged with N₂ for 3 times, and then the mixture was stirred at 100° C. for 1 h under N₂ atmosphere. The reaction mixture was poured into H₂O (20 mL) and extracted with EtOAc (20 mL×3). The combined organic layers were washed with brine (10 mL×2), dried over Na₂SO₄, filtered and concentrated under reduced pressure to afford the title compound (600 mg, crude, 2 Batches in parallel) as brown oil which was used into the next step without further purification.

Step 5: Tert-butyl (3S)-3-[[4-[1-(benzenesulfonyl)-6-(3,5-dimethylisoxazol-4-yl) pyrrolo-[2,3-b]-pyridin-3-yl]-5-(trifluoromethyl)pyrimidin-2-yl]-amino]-piperidine-1-carboxylate

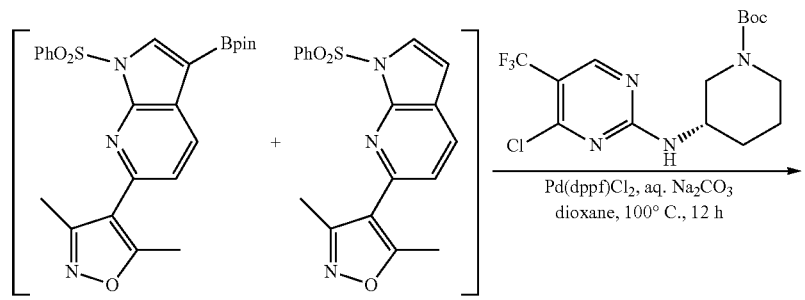

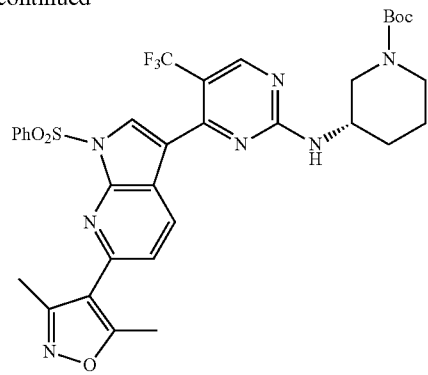

A mixture of 4-[1-(benzenesulfonyl) pyrrolo-[2,3-b]-pyridin-6-yl]-3,5-dimethyl-isoxazole and 4-[1-(benzenesulfonyl)-3-(4,4,5,5-tetramethyl-1,3,2-dioxaborolan-2-yl) pyrrolo-[2,3-b]-pyridin-6-yl]-3,5-dimethyl-isoxazole (600 mg, from previous step), tert-butyl (3S)-3-[[4-chloro-5-(trifluoromethyl)pyrimidin-2-yl]-amino]-piperidine-1-carboxylate ((PCT Int. Appl., WO2014124230); 476.63 mg, 1.25 mmol), Pd(dppf)Cl$_2$ (91.59 mg, 125.17 μmol), Na$_2$CO$_3$ (265.33 mg, 2.50 mmol) in dioxane (10 mL) and H$_2$O (2 mL) was degassed and purged with N$_2$ for 3 times, and then the mixture was stirred at 100° C. for 12 h under N$_2$ atmosphere. The reaction mixture was poured into H$_2$O (30 mL) and extracted with EtOAc (30 mL×4). The combined organic layers were washed with brine (100 mL×2), dried over Na$_2$SO$_4$, filtered and concentrated under reduced pressure to give a residue. The residue was purified by column chromatography (SiO$_2$, PE/EtOAc=10/1 to 2/1) to afford the title compound (0.25 g, 286.65 μmol, 22.90% yield, 80% purity) as yellow solid.

Step 6: Tert-butyl (3S)-3-[[4-[6-(3,5-dimethylisoxazol-4-yl)-1H-pyrrolo-[2,3-b]-pyridin-3-yl]-5-(trifluoromethyl)pyrimidin-2-yl]-amino]-piperidine-1-carboxylate

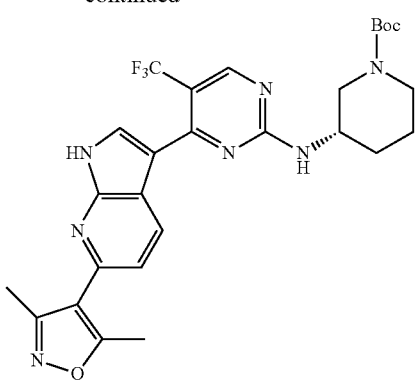

To a solution of tert-butyl (3S)-3-[[4-[1-(benzenesulfonyl)-6-(3,5-dimethylisoxazol-4-yl) pyrrolo-[2,3-b]-pyridin-3-yl]-5-(trifluoromethyl)pyrimidin-2-yl]-amino]-piperidine-1-carboxylate (0.2 g, 286.65 μmol, 1 eq) in MeOH (1 mL) was added NaOH (2 M, 0.8 mL, 5.58 eq). The mixture was stirred at 60° C. for 1 h. The reaction mixture was concentrated under reduced pressure to afford the title compound (0.2 g, crude) as yellow solid, which was used into the next step without further purification.

Step 7: 4-[6-(3,5-dimethylisoxazol-4-yl)-1H-pyrrolo-[2,3-b]-pyridin-3-yl]-N-[(3S)-3-piperidyl]-5-(trifluoromethyl)pyrimidin-2-amine

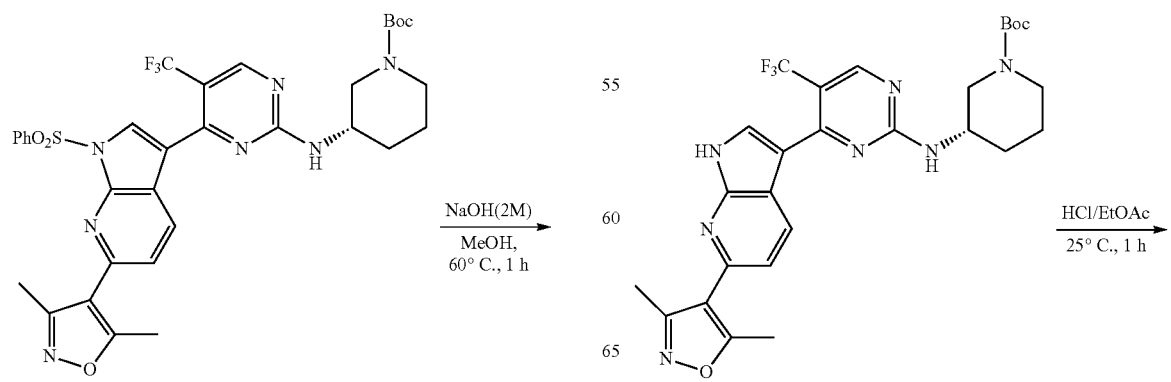

-continued

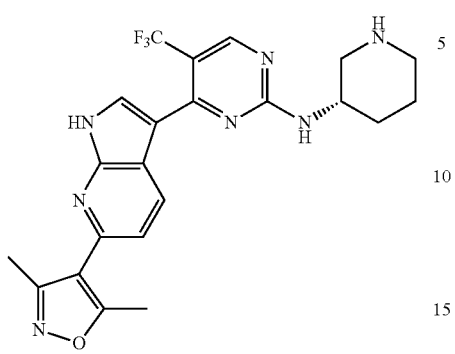

To a solution of tert-butyl (3S)-3-[[4-[6-(3,5-dimethyl-isoxazol-4-yl)-1H-pyrrolo-[2,3-b]-pyridin-3-yl]-5-(trifluoromethyl)pyrimidin-2-yl]-amino]-piperidine-1-carboxylate (0.2 g, 358.70 μmol, 1 eq) in EtOAc (1 mL) was added HCl/EtOAc (4 M, 2 mL, 22.30 eq). The mixture was stirred at 25° C. for 1 h then concentrated under reduced pressure to give a residue that was purified by prep-HPLC (HCl condition) to afford the title compound (31.6 mg, HCl salt, 100% purity) as a yellow solid.

Example 10. Synthesis of 2-[1-(benzenesulfonyl)-3-(4,4,5,5-tetramethyl-1,3,2-dioxaborolan-2-yl)pyrrolo-[2,3-b]pyridin-6-yl]thiazole for use in Synthesizing Compound 108

Step 1: 1-(benzenesulfonyl)-6-bromo-pyrrolo[2,3-b]pyridine

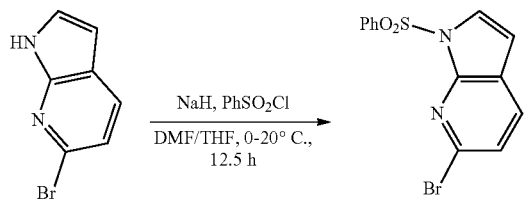

To a solution of 6-bromo-1H-pyrrolo[2,3-b]pyridine (1 g, 5.08 mmol, 1 eq) in DMF (9 mL) and THF (1 mL) was added NaH (243.82 mg, 6.10 mmol, 60% purity, 1.2 eq) at 0° C. for 0.5 h, then benzenesulfonyl chloride (1.17 g, 6.60 mmol, 845.22 μL, 1.3 eq) was added to the solution at 0° C. The mixture was stirred at 20° C. for 12 h. The reaction mixture was diluted with water (100 mL) and extracted with EtOAc (30 mL×3). The combined organic layers were washed with brine (30 mL×3), dried over Na$_2$SO$_4$, filtered and concentrated under reduced pressure to give a residue. The residue was purified by column chromatography (SiO$_2$, PE/EtOAc=5/1) to afford the title compound (1.6 g, 4.27 mmol, 84.07% yield, 90% purity) as a white solid.

Step 2: 2-[1-(benzenesulfonyl)pyrrolo[2,3-b]pyridin-6-yl]thiazole

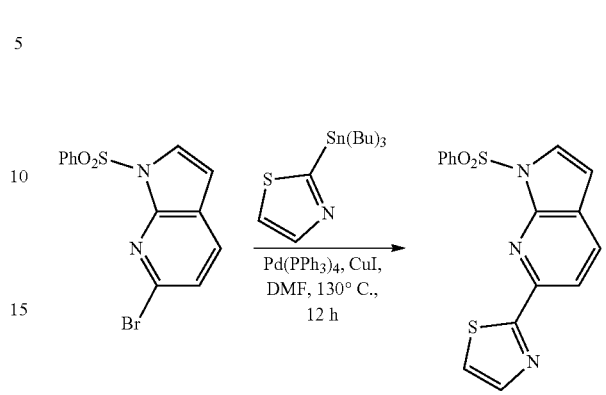

To a solution of 1-(benzenesulfonyl)-6-bromo-pyrrolo[2,3-b]pyridine (0.5 g, 1.48 mmol, 1 eq) in DMF (5 mL) was added tributyl (thiazol-2-yl) stannane (610.32 mg, 1.63 mmol, 1.1 eq), Pd(PPh$_3$)$_4$ (171.35 mg, 148.28 μmol, 0.1 eq) and CuI (28.24 mg, 148.28 μmol, 0.1 eq). The mixture was stirred at 130° C. for 12 h under N$_2$. The reaction mixture was diluted with saturated aqueous of KF (50 mL) and extracted with EtOAc (10 mL×3). The combined organic layers were washed with brine (10 mL×3), dried over Na$_2$SO$_4$, filtered and concentrated under reduced pressure to give a residue. The residue was purified by column chromatography (SiO$_2$, PE/EtOAc=3/1) to afford the title compound (420 mg) as a white solid. (The reaction was combined with another reaction in 50 mg scale for purification.)

Step 3: 2-[1-(benzenesulfonyl)-3-bromo-pyrrolo[2,3-b]pyridin-6-yl]thiazole

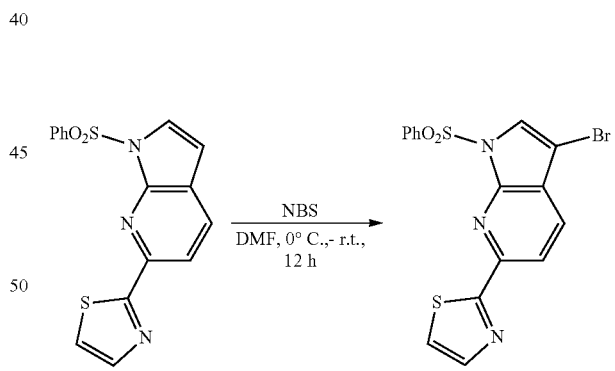

To a solution of 2-[1-(benzenesulfonyl)pyrrolo[2,3-b]pyridin-6-yl]thiazole (0.41 g, 1.20 mmol, 1 eq) in DMF (4 mL) was added NBS (213.74 mg, 1.20 mmol, 1 eq) at 0° C. The mixture was stirred at 20° C. for 12 h. The reaction mixture was diluted with water (50 mL) and extracted with EtOAc (10 mL×3). The combined organic layers were washed with brine (10 mL×3), dried over Na$_2$SO$_4$, filtered and concentrated under reduced pressure to give a residue. The residue was purified by column chromatography (SiO$_2$, PE/EtOAc=6/1 to EtOAc) to afford the title compound (300 mg) as a pink red solid.

Step 4: 2-[1-(benzenesulfonyl)-3-(4,4,5,5-tetramethyl-1,3,2-dioxaborolan-2-yl)pyrrolo-[2,3-b]pyridin-6-yl]thiazole

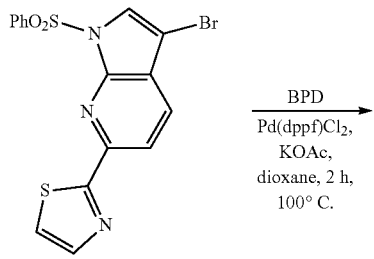

To a solution of 2-[1-(benzenesulfonyl)-3-bromo-pyrrolo[2,3-b]pyridin-6-yl]thiazole (0.8 g, 1.90 mmol, 1 eq) in dioxane (10 mL) was added BPD (725.01 mg, 2.86 mmol, 1.5 eq), KOAc (373.61 mg, 3.81 mmol, 2 eq) and Pd(dppf)Cl$_2$ (139.27 mg, 190.34 µmol, 0.1 eq). The mixture was stirred at 100° C. for 2 h under N$_2$. The reaction mixture was diluted with water (100 mL) and extracted with EtOAc (15 mL×3). The combined organic layers were washed with brine (15 mL×3), dried over Na$_2$SO$_4$, filtered and concentrated under reduced pressure to afford the title compound (1 g) as a brown oil.

Example 11. Synthesis of Tert-butyl (5S)-5-[[4-[1-(benzenesulfonyl)-6-(3,5-dimethylisoxazol-4-yl)pyrrolo[2,3-b]pyridin-3-yl]-5-(trifluoromethyl)pyrimidin-2-yl]amino]-3,3-dimethyl-piperidine-1-carboxylate useful in the synthesis of Compound 115)

Step 1: 4-chloro-2-methylsulfanyl-5-(trifluoromethyl)pyrimidine

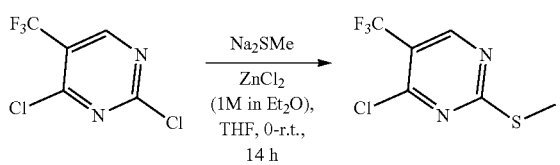

To a solution of 2,4-dichloro-5-(trifluoromethyl)pyrimidine (10 g, 46.09 mmol, 1 eq) in THF (200 mL) was added dropwise ZnCl$_2$ (1 M, 59.91 mL, 1.3 eq) at 0° C. After addition, the mixture was stirred at this temperature for 2 h, and then NaSMe (3.88 g, 55.31 mmol, 3.52 mL, 1.2 eq) was added dropwise at 0° C. The resulting mixture was stirred at 15° C. for 14 h. The mixture was quenched with aq. HCl (150 mL, 1M), and then extracted with EtOAc (60 mL×3), dried over Na$_2$SO$_4$ and concentrated. The residue was purified by column chromatography (SiO$_2$, PE/DCM=1:0 to 50:1) to afford the title compound (10 g, 43.74 mmol, 94.91% yield) as a colorless oil.

Step 2: 4-[1-(benzenesulfonyl)-3-[2-methylsulfanyl-5-(trifluoromethyl)pyrimidin-4-yl]pyrrolo-[2,3-b]pyridin-6-yl]-3,5-dimethylisoxazole

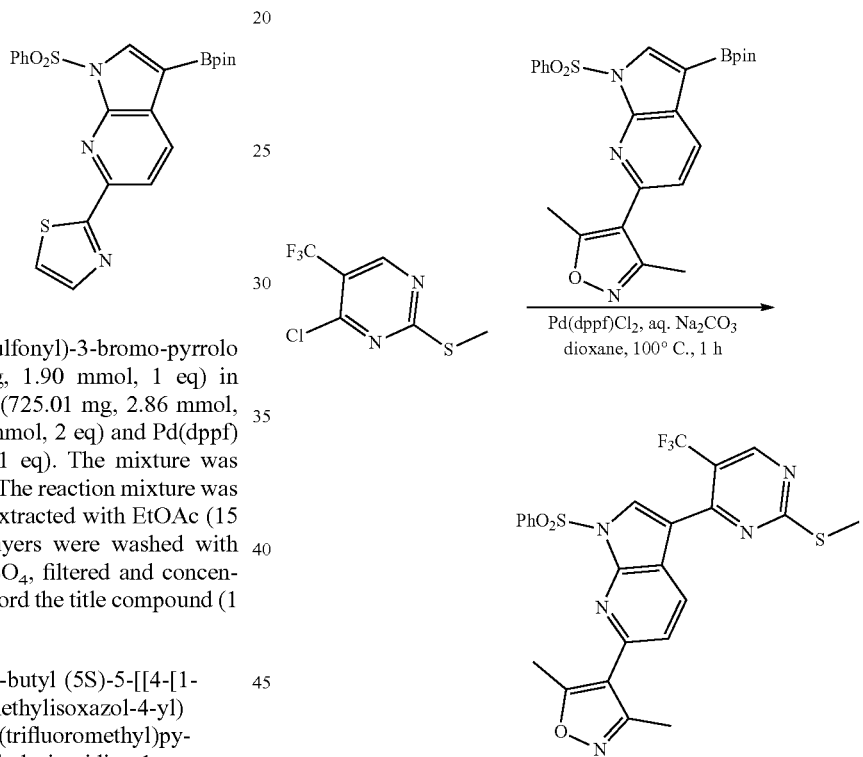

To a solution of 4-[1-(benzenesulfonyl)-3-(4,4,5,5-tetramethyl-1,3,2-dioxaborolan-2-yl)pyrrolo[2,3-b]pyridin-6-yl]-3,5-dimethyl-isoxazole (Example 9; 3 g, 3.76 mmol, 1 eq) and 4-chloro-2-methylsulfanyl-5-(trifluoromethyl)pyrimidine (1.43 g, 5.63 mmol, 1.5 eq) in dioxane (30 mL)/H$_2$O (6 mL) was added Na$_2$CO$_3$ (1.19 g, 11.27 mmol, 3 eq) and Pd(dppf)Cl$_2$ (274.76 mg, 375.50 µmol, 0.1 eq). The mixture was stirred at 100° C. under N$_2$ atmosphere for 1 h. The reaction mixture was poured into water (150 mL). The aqueous phase was extracted with ethyl acetate (50 mL×3). The combined organic phase was washed with brine (50 mL×2), dried over anhydrous Na$_2$SO$_4$, filtered and concentrated in vacuum. The residue was purified by silica gel chromatography (100-200 mesh silica gel, PE/EtOAc=10/1, 4/1) to afford the title compound (0.7 g, 769.86 µmol, 20.50% yield, 60% purity) as a yellow solid.

Step 3: 4-[1-(benzenesulfonyl)-3-[2-methylsulfonyl-5-(trifluoromethyl)pyrimidin-4-yl]pyrrolo[2,3-b]-pyridin-6-yl]-3,5-dimethylisoxazole

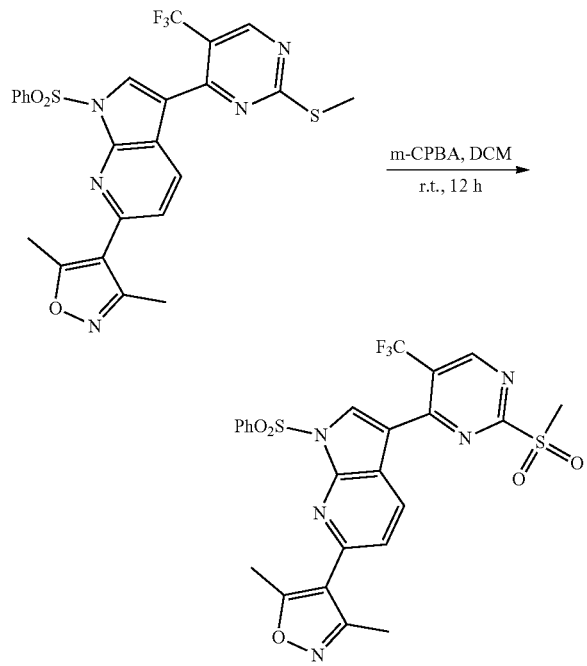

To a solution of 4-[1-(benzenesulfonyl)-3-[2-methylsulfanyl-5-(trifluoromethyl)pyrimidin-4-yl]pyrrolo[2,3-b]pyridin-6-yl]-3,5-dimethyl-isoxazole (0.7 g, 1.28 mmol, 1 eq) in DCM (50 mL) was added m-CPBA (573.08 mg, 2.82 mmol, 2.2 eq). The mixture was stirred at 20° C. for 12 h. The residue was poured into a mixture of Sat.NaHCO₃ (20 mL) and Sat. Na₂SO₃ (20 mL), and the mixture was stirred for 5 min. The aqueous phase was extracted with DCM (30 mL×2). The combined organic phase was dried over anhydrous Na₂SO₄, filtered and concentrated in vacuum. The residue was purified by silica gel chromatography (100-200 mesh silica gel, PE/EtOAc=10/1, 2/1, contained 10% DCM) to afford the title compound (0.5 g, 822.43 µmol, 64.10% yield, 95% purity) as a white solid.

Step 4: Tert-butyl (5S)-5-[[4-[1-(benzenesulfonyl)-6-(3,5-dimethylisoxazol-4-yl) pyrrolo[2,3-b]pyridin-3-yl]-5-(trifluoromethyl)pyrimidin-2-yl]amino]-3,3-dimethyl-piperidine-1-carboxylate

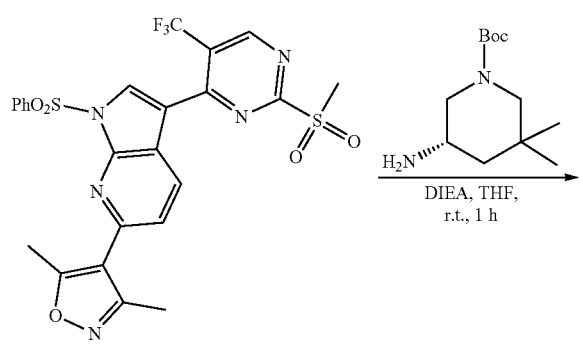

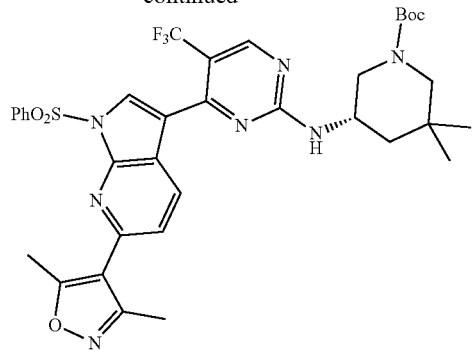

To a solution of 4-[1-(benzenesulfonyl)-3-[2-methylsulfonyl-5-(trifluoromethyl)pyrimidin-4-yl]pyrrolo[2,3-b]pyridin-6-yl]-3,5-dimethyl-isoxazole (0.1 g, 173.14 µmol, 1 eq), tert-butyl (5S)-5-amino-3,3-dimethyl-piperidine-1-carboxylate (114.01 mg, 207.77 µmol, 1.2 eq, FA) in THF (3 mL) was added DIEA (111.89 mg, 865.72 µmol, 150.79 µL, 5 eq). The mixture was stirred at 20° C. under N₂ atmosphere for 1 h. The reaction mixture was poured into water (30 mL). The aqueous phase was extracted with EtOAc (20 mL×3). The combined organic phase was washed with brine (20 mL×2), dried over anhydrous Na₂SO₄, filtered and concentrated in vacuum. The residue was purified by silica gel chromatography (100-200 mesh silica gel, PE/EtOAc=10/1, 2/1) to afford the title compound (0.12 g) as yellow solid.

Example 12. Synthesis of 4-[6-(3,5-dimethylisoxazol-4-yl)-1H-pyrazolo-[3,4-b]-pyridin-3-yl]-N-[(3S)-3-piperidyl]-5-(trifluoromethyl)pyrimidin-2-amine (Compound 118)

Step 1: 3,5-dimethyl-4-(1H-pyrazolo-[3,4-b]-pyridin-6-yl) isoxazole

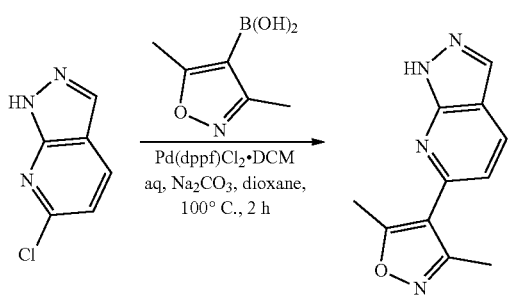

A mixture of 6-chloro-1H-pyrazolo-[3,4-b]-pyridine (1 g, 6.51 mmol, 1 eq), (3,5-dimethylisoxazol-4-yl) boronic acid (1.38 g, 9.77 mmol, 1.5 eq), Pd(dppf)Cl₂.CH₂Cl₂ (531.77 mg, 651.17 µmol, 0.1 eq), K₂CO₃ (5 M, 3.91 mL, 3 eq) in dioxane (20 mL) was degassed and purged with N₂ for 3 times, and then the mixture was stirred at 100° C. for 2 h under N₂ atmosphere. The reaction mixture was poured into water (100 mL), and then extracted with EtOAc (30 mL×3). The combined organic layers were washed with brine (200 mL), dried over Na₂SO₄, filtered and concentrated under reduced pressure to give a residue. The residue was purified by column chromatography (SiO₂, PE/EtOAc=10/1 to 1/1) to afford the title compound (1 g) as a yellow solid.

Step 2: 4-(3-iodo-1H-pyrazolo-[3,4-b]-pyridin-6-yl)-3,5-dimethyl-isoxazole

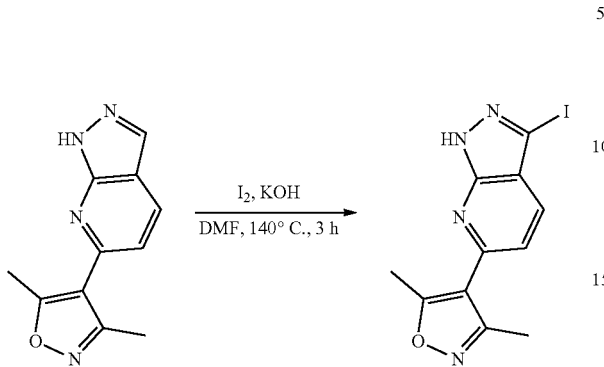

To a solution of 3,5-dimethyl-4-(1H-pyrazolo-[3,4-b]-pyridin-6-yl) isoxazole (0.9 g, 4.20 mmol, 1 eq) in DMF (10 mL) was added KOH (942.92 mg, 16.80 mmol, 4 eq) and molecular iodine (2.13 g, 8.40 mmol, 1.69 mL, 2 eq). The mixture was stirred at 140° C. for 3 h. The reaction mixture was quenched by addition 10% Na$_2$SO$_3$ (100 mL) at 15° C., then extracted with EtOAc (50 mL×3), dried over Na$_2$SO$_4$ and concentrated to afford the title compound (1 g, crude) as a yellow solid.

Step 3: 4-(3-iodo-1-tetrahydropyran-2-yl-pyrazolo-[3,4-b]-pyridin-6-yl)-3,5-dimethyl-isoxazole

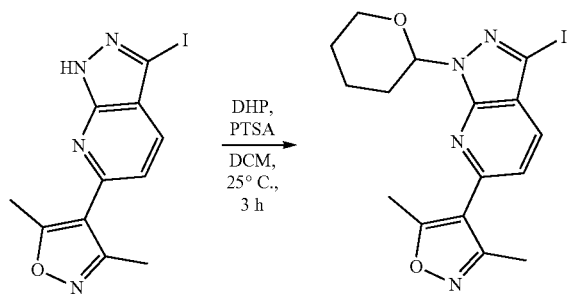 [SMILES: Cc1noc(C)c1-c1ccc2c(I)n[nH]c2n1 ; Cc1noc(C)c1-c1ccc2c(I)nn(C3CCCCO3)c2n1]

To a solution of 4-(3-iodo-1H-pyrazolo-[3,4-b]-pyridin-6-yl)-3,5-dimethyl-isoxazole (0.9 g, 2.65 mmol, 1 eq) in DCM (1 mL) was added 3,4-dihydro-2H-pyran (267.10 mg, 3.18 mmol, 290.32 μL, 1.2 eq) and PTSA (p-toluenesulfonic acid; 45.57 mg, 264.61 μmol, 0.1 eq). The mixture was stirred at 25° C. for 3 h. The mixture was washed with Sat.NaHCO$_3$ (100 mL×2) and brine (200 mL), dried over Na$_2$SO$_4$, filtered and the filtrate was evaporated. The residue was purified by column chromatography (SiO$_2$, PE/EtOAc=10/1 to 1/1) to afford the title compound (0.8 g, 90% purity) as a white solid.

Step 4: 3,5-dimethyl-4-[3-[2-methylsulfanyl-5-(trifluoromethyl)pyrimidin-4-yl]-1-tetrahydropyran-2-yl-pyrazolo-[3,4-b]-pyridin-6-yl]-isoxazole

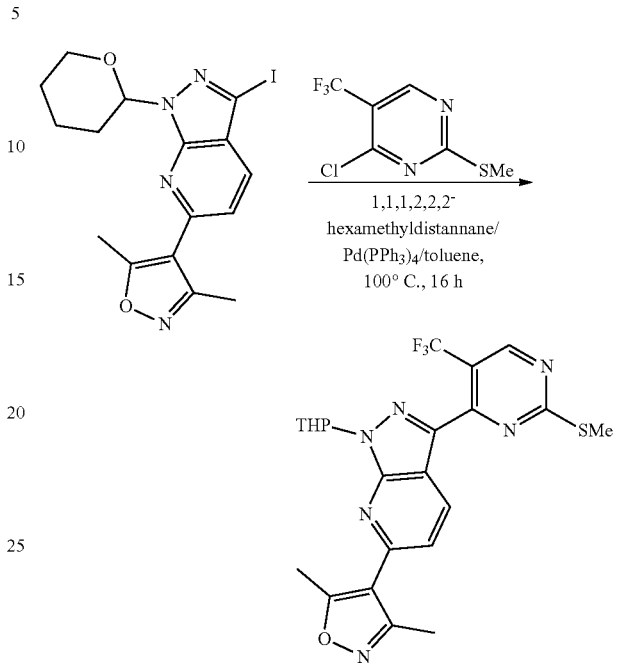

A mixture of 4-(3-iodo-1-tetrahydropyran-2-yl-pyrazolo-[3,4-b]-pyridin-6-yl)-3,5-dimethyl-isoxazole (0.25 g, 589.30 μmol, 1 eq), 4-chloro-2-methylsulfanyl-5-(trifluoromethyl)pyrimidine (134.73 mg, 589.30 μmol, 1 eq), Pd(PPh$_3$)$_4$ (68.10 mg, 58.93 μmol, 0.1 eq), trimethyl (trimethylstannyl) stannane (193.07 mg, 589.30 μmol, 122.20 μL, 1 eq) in Tol. (2 mL) was degassed and purged with N$_2$ for 3 times, and then the mixture was stirred at 100° C. for 16 h under N$_2$ atmosphere. The reaction mixture was poured into aq. KF (50 mL), and then extracted with EtOAc (20 mL×3). The combined organic layers were washed with brine (100 mL), dried over Na$_2$SO$_4$, filtered and concentrated under reduced pressure to give a residue. The residue was purified by column chromatography (SiO$_2$, PE/EtOAc=10/1 to 3/1) to afford the title compound (150 mg, 305.81 μmol, 51.89% yield) as a yellow solid.

Step 5: 3,5-dimethyl-4-[3-[2-methylsulfonyl-5-(trifluoromethyl)pyrimidin-4-yl]-1-tetrahydropyran-2-yl-pyrazolo-[3,4-b]-pyridin-6-yl]-isoxazole

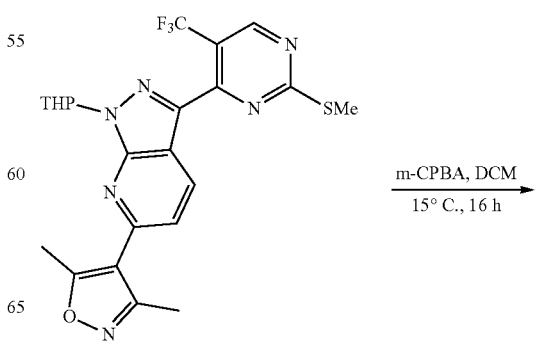

-continued

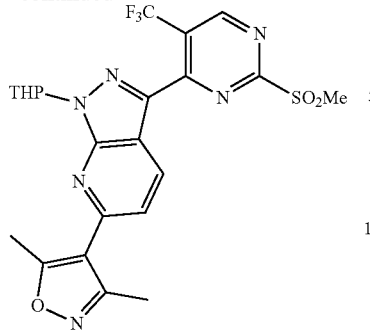

To a solution of 3,5-dimethyl-4-[3-[2-methylsulfanyl-5-(trifluoromethyl)pyrimidin-4-yl]-1-tetrahydropyran-2-yl-pyrazolo-[3,4-b]-pyridin-6-yl]-isoxazole (0.15 g, 305.81 μmol, 1 eq) in DCM (1 mL) was added m-CPBA (155.22 mg, 764.53 μmol, 85% purity, 2.5 eq). The mixture was stirred at 15° C. for 16 h. The reaction mixture was quenched by addition Sat.Na₂SO₃ (5 mL) and NaHCO₃ (5 mL), stirred at this temperature for 10 min and then extracted with DCM (10 mL×2). The combined organic layers were washed with brine (30 mL), dried over Na₂SO₄, filtered and concentrated under reduced pressure to give a residue. The residue was triturated with PE:EtOAc (5:1.5 mL). The solid was filtered and dried to afford the title compound (100 mg, 191.39 μmol, 62.58% yield) as a yellow solid.

Step 6: Tert-butyl (3S)-3-[[4-[6-(3,5-dimethylisoxazol-4-yl)-1-tetrahydropyran-2-yl-pyrazolo-[3,4-b]-pyridin-3-yl]-5-(trifluoromethyl)pyrimidin-2-yl]-amino]-piperidine-1-carboxylate A mixture of 3,5-dimethyl-4-[3-[2-methylsulfonyl-5-(trifluoromethyl)pyrimidin-4-yl]-1-tetrahydropyran-2-yl-pyrazolo-[3,4-b]-pyridin-6-yl]-isoxazole (0.1 g, 191.39 μmol, 1 eq), tert-butyl (3S)-3-aminopiperidine-1-carboxylate (57.50 mg, 287.08 μmol, 1.5 eq), DIEA (74.20 mg, 574.16 μmol, 100.01 μL, 3 eq) in THF (1 mL) was as stirred at 15° C. for 3 h. It was concentrated. The residue was purified by column chromatography (SiO₂, PE/EtOAc=10/1 to 1/1) to afford the title compound (100 mg) as a yellow gum.

Step 7: 4-[6-(3,5-dimethylisoxazol-4-yl)-1H-pyrazolo-[3,4-b]-pyridin-3-yl]-N-[(3S)-3-piperidyl]-5-(trifluoromethyl)pyrimidin-2-amine

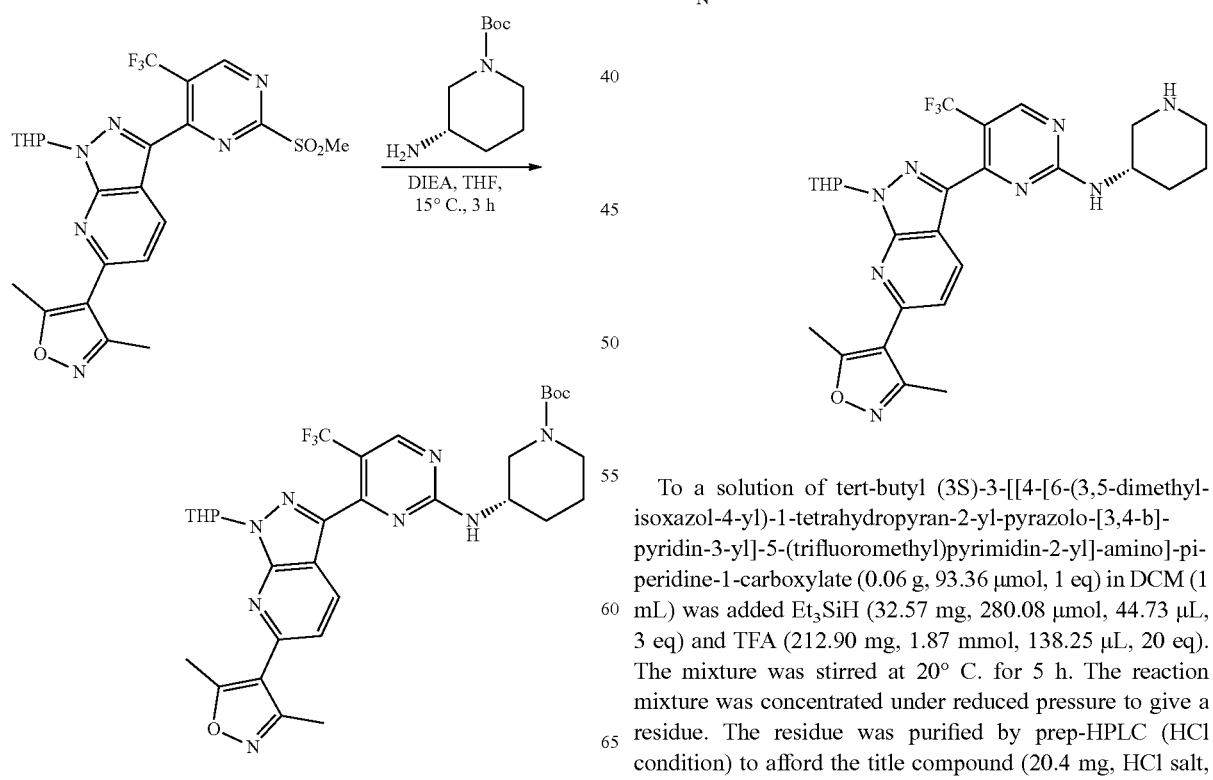

To a solution of tert-butyl (3S)-3-[[4-[6-(3,5-dimethyl-isoxazol-4-yl)-1-tetrahydropyran-2-yl-pyrazolo-[3,4-b]-pyridin-3-yl]-5-(trifluoromethyl)pyrimidin-2-yl]-amino]-piperidine-1-carboxylate (0.06 g, 93.36 μmol, 1 eq) in DCM (1 mL) was added Et₃SiH (32.57 mg, 280.08 μmol, 44.73 μL, 3 eq) and TFA (212.90 mg, 1.87 mmol, 138.25 μL, 20 eq). The mixture was stirred at 20° C. for 5 h. The reaction mixture was concentrated under reduced pressure to give a residue. The residue was purified by prep-HPLC (HCl condition) to afford the title compound (20.4 mg, HCl salt, 100% purity) as a yellow solid.

Example 13. Synthesis of (3R,5S)-5-[[4-[6-(3,5-dimethylisoxazol-4-yl)-1H-pyrrolo[2,3-b]pyridin-3-yl]-5-(trifluoromethyl)pyrimidin-2-yl]amino]-N,N-dimethyl-piperidine-3-carboxamide (Compound 119)

Step 1: O1-tert-butyl-O3-methyl(3R,5S)-5-[[4-[1-(benzenesulfonyl)-6-(3,5-dimethylisoxazol-4-yl)-pyrrolo[2,3-b]pyridin-3-yl]-5-(trifluoromethyl)pyrimidin-2-yl]amino]piperidine-1,3-dicarboxylate

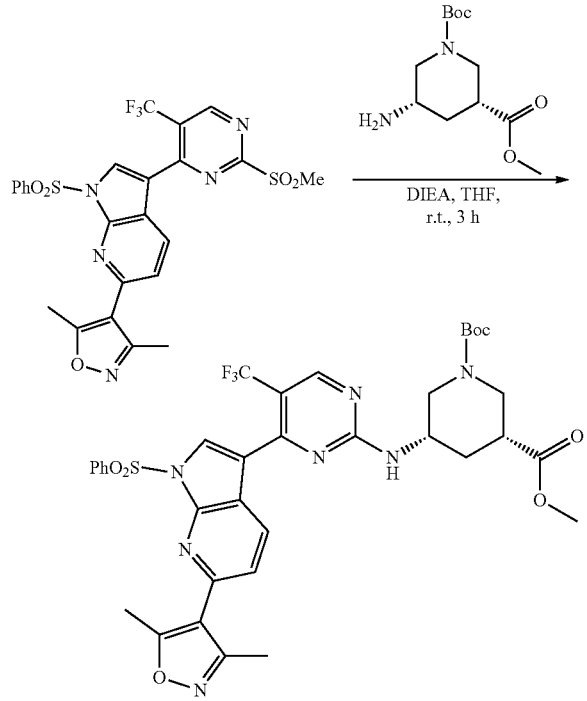

To a solution of 4-[1-(benzenesulfonyl)-3-[2-methylsulfonyl-5-(trifluoromethyl)pyrimidin-4-yl]-pyrrolo[2,3-b]pyridin-6-yl]-3,5-dimethyl-isoxazole (Example 11; 260 mg, 450.17 µmol, 1 eq) in THF (5 mL) was added DIPEA (290.91 mg, 2.25 mmol, 392.06 µL, 5 eq) and O1-tert-butyl O3-methyl (3R,5S)-5-aminopiperidine-1,3-dicarboxylate (174.43 mg, 675.26 µmol, 1.5 eq). The mixture was stirred at 15° C. for 1 h. The reaction mixture was diluted with H₂O (15 mL), and then extracted with EtOAc (15 mL×3). The combined organic layers were washed with brine (40 mL), dried over Na₂SO₄, filtered and concentrated under reduced pressure to give a residue. The residue was purified by column chromatography (SiO₂, PE/EtOAc=10:1 to 1:1) to afford the title compound (240 mg) as a yellow solid.

Step 2: (3R,5S)-1-tert-butoxycarbonyl-5-[[4-[6-(3,5-dimethylisoxazol-4-yl)-1H-pyrrolo[2,3-b]pyridin-3-yl]-5-(trifluoromethyl)pyrimidin-2-yl]amino]piperidine-3-carboxylic acid

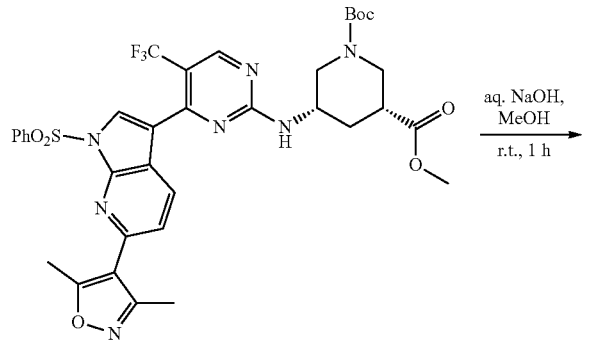

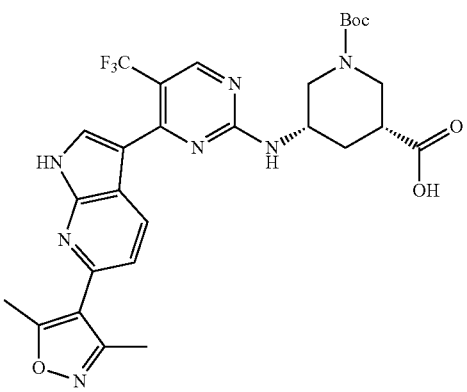

To a solution of O1-tert-butyl-O3-methyl(3R,5S)-5-[[4-[1-(benzenesulfonyl)-6-(3,5-dimethylisoxazol-4-yl)-pyrrolo[2,3-b]pyridin-3-yl]-5-(trifluoromethyl)pyrimidin-2-yl]amino]piperidine-1,3-dicarboxylate (220 mg, 291.10 µmol, 1 eq) in MeOH (2 mL) was added NaOH (2 M, 2.00 mL, 13.74 eq). The mixture was stirred at 15° C. for 1 h. The reaction mixture was concentrated under reduced pressure to remove MeOH. The residue was diluted with H₂O (15 mL) and acidified by 2N HCl to pH=2 and extracted with EtOAc (15 mL×3). The combined organic layers were washed with brine (30 mL), dried over Na₂SO₄, filtered and concentrated under reduced pressure to afford the title compound (140 mg) as a yellow solid.

Step 3: tert-butyl(3R,5S)-3-(dimethylcarbamoyl)-5-[[4-[6-(3,5-dimethylisoxazol-4-yl)-1H-pyrrolo[2,3-b]pyridin-3-yl]-5-(trifluoromethyl)pyrimidin-2-yl]amino]piperidine-1-carboxylate

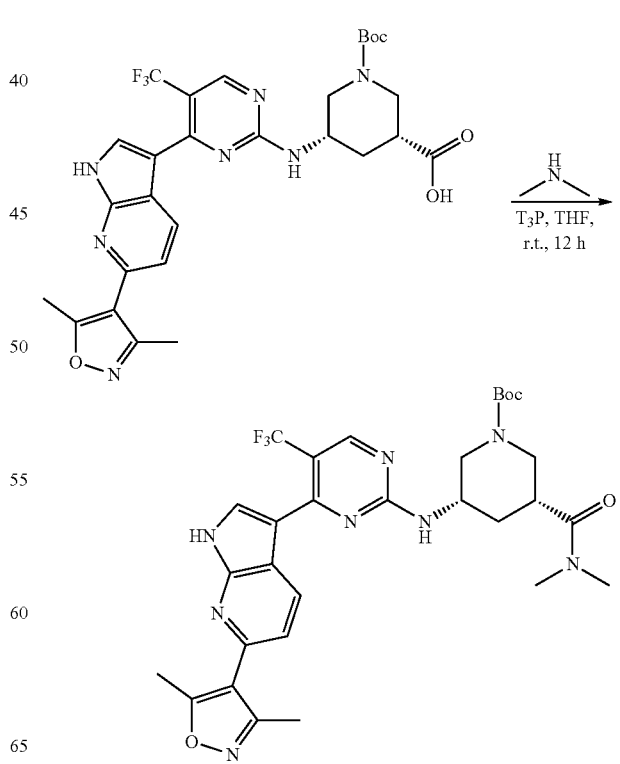

To a solution of (3R,5S)-1-tert-butoxycarbonyl-5-[[4-[6-(3,5-dimethylisoxazol-4-yl)-1H-pyrrolo[2,3-b]pyridin-3-yl]-5-(trifluoromethyl)pyrimidin-2-yl]amino]piperidine-3-carboxylic acid (60 mg, 99.74 μmol, 1 eq) in THF (1 mL) was added T₃P (190.41 mg, 299.21 μmol, 177.95 μL, 50% purity, 3 eq), DIPEA (64.45 mg, 498.69 μmol, 86.86 μL, 5 eq) and N-methylmethanamine (2 M, 249.35 μL, 5 eq). The mixture was stirred at 15° C. for 12 h. The reaction mixture was diluted with H₂O (15 mL), and then extracted with EtOAc (15 mL×3). The combined organic layers were washed with brine (40 mL), dried over Na₂SO₄, filtered and concentrated under reduced pressure to afford the title compound (50 mg) as yellow solid.

Step 4: (3R,5S)-5-[[4-[6-(3,5-dimethylisoxazol-4-yl)-1H-pyrrolo[2,3-b]pyridin-3-yl]-5-(trifluoromethyl)pyrimidin-2-yl]amino]-N,N-dimethyl-piperidine-3-carboxamide

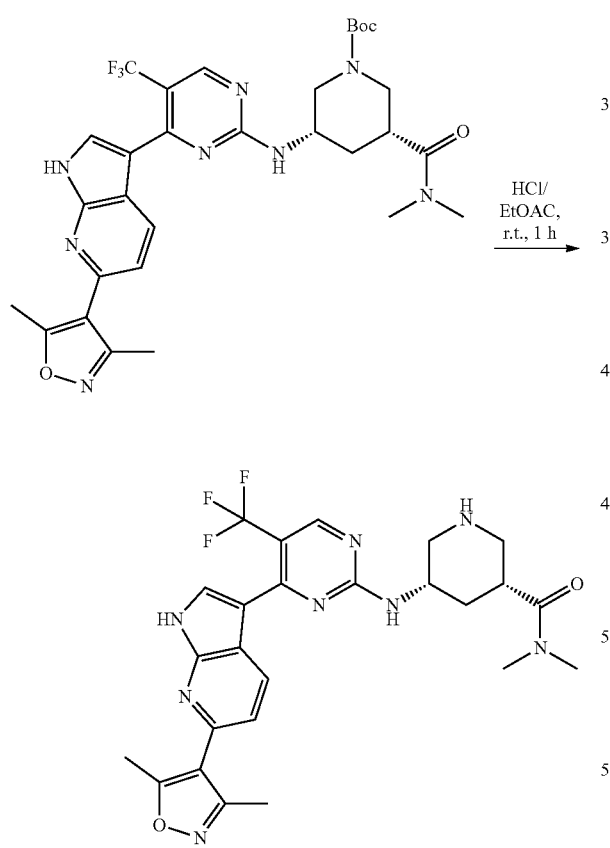

To a solution of tert-butyl(3R,5S)-3-(dimethylcarbamoyl)-5-[[4-[6-(3,5-dimethylisoxazol-4-yl)-1H-pyrrolo[2,3-b]pyridin-3-yl]-5-(trifluoromethyl)pyrimidin-2-yl]amino]piperidine-1-carboxylate (40 mg, 63.63 μmol, 1 eq) was added HCl/EtOAc (4 M, 2 mL). The mixture was stirred at 15° C. for 1 h. The reaction mixture was concentrated under reduced pressure to give a residue. The residue was purified by prep-HPLC to afford the title compound (13.4 mg, FA) as white solid.

Example 14. Synthesis of Tert-butyl (3S,5R)-3-[[4-[6-(3,5-dimethylisoxazol-4-yl)-1H-pyrrolo[2,3-b]pyridin-3-yl]-5-(trifluoromethyl)pyrimidin-2-yl]amino]-5-(methylcarbamoyl)piperidine-1-carboxylate Useful in the Synthesis of Compound 120

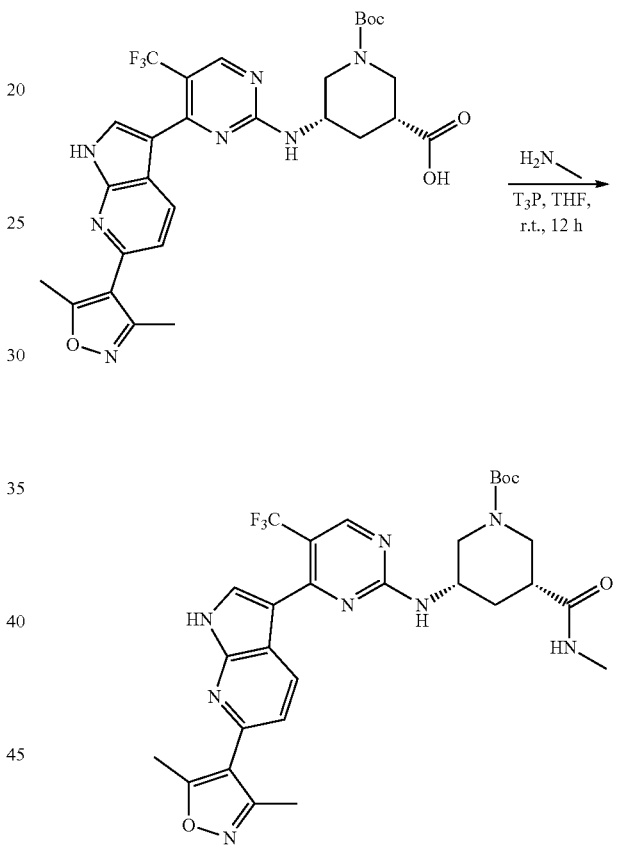

To a solution of (3R,5S)-1-tert-butoxycarbonyl-5-[[4-[6-(3,5-dimethylisoxazol-4-yl)-1H-pyrrolo[2,3-b]pyridin-3-yl]-5-(trifluoromethyl)pyrimidin-2-yl]amino]piperidine-3-carboxylic acid (60 mg, 99.74 μmol, 1 eq) in THF (1 mL) was added T₃P (190.41 mg, 299.21 μmol, 177.95 μL, 50% purity, 3 eq), DIPEA (64.45 mg, 498.69 μmol, 86.86 μL, 5 eq) and methanamine (2M, 249.35 μL, 5 eq). The mixture was stirred at 15° C. for 12 h. The reaction mixture was diluted with H₂O (10 mL) and extracted with EtOAc (10 mL×3). The combined organic layers were washed with brine (20 mL), dried over Na₂SO₄, filtered and concentrated under reduced pressure to give a residue. The residue was purified by column chromatography (SiO₂, Petroleum ether/Ethyl acetate=1:1 to 1:20) to afford the title compound (50 mg) as white solid.

Example 15. Synthesis of (3R,5S)-5-[[4-[6-(3,5-dimethylisoxazol-4-yl)-1H-indol-3-yl]-5-(trifluoromethyl)pyrimidin-2-yl]-amino]-N, N-dimethyl-piperidine-3-carboxamide (Compound 112)

Step 1: 2-[[6-bromo-3-[2-chloro-5-(trifluoromethyl)pyrimidin-4-yl]-indol-1-yl]-methoxy]-ethyl-trimethyl-silane

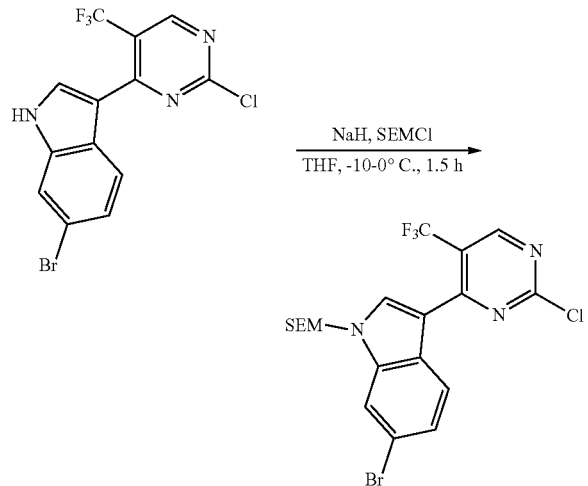

To a solution of 6-bromo-3-[2-chloro-5-(trifluoromethyl)pyrimidin-4-yl]-1H-indole (Example 19, step 1; 2 g, 5.31 mmol, 1 eq) in THF (20 mL) was added NaH (254.94 mg, 6.37 mmol, 60% purity, 1.2 eq) at −10° C. After addition, the mixture was stirred at this temperature for 30 min, and then 2-(chloromethoxy) ethyl-trimethyl-silane (1.33 g, 7.97 mmol, 1.41 mL, 1.5 eq) was added dropwise at −10° C. The resulting mixture was stirred at 0° C. for 1 h. The reaction mixture was diluted with water (150 mL) and extracted with ethyl acetate (80 mL×2). The combined organic layers were washed with brine (200 mL×2), dried over Na$_2$SO$_4$, filtered and concentrated under reduced pressure to give a residue. The residue was purified by column chromatography (SiO$_2$, Petroleum ether/Ethyl acetate=50:1 to 20:1) to afford the title compound (2.6 g) as a white solid.

Step 2: O1-tert-butyl-O3-methyl-(3R,5S)-5-[[4-[6-bromo-1-(2-trimethylsilylethoxymethyl) indol-3-yl]-5-(trifluoromethyl)pyrimidin-2-yl]-amino]-piperidine-1,3-dicarboxylate

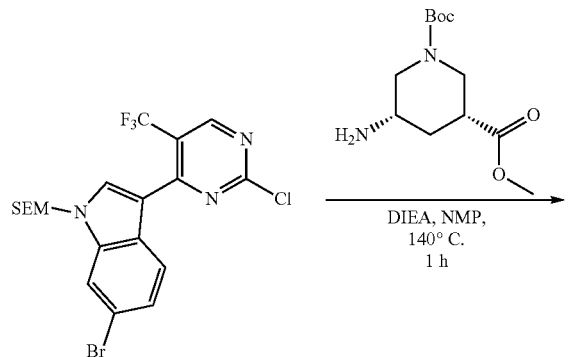

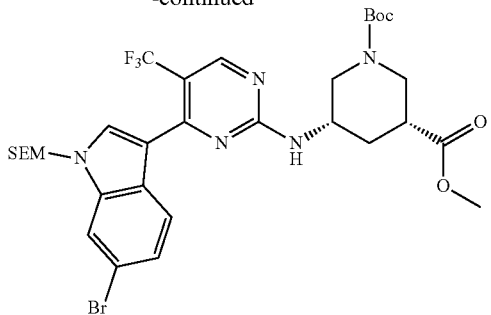

A mixture of 2-[[6-bromo-3-[2-chloro-5-(trifluoromethyl)pyrimidin-4-yl]-indol-1-yl]-methoxy]-ethyl-trimethyl-silane (1.46 g, 2.87 mmol, 1 eq), O1-tert-butyl-O3-methyl-(3R,5S)-5-aminopiperidine-1,3-dicarboxylate (0.89 g, 3.45 mmol, 1.2 eq) and DIEA (1.11 g, 8.61 mmol, 1.50 mL, 3 eq) in NMP (15 mL) was stirred at 140° C. for 1 h. The reaction mixture was diluted with water (100 mL) and extracted with EtOAc (50 mL×2). The combined organic layers were washed with brine (100 mL×2), dried over Na$_2$SO$_4$, filtered and concentrated under reduced pressure to give a residue. The residue was purified by column chromatography (SiO2, PE/EtOAc=30:1 to 5:1) to afford the title compound (1.68 g, 2.21 mmol, 77.09% yield, 96% purity) as a white solid.

Step 3: O1-tert-butyl-O3-methyl-(3R,5S)-5-[[4-[6-(3,5-dimethylisoxazol-4-yl)-1-(2-trimethylsilylethoxymethyl)indol-3-yl]-5-(trifluoromethyl)pyrimidin-2-yl]-amino]-piperidine-1,3-dicarboxylate

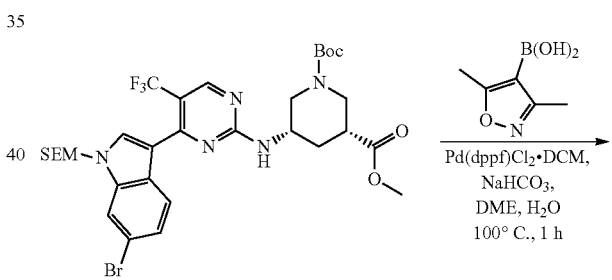

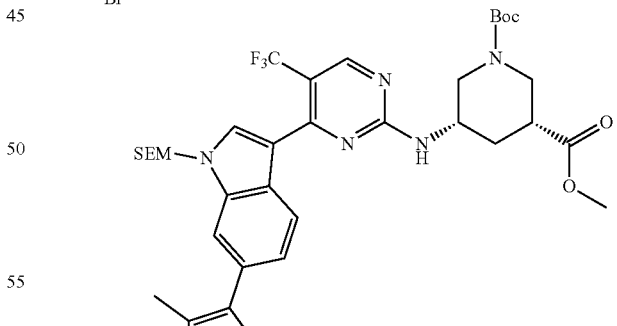

A mixture of O1-tert-butyl-O3-methyl-(3R,5S)-5-[[4-[6-bromo-1-(2-trimethylsilylethoxymethyl)indol-3-yl]-5-(trifluoromethyl)pyrimidin-2-yl]-amino]-piperidine-1,3-dicarboxylate (0.7 g, 960.65 μmol, 1 eq), (3,5-dimethylisoxazol-4-yl)boronic acid (270.77 mg, 1.92 mmol, 2 eq), Pd(dppf)Cl$_2$·CH$_2$Cl$_2$ (78.45 mg, 96.07 μmol, 0.1 eq) and NaHCO$_3$ (242.11 mg, 2.88 mmol, 112.09 μL, 3 eq) in DME (9 mL), H₂O (3 mL) was degassed and purged with N₂ for 3 times, and then the mixture was stirred at 100° C. for 1 h under N₂ atmosphere. The reaction mixture was diluted with water (100 mL) and extracted with EtOAc (50 mL×2). The combined organic layers were washed with brine (100 mL×2), dried over Na₂SO₄, filtered and concentrated under reduced pressure to give a residue. The residue was purified by column chromatography (SiO₂, PE/EtOAc=10:1 to 5:1) to afford the title compound (600 mg) as a yellow solid.

Step 4: (3R,5S)-1-tert-butoxycarbonyl-5-[[4-[6-(3,5-dimethylisoxazol-4-yl]-1-(2-trimethylsilylethoxymethyl) indol-3-yl]-5-(trifluoromethyl)pyrimidin-2-yl]-amino]-piperidine-3-carboxylic Acid

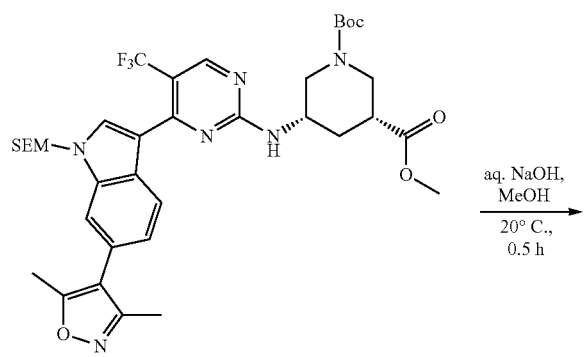

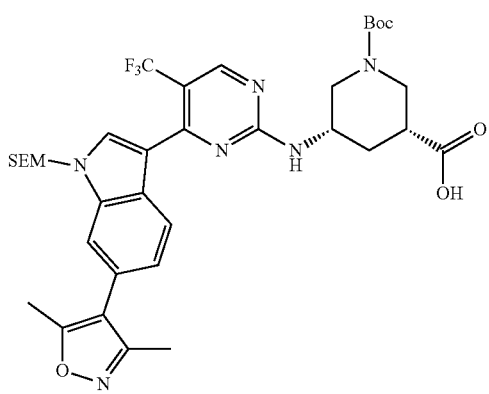

To a solution of O1-tert-butyl-O3-methyl-(3R,5S)-5-[[4-[6-(3,5-dimethylisoxazol-4-yl)-1-(2-trimethylsilylethoxymethyl)indol-3-yl]-5-(trifluoromethyl)pyrimidin-2-yl]-amino]-piperidine-1,3-dicarboxylate (550 mg, 738.38 μmol, 1 eq) in MeOH (6 mL) was added NaOH (2 M, 3.69 mL, 10 eq). The mixture was stirred at 20° C. for 0.5 h. The reaction mixture was adjusted pH to 4 with aqueous HCl (0.5 M, 80 mL) and extracted with EtOAc (30 mL×3). The combined organic layers were washed with brine (90 mL×2), dried over Na₂SO₄, filtered and concentrated under reduced pressure to give a residue to afford the title compound (600 mg, crude) was used into the next step without further purification.

Step 5: Tert-butyl (3R,5S)-3-(dimethylcarbamoyl)-5-[[4-[6-(3,5-dimethylisoxazol-4-yl)-1-(2-trimethyl-silylethoxymethyl) indol-3-yl]-5-(trifluoromethyl) pyrimidin-2-ylamino]-piperidine-1-carboxylate

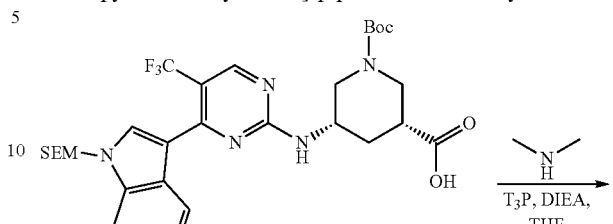

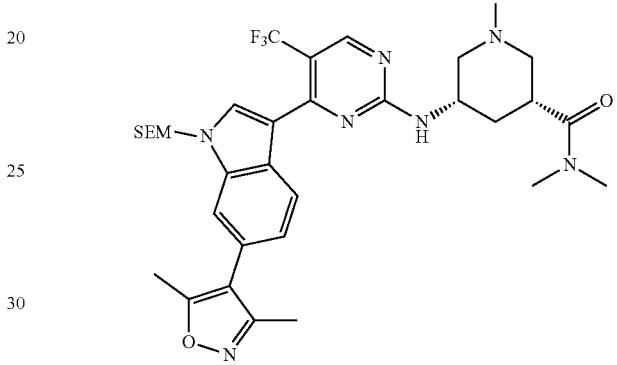

To a solution of (3R,5S)-1-tert-butoxycarbonyl-5-[[4-[6-(3,5-dimethylisoxazol-4-yl)-1-(2-trimethylsilylethoxymethyl) indol-3-yl]-5-(trifluoromethyl)pyrimidin-2-yl]-amino]-piperidine-3-carboxylic acid (0.2 g, 273.65 μmol, 1 eq) in THF (2 mL) was added T₃P (1.74 g, 2.74 mmol, 1.63 mL, 50% purity, 10 eq) and DIEA (530.51 mg, 4.10 mmol, 714.97 μL, 15 eq), N-methylmethanamine (2 M, 2.74 mL, 20 eq). The mixture was stirred at 20° C. for 1 h. The reaction mixture was diluted with water (100 mL) and extracted with EtOAc (50 mL×2). The combined organic layers were washed with brine (100 mL×2), dried over Na₂SO₄, filtered and concentrated under reduced pressure to give a residue. The residue was purified by column chromatography (SiO₂, PE/EtOAc=5:1 to 1:1) to afford the title compound (200 mg) as a colorless oil.

Step 6: (3R,5S)-5-[[4-[6-(3,5-dimethylisoxazol-4-yl)-1H-indol-3-yl]-5-(trifluoromethyl)pyrimidin-2-yl]-amino]-N, N-dimethyl-piperidine-3-carboxamide

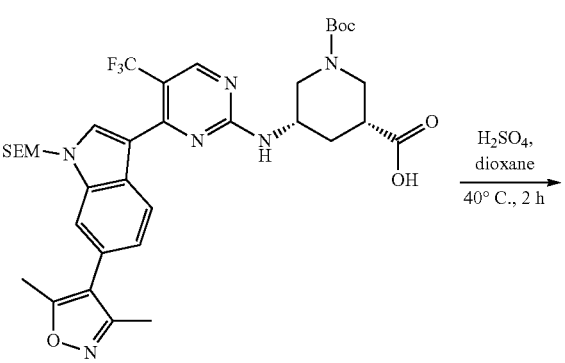

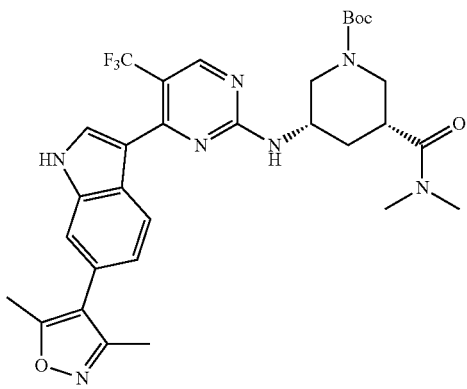

To a solution of tert-butyl (3R,5S)-3-(dimethylcarbamoyl)-5-[[4-[6-(3,5-dimethylisoxazol-4-yl)-1-(2-trimethylsilylethoxymethyl) indol-3-yl]-5-(trifluoromethyl)pyrimidin-2-yl]-amino]-piperidine-1-carboxylate (0.18 g, 237.49 μmol, 1 eq) in dioxane (2 mL) was added H$_2$SO$_4$ (232.93 mg, 2.37 mmol, 126.59 μL, 10 eq). The mixture was stirred at 40° C. for 2 h. The mixture was adjusted pH to 8 with saturated aqueous K$_2$CO$_3$ and extracted with EtOAc (20 mL×3). The combined organic layers were washed with brine (30 mL×2), dried over Na$_2$SO$_4$, filtered and concentrated under reduced pressure to give a residue. The residue was purified by prep-HPLC (HCl condition) to afford the title compound (28.6 mg, HCl salt) as a yellow solid.

Example 16. Synthesis of Tert-butyl (3S,5R)-3-[[4-[6-(3,5-dimethylisoxazol-4-yl)-1-(2-trimethylsilylethoxymethyl) indol-3-yl]-5-(trifluoromethyl)pyrimidin-2-yl]-amino]-5-(methylcarbamoyl) piperidine-1-carboxylate Useful in the Synthesis of Compound 113

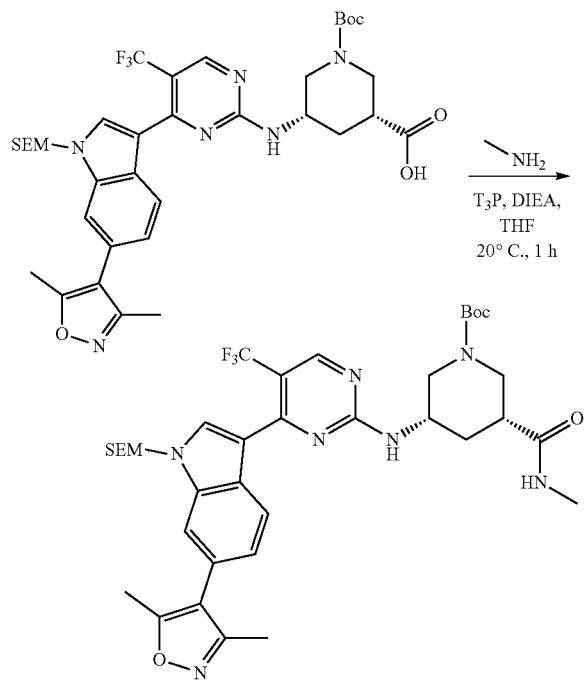

To a solution of (3R,5S)-1-tert-butoxycarbonyl-5-[[4-[6-(3,5-dimethylisoxazol-4-yl)-1-(2-trimethylsilylethoxymethyl) indol-3-yl]-5-(trifluoromethyl)pyrimidin-2-yl]-amino]-piperidine-3-carboxylic acid (0.2 g, 273.65 μmol, 1 eq) in THF (5 mL) was added T$_3$P (1.74 g, 2.74 mmol, 1.63 mL, 50% purity, 10 eq) and DIEA (530.51 mg, 4.10 mmol, 714.97 μL, 15 eq), methanamine (2 M, 2.74 mL, 20 eq). The mixture was stirred at 20° C. for 1 h. The reaction mixture was diluted with water (100 mL) and extracted with ethyl acetate (50 mL×2). The combined organic layers were washed with brine (100 mL×2), dried over Na$_2$SO$_4$, filtered and concentrated under reduced pressure to give a residue. The residue was purified by column chromatography (SiO$_2$, Petroleum ether/Ethyl acetate=5:1 to 1:1) to afford the title compound (200 mg) as a white solid.

Example 17. Synthesis of Tert-butyl(5S)-3,3-dimethyl-5-[[4-[6-thiazol-2-yl-1-(2-trimethylsilylethoxymethyl)indol-3-yl]-5-(trifluoromethyl)pyrimidin-2-yl]amino]piperidine-1-carboxylate Useful in the Synthesis of Compound 109

Step 1: N-[(3S)-1-benzyl-5,5-dimethyl-3-piperidyl]-4-[6-bromo-1-(2-trimethylsilylethoxy methyl)indol-3-yl]-5-(trifluoromethyl)pyrimidin-2-amine

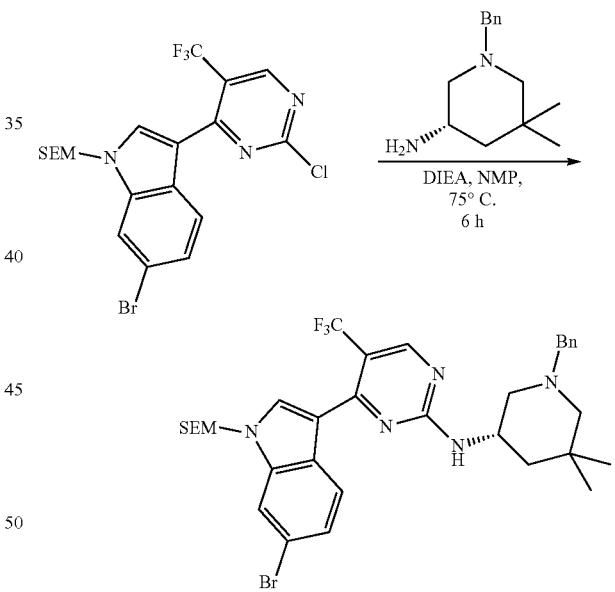

A mixture of 2-[[6-bromo-3-[2-chloro-5-(trifluoromethyl)pyrimidin-4-yl]indol-1-yl]methoxy ethyl-trimethyl-silane (270 mg, 532.74 μmol, 1 eq), (3S)-1-benzyl-5,5-dimethyl-piperidin-3-amine (135.74 mg, 532.74 μmol, 1 eq, HCl) and DIEA (344.26 mg, 2.66 mmol, 463.96 μL, 5 eq) in NMP (2.7 mL) was heated to 75° C. and stirred for 6 h. The mixture was poured into water 20 mL, and extracted with EtOAc (20 mL×3). The combined organic layer was washed with brine (50 mL), dried over Na$_2$SO$_4$, filtered. The filtrate was concentrated under reduced pressure to give a residue. The residue was purified by MPLC (SiO$_2$, PE/EtOAc=10/1 to 1:1) to afford the title compound (230 mg, 91.5% purity) as yellow oil.

Step 2 N-[(3S)-1-benzyl-5,5-dimethyl-3-piperidyl]-4-[6-thiazol-2-yl-1-(2-trimethylsilylethoxymethyl)indol-3-yl]-5-(trifluoromethyl)pyrimidin-2-amine

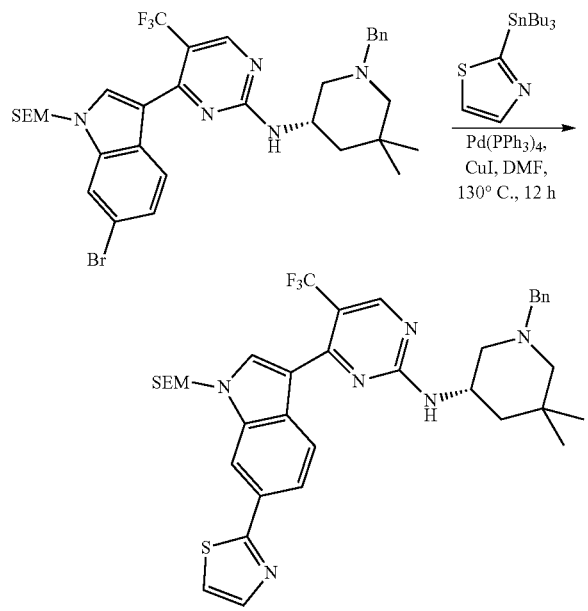

To a mixture of N-[(3S)-1-benzyl-5,5-dimethyl-3-piperidyl]-4-[6-bromo-1-(2-trimethylsilylethoxymethyl)indol-3-yl]-5-(trifluoromethyl)pyrimidin-2-amine (200 mg, 290.40 µmol, 1 eq) in DMF (0.5 mL) was added tributyl (thiazol-2-yl)stannane (325.98 mg, 871.21 µmol, 3 eq), CuI (5.53 mg, 29.04 µmol, 0.1 eq) and Pd(PPh₃)₄ (33.56 mg, 29.04 µmol, 0.1 eq). The mixture was heated to 130° C. and stirred for 12 h under N₂. Saturated KF solution (20 mL) was added and the reaction mixture was stirred for about 1 hr. Then the reaction mixture was extracted by EtOAc (20 mL×3). The organic layer was combined, washed by brine (100 mL), dried over Na₂SO₄, filtered and evaporated to afford the residue. The residue was purified by MPLC (SiO₂, PE/EtOAc=10/1 to 1:1) to afford the title compound (125 mg, 85.2% purity) as yellow solid.

Step 3: tert-butyl(5S)-3,3-dimethyl-5-[[4-[6-thiazol-2-yl-1-(2-trimethylsilylethoxymethyl)indol-3-yl]-5-(trifluoromethyl)pyrimidin-2-yl]amino]piperidine-1-carboxylate

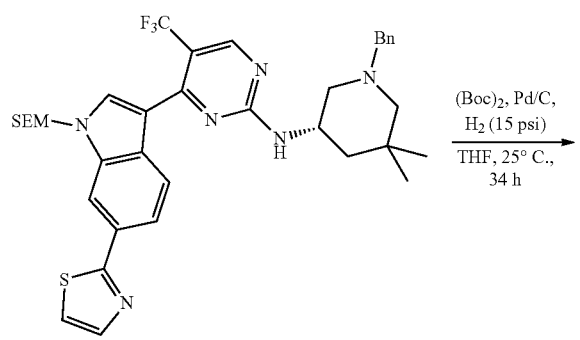

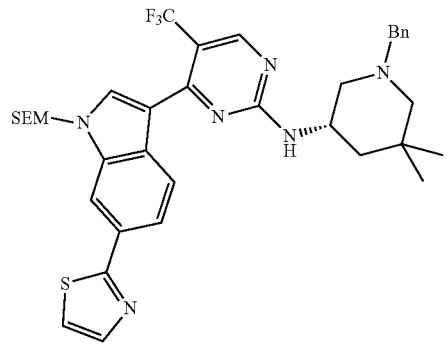

To a mixture of N-[(3S)-1-benzyl-5,5-dimethyl-3-piperidyl]-4-[6-thiazol-2-yl-1-(2-trimethylsilylethoxymethyl)indol-3-yl]-5-(trifluoromethyl)pyrimidin-2-amine (95 mg, 137.10 µmol, 1 eq) and Boc₂O (di-t-butyl dicarbonate; 149.61 mg, 685.51 µmol, 157.49 µL, 5 eq) in THF (1 mL) was added Pd/C (15 mg, 10% purity) under N₂. The suspension was degassed under vacuum and purged with H₂ several times. The mixture was stirred for 34 h at 25° C. under H₂ (15 psi). The mixture was filtered, and the filtrate was concentrated to afford the title compound (200 mg, crude, 73.4% purity) as brown oil.

Example 18. Synthesis of (3R,5S)-5-[[4-[6-(3,5-dimethylisoxazol-4-yl)-1H-indol-3-yl]-5-(trifluoromethyl)pyrimidin-2-yl]amino]piperidin-3-ol (Compound 105)

Step 1: tert-butyl N-[(3S,5R)-1-benzyl-5-hydroxy-3-piperidyl]carbamate

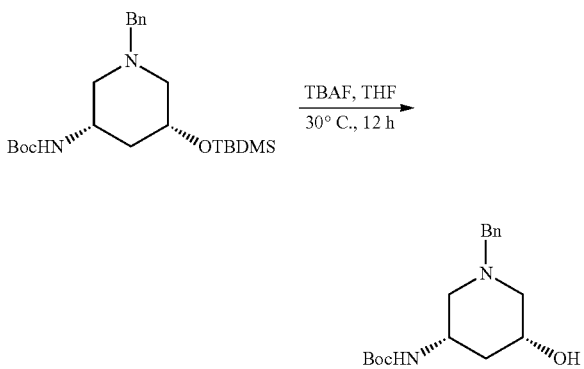

To a solution of tert-butyl N-[(3S,5R)-1-benzyl-5-[tert-butyl(dimethyl)silyl]oxy-3-piperidyl]carbamate (8.6 g, 20.44 mmol, 1 eq) in THF (50 mL) was added TBAF (1 M, 22.49 mL, 1.1 eq). The reaction mixture was stirred at 30° C. for 12 h. The reaction mixture was evaporated to afford a residue. The residue was purified by column chromatography (SiO₂, PE/EtOAc=3/1) to afford the title compound (5.4 g, 17.45 mmol, 85.34% yield, 99% purity) as white solid.

Step 2: (3R,5S)-5-amino-1-benzyl-piperidin-3-ol

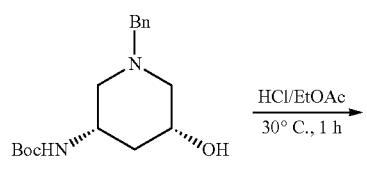

Tert-butyl N-[(3S,5R)-1-benzyl-5-hydroxy-3-piperidyl]carbamate (5.4 g, 17.62 mmol, 1 eq) dissolved in HCl/EtOAc (25 mL) was stirred at 30° C. for 1 h under $N_2$ atmosphere. The reaction mixture was evaporated to afford the product to afford the title compound (4.2 g, 16.61 mmol, 94.25% yield, 96% purity, HCl salt) as pink solid. It will be used directly in next step.

Step 3: (3R,5S)-1-benzyl-5-[[4-(6-bromo-1H-indol-3-yl)-5-(trifluoromethyl)pyrimidin-2-yl]amino]piperidin-3-ol

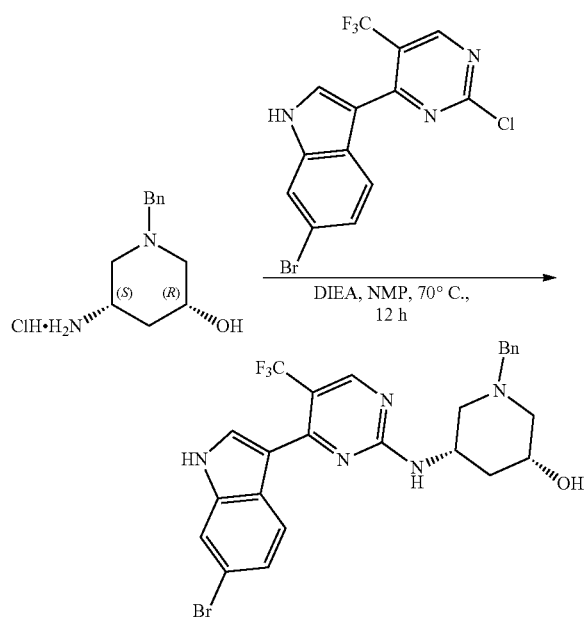

A flask was fitted with 6-bromo-3-[2-chloro-5-(trifluoromethyl)pyrimidin-4-yl]-1H-indole (Example 19; 500 mg, 1.33 mmol, 1 eq), (3R,5S)-5-amino-1-benzyl-piperidin-3-ol (322.32 mg, 1.33 mmol, 1 eq, HCl) and DIPEA (858.05 mg, 6.64 mmol, 1.16 mL, 5 eq) in NMP (1 mL). The reaction mixture was heated to 70° C. for 12 h. The combined mixture was poured into $H_2O$ (50 mL). EtOAc (40 mL×3) was used to extract the product. The organic layer was washed by brine (30 mL), dried over $Na_2SO_4$, filtered and evaporated to afford the crude product. The crude product was purified by MPLC ($SiO_2$, PE/EtOAc=3/1-1/1) to afford the title compound (1 g, 32.6% purity) as light yellow oil.

Step 4: (3R,5S)-1-benzyl-5-[[4-[6-(3,5-dimethyl-isoxazol-4-yl)-1H-indol-3-yl]-5-(trifluoromethyl)pyrimidin-2-yl]amino]piperidin-3-ol

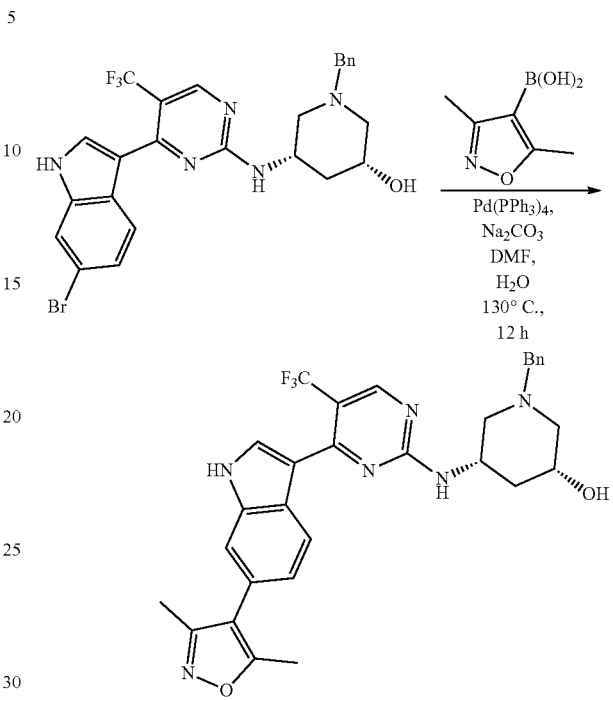

(3R,5S)-1-benzyl-5-[[4-(6-bromo-1H-indol-3-yl)-5-(trifluoromethyl)pyrimidin-2-yl]amino]piperidin-3-ol (700 mg, 1.28 mmol, 1 eq), (3,5-dimethylisoxazol-4-yl)boronic acid (361.11 mg, 2.56 mmol, 2 eq), $Pd(PPh_3)_4$ (296.09 mg, 256.23 μmol, 0.2 eq) and $Na_2CO_3$ (271.58 mg, 2.56 mmol, 2 eq) in DMF (10 mL) and $H_2O$ (2 mL) was de-gassed and then heated to 130° C. for 12 h under $N_2$. The combined reaction mixture was poured into $H_2O$ (40 mL). EtOAc (40 mL×3) was used to extract the product. The organic layer was washed by brine (30 mL), dried over $Na_2SO_4$, filtered and evaporated to afford the crude product. The crude product was purified by MPLC ($SiO_2$, PE/EtOAc=1/1) to afford the title compound (460 mg, 44.2% purity) as yellow solid. It contains some TPPO.

Step 5: tert-butyl (3S,5R)-3-[[4-[6-(3,5-dimethyl-isoxazol-4-yl)-1H-indol-3-yl]-5-(trifluoromethyl)pyrimidin-2-yl]amino]-5-hydroxypiperidine-carboxylate

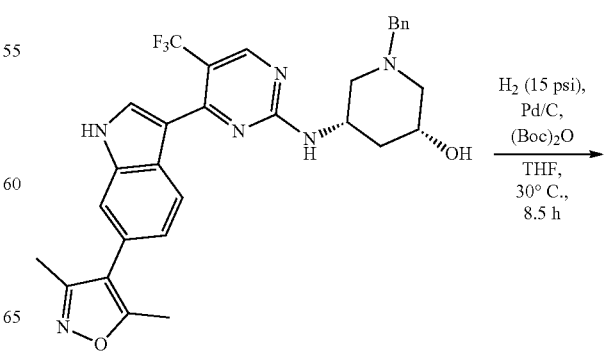

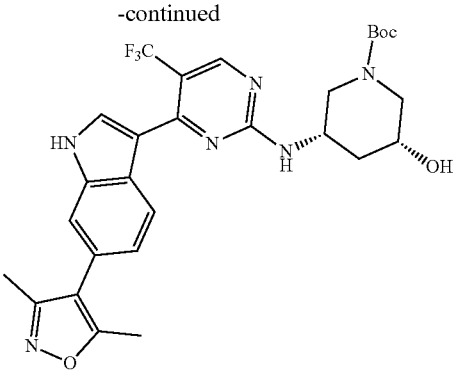

To a solution of (3R,5S)-1-benzyl-5-[[4-[6-(3,5-dimethylisoxazol-4-yl)-1H-indol-3-yl]-5-(trifluoromethyl)pyrimidin-2-yl]amino]piperidin-3-ol (360 mg, 639.90 μmol, 1 eq) and Boc$_2$O (279.31 mg, 1.28 mmol, 294.01 μL, 2 eq) in THF (10 mL) was added Pd/C (120 mg, 10% purity) under N$_2$. The suspension was degassed under vacuum and purged with H$_2$ several times. The mixture was stirred under H$_2$ (15 psi) at 30° C. for 8.5 h. The reaction mixture was filtered through celite and the cake was washed by THF (15 mL). The filtrate was evaporated to afford the title compound (400 mg, crude) as yellow oil. It contains some TPPO and was used directly in next step without any further purification.

Step 6: (3R,5S)-5-[[4-[6-(3,5-dimethylisoxazol-4-yl)-1H-indol-3-yl]-5-(trifluoromethyl)pyrimidin-2-yl]amino]piperidin-3-ol A mixture of tert-butyl (3S,5R)-3-[[4-[6-(3,5-dimethylisoxazol-4-yl)-1H-indol-3-yl]-5-(trifluoromethyl)pyrimidin-2-yl]amino]-5-hydroxy-piperidine-1-carboxylate (400 mg, 698.60 μmol, 1 eq) in HCl/EtOAc (15 mL) was stirred at 30° C. for 1 h. The reaction mixture was evaporated to afford a residue. Then H$_2$O (10 mL) was added to the mixture and PE/EtOAc (10/1, 15 mL×3) was used to extract undesired TPPO. The aqueous was evaporated to afford the crude product. The combined crude product was purified by acidic prep-HPLC (HCl condition). The separated solution was lyophilized after removing MeCN to afford the title compound (53.3 mg, 99.7% purity, HCl salt) as yellow solid.

Example 19. Synthesis of N-[(3S)-1-benzyl-5,5-dimethyl-3-piperidyl]-4-(6-bromo-1H-indol-3-yl)-5-(trifluoromethyl)pyrimidin-2-amine Useful in the Synthesis of Compound 102)

Step 1: 6-bromo-3-[2-chloro-5-(trifluoromethyl)pyrimidin-4-yl]-1H-indole

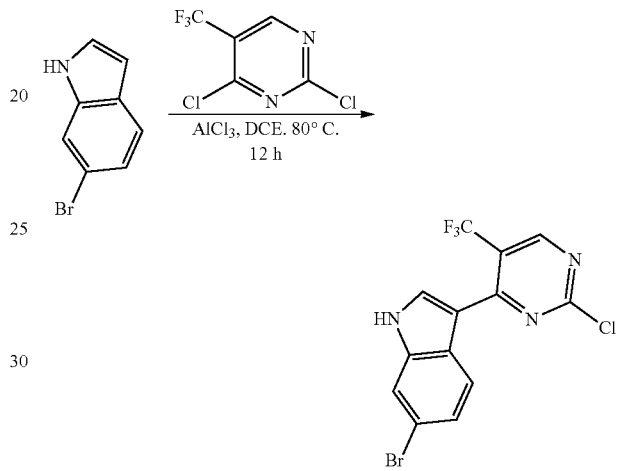

To a solution of 2,4-dichloro-5-(trifluoromethyl)pyrimidine (22.58 g, 104.06 mmol, 1.2 eq) in DCE (1,2-dichloroethane; 200 mL) was added AlCl$_3$ (15.03 g, 112.73 mmol, 6.16 mL, 1.3 eq). The mixture was stirred at 80° C. for 0.5 h. Then 6-bromo-1H-indole (17 g, 86.72 mmol, 1 eq) was added to the solution at 80° C. The mixture was stirred at 80° C. for 11.5 h. The reaction mixture was diluted with water (1500 mL) and extracted with EtOAc (500 mL×3). The combined organic layers were washed with brine (200 mL×3), dried over Na$_2$SO$_4$, filtered and concentrated under reduced pressure to give a residue. The residue was purified by column chromatography (SiO$_2$, PE/EtOAc=10/1 to 3/1), then the residue was washed with MeOH (200 mL), filtered to afford the title compound (9.9 g, 26.29 mmol, 30.32% yield, 100% purity) as white solid.

Step 2: N-[(3S)-1-benzyl-5,5-dimethyl-3-piperidyl]-4-(6-bromo-1H-indol-3-yl)-5-(trifluoromethyl)pyrimidin-2-amine

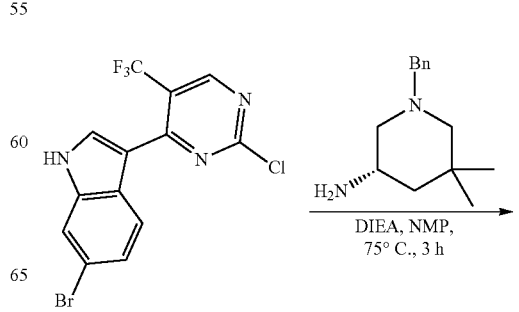

-continued

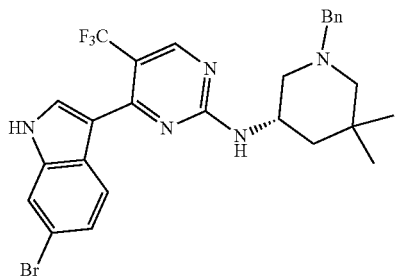

A mixture of (3S)-1-benzyl-5,5-dimethyl-piperidin-3-amine (676.65 mg, 2.66 mmol, 1 eq, HCl), 6-bromo-3-[2-chloro-5-(trifluoromethyl)pyrimidin-4-yl]-1H-indole (1 g, 2.66 mmol, 1 eq) and DIEA (1.72 g, 13.28 mmol, 2.31 mL, 5 eq) in NMP (3 mL) was heated to 75° C. and stirred for 3 h under N₂. The mixture was poured into water 20 mL, and extracted with EtOAc (20 mL×3). The combined organic layer was washed with brine (50 mL), dried over Na₂SO₄, filtered. The filtrate was concentrated under reduced pressure to give a residue. The residue was purified by MPLC (SiO₂, PE/EtOAc=7/1, 1500 mL) to afford the title compound as yellow solid.

Example 20. Synthesis of (3R,5S)-1-benzyl-5-[[4-[6-thiazol-2-yl-1-(2-trimethylsilylethoxymethyl)indol-3-yl]-5-(trifluoromethyl)pyrimidin-2-yl]-amino]-piperidin-3-ol Useful in the Synthesis of Compound 107)

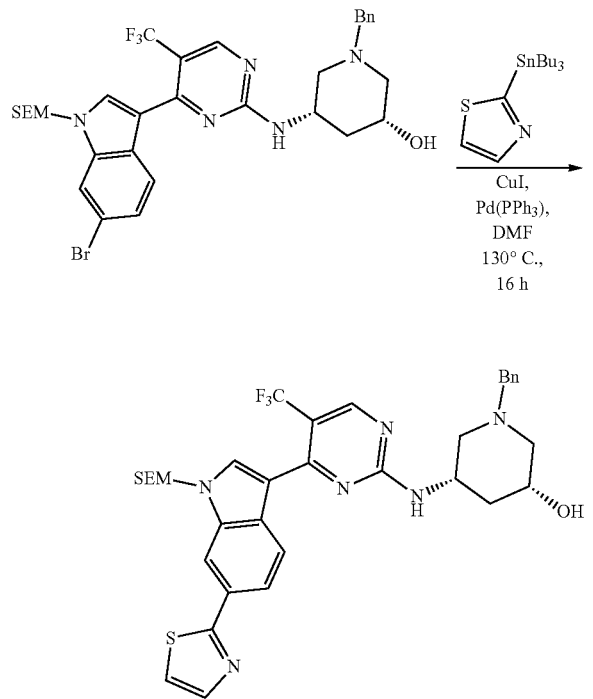

A mixture of (3R,5S)-1-benzyl-5-[[4-[6-bromo-1-(2-trimethylsilylethoxymethyl) indol-3-yl]-5-(trifluoromethyl)pyrimidin-2-yl]-amino]-piperidin-3-ol (400 mg, 591.16 μmol, 1 eq), tributyl (thiazol-2-yl) stannane (663.58 mg, 1.77 mmol, 3 eq), CuI (11.26 mg, 59.12 μmol, 0.1 eq), Pd(PPh₃)₄ (68.31 mg, 59.12 μmol, 0.1 eq) and in DMF (5 mL) was degassed and purged with N₂ for 3 times, and then the mixture was stirred at 130° C. for 16 h under N₂ atmosphere. The reaction mixture was quenched by addition saturated CsF solution (20 mL), extracted with EtOAc (20 mL×3). The combined organic layers were washed with brine 20 mL, dried over Na₂SO₄, filtered and concentrated under reduced pressure to give a residue. The residue was purified by column chromatography (SiO₂, PE/EtOAc=5/1 to 4/1) to afford the title compound (328 mg) as a yellow solid.

Example 21. Synthesis of 4-[6-(3-methyl-1,2,4-oxadiazol-5-yl)-1H-indol-3-yl]-N-[(3S)-3-piperidyl]-5 (trifluoromethyl)pyrimidin-2-amine (Compound 121)

Step 1: Methyl 3-[2-chloro-5-(trifluoromethyl)pyrimidin-4-yl]-1H-indole-6-carboxylate

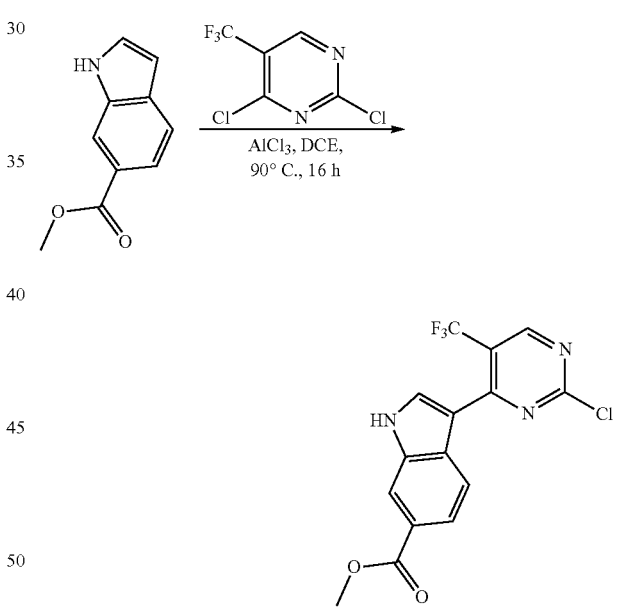

To a solution of 2, 4-dichloro-5-(trifluoromethyl) pyrimidine (24.77 g, 114.16 mmol, 2.00 eq) in DCE (200.00 mL) was added AlCl₃ (15.98 g, 119.87 mmol, 6.55 mL, 2.10 eq). The mixture was stirred at 90° C. for 30 min, and then methyl 1H-indole-6-carboxylate (10.00 g, 57.08 mmol, 1.00 eq) was added at 90° C. The resulting mixture was stirred at 90° C. for 15.5 h. The reaction mixture was filtered. The filtrate was diluted with water (200 mL) and extracted with DCM (80 mL×3). The combined organic layers were washed with brine (200 mL×2), dried over Na₂SO₄, filtered and concentrated under reduced pressure to give a residue. The residue was washed with MeOH (50 mL) and filtered to afford the title compound (4.00 g, 10.57 mmol, 18.52% yield, 94% purity) as a yellow solid.

Step 2: Methyl 3-[2-[[(3S)-1-tert-butoxycarbonyl-3-piperidyl] amino]-5-(trifluoromethyl) pyrimidin-4-yl]-1H-indole-6-carboxylate

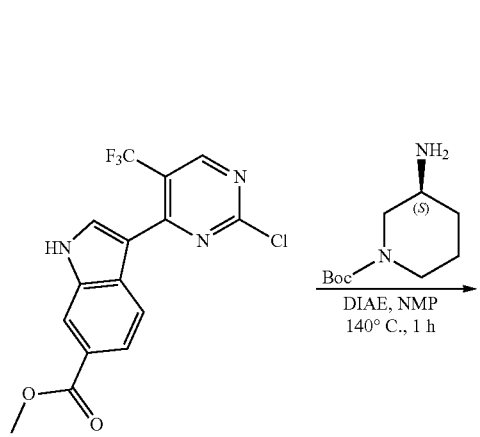

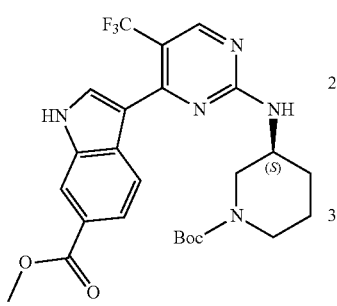

A mixture of methyl 3-[2-chloro-5-(trifluoromethyl)pyrimidin-4-yl]-1H-indole-6-carboxylate (2.50 g, 7.03 mmol, 1.00 eq), tert-butyl (3S)-3-aminopiperidine-1-carboxylate (1.83 g, 9.14 mmol, 1.30 eq), DIEA (4.54 g, 35.15 mmol, 6.14 mL, 5.00 eq) in NMP (10.00 mL) was stirred at 140° C. for 1 h. The reaction mixture was poured into water 200 mL, and then extracted with EtOAc (70 mL×3). The combined organic layers were washed with brine (300 mL), dried over Na$_2$SO$_4$, filtered and concentrated under reduced pressure to give a residue. The residue was purified by column chromatography (SiO$_2$, PE/EtOAc=5:1 to 1:1) to afford the title compound (2.20 g, 3.39 mmol, 48.19% yield, 80% purity) as a yellow solid.

Step 3: 3-[2-[[(3S)-1-tert-butoxycarbonyl-3-piperidyl] amino]-5-(trifluoromethyl) pyrimidin-4-yl]-1H-indole-6-carboxylic Acid

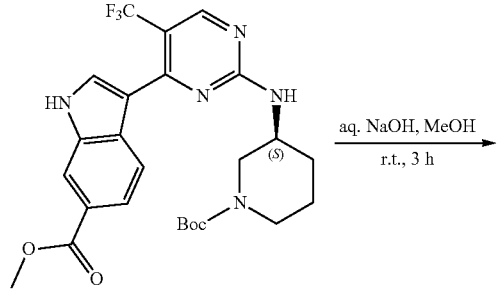

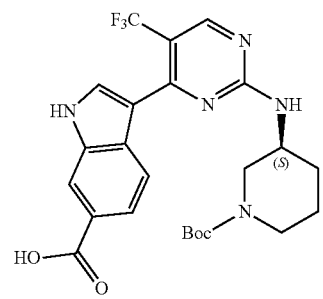

A mixture of methyl 3-[2-[[(3S)-1-tert-butoxycarbonyl-3-piperidyl] amino]-5-(trifluoromethyl) pyrimidin-4-yl]-1H-indole-6-carboxylate (2.20 g, 4.23 mmol, 1.00 eq), LiOH (5 M, 1.69 mL, 2.00 eq) in MeOH (20.00 mL) was stirred at 25° C. for 3 h. The reaction mixture was concentrated, and then diluted with water 100 mL and extracted with EtOAc (50 mL×3). The organic layers was removed, and the aqueous phase was adjusted pH to 1 by HCl (1M), extracted with EtOAc (50 mL×3). The combined organic layers were washed with brine (300 mL), dried over Na$_2$SO$_4$, filtered and concentrated under reduced pressure to afford the title compound (1.80 g, 3.20 mmol, 75.57% yield, 90% purity) as a yellow solid.

Step 4: Tert-butyl (3S)-3-[[4-[6-[[(Z)—N-hydroxy-C-methyl-carbonimidoyl]-carbamoyl]-1H-indol-3-yl]-5-(trifluoromethyl)pyrimidin-2-yl]-amino]-piperidine-1-carboxylate

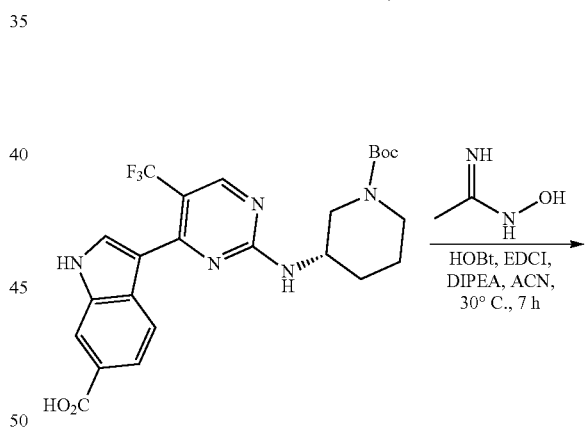

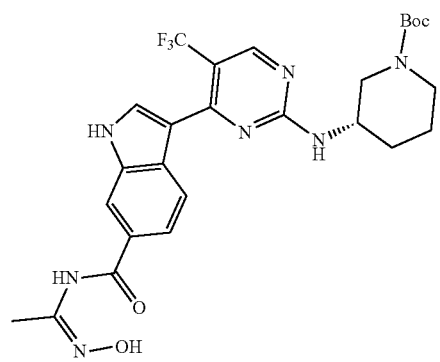

A mixture of 3-[2-[[(3S)-1-tert-butoxycarbonyl-3-piperidyl]-amino]-5-(trifluoromethyl)pyrimidin-4-yl]-1H-indole-6-carboxylic acid (200 mg, 395.66 μmol, 1 eq), N-hydroxyacetamidine (58.62 mg, 791.31 μmol, 2 eq), HOBt (1-hydroxybenzotriazole; 106.92 mg, 791.31 μmol, 2 eq), EDCI (151.70 mg, 791.31 μmol, 2 eq) and DIPEA (255.68 mg, 1.98 mmol, 344.58 μL, 5 eq) in acetonitrile (ACN; 9 mL). The mixture was stirred at 30° C. for 7 h. The reaction mixture was concentrated under reduced pressure to afford the title compound (240 mg, crude) as white solid. The crude product was used directly into the next step without purification.

Step 5: Tert-butyl (3S)-3-[[4-[6-(3-methyl-1,2,4-oxadiazol-5-yl)-1H-indol-3-yl]-5-(trifluoromethyl)pyrimidin-2-yl]-amino]-piperidine-1-carboxylate

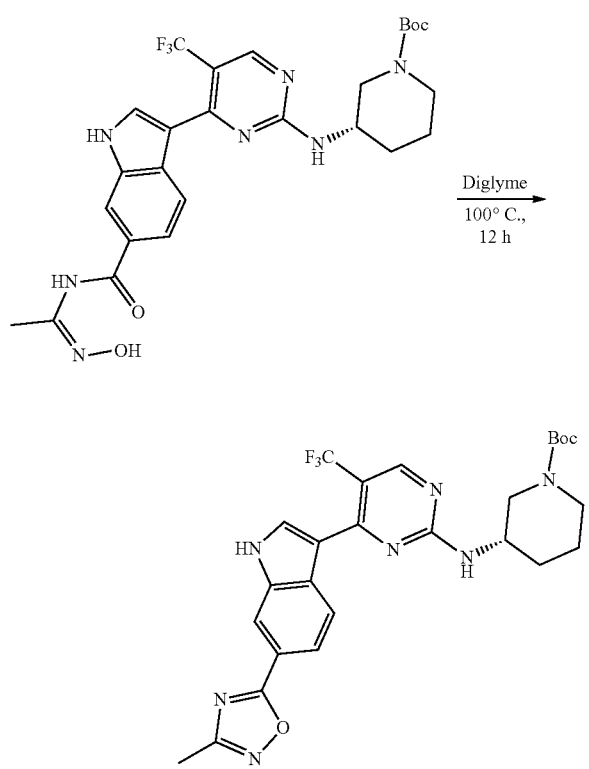

Diglyme
100° C.,
12 h

A solution of tert-butyl (3S)-3-[[4-[6-[[(Z)—N-hydroxy-C-methyl-carbonimidoyl]-carbamoyl]-1H-indol-3-yl]-5-(trifluoromethyl)pyrimidin-2-yl]-amino]-piperidine-1-carboxylate (240 mg, 427.38 μmol, 1 eq) in Diglyme (10 mL) was stirred at 100° C. for 12 h. The reaction mixture was concentrated under reduced pressure to remove digylme. The residue was diluted with H₂O (50 mL) and extracted with EtOAc (20 mL×3). The combined organic layers were washed with brine (60 mL), dried over Na₂SO₄, filtered and concentrated under reduced pressure to give a residue. The residue was purified by column chromatography (SiO₂, PE/EtOAc=5/1 to 1/1) to afford the title compound (100 mg) as yellow solid.

(The reaction was combined with another reaction in 70 mg scale for purification and work up.)

Step 6: 4-[6-(3-methyl-1,2,4-oxadiazol-5-yl)-1H-indol-3-yl]-N-[(3S)-3-piperidyl]-5-(trifluoromethyl)pyrimidin-2-amine

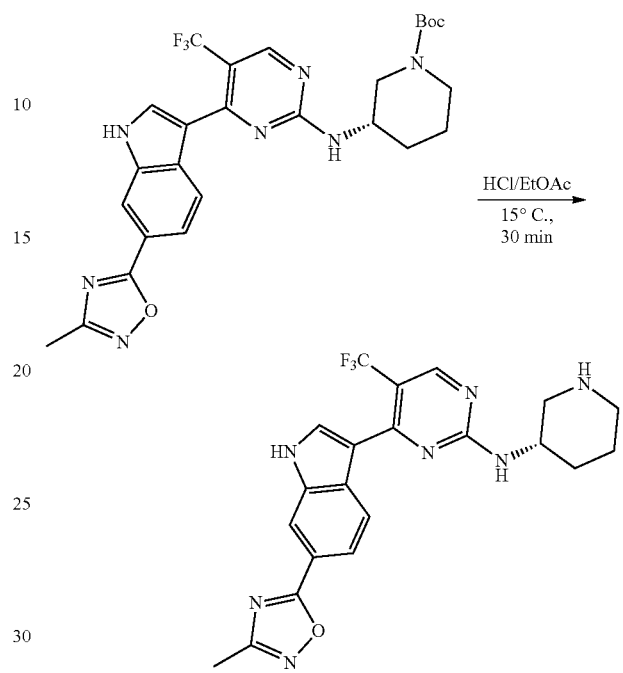

HCl/EtOAc
15° C.,
30 min

A solution of tert-butyl (3S)-3-[[4-[6-(3-methyl-1,2,4-oxadiazol-5-yl)-1H-indol-3-yl]-5-(trifluoromethyl)pyrimidin-2-yl]-amino]-piperidine-1-carboxylate (80 mg, 147.18 μmol, 1 eq) in HCl/EtOAc (4 M, 8.00 mL, 217.42 eq) was stirred at 15° C. for 30 min. The reaction mixture was concentrated under reduced pressure to give a residue. The residue was purified by prep-HPLC (FA condition) to afford the title compound (64 mg, FA, 100% purity) as white solid.

(The reaction was combined with another reaction in 20 mg scale for purification and work-up.)

Example 22. Synthesis of 4-[6-(3,5-dimethylisoxazol-4-yl)-1H-indazol-3-yl]-N-[(3S)-3-piperidyl]-5-(trifluoromethyl)pyrimidin-2-amine (Compound 100)

Step 1: Tert-butyl (3S)-3-[[4-[6-(3,5-dimethylisoxazol-4-yl)-1-(2-trimethylsilylethoxy methyl) indazol-3-yl]-5-(trifluoromethyl)pyrimidin-2-yl]-amino]-piperidine-1-carboxylate

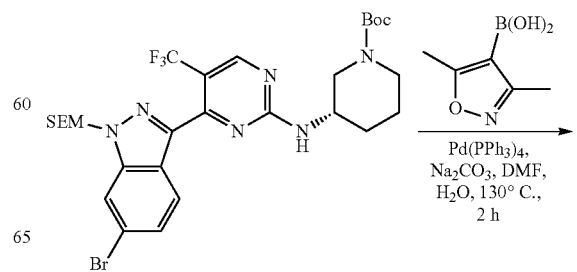

Pd(PPh₃)₄,
Na₂CO₃, DMF,
H₂O, 130° C.,
2 h

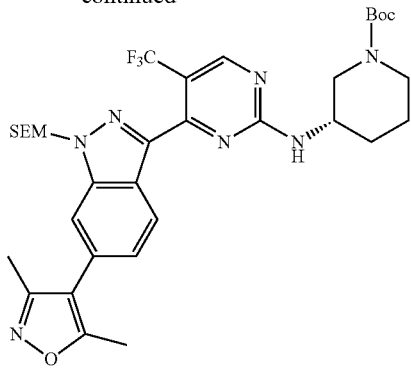

A mixture of tert-butyl (3S)-3-[[4-[6-bromo-1-(2-trimethylsilylethoxymethyl)indazol-3-yl]-5-(trifluoromethyl)pyrimidin-2-yl]amino]piperidine-1-carboxylate (0.3 g, 446.68 µmol, 1 eq), (3,5-dimethylisoxazol-4-yl)boronic acid (75.54 mg, 536.02 µmol, 1.2 eq), Pd(PPh$_3$)$_4$ (51.62 mg, 44.67 µmol, 0.1 eq) and Na$_2$CO$_3$ (94.69 mg, 893.36 µmol, 2 eq) in DMF (20 mL), H$_2$O (4 mL) was degassed and purged with N$_2$ for 3 times, and then the mixture was stirred at 130° C. for 2 h under N$_2$ atmosphere. The reaction mixture was diluted with water (50 mL) and extracted with EtOAc (20 ml×3). The combined organic layers were washed with brine (50 mL×2), dried over Na$_2$SO$_4$, filtered and concentrated under reduced pressure to give a residue. The residue was purified by column chromatography (SiO$_2$, PE/EtOAc=10:1 to 5:1) to afford the title compound (260 mg) as a yellow oil.

(The reaction was combined with another reaction in 50 mg scale for purification.)

Step 2: 4-[6-(3,5-dimethylisoxazol-4-yl)-1H-indazol-3-yl]-N-[(3S)-3-piperidyl]-5-(trifluoromethyl)pyrimidin-2-amine

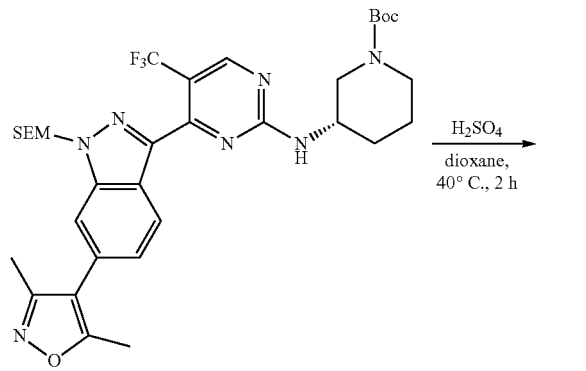

To a solution of tert-butyl (3S)-3-[[4-[6-(3,5-dimethylisoxazol-4-yl)-1-(2-trimethylsilylethoxymethyl) indazol-3-yl]-5-(trifluoromethyl)pyrimidin-2-yl]-amino]-piperidine-1-carboxylate (210 mg, 305.31 µmol, 1 eq) in dioxane (4 mL) was added H$_2$SO$_4$ (299.45 mg, 3.05 mmol, 162.74 µL, 10 eq). The mixture was stirred at 40° C. for 2 h. The reaction mixture was adjusted pH to 8 with saturated aqueous Na$_2$CO$_3$ and extracted with EtOAc (10 mL×3). The combined organic layers were washed with brine (30 mL×2), dried over Na$_2$SO$_4$, filtered and concentrated under reduced pressure to give a residue. The residue was purified by prep-HPLC (FA condition) to afford the title compound (49.4 mg, FA, purity 98.479%) as a white solid.

Example 23. Synthesis of Tert-butyl (3S)-3-[[4-[6-thiazol-2-yl-1-(2-trimethylsilylethoxymethyl) indazol-3-yl]-5-(trifluoromethyl)pyrimidin-2-yl]amino] piperidine-1-carboxylate useful in the Synthesis of Compound 103

Step 1: Tert-butyl(3S)-3-[[4-[6-(4,4,5,5-tetramethyl-1,3,2-dioxaborolan-2-yl)-1-(2-trimethylsilylethoxymethyl)indazol-3-yl]-5-(trifluoromethyl)pyrimidin-2-yl]amino]piperidine-1-carboxylate

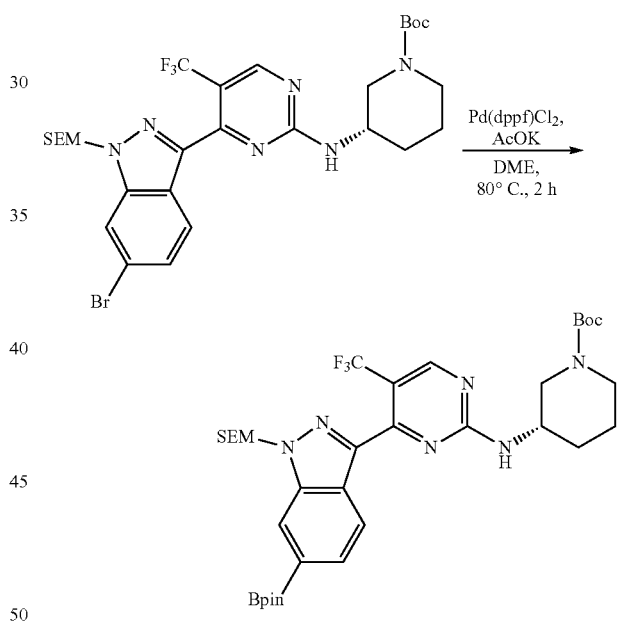

A mixture of tert-butyl (3S)-3-[[4-[6-bromo-1-(2-trimethylsilylethoxymethyl)indazol-3-yl]-5-(trifluoromethyl)pyrimidin-2-yl]amino]piperidine-1-carboxylate (400 mg, 595.57 µmol, 1 eq), 4,4,5,5-tetramethyl-2-(4,4,5,5-tetramethyl-1,3,2-dioxaborolan-2-yl)-1,3,2-dioxaborolane (302.48 mg, 1.19 mmol, 2 eq), Pd(dppf)Cl$_2$ (43.58 mg, 59.56 µmol, 0.1 eq) and AcOK (175.35 mg, 1.79 mmol, 3 eq) in DME (4 mL) was degassed and purged with N$_2$ for 3 times, and then the mixture was stirred at 80° C. for 2 h under N$_2$ atmosphere. The reaction mixture was diluted with water 40 mL and extracted with EtOAc (20 mL×3). The combined organic layers were washed with brine (80 mL×1), dried over Na$_2$SO$_4$, filtered and concentrated under reduced pressure to give a residue. The residue was purified by column chromatography (SiO$_2$, PE/EtOAc=20:1 to 10:1) to afford the title compound (400 mg) as a yellow oil.

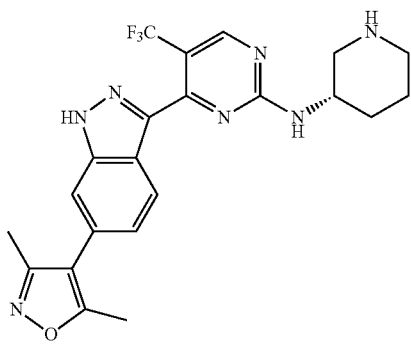

Step 2: Tert-butyl (3S)-3-[[4-[6-thiazol-2-yl-1-(2-trimethylsilylethoxymethyl) indazol-3-yl]-5-(trifluoromethyl)pyrimidin-2-yl]amino]piperidine-1-carboxylate

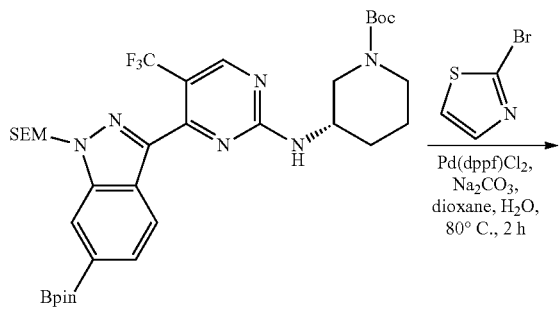

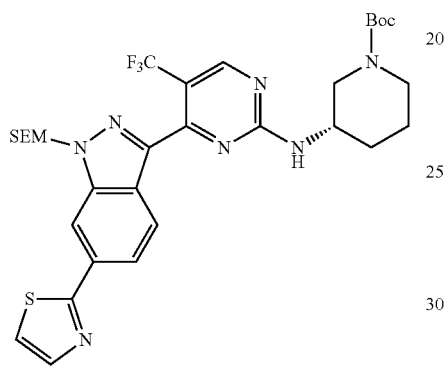

A mixture of tert-butyl (3S)-3-[[4-[6-(4,4,5,5-tetramethyl-1,3,2-dioxaborolan-2-yl)-1-(2-trimethylsilylethoxymethyl) indazol-3-yl]-5-(trifluoromethyl)pyrimidin-2-yl]amino]piperidine-1-carboxylate (350 mg, 487.00 μmol, 1 eq), 2-bromothiazole (103.84 mg, 633.10 μmol, 57.06 μL, 1.3 eq), Pd(dppf)Cl₂ (35.63 mg, 48.70 μmol, 0.1 eq) and Na₂CO₃ (51.62 mg, 487.00 μmol, 1 eq) in dioxane (5 mL), H₂O (1 mL) as degassed and purged with N₂ for 3 times, and then the mixture was stirred at 80° C. for 2 h under N₂ atmosphere. The reaction mixture was diluted with water 20 mL and extracted with EtOAc (10 mL×3). The combined organic layers were washed with brine (30 mL×2), dried over Na₂SO₄, filtered and concentrated under reduced pressure to give a residue. The residue was purified by column chromatography (SiO₂, Petroleum ether/Ethyl acetate=10:1 to 2:1) to give a residue. The residue was purified again by prep-TLC (thin layer chromatography; SiO₂, PE:EtOAc=3:1) to afford the title compound (160 mg) as a yellow solid.

Example 24. Synthesis of 4-[6-(1-methyltetrazol-5-yl)-1Hindol-3-yl]-N-[(3S)-3-piperidyl]-5-(trifluoromethyl)pyrimidin-2-amine (Compound 122)

Step 1: 5-bromo-1-methyl-tetrazole

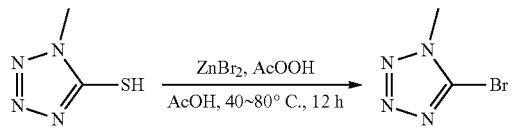

A suspension of 1-methyltetrazole-5-thiol (0.5 g, 4.30 mmol, 1 eq), ZnBr₂ (1.94 g, 8.61 mmol, 430.88 μL, 2 eq) in AcOH (10 mL) was heated to 40° C. for 0.5 h, then peroxyacetic acid (13.10 g, 25.83 mmol, 11.39 mL, 6 eq) was added to the above carefully and the resulting mixture was stirred at 80° C. for 11.5 h. The reaction mixture was cooled to 15° C. and poured into ice-water (1000 mL) and adjusted pH to 9 with NaHCO₃ (50 g). The aqueous phase was extracted with EtOAc (200 mL×3). The combined organic phase was washed with Sat. Na₂SO₃ (500 mL×2). The combined organic phase was dried over anhydrous Na₂SO₄, filtered and concentrated in vacuum to afford the title compound (0.45 g, crude) as white solid and used directly.

Step 2: Tert-butyl (3S)-3-[[4-[6-(1-methyltetrazol-5-yl)-1H-indol-3-yl]-5-(trifluoromethyl)pyrimidin-2-yl]-amino]-piperidine-1-carboxylate

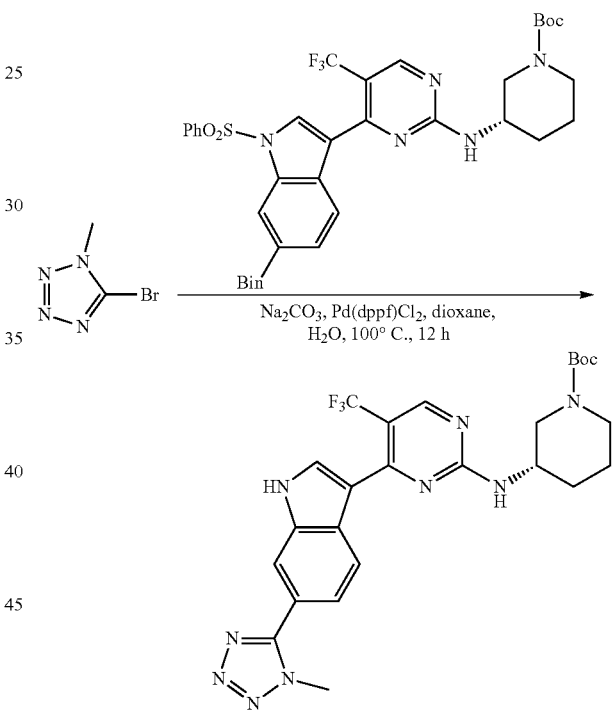

To a solution of (S)-tert-butyl 3-((4-(1-(phenylsulfonyl)-6-(4,4,5,5-tetramethyl-1,3,2-dioxaborolan-2-yl)-1H-indol-3-yl)-5-(trifluoromethyl)pyrimidin-2-yl)amino)piperidine-1-carboxylate (Example 8; 0.1 g, 137.44 μmol, 1 eq), 5-bromo-1-methyl-tetrazole (33.60 mg, 206.16 μmol, 1.5 eq) in dioxane (2 mL)/H₂O (0.4 mL) was added Pd(dppf)Cl₂ (10.06 mg, 13.74 μmol, 0.1 eq) and Na₂CO₃ (43.70 mg, 412.31 μmol, 3 eq). The mixture was stirred at 100° C. under N₂ atmosphere for 12 h. The reaction mixture was cooled to 15° C. and poured into water (20 mL). The aqueous phase was extracted with EtOAc (20 mL×3). The combined organic phase was dried over anhydrous Na₂SO₄, filtered and concentrated in vacuum. The residue was purified by silica gel chromatography (100-200 mesh silica gel, PE/EtOAc=5/1, 1/1) to afford the title compound (40 mg, 58.87 μmol, 42.84% yield, 80% purity) as yellow solid.

87

Step 3: 4-[6-(1-methyltetrazol-5-yl)-1Hindol-3-yl]-N-[(3S)-3-piperidyl]-5-(trifluoromethyl)pyrimidin-2-amine

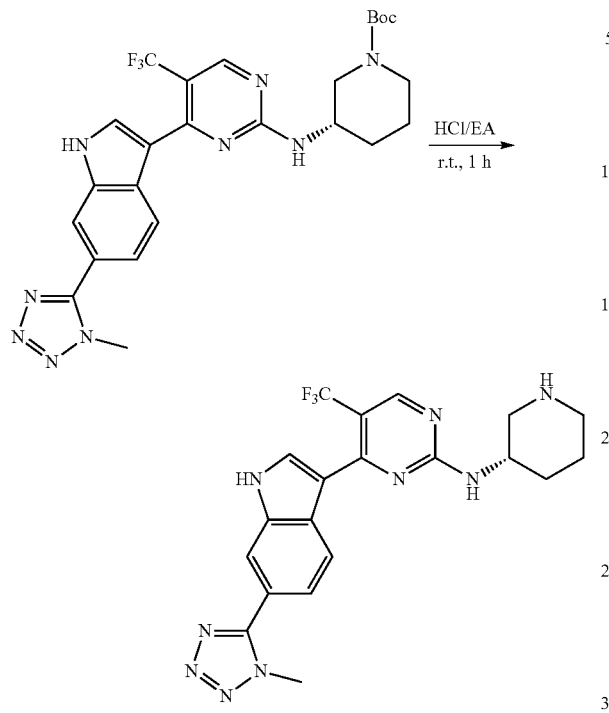

A solution of tert-butyl (3S)-3-[[4-[6-(1-methyltetrazol-5-yl)-1H-indol-3-yl]-5-(trifluoromethyl)pyrimidin-2-yl]-amino]-piperidine-1-carboxylate (40 mg, 73.59 µmol, 1 eq) in HCl/EtOAc (10 mL) was stirred at 15° C. for 1 h. The reaction mixture was concentrated in vacuum. The residue was purified by twice prep-HPLC (HCl condition) to afford the title compound (9 mg, HCl salt 99% purity) as a yellow solid. The reaction was combined with another reaction in 30 mg scale for purification.

Example 25. Synthesis of 4-[6-(3,5-dimethylisoxazol-4-yl)-1H-pyrrolo-[2,3-b]-pyridin-3-yl]-N-[(3S,6S)-6-methyl-3-piperidyl]-5-(trifluoromethyl)pyrimidin-2-amine (Compound 124) and 4-[6-(3,5-dimethylisoxazol-4-yl)-1H-pyrrolo-[2,3-b]-pyridin-3-yl]-N-[(3R,6R)-6-methyl-3-piperidyl]-5-(trifluoromethyl)pyrimidin-2-amine (Compound 125)

Step 1: 4-[1-(benzenesulfonyl)-6-(3,5-dimethyl-isoxazol-4-yl) pyrrolo-[2,3-b]-pyridin-3-yl]-5-(trifluoromethyl)pyrimidin-2-ol

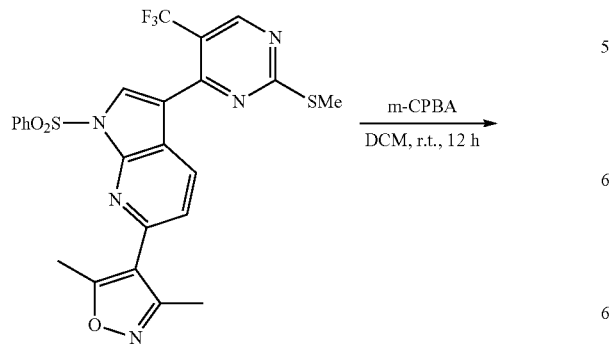

88

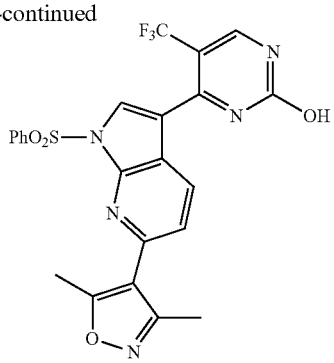

To a solution of 4-[1-(benzenesulfonyl)-3-[2-methylsulfanyl-5-(trifluoromethyl)pyrimidin-4-yl]-pyrrolo[2,3-b]-pyridin-6-yl]-3,5-dimethyl-isoxazole (Example 11; 1.9 g, 2.44 mmol, 1 eq) in DCM (50 mL) was added m-CPBA (1.16 g, 5.36 mmol, 2.2 eq). The mixture was stirred at 20° C. for 12 h. The residue was poured into a mixture of Sat.NaHCO₃ (20 mL) and Sat. Na₂SO₃ (20 mL), and the mixture was stirred for 5 min. The aqueous phase was extracted with DCM (30 mL×2). The combined organic phase was dried over anhydrous Na₂SO₄, filtered and concentrated in vacuum. The residue was washed with a mixture of PE:EtOAc=5:1 (20 mL), filtered and the filter cake was collected to afford the title compound (1 g, crude) as yellow solid and used directly.

Step 2: 4-[1-(benzenesulfonyl)-3-[2-chloro-5-(trifluoromethyl)pyrimidin-4-yl]-pyrrolo-[2,3-b]-pyridin-6-yl]-3,5-dimethylisoxazle

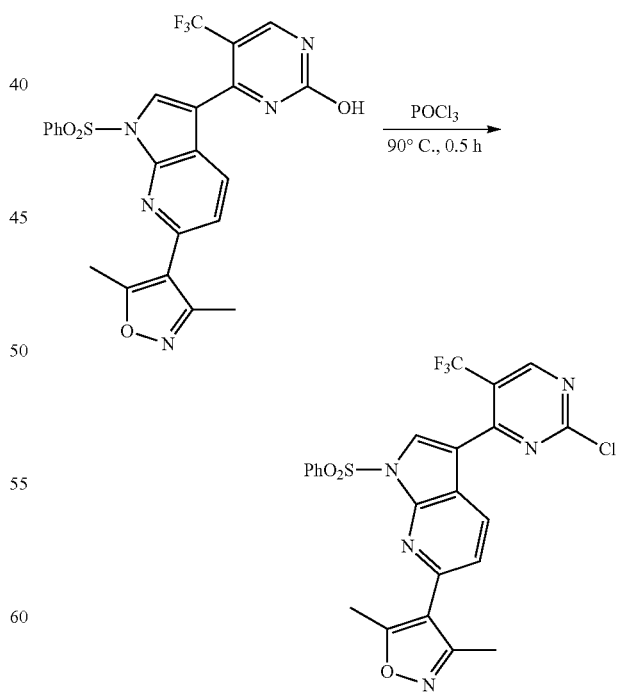

A solution of 4-[1-(benzenesulfonyl)-6-(3,5-dimethyl-isoxazol-4-yl) pyrrolo-[2,3-b]-pyridin-3-yl]-5-(trifluoromethyl)pyrimidin-2-ol (1 g, 1.94 mmol, 1 eq) in POCl₃ (15 mL) was stirred at 90° C. for 0.5 h. The solution was cooled to 15° C. and concentrated in vacuum. The residue was adjusted pH to 9 with sat. NaHCO₃ and extracted with ethyl acetate (50 mL×3). The combined organic phase was dried over anhydrous Na₂SO₄, filtered and concentrated in vacuum to afford the title compound (0.6 g, crude) as a yellow solid and used directly.

Step 3: Benzyl (2S,5S)-5-[[4-[1-(benzenesulfonyl)-6-(3,5-dimethylisoxazol-4-yl)pyrrolo[2,3-b]-pyridin-3-yl]-5-(trifluoromethyl)pyrimidin-2-yl]amino]-2-methyl-piperidine-1-carboxylate and Benzyl (2R, 5R)-5-[[4-[1-(benzenesulfonyl)-6-(3,5-dimethylisoxazol-4-yl) pyrrolo[2,3-b]-pyridin-3-yl]-5-(trifluoromethyl)pyrimidin-2-yl]amino]-2-methyl-piperidine-1-carboxylate

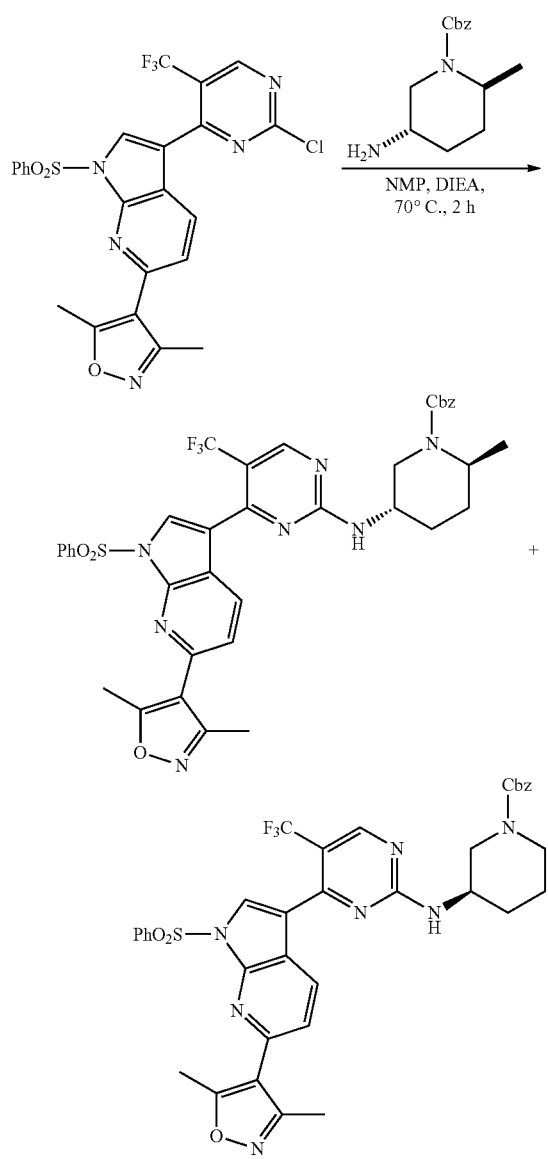

To a solution of 4-[1-(benzenesulfonyl)-3-[2-chloro-5-(trifluoromethyl)pyrimidin-4-yl]-pyrrolo-[2,3-b]pyridin-6-yl]-3,5-dimethyl-isoxazole (0.26 g, 486.97 μmol, 1 eq) and benzyl 5-amino-2-methyl-piperidine-1-carboxylate (241.85 mg, 973.95 μmol, 2 eq) in NMP (0.4 mL) was added DIEA (314.69 mg, 2.43 mmol, 424.11 μL, 5 eq). The mixture was stirred at 70° C. for 2 h. The solution was cooled to 15° C., diluted with water (50 mL) and extracted with EtOAc (20 mL×3). The combined organic phase was washed with brine (30 mL×2), dried over anhydrous Na₂SO₄, filtered and concentrated in vacuum. The residue was purified by silica gel chromatography (100-200 mesh silica gel, PE/EtOAc=5/1, 2/1) to give a racemate product (0.25 g) as a yellow solid. The product was separated by SFC (column: Chiralpak AS-H 250*30 mm i.d. 5 u Mobile phase: A for CO₂ and B for MeOH (0.1% NH₃H₂O) Gradient: B %=40% Flow rate: 70 g/min Wavelength: 220 nm. Column temperature: 40° C. System back pressure: 100 bar Cycle time: 5 min) to afford the title compound 1 (Peak 1, RT=1.74 min, 120 mg, 160.91 μmol, 33.04% yield) as a yellow solid. Compound 2 (Peak 2, 100 mg, 134.09 μmol, 27.54% yield. It was used for example 4) as a yellow solid.

Step 4: Benzyl (2S,5S)-5-[[4-[6-(3,5-dimethylisoxazol-4-yl)-1H-pyrrolo-[2,3-b]-pyridin-3-yl]-5-(trifluoromethyl)pyrimidin-2-yl]amino]-2-methyl-piperidine-1-carboxylate

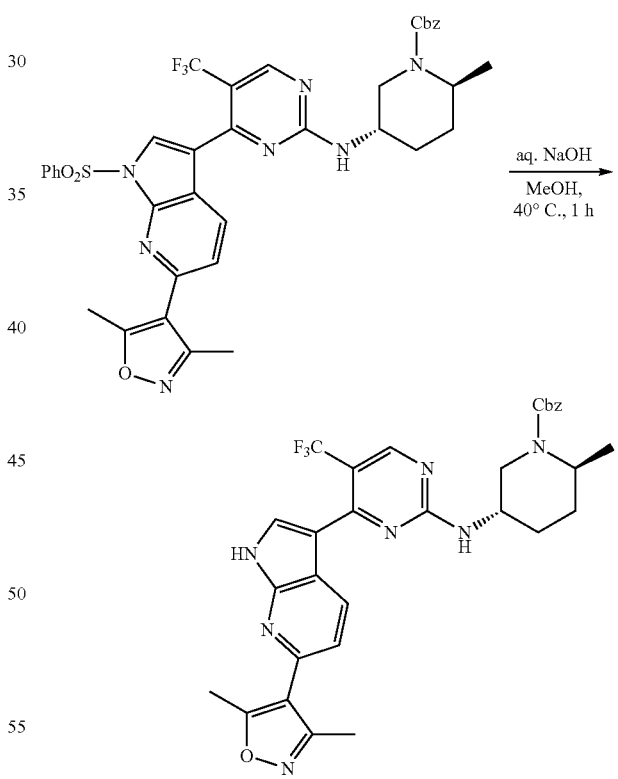

To a solution of benzyl (2S,5S)-5-[[4-[1-(benzenesulfonyl)-6-(3,5-dimethylisoxazol-4-yl) pyrrolo[2,3-b]pyridin-3-yl]-5-(trifluoromethyl)pyrimidin-2-yl]amino]-2-methyl-piperidine-1-carboxylate (0.1 g, 134.09 μmol, 1 eq) in MeOH (3 mL) was added NaOH (2 M, 670.45 μL, 10 eq). The mixture was stirred at 40° C. for 1 h. The solution was cooled to 15° C. and poured into water (10 mL). The aqueous phase was extracted with EtOAc (10 mL×2). The combined organic phase was washed with brine (10 mL×2), dried over anhydrous Na$_2$SO$_4$, filtered and concentrated in vacuum to afford the title compound (70 mg, crude) as a yellow solid and used directly.

Step 5: 4-[6-(3,5-dimethylisoxazol-4-yl)-1H-pyrrolo-[2,3-b]-pyridin-3-yl]-N-[(3S,6S)-6-methyl-3-piperidyl]-5-(trifluoromethyl)pyrimidin-2-amine

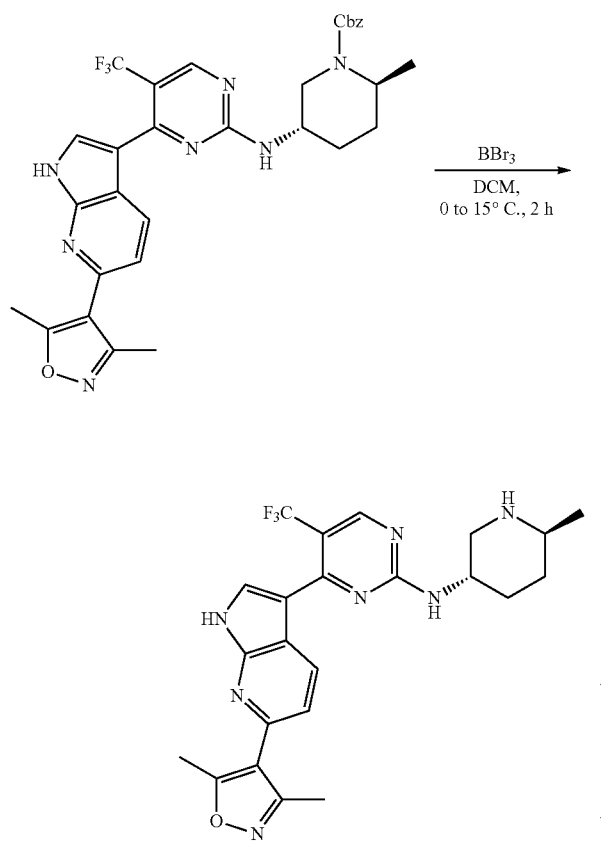

To a solution of benzyl (2S,5S)-5-[[4-[6-(3,5-dimethylisoxazol-4-yl)-1H-pyrrolo-[2,3-b]-pyridin-3-yl]-5-(trifluoromethyl)pyrimidin-2-yl]-amino]-2-methyl-piperidine-1-carboxylate (70 mg, 115.59 μmol, 1 eq) in DCM (5 mL) was added BBr$_3$ (115.83 mg, 462.34 μmol, 44.55 μL, 4 eq) at 0° C. The mixture was stirred at 15° C. for 2 h. The reaction mixture was concentrated in vacuum. The residue was washed with PE (10 mL), filtered and the filter cake was collected. The residue was purified by prep-HPLC (HCl condition) to afford the title compound (26.8 mg, 100% purity, HCl salt) as a yellow solid.

4-[6-(3,5-dimethylisoxazol-4-yl)-1H-pyrrolo-[2,3-b]-pyridin-3-yl]-N-[(3R,6R)-6-methyl-3-piperidyl]-5-(trifluoromethyl)pyrimidin-2-amine is produced following steps 4 and 5, but starting with benzyl (2R,5R)-5-[[4-[1-(benzenesulfonyl)-6-(3,5-dimethylisoxazol-4-yl) pyrrolo[2,3-b]pyridin-3-yl]-5-(trifluoromethyl)pyrimidin-2-yl]amino]-2-methyl-piperidine-1-carboxylate.

Example 26. Synthesis of Tert-butyl (3S)-3-[[4-[1-(benzenesulfonyl)-6-(3-methyltriazol-4-yl)indol-3-yl]-5-(trifluoromethyl)pyrimidin-2-yl]amino]piperidine-1-carboxylate Useful in the Synthesis of Compound 126)

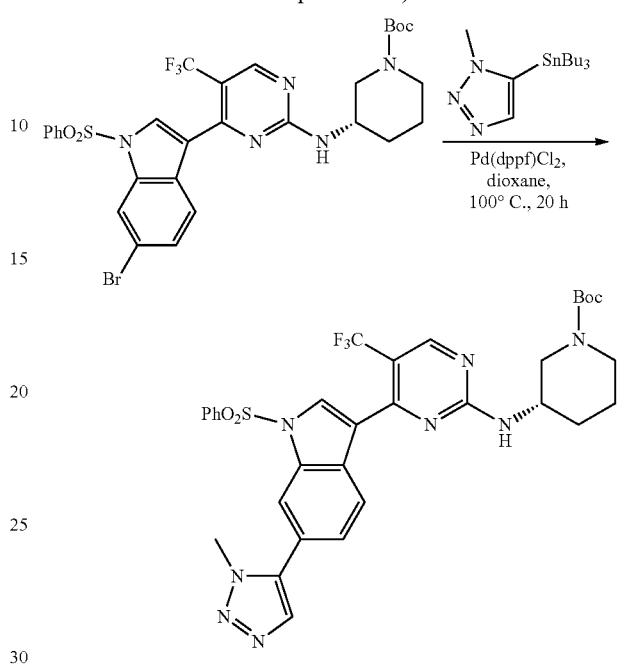

A mixture of tert-butyl (3S)-3-[[4-[1-(benzenesulfonyl)-6-bromo-indol-3-yl]-5-(trifluoromethyl)pyrimidin-2-yl]amino]piperidine-1-carboxylate (300 mg, 440.83 μmol, 1 eq), tributyl-(3-methyltriazol-4-yl)stannane (1.31 g, 1.76 mmol, 4 eq) and Pd(dppf)Cl$_2$ (32.26 mg, 44.08 μmol, 0.1 eq) in dioxane (0.5 mL) was stirred for 20 h at 100° C. under N$_2$. The mixture was cooled to 15° C. and poured into water (10 mL) and extracted with EtOAc (20 mL×3). The combined organic layer was washed with brine (20 mL×3), dried over Na$_2$SO$_4$, filtered. The filtrate was concentrated under reduced pressure to give a residue. The residue was purified by MPLC (SiO$_2$, PE:EtOAc=4/1 to 1/1) to afford the title compound (280 mg, 83.6% purity) as a yellow solid. The reaction was combined with another reaction in 20 mg scale for work up.

Example 27. Synthesis of 4-[6-(5-methyl-1,2,4-oxadiazol-3-yl)-1H-indol-3-yl]-N-[(3S)-3-piperidyl]-5-(trifluoromethyl)pyrimidin-2-amine (Compound 129)

Step 1: 3-[2-chloro-5-(trifluoromethyl) pyrimidin-4-yl]-1H-indole-6-carbonitrile

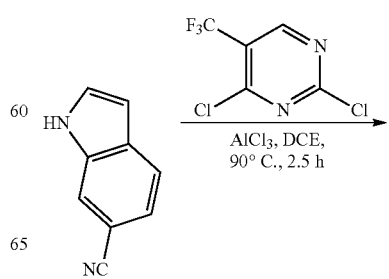

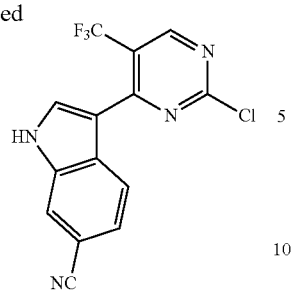

To a solution of 2, 4-dichloro-5-(trifluoromethyl) pyrimidine (30.53 g, 140.69 mmol, 2 eq) in DCE (250 mL) was added AlCl₃ (19.70 g, 147.72 mmol, 8.07 mL, 2.1 eq). The mixture was stirred at 90° C. for 0.5 h. Then 1H-indole-6-carbonitrile (10 g, 70.34 mmol, 1 eq) was added and the resulting solution was stirred at 90° C. for 2 h. The residue was dissolved in MeOH (100 mL) and poured into ice-water (1000 mL) and stirred for 5 min. The solids were formed and filtered to collect the cake. The cake was washed with MeOH (500 mL), filtered and concentrated in vacuum. The residue was purified by silica gel chromatography (PE:EtOAc=1:1) to afford the title compound (10 g, 26.34 mmol, 37.45% yield, 85% purity) as yellow solid.

Step 2: 3-[2-chloro-5-(trifluoromethyl) pyrimidin-4-yl]-1-(2-trimethylsilylethoxymethyl)indole-6-carbonitrile

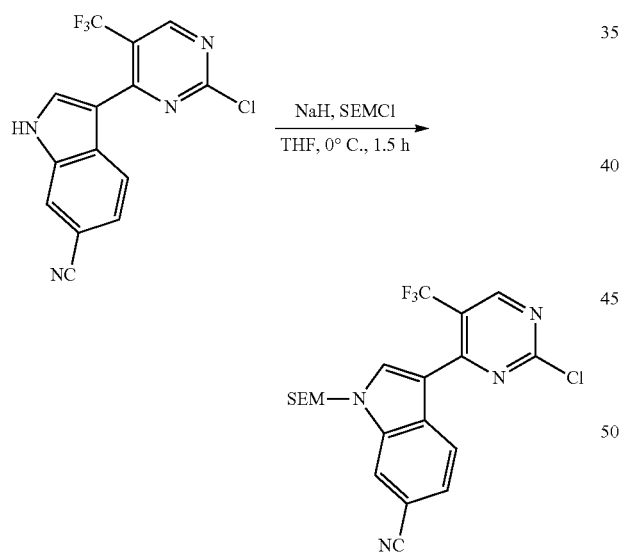

To a solution of 3-[2-chloro-5-(trifluoromethyl) pyrimidin-4-yl]-1H-indole-6-carbonitrile (1 g, 3.10 mmol, 1 eq) in THF (20 mL) was added NaH (185.93 mg, 4.65 mmol, 60% purity, 1.5 eq) at 0° C. The mixture was stirred at 0° C. for 0.5 h. Then SEMCl (775.03 mg, 4.65 mmol, 822.75 μL, 1.5 eq) was added and the mixture was stirred at 0° C. for 1 h. The residue was poured into ice-water (50 mL). The aqueous phase was extracted with EtOAc (50 mL×3). The combined organic phase was washed with brine (50 mL×2), dried with anhydrous Na₂SO₄, filtered and concentrated in vacuum. The residue was purified by silica gel chromatography PE:EtOAc=20:1-10:1-8:1 to afford the title compound (0.7 g, 1.53 mmol, 49.37% yield, 99% purity) as white solid.

Step 3: Tert-butyl (3S)-3-[[4-[6-cyano-1-(2-trimethylsilylethoxymethyl)indol-3-yl]-5-(trifluoromethyl) pyrimidin-2-yl]amino]piperidine-1-carboxylate

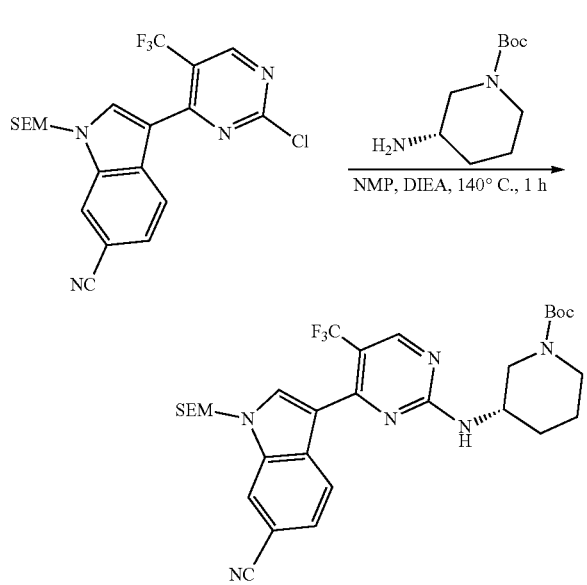

A mixture of 3-[2-chloro-5-(trifluoromethyl)pyrimidin-4-yl]-1-(2-trimethylsilylethoxymethyl)indole-6-carbonitrile (0.5 g, 1.10 mmol, 1 eq), tert-butyl (3S)-3-aminopiperidine-1-carboxylate (287.42 mg, 1.44 mmol, 1.3 eq) and DIEA (428.01 mg, 3.31 mmol, 576.83 μL, 3 eq) in NMP (5 mL) was stirred at 140° C. for 1 h. The reaction mixture was diluted with H₂O (80 mL) and extracted with EtOAc (30 mL×2). The combined organic layers were washed with brine (100 mL×2), dried over Na₂SO₄, filtered and concentrated. The residue was purified by column chromatography (SiO₂, PE:EtOAc=10:1 to 2:1) to afford the title compound (0.63 g, 817.19 umol, 74.03% yield, 80% purity) as a yellow oil.

Step 4: Tert-butyl (3S)-3-[[4-[6-[(Z)—N'-hydroxycarbamimidoyl]-1-(2-trimethylsilylethoxymethyl)indol-3-yl]-5-(trifluoromethyl)pyrimidin-2-yl]amino]piperidine-1-carboxylate

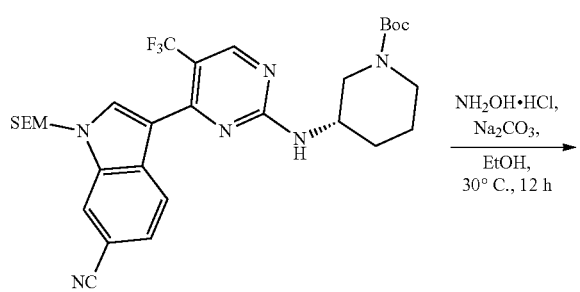

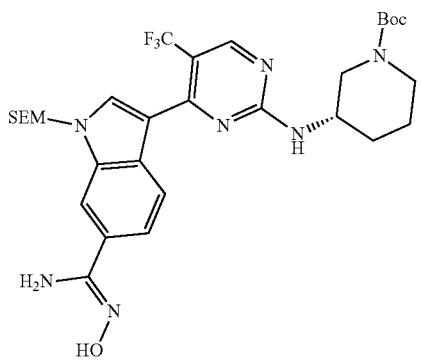

To a solution of tert-butyl (3S)-3-[[4-[6-cyano-1-(2-trimethylsilylethoxymethyl)indol-3-yl]-5-(trifluoromethyl)pyrimidin-2-yl]amino]piperidine-1-carboxylate (0.5 g, 810.70 µmol, 1 eq) in EtOH (5 mL) was added hydroxylamine hydrochloride (563.36 mg, 8.11 mmol, 10 eq), $Na_2CO_3$ (687.41 mg, 6.49 mmol, 8 eq) and the mixture was stirred at 30° C. for 12 h. The reaction mixture was diluted with $H_2O$ (50 mL) and extracted with EtOAc (30 mL×3). The combined organic layers were washed with brine (50 mL×2), dried over $Na_2SO_4$, filtered and concentrated under reduced pressure to afford the title compound (0.56 g, crude) as a yellow solid.

Step 5: Tert-butyl (3S)-3-[[4-[6-(5-methyl-1,2,4-oxadiazol-3-yl)-1-(2-trimethylsilylethoxymethyl)indol-3-yl]-5-(trifluoromethyl)pyrimidin-2-yl]amino]piperidine-1-carboxylate

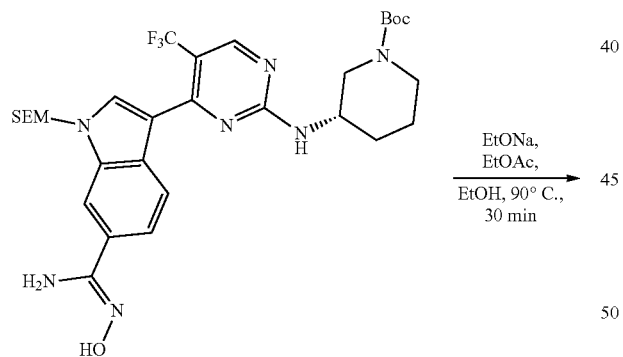

To a solution of tert-butyl (3S)-3-[[4-[6-[(Z)—N'-hydroxycarbamimidoyl]-1-(2-trimethylsilylethoxymethyl)indol-3-yl]-5-(trifluoromethyl)pyrimidin-2-yl]amino]piperidine-1-carboxylate (0.5 g, 769.49 µmol, 1 eq) in EtOH (6 mL) and EtOAc (2 mL) was added EtONa (104.73 mg, 1.54 mmol, 2 eq). The mixture was stirred at 90° C. for 30 min. The reaction mixture was concentrated to give a residue. The residue was purified by column chromatography ($SiO_2$, Petroleum ether/Ethyl acetate=5:1 to 2:1) to afford the title compound (300 mg) as a yellow oil. (The reaction was combined with another reaction in 80 mg scale for purification.)

Step 6: 4-[6-(5-methyl-1,2,4-oxadiazol-3-yl)-1H-indol-3-yl]-N-[(3S)-3-piperidyl]-5-(trifluoromethyl)pyrimidin-2-amine

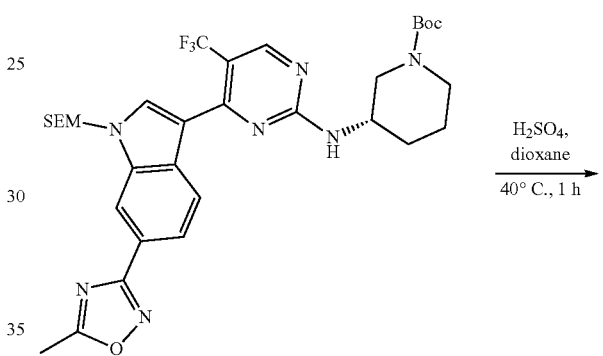

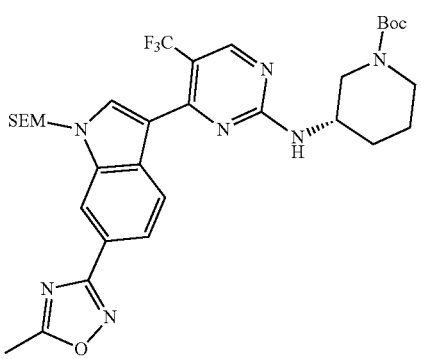

A mixture of tert-butyl (3S)-3-[[4-[6-(5-methyl-1,2,4-oxadiazol-3-yl)-1-(2-trimethylsilylethoxymethyl)indol-3-yl]-5-(trifluoromethyl)pyrimidin-2-yl]amino]piperidine-1-carboxylate (0.25 g, 371.03 µmol, 1 eq) and $H_2SO_4$ (363.91 mg, 3.71 mmol, 197.78 µL, 10 eq) in dioxane (5 mL) was stirred at 40° C. for 1 h. The mixture was adjusted pH to 8 with saturated aqueous $Na_2CO_3$ and stirred at 20° C. for 20 min. Then the aqueous was extracted with EtOAc (20 mL×3). The combined organic layers were washed with brine (30 mL×2), dried over $Na_2SO_4$, filtered and concentrated under reduced pressure to give a residue. The residue was purified by prep-HPLC (FA condition) to afford title compound (50.7 mg, FA) as a white solid.

Example 28. Synthesis of Benzyl (3S,5R)-3-amino-5-methoxy-piperidine-1-carboxylate Useful in the Synthesis of Compound 131

Step 1: benzyl (3S,5R)-3-(tert-butoxycarbonylamino)-5-methoxy-piperidine-1-carboxylate

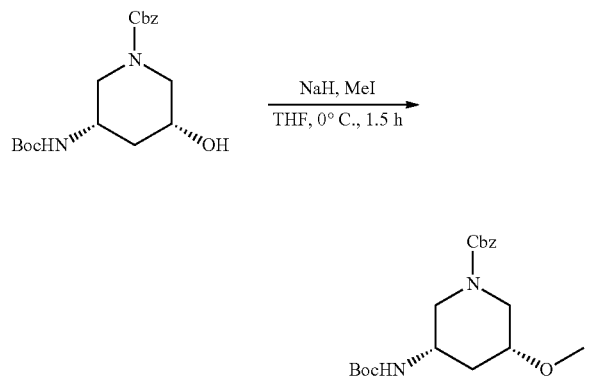

A benzyl (3S,5R)-3-(tert-butoxycarbonylamino)-5-hydroxy-piperidine-1-carboxylate (500 mg, 1.43 mmol, 1 eq) in THF (5 mL) was added NaH (74.19 mg, 1.85 mmol, 60% purity, 1.3 eq) at 0° C. The mixture was stirred at 0° C. for 0.5 h. Then MeI (222.79 mg, 1.57 mmol, 97.71 μL, 1.1 eq) was added. The mixture was stirred for another 1 h at 15° C. It was poured into water (15 mL) and extracted with EtOAc (25 mL×3). The combined organic layer was washed with brine (25 mL×3), dried over $Na_2SO_4$, filtered. The filtrate was concentrated under reduced pressure to give a residue. The residue was purified by MPLC ($SiO_2$, PE:EtOAc=4/1 to 1/1) to afford the title compound (450 mg, 987.83 μmol, 69.23% yield, 80% purity) as brown solid.

Step 2: benzyl (3S,5R)-3-amino-5-methoxy-piperidine-1-carboxylate

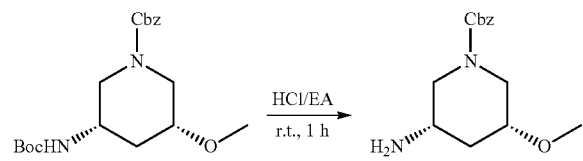

A solution of benzyl (3S,5R)-3-(tert-butoxycarbonylamino)-5-methoxy-piperidine-1-carboxylate (450 mg, 1.23 mmol, 1 eq) in HCl/EtOAc (50 mL) was stirred at 15° C. for 1 h. The reaction mixture was concentrated in vacuum, the residue was dissolved into MeOH (15 mL) and adjusted pH to 9 by Amberlyst 21 to afford the title compound (350 mg, crude) as brown solid. It will be used next step without further purification.

Example 29. Synthesis of (3R,5S)-5-[[4-[6-(3,5-dimethylisoxazol-4-yl)-1H-pyrrolo[2,3-b]pyridin-3-yl]-5-(trifluoromethyl)pyrimidin-2-yl]amino]piperidin-3-ol (Compound 133)

Step 1: (3R,5S)-5-[[4-[1-(benzenesulfonyl)-6-(3,5-dimethylisoxazol-4-yl)pyrrolo[2,3-b]pyridin-3-yl]-5-(trifluoromethyl)pyrimidin-2-yl]amino]-1-benzyl-piperidin-3-ol

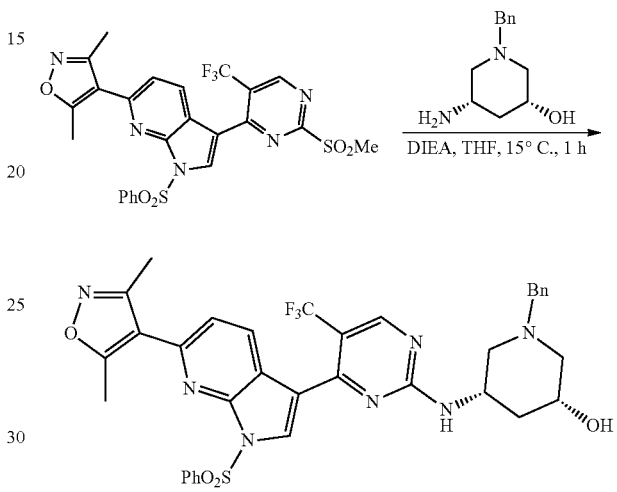

A mixture of 4-[1-(benzenesulfonyl)-3-[2-methylsulfonyl-5-(trifluoromethyl)pyrimidin-4-yl]pyrrolo[2,3-b]pyridin-6-yl]-3,5-dimethyl-isoxazole (280 mg, 484.80 umol, 1 eq), (3R,5S)-5-amino-1-benzyl-piperidin-3-ol (130.01 mg, 630.24 umol, 1.3 eq) and DIEA (313.29 mg, 2.42 mmol, 422.22 uL, 5 eq) in THF (3 mL) was stirred at 15° C. for 1 h. It was poured into water (10 mL) and extracted with EtOAc (20 mL×3). The combined organic layer was washed with brine (20 mL×3), dried over $Na_2SO_4$, filtered. The filtrate was concentrated under reduced pressure. The residue was purified by MPLC ($SiO_2$, PE/EtOAc=3/1 to 1/1) to afford the title compound (170 mg, 94% purity) as brown solid.

(Note: The reaction was combined with another reaction in 20 mg scale for work up)

Step 2: tert-butyl (3S,5R)-3-[[4-[1-(benzenesulfonyl)-6-(3,5-dimethylisoxazol-4-yl)pyrrolo[2,3-b]pyridin-3-yl]-5-(trifluoromethyl)pyrimidin-2-yl]amino]-5-hydroxy-piperidine-1-carboxylate

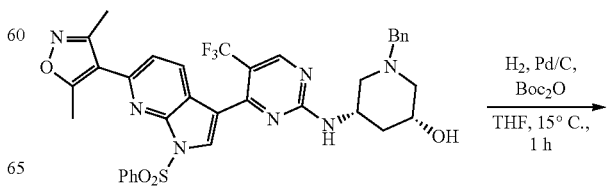

-continued

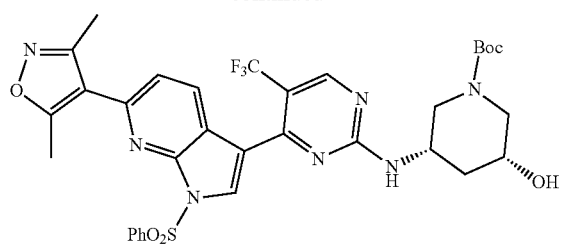

To a solution of (3R,5S)-5-[[4-[1-(benzenesulfonyl)-6-(3,5-dimethylisoxazol-4-yl)pyrrolo[2,3-b]pyridin-3-yl]-5-(trifluoromethyl)pyrimidin-2-yl]amino]-1-benzyl-piperidin-3-ol (150 mg, 213.15 umol, 1 eq) and Boc$_2$O (69.78 mg, 319.72 umol, 73.45 uL, 1.5 eq) in THF (2 mL) was added Pd/C (20 mg, 10% purity) under N$_2$. The suspension was degassed under vacuum and purged with H$_2$ several times. It was stirred under H$_2$ (15 psi) at 15° C. for 1 h. Then the mixture was filtered though a pad of celite. The filtrate was concentrated under reduced pressure to give a residue. It was purified by MPLC (SiO$_2$, PE/EtOAc=4/1 to 1/1) to afford the title compound (100 mg) as yellow solid. (Note: The reaction was combined with another reaction in 20 mg scale for work up).

Step 3: tert-butyl (3S,5R)-3-[[4-[6-(3,5-dimethylisoxazol-4-yl)-1H-pyrrolo[2,3-b]pyridin-3-yl]-5-(trifluoromethyl)pyrimidin-2-yl]amino]-5-hydroxy-piperidine-1-carboxylate

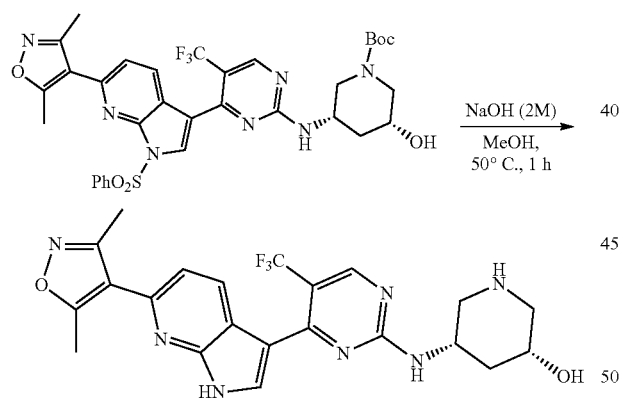

A mixture of tert-butyl (3S,5R)-3-[[4-[1-(benzenesulfonyl)-6-(3,5-dimethylisoxazol-4-yl)pyrrolo[2,3-b]pyridin-3-yl]-5-(trifluoromethyl)pyrimidin-2-yl]amino]-5-hydroxy-piperidine-1-carboxylate (75 mg, 105.08 umol, 1 eq) and NaOH (2 M, 262.71 uL, 5 eq) in MeOH (0.2 mL) was stirred at 50° C. for 1 h and then cooled to the room temperature. It was poured into the water (10 mL), and extracted with EtOAc (20 mL×3). The combined organic layer was washed with brine (20 mL×3), dried over Na$_2$SO$_4$, filtered. The filtrate was concentrated under reduced pressure to afford the title compound (70 mg, crude) as brown solid which was used in next step without further purification (Note: The reaction was combined with another reaction in 10 mg scale for work up)

Step 4: (3R,5S)-5-[[4-[6-(3,5-dimethylisoxazol-4-yl)-1H-pyrrolo[2,3-b]pyridin-3-yl]-5-(trifluoromethyl)pyrimidin-2-yl]amino]piperidin-3-ol

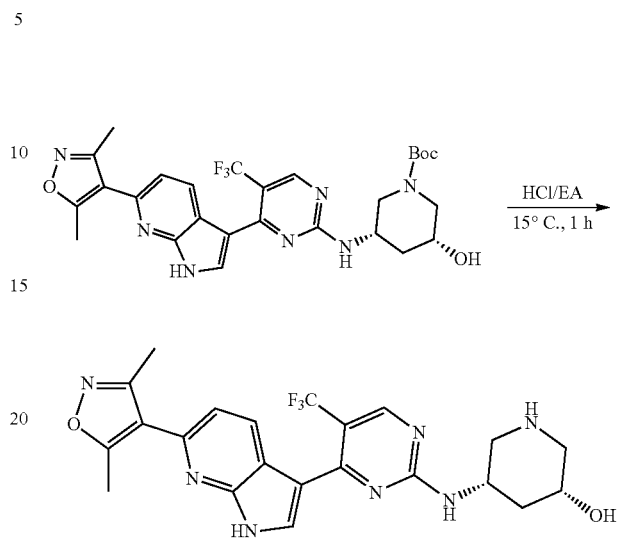

A solution of tert-butyl (3S,5R)-3-[[4-[6-(3,5-dimethylisoxazol-4-yl)-1H-pyrrolo[2,3-b]pyridin-3-yl]-5-(trifluoromethyl)pyrimidin-2-yl]amino]-5-hydroxy-piperidine-1-carboxylate (50 mg, 87.17 umol, 1 eq) in HCl/EtOAc (5 mL) was stirred at 15° C. for 1 h. It was concentrated. The crude product was purified by prep-HPLC (HCl condition) to afford the title compound (10 mg, 95.1% purity, HCl, 100% ee) as yellow solid.

(Note: The reaction was combined with another reaction in 20 mg scale for work up)

Example 30. Synthesis of 4-[6-(3-methyl-1,2,4-oxadiazol-5-yl)-1H-pyrrolo[2,3-b]pyridin-3-yl]-N-[(3S)-3-piperidyl]-5-(trifluoromethyl)pyrimidin-2-amine (Compound 136)

Step 1: 1H-pyrrolo[2,3-b]pyridine-6-carboxylic Acid

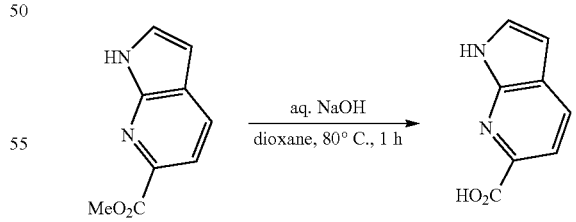

To a solution of ethyl 1H-pyrrolo[2,3-b]pyridine-6-carboxylate (4.3 g, 22.61 mmol, 1 eq) in dioxane (40 mL) was added NaOH (2 M, 50 mL, 4.42 eq). The mixture was stirred at 80° C. for 1 h. The solution was concentrated under reduced pressure to remove dioxane and water. The residue was diluted with H$_2$O (50 mL) and adjusted pH to 2 with HCl (1M), with a lot of solid production, filtered to afford the title compound (3.5 g, crude) as a yellow solid.

Step 2: N-[(E)-N-hydroxy-C-methyl-carbonimi-doyl]-1H-pyrrolo[2,3-b]pyridine-6-carboxamide

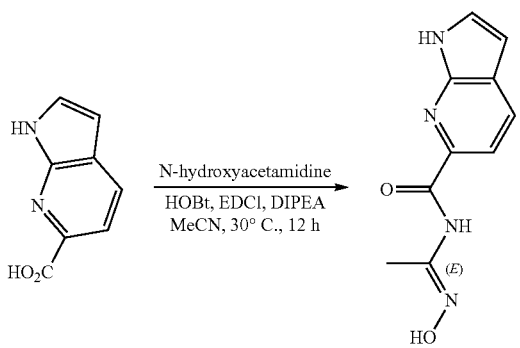 [SMILES: O=C(O)c1ccc2cc[nH]c2n1 ; C/C(=N\O)NC(=O)c1ccc2cc[nH]c2n1]

To a solution of 1H-pyrrolo[2,3-b]pyridine-6-carboxylic acid (1 g, 6.17 mmol, 1 eq) in MeCN (10 mL) was added HOBt (1.67 g, 12.33 mmol, 2 eq), EDCI (2.36 g, 12.33 mmol, 2 eq), N-hydroxyacetamidine (913.77 mg, 12.33 mmol, 2 eq), and DIPEA (3.99 g, 30.84 mmol, 5.37 mL, 5 eq). The mixture was stirred at 30° C. for 12 h. Then it was concentrated under reduced pressure to afford the title compound (1.5 g, crude) as white solid which was used directly without further purification.

Step 3: 3-methyl-5-(1H-pyrrolo[2,3-b]pyridin-6-yl)-1,2,4-oxadiazole

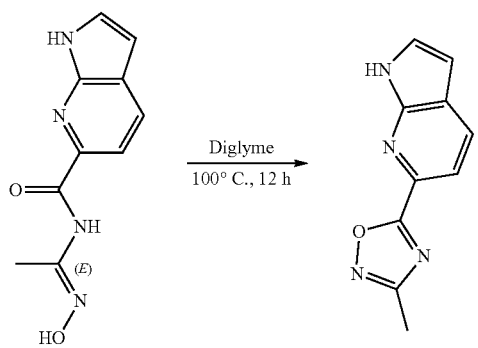 [SMILES: C/C(=N\O)NC(=O)c1ccc2cc[nH]c2n1 ; Cc1noc(-c2ccc3cc[nH]c3n2)n1]

A solution of N-[(E)-N-hydroxy-C-methyl-carbonimi-doyl]-1H-pyrrolo[2,3-b]pyridine-6-carboxamide (1.5 g, 6.87 mmol, 1 eq) in Diglyme (20 mL) was stirred at 100° C. for 12 h. The reaction mixture was poured into water (200 mL) and the solid was formed. It was filtered to afford the title compound (0.4 g, crude) as brown solid.

Step 4: 5-(3-bromo-1H-pyrrolo[2,3-b]pyridin-6-yl)-3-methyl-1,2,4-oxadiazole

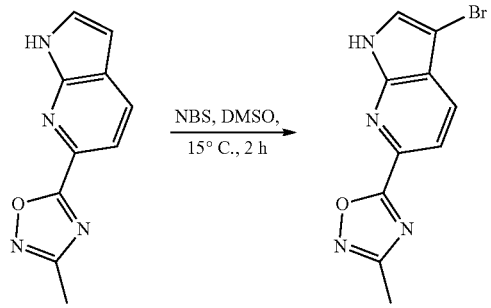 [SMILES: Cc1noc(-c2ccc3cc[nH]c3n2)n1 ; Cc1noc(-c2ccc3c(Br)c[nH]c3n2)n1]

To a solution of 3-methyl-5-(1H-pyrrolo[2,3-b]pyridin-6-yl)-1,2,4-oxadiazole (0.4 g, 2.00 mmol, 1 eq) in DMSO (dimethylsulfoxide; 4 mL) was added NBS (391.18 mg, 2.20 mmol, 1.1 eq). The mixture was stirred at 15° C. for 2 h. It was diluted with H₂O (30 mL), with a lot of solid formed. It was filtered to afford the title compound (480 mg, crude) as brown solid.

Step 5: 5-[1-(benzenesulfonyl)-3-bromo-pyrrolo[2,3-b]pyridin-6-yl]-3-methyl-1,2,4-oxadiazole

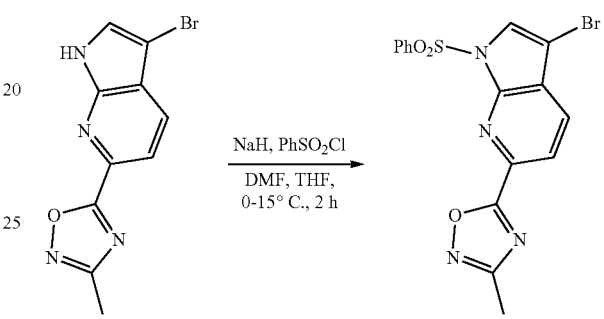

To a solution of 5-(3-bromo-1H-pyrrolo[2,3-b]pyridin-6-yl)-3-methyl-1,2,4-oxadiazole (675 mg, 2.42 mmol, 1 eq) in DMF (7 mL) was added NaH (125.76 mg, 3.14 mmol, 60% purity, 1.3 eq). The mixture was stirred at 0° C. for 0.5 h. Then the benzenesulfonyl chloride (640.75 mg, 3.63 mmol, 464.31 uL, 1.5 eq) was added, the resulting mixture was stirred at 15° C. for 1.5 h. Then it was quenched by addition water (40 mL), with a lot of solid formed, and then it was filtered to afford the crude product. The crude product was purified by column chromatography (SiO₂, EtOAc) to afford the title compound (480 mg, 801.43 umol, 33% yield, 70% purity) as an orange solid.

Step 6: 5-[1-(benzenesulfonyl)-3-(4, 4,5, 5-tetramethyl-1,3,2-dioxaborolan-2-yl) pyrrolo[2,3-b]pyridin-6-yl]-3-methyl-1,2,4-oxadiazole

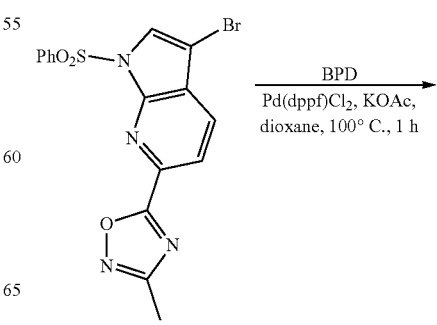

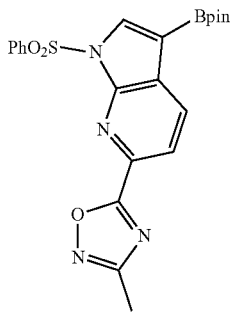

A mixture of 5-[1-(benzenesulfonyl)-3-bromo-pyrrolo[2,3-b]pyridin-6-yl]-3-methyl-1,2,4-oxadiazole (410 mg, 977.93 umol, 1 eq), BPD (372.50 mg, 1.47 mmol, 1.5 eq), KOAc (191.95 mg, 1.96 mmol, 2 eq), Pd(dppf)Cl₂ (107.33 mg, 146.69 umol, 0.15 eq) in dioxane (4 mL) was degassed and purged with N₂ for 5 times, and then the mixture was stirred at 100° C. for 1 h under N₂ atmosphere. The solution was diluted with H₂O (25 mL) and extracted with EtOAc (15 mL×3). The combined organic layers were washed with brine (45 mL), dried over Na₂SO₄, filtered and concentrated under reduced pressure to give a residue. The residue was purified by column chromatography (SiO₂, PE/EtOAc=10/1 to 5/1) to afford the title compound (240 mg, 411.74 umol, 42% yield, 80% purity) as a yellow solid.

Step 7: Tert-butyl (3S)-3-[[4-[1-(benzenesulfonyl)-6-(3-methyl-1,2,4-oxadiazol-5-yl) pyrrolo[2,3-b]pyridin-3-yl]-5-(trifluoromethyl)pyrimidin-2-yl]amino]piperidine-1-carboxylate

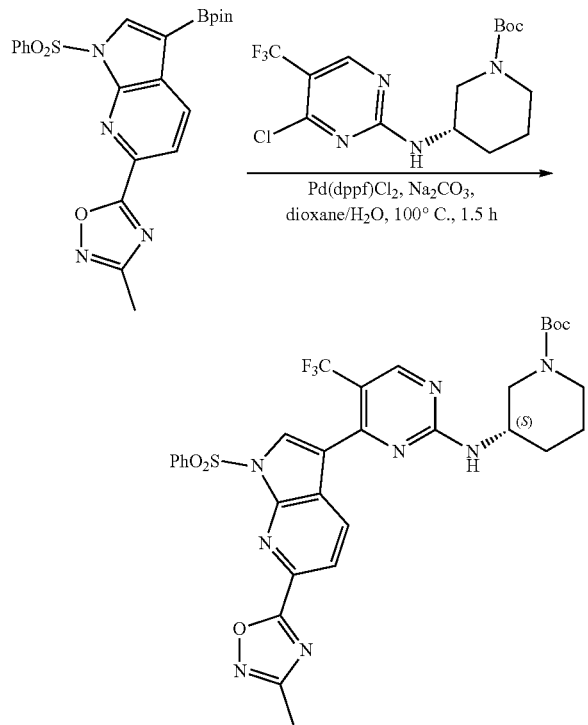

A mixture of 5-[1-(benzenesulfonyl)-3-(4, 4, 5, 5-tetramethyl-1, 3, 2-dioxaborolan-2-yl)pyrrolo[2,3-b]pyridin-6-yl]-3-methyl-1,2,4-oxadiazole (240 mg, 411.74 umol, 1 eq), tert-butyl (3S)-3-[[4-chloro-5-(trifluoromethyl)pyrimidin-2-yl]amino]piperidine-1-carboxylate (172.46 mg, 452.91 umol, 1.1 eq), Na₂CO₃ (87.28 mg, 823.47 umol, 2 eq), Pd(dppf)Cl₂ (45.19 mg, 61.76 umol, 0.15 eq) in dioxane (2.5 mL) and H₂O (0.5 mL) was degassed and purged with N₂ for 3 times, and then the mixture was stirred at 100° C. for 1.5 h under N₂ atmosphere. The solution was concentrated under reduced pressure to remove dioxane. The residue was diluted with H₂O (30 mL) and extracted with EtOAc (15 mL×2). The combined organic layers were washed with brine (30 mL), dried over Na₂SO₄, filtered and concentrated under reduced pressure to give a residue. The residue was purified by column chromatography (SiO₂, PE/EtOAc=3/1 to 1/1) to afford the title compound (340 mg, 70% purity) as yellow solid.

Step 8: Tert-butyl (3S)-3-[[4-[6-(3-methyl-1,2,4-oxadiazol-5-yl)-1H-pyrrolo[2,3-b]pyridin-3-yl]-5-(trifluoromethyl)pyrimidin-2-yl]amino]piperidine-1-carboxylate

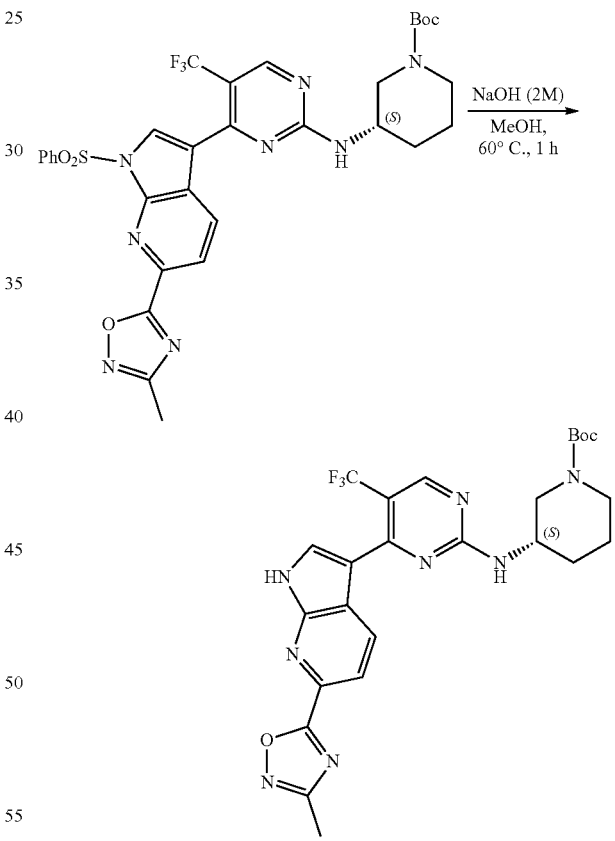

To a solution of tert-butyl (3S)-3-[[4-[1-(benzenesulfonyl)-6-(3-methyl-1,2,4-oxadiazol-5-yl)pyrrolo[2,3-b]pyridin-3-yl]-5-(trifluoromethyl)pyrimidin-2-yl]amino]piperidine-1-carboxylate (80 mg, 116.84 umol, 1 eq) in MeOH (2.5 mL) was added NaOH (2 M, 292.10 uL, 5 eq). The mixture was stirred at 60° C. for 1 h. The solution was concentrated under reduced pressure to remove MeOH. The residue was diluted with H₂O (15 mL) and adjusted pH to 7 by added HCl (1M), then extracted with EtOAc (15 mL×2). The combined organic layers were washed with brine (30 mL), dried over Na₂SO₄, filtered and concentrated under reduced pressure to afford the crude product (80 mg, crude) as yellow solid.

Step 9: 4-[6-(3-methyl-1,2,4-oxadiazol-5-yl)-1H-pyrrolo[2,3-b]pyridin-3-yl]-N-[(3S)-3-piperidyl]-5-(trifluoromethyl)pyrimidin-2-amine

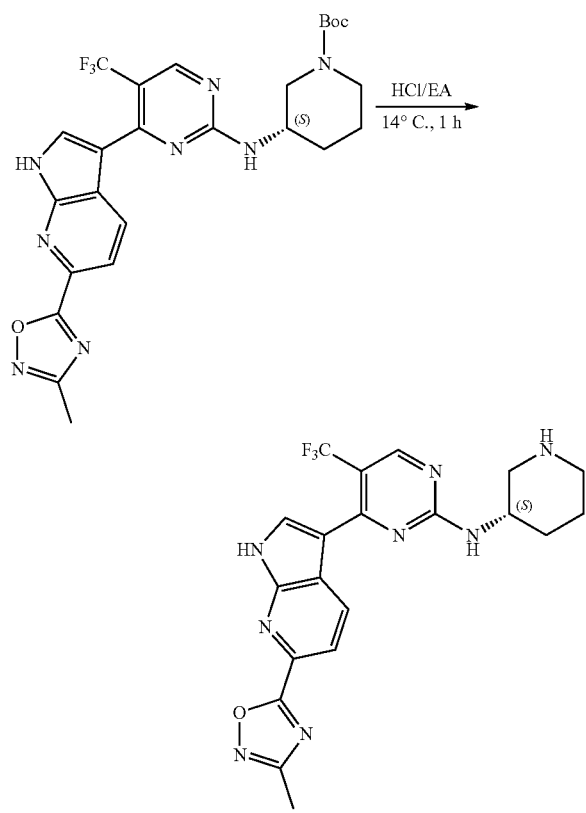

To a solution of tert-butyl (3S)-3-[[4-[6-(3-methyl-1,2,4-oxadiazol-5-yl)-1H-pyrrolo[2,3-b]pyridin-3-yl]-5-(trifluoromethyl)pyrimidin-2-yl]amino]piperidine-1-carboxylate (60 mg, 110.19 umol, 1 eq) in EtOAc (0.5 mL) was added HCl/EtOAc (4 M, 1 mL, 36.30 eq). The mixture was stirred at 14° C. for 1 h. The solution was concentrated under reduced pressure to give a residue. The residue was purified by prep-HPLC (FA condition) to afford the title compound (27.3 mg, FA, 99% purity) as white solid.

Example 31. Synthesis of N-[(3S)-5, 5-dimethyl-3-piperidyl]-4-(6-thiazol-2-yl-1H-pyrrolo[2,3-b]pyridin-3-yl)-5-(trifluoromethyl)pyrimidin-2-amine (Compound 137)

Step 1: 2-[1-(benzenesulfonyl)pyrrolo[2,3-b]pyridin-6-yl]thiazole

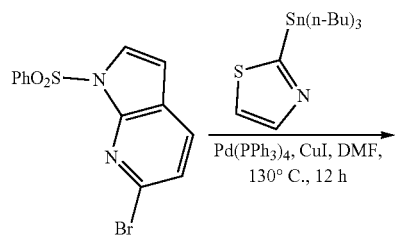

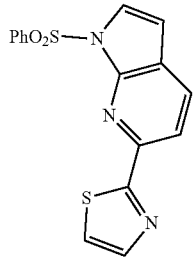

A mixture of 1-(benzenesulfonyl)-6-bromo-pyrrolo[2,3-b]pyridine (3.1 g, 9.19 mmol, 1 eq), tributyl(thiazol-2-yl)stannane (3.78 g, 10.11 mmol, 1.1 eq), CuI (175.09 mg, 919.36 umol, 0.1 eq) and Pd(PPh₃)₄ (1.06 g, 919.36 umol, 0.1 eq) in DMF (30 mL) was degassed and purged with N₂ for 3 times, and then the mixture was stirred at 130° C. for 12 h under N₂ atmosphere. The mixture was poured into water (300 mL) and EtOAc (200 mL), and filtered to remove the CuI.

The organic layers were separated, washed with brine (150 mL), dried over Na₂SO₄ and concentrated to give a residue. It was suspended in MeOH (20 mL), and stirred 10 min at room temperature and filtered. The filter cake was collected and dried to dryness to afford the title compound (2 g, 5.27 mmol, 57% yield, 90% purity) as a brown solid.

Step 2: 2-[1-(benzenesulfonyl)-3-bromo-pyrrolo[2,3-b]pyridin-6-yl]thiazole

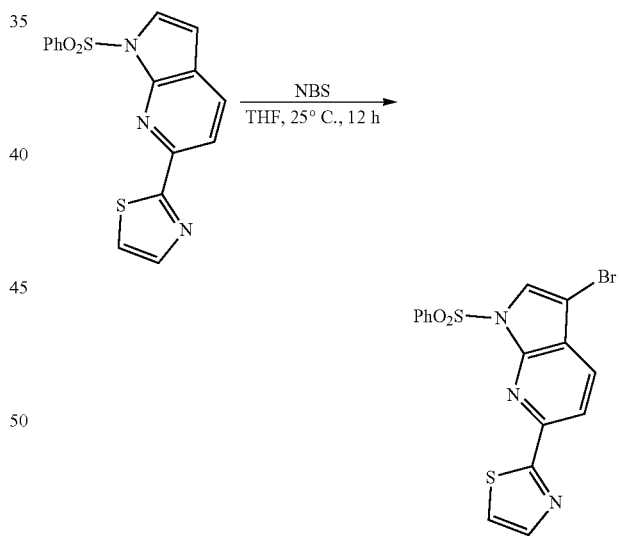

To a solution of 2-[1-(benzenesulfonyl)pyrrolo[2,3-b]pyridin-6-yl]thiazole (1.8 g, 5.27 mmol, 1 eq) in THF (18 mL) was added NBS (0.94 g, 5.27 mmol, 1 eq). The mixture was stirred at 25° C. for 12 h under N₂ atmosphere. The mixture was poured into water (80 mL) and extracted with EtOAc (30 mL×2). The organic layers were separated, washed with brine (150 mL), dried over Na₂SO₄ and concentrated to give a residue. The residue was purified by column chromatography (SiO₂, Petroleum ether/Ethyl acetate=10/1 to 3/1) to afford the title compound (1.5 g) as a yellow solid.

Step 3: 2-[1-(benzenesulfonyl)-3-(4,4,5,5-tetramethyl-1,3,2-dioxaborolan-2-yl)pyrrolo[2,3-b]pyridin-6-yl]thiazole

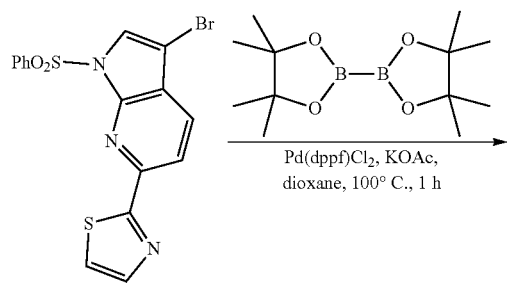

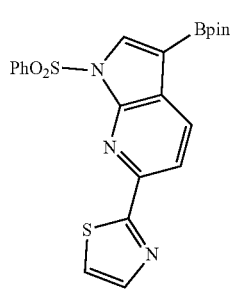

A mixture of 2-[1-(benzenesulfonyl)-3-bromo-pyrrolo[2,3-b]pyridin-6-yl]thiazole (0.95 g, 2.26 mmol, 1 eq), 4,4,5,5-tetramethyl-2-(4,4,5,5-tetramethyl-1,3,2-dioxaborolan-2-yl)-1,3,2-dioxaborolane (1.15 g, 4.52 mmol, 2 eq), Pd(dppf)Cl$_2$ (165.39 mg, 226.03 umol, 0.1 eq) and KOAc (443.65 mg, 4.52 mmol, 2 eq) in dioxane (10 mL) was degassed and purged with N$_2$ for 3 times, and then the mixture was stirred at 100° C. for 2 h under N$_2$ atmosphere. The mixture was poured into water (50 mL) and extracted with EtOAc (20 mL×2). The organic layers were separated, washed with brine (150 mL), dried over Na$_2$SO$_4$ and concentrated to give a residue. It was purified by column chromatography (SiO$_2$, Petroleum ether/Ethyl acetate=10/1 to 4/1) to afford the title compound (0.63 g, 1.15 mmol, 50% yield, 85% purity) as a yellow solid.

Step 4: 2-[1-(benzenesulfonyl)-3-[2-methylsulfanyl-5-(trifluoromethyl)pyrimidin-4-yl]pyrrolo[2,3-b]pyridin-6-yl]thiazole

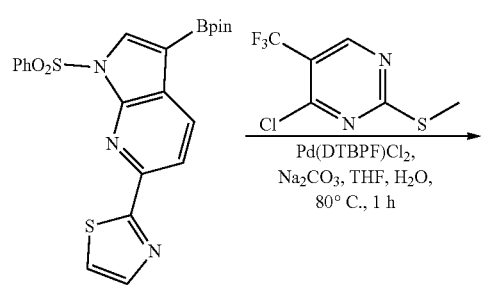

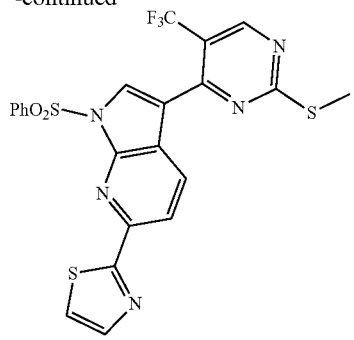

A mixture of 2-[1-(benzenesulfonyl)-3-(4,4,5,5-tetramethyl-1,3,2-dioxaborolan-2-yl) pyrrolo[2,3-b]pyridin-6-yl]thiazole (0.05 M, 26.96 mL, 1 eq), 4-chloro-2-methylsulfanyl-5-(trifluoromethyl)pyrimidine (462.27 mg, 2.02 mmol, 1.5 eq), Na$_2$CO$_3$ (285.74 mg, 2.70 mmol, 2 eq) and ditert-butyl(cyclopentyl)phosphane:dichloropalladium:iron (87.85 mg, 134.80 umol, 0.1 eq) in THF (20 mL) and H$_2$O (2 mL) was degassed and purged with N$_2$ for 3 times, and then the mixture was stirred at 80° C. for 1 h under N$_2$ atmosphere. The reaction mixture was diluted with addition H$_2$O (100 mL), and extracted with EtOAc (50 mL×3), dried over Na$_2$SO$_4$, filtered and concentrated under reduced pressure to give a residue. The residue was purified by column chromatography (SiO$_2$, Petroleum ether/Ethyl acetate=10/1 to 3/1) to afford the title compound (300 mg) as a yellow solid.

(Note: The reaction was combined with another reaction in 50 mg scale for work up)

Step 5: 2-[1-(benzenesulfonyl)-3-[2-methylsulfonyl-5-(trifluoromethyl)pyrimidin-4-yl]pyrrolo[2,3-b]pyridin-6-yl]thiazole

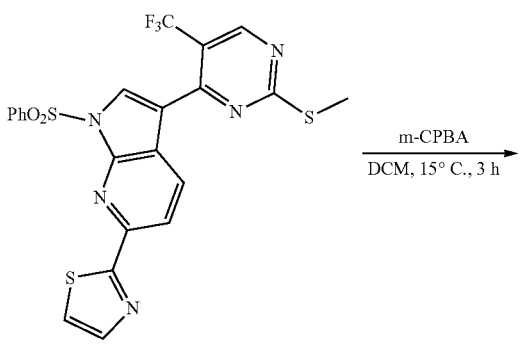

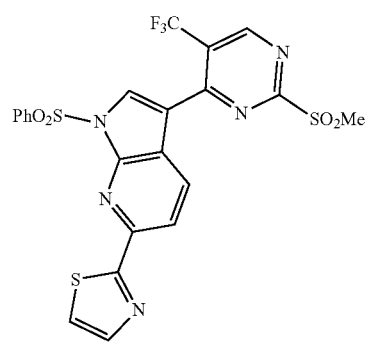

A mixture of 2-[1-(benzenesulfonyl)-3-[2-methylsulfanyl-5-(trifluoromethyl)pyrimidin-4-yl]pyrrolo[2,3-b]pyridin-6-yl]thiazole (0.28 g, 524.77 umol, 1 eq) and m-CPBA (266.35 mg, 1.31 mmol, 85% purity, 2.5 eq) in DCM (3 mL) was stirred at 15° C. for 3 h. The solution was washed with sat.Na$_2$SO$_3$ (30 mL), Sat.NaHCO$_3$ (30 mL) and brine (50 mL). The organic layers were dried over Na$_2$SO$_4$ and concentrated. The residue was washed with PE/EtOAc=3/1 (4 mL), and filtered to afford the title compound (180 mg) as a yellow solid.

(Note: The reaction was combined with another reaction in 20 mg scale for work up).

Step 6: Tert-butyl (5S)-5-[[4-[1-(benzenesulfonyl)-6-thiazol-2-yl-pyrrolo[2,3-b]pyridin-3-yl]-5-(trifluoromethyl)pyrimidin-2-yl]amino]-3,3-dimethyl-piperidine-1-carboxylate

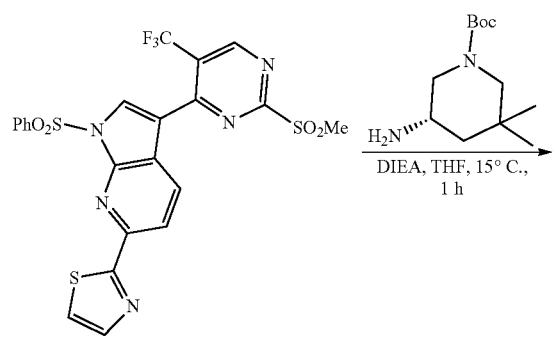

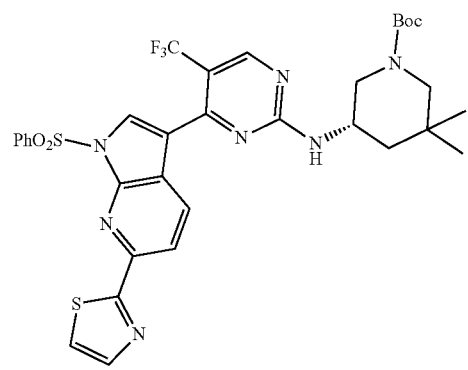

A mixture of 2-[1-(benzenesulfonyl)-3-[2-methylsulfonyl-5-(trifluoromethyl)pyrimidin-4-yl]pyrrolo[2,3-b]pyridin-6-yl]thiazole (0.16 g, 282.90 umol, 1 eq), tert-butyl (5S)-5-amino-3,3-dimethyl-piperidine-1-carboxylate (96.89 mg, 424.35 umol, 1.5 eq) and DIEA (109.69 mg, 848.71 umol, 147.83 uL, 3 eq) in THF (2 mL) was stirred at 15° C. for 1 h. The reaction mixture was concentrated to afford the title compound (300 mg) as a yellow solid.

(Note: The reaction was combined with another reaction in 10 mg scale for work up)

Step 7: Tert-butyl (5S)-3,3-dimethyl-5-[[4-(6-thiazol-2-yl-1H-pyrrolo[2,3-b]pyridin-3-yl)-5-(trifluoromethyl)pyrimidin-2-yl]amino]piperidine-1-carboxylate

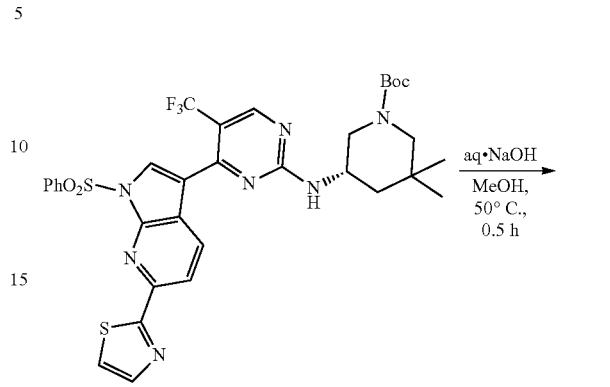

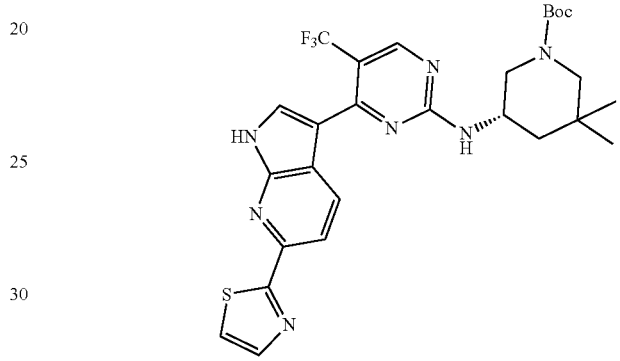

A mixture of tert-butyl (5S)-5-[[4-[1-(benzenesulfonyl)-6-thiazol-2-yl-pyrrolo[2,3-b]pyridin-3-yl]-5-(trifluoromethyl)pyrimidin-2-yl]amino]-3,3-dimethyl-piperidine-1-carboxylate (0.25 g, 350.24 umol, 1 eq) and NaOH (2 M, 1.75 mL, 10 eq) in MeOH (3 mL) was stirred at 50° C. for 0.5 h. It was diluted with H$_2$O (30 mL) and extracted with EtOAc (15 mL×3). The combined organic layers were washed with brine (30 mL×2), dried over Na$_2$SO$_4$, filtered and concentrated under reduced pressure to give a residue. It was purified by column chromatography (SiO$_2$, Petroleum ether/Ethyl acetate=10/1 to 3/1) to afford the title compound (160 mg) as a yellow solid. (Note: The reaction was combined with another reaction in 50 mg scale for work up.)

Step 8: N-[(3S)-5,5-dimethyl-3-piperidyl]-4-(6-thiazol-2-yl-1H-pyrrolo[2,3-b]pyridin-3-yl)-5-(trifluoromethyl)pyrimidin-2-amine

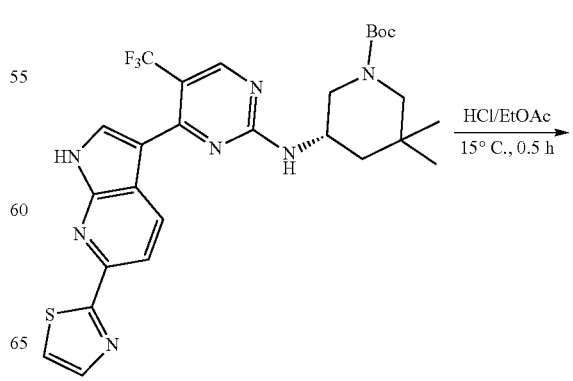

Step 2: 5-methyl-3-(1H-pyrrolo[2,3-b]pyridin-6-yl)-1,2,4-oxadiazole

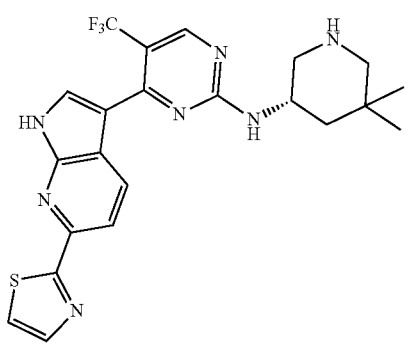

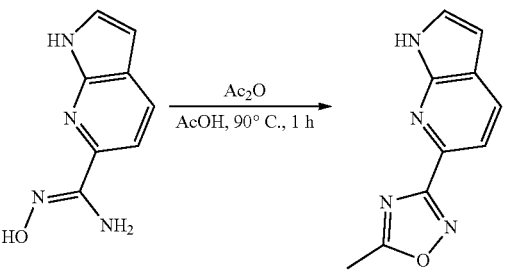

A mixture of tert-butyl (5S)-3,3-dimethyl-5-[[4-(6-thiazol-2-yl-1H-pyrrolo[2,3-b]pyridin-3-yl)-5-(trifluoromethyl)pyrimidin-2-yl]amino]piperidine-1-carboxylate (150 mg, 261.49 umol, 1 eq) and HCl/EtOAc (4 M, 2 mL) was stirred at 15° C. for 0.5 h. The reaction mixture was concentrated to give a residue. The residue was purified by prep-HPLC (HCl condition) to afford the title compound (21.7 mg, HCl) as a yellow solid.

(Note: The reaction was combined with another reaction in 10 mg scale for purification.)

To a solution of N'-hydroxy-1H-pyrrolo[2,3-b]pyridine-6-carboxamidine (1.2 g, 6.81 mmol, 1 eq) in AcOH (12 mL) was added Ac₂O (1.39 g, 13.62 mmol, 1.28 mL, 2 eq). The mixture was stirred at 90° C. for 1 h. The solution was poured into H₂O (100 mL) and the yellow solid was formed. It was filtered and dried to afford the title compound (0.85 g, crude) as yellow solid, which was used into the next step without further purification.

Example 32. Synthesis of 4-[6-(5-methyl-1,2,4-oxadiazol-3-yl)-1H-pyrrolo[2,3-b]pyridin-3-yl]-N-[(3S)-3-piperidyl]-5-(trifluoromethyl)pyrimidin-2-amine (Compound 139)

Step 3: 3-(3-bromo-1H-pyrrolo[2,3-b]pyridin-6-yl)-5-methyl-1,2,4-oxadiazole

Step 1: N'-hydroxy-1H-pyrrolo[2,3-b]pyridine-6-carboxamidine

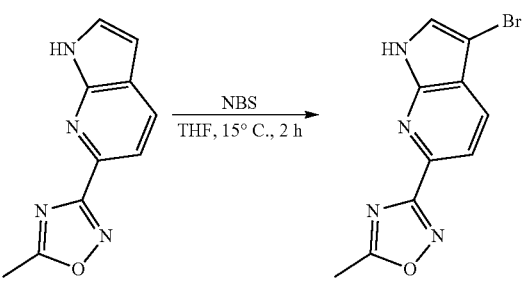

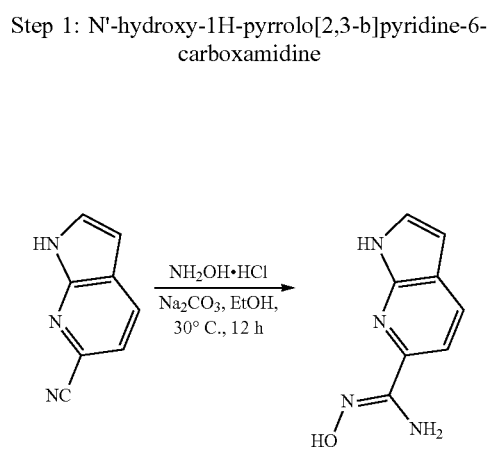

To a solution of 1H-pyrrolo[2,3-b]pyridine-6-carbonitrile (1 g, 6.99 mmol, 1 eq) in EtOH (30 mL) was added NH₂OH.HCl (4.85 g, 69.86 mmol, 10 eq) and Na₂CO₃ (8.89 g, 83.83 mmol, 12 eq). The mixture was stirred at 30° C. for 12 h. The suspension was filtered and concentrated under reduced pressure to afford the title compound (1.3 g, crude) as yellow solid, which was used into the next step without further purification.

To a solution of 5-methyl-3-(1H-pyrrolo[2,3-b]pyridin-6-yl)-1,2,4-oxadiazole (0.8 g, 4.00 mmol, 1 eq) in THF (80 mL) was added NBS (711.24 mg, 4.00 mmol, 1 eq). The mixture was stirred at 15° C. for 2 h. The solution was poured into H₂O (100 mL), while the yellow solid was formed. It was filtered to give a residue. It was purified by column chromatography (SiO₂, PE/EtOAc=1/1 to 0/1) to afford the title compound (0.4 g, 1.15 mmol, 28% yield, 80% purity) as yellow solid.

(Note: The reaction was combined with another reaction in 150 mg scale for work up)

Step 4: 3-[1-(benzenesulfonyl)-3-bromo-pyrrolo[2,3-b]pyridin-6-yl]-5-methyl-1,2,4-oxadiazole

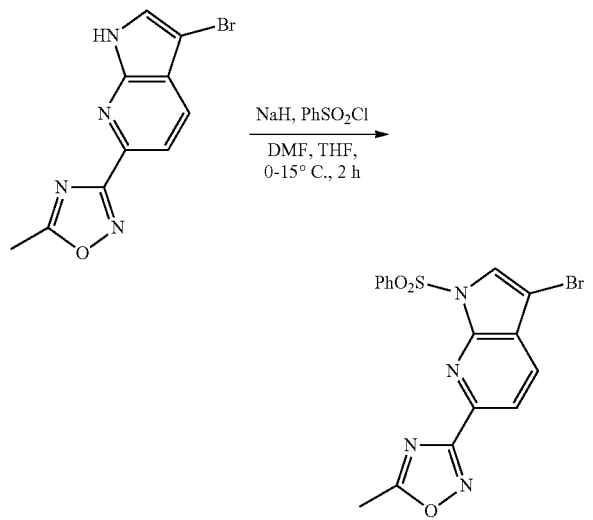

To a solution of 3-(3-bromo-1H-pyrrolo[2,3-b]pyridin-6-yl)-5-methyl-1,2,4-oxadiazole (0.3 g, 1.07 mmol, 1 eq) in DMF (3 mL) was added NaH (64.49 mg, 1.61 mmol, 60% purity, 1.5 eq) at 0° C. The reaction mixture was stirred at 0° C. for 0.5 h. Then the benzenesulfonyl chloride (227.82 mg, 1.29 mmol, 165.09 uL, 1.2 eq) was added to the above mixture, and stirred at 15° C. for another 1.5 h. After the material was converted completely, the solution was poured into H$_2$O (20 mL), while the yellow solid formed. It was filtered to give the crude product. It was purified by column chromatography (SiO$_2$, PE/EtOAc=10/1 to 1/1) to afford the title compound (0.2 g, 429.34 umol, 39% yield, 90% purity) as yellow solid.

Step 5: 3-[1-(benzenesulfonyl)-3-(4,4,5,5-tetramethyl-1,3 2-dioxaborolan-2-yl) pyrrolo[2,3-b]pyridin-6-yl]-5-methyl-1,2,4-oxadiazole

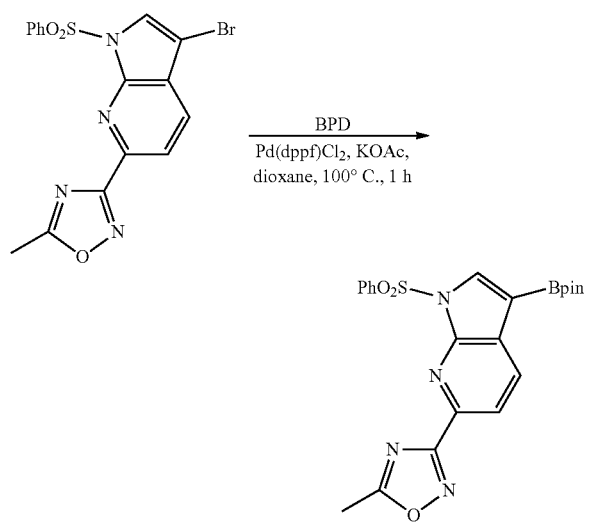

A mixture of 3-[1-(benzenesulfonyl)-3-bromo-pyrrolo[2,3-b]pyridin-6-yl]-5-methyl-1,2,4-oxadiazole (0.2 g, 477.04 umol, 1 eq), BPD (181.71 mg, 715.56 umol, 1.5 eq), Pd(dppf)Cl$_2$ (34.91 mg, 47.70 umol, 0.1 eq), KOAc (93.64 mg, 954.08 umol, 2 eq) in dioxane (2 mL) was degassed and purged with N$_2$ for 3 times, and then the mixture was stirred at 100° C. for 1 h under N$_2$ atmosphere. The solution was poured into H$_2$O (20 mL) and extracted with EtOAc (20 mL×2). The combined organic layers were washed with brine (40 mL×2), dried over Na$_2$SO$_4$, filtered and concentrated under reduced pressure to give a residue. The residue was purified by column chromatography (SiO$_2$, PE/EtOAc=10/1 to 2/1) to afford the title compound (140 mg) as brown solid.

Step 6: Tert-butyl (3S)-3-[[4-[1-(benzenesulfonyl)-6-(5-methyl-1,2,4-oxadiazol-3-yl) pyrrolo[2,3-b]pyridin-3-yl]-5-(trifluoromethyl)pyrimidin-2-yl]amino]piperidine-1-carboxylate

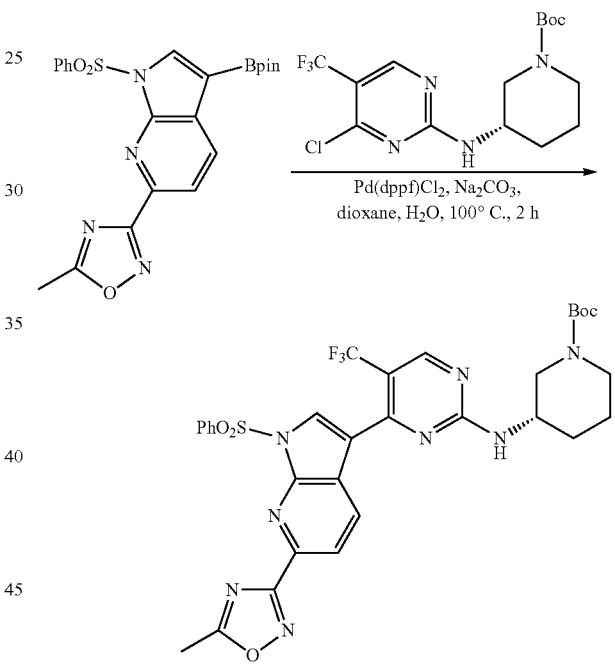

A mixture of 3-[1-(benzenesulfonyl)-3-(4,4,5,5-tetramethyl-1,3,2-dioxaborolan-2-yl) pyrrolo[2,3-b]pyridin-6-yl]-5-methyl-1,2,4-oxadiazole (0.12 g, 257.34 umol, 1 eq), tert-butyl (3S)-3-[[4-chloro-5-(trifluoromethyl)pyrimidin-2-yl]amino]piperidine-1-carboxylate (97.99 mg, 257.34 umol, 1 eq), Pd(dppf)Cl$_2$ (18.83 mg, 25.73 umol, 0.1 eq), Na$_2$CO$_3$ (54.55 mg, 514.67 umol, 2 eq) in dioxane (1.5 mL) and H$_2$O (0.3 mL) was degassed and purged with N$_2$ for 3 times, and then the mixture was stirred at 100° C. for 2 h under N$_2$ atmosphere. The solution was poured into H$_2$O (20 mL), and extracted with EtOAc (20 mL×3). The combined organic layers were washed by brine (60 mL×2), dried over Na$_2$SO$_4$, filtered and concentrated under reduced pressure to give the residue. The residue was purified by column chromatography (SiO$_2$, PE/EtOAc=3/1 to 1/1) to afford the title compound (60 mg) as yellow solid.

(Note: The reaction mixture was combined with another reaction in 20 mg scale for work-up and purification).

115

Step 7: Tert-butyl (3S)-3-[[4-[6-(5-methyl-1,2,4-oxadiazol-3-yl)-1H-pyrrolo[2,3-b]pyridin-3-yl]-5-(trifluoromethyl)pyrimidin-2-yl]amino]piperidine-1-carboxylate

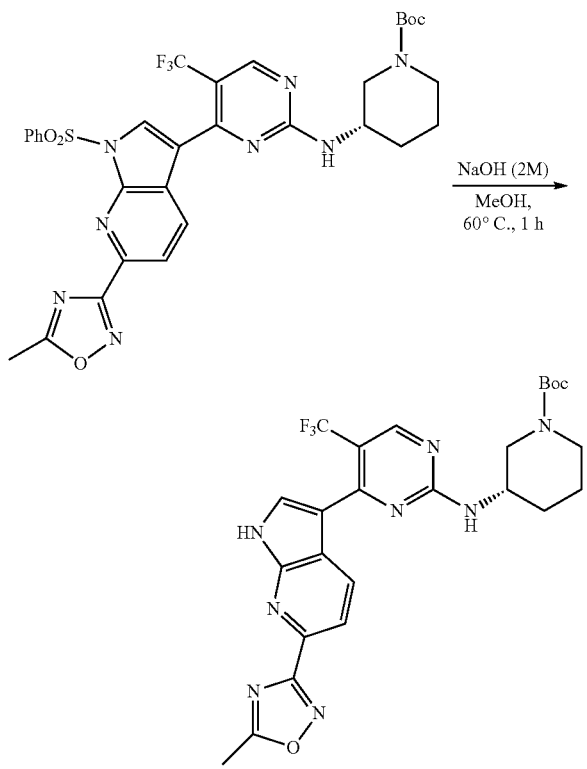

To a solution of tert-butyl (3S)-3-[[4-[1-(benzenesulfonyl)-6-(5-methyl-1,2,4-oxadiazol-3-yl)pyrrolo[2,3-b]pyridin-3-yl]-5-(trifluoromethyl)pyrimidin-2-yl]amino]piperidine-1-carboxylate (0.04 g, 58.42 umol, 1 eq) in MeOH (0.5 mL) was added NaOH (2 M, 0.5 mL, 17.12 eq). The mixture was stirred at 60° C. for 1 h. The solution was concentrated under reduced pressure to afford the title compound (40 mg, crude) as yellow solid, which was used into the next step without further purification.

(Note: The reaction was combined with another reaction in 20 mg scale for work up)

Step 8: 4-[6-(5-methyl-1,2,4-oxadiazol-3-yl)-1H-pyrrolo[2,3-b]pyridin-3-yl]-N-[(3S)-3-piperidyl]-5-(trifluoromethyl)pyrimidin-2-amine

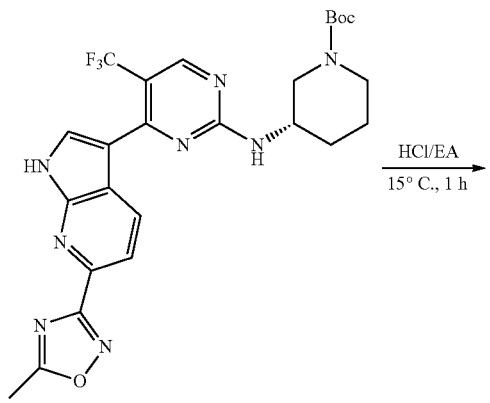

116

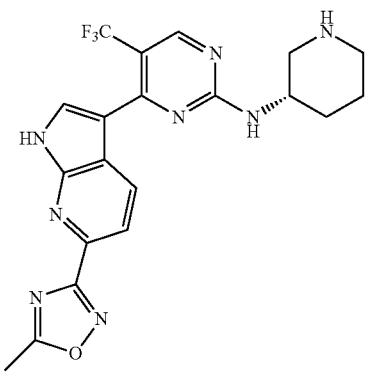

A solution of tert-butyl (3S)-3-[[4-[6-(5-methyl-1,2,4-oxadiazol-3-yl)-1H-pyrrolo[2,3-b]pyridin-3-yl]-5-(trifluoromethyl)pyrimidin-2-yl]amino]piperidine-1-carboxylate (30 mg, 55.09 umol, 1 eq) in HCl/EtOAc (4 M, 1.50 mL, 108.91 eq) was stirred at 15° C. for 1 h. The solution was concentrated under reduced pressure to give a residue. The residue was purified by prep-HPLC to afford the title compound (8.2 mg, FA salt, 98.14% purity) as a white solid (Note: The reaction was combined with another reaction in 10 mg scale for work up)

Example 33. Synthesis of 4-[6-(3,5-dimethyl-1,2,4-triazol-4-yl)-1H-pyrrolo[2,3-b]pyridin-3-yl]-N-[(3S)-3-piperidyl]-5-(trifluoromethyl)pyrimidin-2-amine (Compound 140)

Step 1: 6-(3,5-dimethyl-1,2,4-triazol-4-yl)-1H-pyrrolo[2,3-b]pyridine

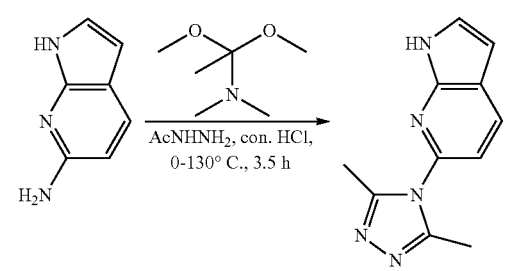

A mixture of 1H-pyrrolo[2,3-b]pyridin-6-amine (2 g, 15.02 mmol, 1 eq), 1,1-dimethoxy-N,N-dimethylethanamine (18.22 g, 136.80 mmol, 20.00 mL, 9.11 eq) was stirred at 130° C. for 1 h. The mixture was cooled to 0° C., conc. HCl (4 mL) was added dropwise, followed by acetohydrazide (6.68 g, 90.12 mmol, 6 eq) and the resulting mixture was stirred at 0° C. for 30 min. Then, the temperature was raised to 130° C. and the solution was stirred for another 2 h. The resulting solution was concentrated. The residue was purified by column chromatography (SiO$_2$, DCM/MeOH=70/1 to 7/1) to afford the title compound (10.5 g, crude, HCl) as a yellow oil.

(Note: The reaction was combined with another reaction in 200 mg scale for work up)

Step 2: 3-bromo-6-(3,5-dimethyl-1,2,4-triazol-4-yl)-1H-pyrrolo[2,3-b]pyridine

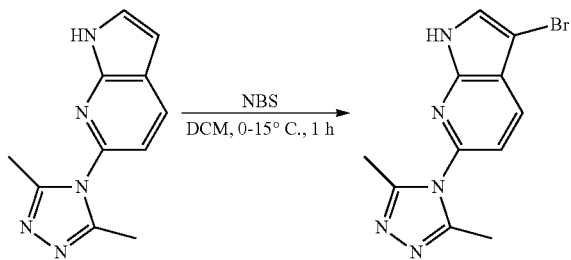

To a solution of 6-(3,5-dimethyl-1,2,4-triazol-4-yl)-1H-pyrrolo[23-b]pyridine (10 g, 46.90 mmol, 1 eq) in DCM (200 mL) was added NBS (4.17 g, 23.45 mmol, 0.5 eq) at 0° C. The mixture was stirred at 15° C. for 1 h. The reaction mixture was diluted with $H_2O$ (800 mL) and extracted with EtOAc (300 mL×2). The combined organic layers were washed with brine (1000 mL×2), dried over $Na_2SO_4$, filtered and concentrated under reduced pressure to give a residue. The residue was purified by column chromatography ($SiO_2$, DCM/MeOH=50/1 to 10/1) to afford the title compound (5.5 g, 13.74 mmol, 73% purity) as a yellow solid.

(Note: The reaction was combined with another reaction in 500 mg scale for work up).

Step 3: 1-(benzenesulfonyl)-3-bromo-6-(3,5-dimethyl-1,2,4-triazol-4-yl)pyrrolo[2,3-b]pyridine

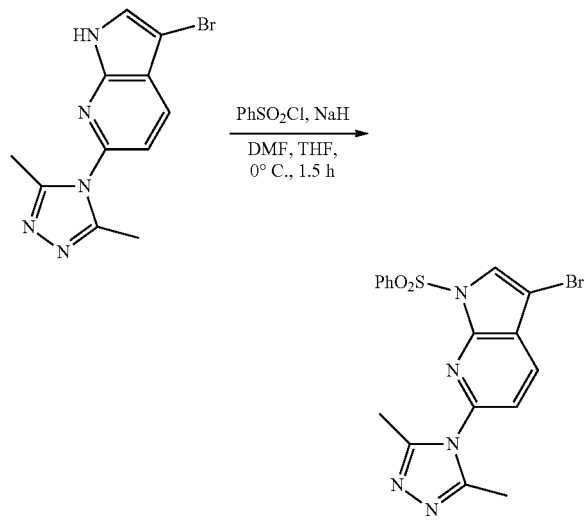

To a solution of 3-bromo-6-(3,5-dimethyl-1,2,4-triazol-4-yl)-1H-pyrrolo[2,3-b]pyridine (5 g, 17.12 mmol, 1 eq) in DMF (90 mL) and THF (10 mL) was added NaH (821.54 mg, 20.54 mmol, 60% purity, 1.2 eq) at 0° C. batch wise. After addition, the mixture was stirred at this temperature for 0.5 h, and then benzenesulfonyl chloride (3.93 g, 22.25 mmol, 2.85 mL, 1.3 eq) was added dropwise at 0° C. The resulting mixture was stirred at 0° C. for 1 h. The resulting mixture was diluted with $H_2O$ (500 mL) and extracted with EtOAc (100 mL×3). The combined organic layers were washed with brine (300 mL×2), dried over $Na_2SO_4$, filtered and concentrated under reduced pressure to give a residue. It was purified by column chromatography ($SiO_2$, DCM/MeOH=10/1) to afford the title compound (3.6 g) as a black brown solid.

(Note: The reaction was combined with another reaction in 500 mg scale for work up)

Step 4: [1-(benzenesulfonyl)-6-(3, 5-dimethyl-1,2,4-triazol-4-yl) pyrrolo[2,3-b]pyridin-3-yl]boronic Acid

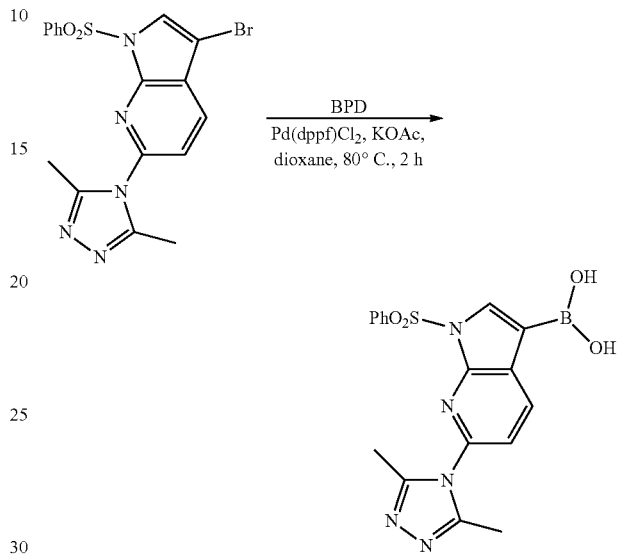

A mixture of 1-(benzenesulfonyl)-3-bromo-6-(3,5-dimethyl-1,2,4-triazol-4-yl) pyrrolo[2,3-b]pyridine (0.8 g, 1.85 mmol, 1 eq), 4,4,5,5-tetramethyl-2-(4,4,5,5-tetramethyl-1,3,2-dioxaborolan-2-yl)-1,3,2-dioxaborolane (939.87 mg, 3.70 mmol, 2 eq), Pd(dppf)Cl$_2$ (135.41 mg, 185.06 umol, 0.1 eq) and KOAc (363.23 mg, 3.70 mmol, 2 eq) in dioxane (3 mL) was degassed and purged with N$_2$ for 3 times, and then the mixture was stirred at 80° C. for 2 h under N$_2$ atmosphere. The solution was diluted with H$_2$O 100 (mL) and extracted with EtOAc (30 mL×3). The combined organic layers were washed with brine (100 mL×2), dried over Na$_2$SO$_4$, filtered and concentrated under reduced pressure to give a residue to afford the title compound (3.2 g, crude) as a brown oil.

Step 5: Tert-butyl (3S)-3-[[4-[1-(benzenesulfonyl)-6-(3,5-dimethyl-1,2,4-triazol-4-yl) pyrrolo[2,3-b]pyridin-3-yl]-5-(trifluoromethyl)pyrimidin-2-yl]amino]piperidine-1-carboxylate

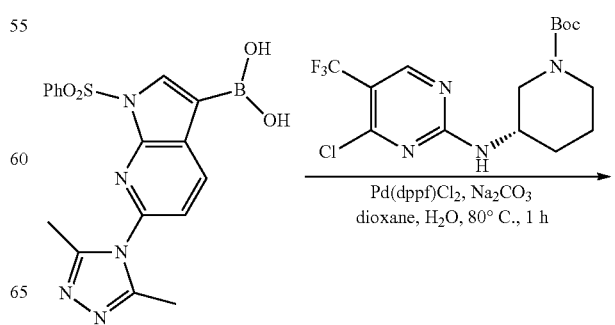

-continued

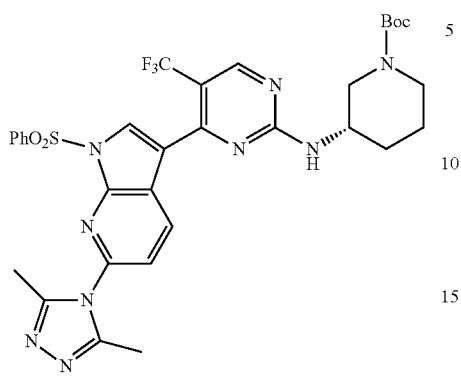

A mixture of [1-(benzenesulfonyl)-6-(3,5-dimethyl-1,2,4-triazol-4-yl)pyrrolo[2,3-b]pyridin-3-yl]boronic acid (2.7 g, 6.80 mmol, 1 eq), tert-butyl (3S)-3-[[4-chloro-5-(trifluoromethyl)pyrimidin-2-yl]amino]piperidine-1-carboxylate (864.00 mg, 2.27 mmol, 3.34e-1 eq), Na$_2$CO$_3$ (1.44 g, 13.59 mmol, 2 eq) and Pd(dppf)Cl$_2$ (497.37 mg, 679.73 umol, 0.1 eq) in dioxane (5 mL) and H$_2$O (1 mL) was degassed and purged with N$_2$ for 3 times, and then the mixture was stirred at 80° C. for 1 h under N$_2$ atmosphere. It was diluted with H$_2$O (100 mL) and extracted with EtOAc (30 mL×3). The combined organic layers were washed with brine (100 mL×2), dried over Na$_2$SO$_4$, filtered and concentrated under reduced pressure to give a residue. It was purified by column chromatography (SiO$_2$, DCM/MeOH=50/1 to 7/1) to afford the title compound (800 mg, crude) as a black brown oil.

(Note: The reaction was combined with another reaction in 500 mg scale for work up)

Step 6: Tert-butyl (3S)-3-[[4-[6-(3,5-dimethyl-1,2,4-triazol-4-yl)-1H-pyrrolo[2,3-b]pyridin-3-yl]-5-(trifluoromethyl)pyrimidin-2-yl]amino]piperidine-1-carboxylate

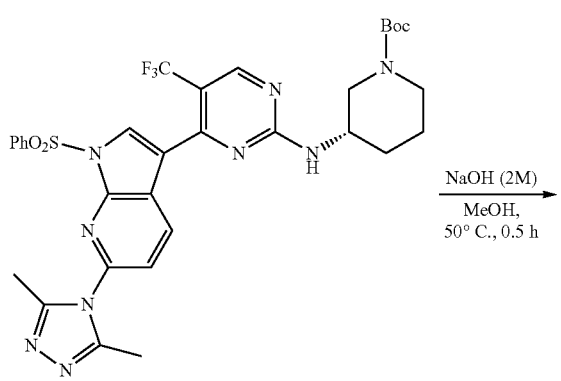

-continued

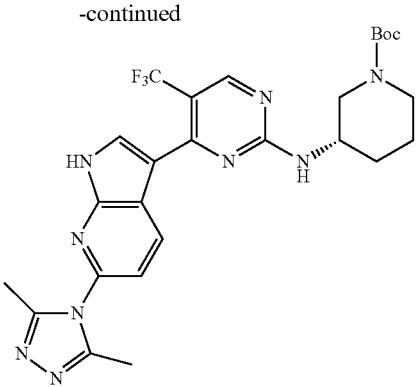

A mixture of tert-butyl (3S)-3-[[4-[1-(benzenesulfonyl)-6-(3,5-dimethyl-1,2,4-triazol-4-yl) pyrrolo[2,3-b]pyridin-3-yl]-5-(trifluoromethyl)pyrimidin-2-yl]amino]piperidine-1-carboxylate (0.7 g, 1.00 mmol, 1 eq) and NaOH (2 M, 5.02 mL, 10 eq) in MeOH (10 mL) was stirred at 50° C. for 0.5 h. The reaction mixture was diluted with H$_2$O 30 mL and extracted with EtOAc (15 mL×3). The combined organic layers were washed with brine (30 mL×2), dried over Na$_2$SO$_4$, filtered and concentrated under reduced pressure to give a residue that was purified by column chromatography (SiO$_2$, DCM:MeOH=50/1 to 10/1) to afford the title compound (180 mg) as a black brown oil.

(Note: The reaction was combined with another reaction in 100 mg scale for purification).

Step 7: 4-[6-(3, 5-dimethyl-1,2, 4-triazol-4-yl)-1H-pyrrolo[2,3-b]pyridin-3-yl]-N-[(3S)-3-piperidyl]-5-(trifluoromethyl)pyrimidin-2-amine

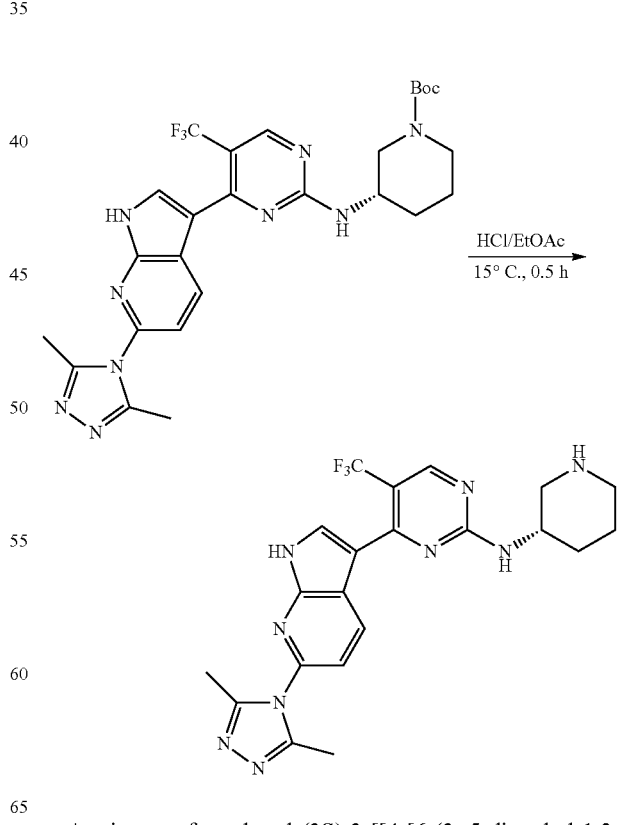

A mixture of tert-butyl (3S)-3-[[4-[6-(3, 5-dimethyl-1,2, 4-triazol-4-yl)-1H-pyrrolo[2,3-b]pyridin-3-yl]-5-(trifluoromethyl)pyrimidin-2-yl]amino]piperidine-1-carboxylate (0.16 g, 286.96 umol, 1 eq) and HCl/EtOAc (4 M, 3 mL, 41.82 eq) was stirred at 15° C. for 0.5 h. The mixture was concentrated to give a residue. The residue was purified by prep-HPLC (neutral condition) to afford the title compound (19.9 mg, free) as a white solid. (Note: The reaction was combined with another reaction in 20 mg scale for purification.)

Example 34. Synthesis of 4-[6-(5-methyltetrazol-1-yl)-1H-pyrrolo[2,3-b]pyridin-3-yl]-N-[(3S)-3-piperidyl]-5-(trifluoromethyl)pyrimidin-2-amine (Compound 141)

Step 1: 2-[(6-bromopyrrolo[2,3-b]pyridin-1-yl)methoxy]ethyl-trimethyl-silane

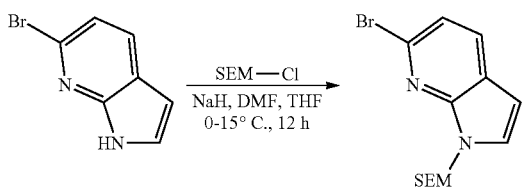 [SMILES: Brc1ccc2cc[nH]c2n1 ; C[Si](C)(C)CCOCCl ; C[Si](C)(C)CCOCn1ccc2ccc(Br)nc21]

To a solution of 6-bromo-1H-pyrrolo[2,3-b]pyridine (1.5 g, 7.61 mmol, 1 eq) in DMF (13.5 mL) and THF (1.5 mL) was added NaH (365.42 mg, 9.14 mmol, 60% purity, 1.2 eq) at 0° C., the mixture was stirred at 0° C. for 0.5 h. Then SEM-Cl (1.65 g, 9.90 mmol, 1.75 mL, 1.3 eq) was added, the mixture was stirred at 15° C. for 11.5 h. The reaction mixture was diluted with $H_2O$ (60 mL) and extracted with EtOAc (30 mL×3). The combined organic layers were washed with brine (50 mL), dried over $Na_2SO_4$, filtered and concentrated under reduced pressure to give a residue. The residue was purified by flash silica gel chromatography (ISCO®; 20 g SepaFlash® Silica Flash Column, Eluent of 0~8% Ethyl acetate/Petroleum ether gradient @ 75 mL/min) to afford the title compound (2.1 g, 6.42 mmol, 84.28% yield) as yellow oil.

Step 2: trimethyl-[2-[[6-(5-methyltetrazol-1-yl)pyrrolo[2,3-b]pyridin-1-yl]methoxy]ethyl]silane

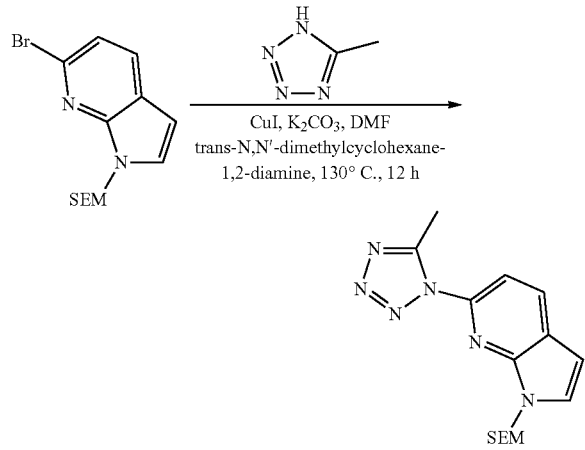

A mixture of 2-[(6-bromopyrrolo[2,3-b]pyridin-1-yl)methoxy]ethyl-trimethyl-silane (2.1 g, 6.42 mmol, 1 eq), 5-methyl-1H-tetrazole (539.48 mg, 6.42 mmol, 1 eq), CuI (488.79 mg, 2.57 mmol, 0.4 eq), $K_2CO_3$ (2.13 g, 15.40 mmol, 2.4 eq) and (1S,2S)—N1,N2-dimethylcyclohexane-1,2-diamine (365.06 mg, 2.57 mmol, 0.4 eq) in DMF (20 mL) was degassed and purged with $N_2$ for 3 times, and then the mixture was stirred at 130° C. for 12 h under $N_2$ atmosphere. It was cooled to the room temperature. The mixture was diluted with $H_2O$ (70 mL) and extracted with EtOAc (50 mL×3). The combined organic layers were washed with brine (80 mL), dried over $Na_2SO_4$, filtered and concentrated under reduced pressure to give a residue. It was purified by flash silica gel chromatography (ISCO®; 40 g SepaFlash® Silica Flash Column, Eluent of 0~35% Ethyl acetate/Petroleum ether gradient @ 100 mL/min) to afford the title compound (1.2 g, 3.63 mmol, 56.60% yield) as a yellow solid.

Step 3: 2-[[3-bromo-6-(5-methyltetrazol-1-yl)pyrrolo[2,3-b]pyridin-1-yl]methoxy]ethyl-trimethyl-silane

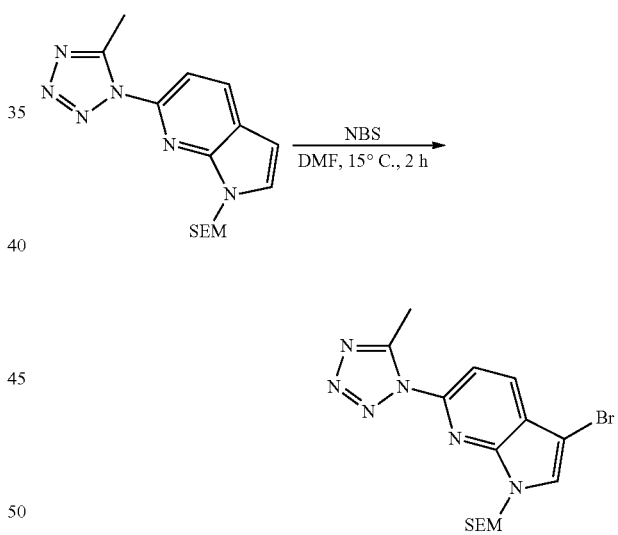

To a solution of trimethyl-[2-[[6-(5-methyltetrazol-1-yl)pyrrolo[2,3-b]pyridin-1-yl]methoxy]ethyl]silane (1.2 g, 3.63 mmol, 1 eq) in DMF (4.5 mL) was added NBS (710.95 mg, 3.99 mmol, 1.1 eq). The mixture was stirred at 15° C. for 2 h. The solution was diluted with $H_2O$ (60 mL) and extracted with EtOAc (30 mL×3). The combined organic layers were washed with brine (50 mL), dried over $Na_2SO_4$, filtered and concentrated under reduced pressure to give a residue. It was purified by flash silica gel chromatography (ISCO®; 20 g SepaFlash® Silica Flash Column, Eluent of 0~8% Ethyl acetate/Petroleum ether gradient @ 75 mL/min) to afford the title compound (1 g, 2.44 mmol, 67% yield) as a yellow solid.

Step 4: Trimethyl-[2-[[6-(5-methyltetrazol-1-yl)-3-(4,4,5,5-tetramethyl-1,3,2-dioxaborolan-2-yl)pyrrolo[2,3-b]pyridin-1-yl]methoxy]ethyl]silane

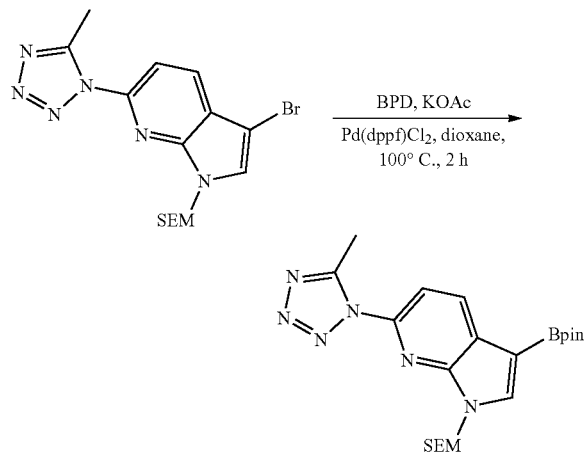

A mixture of 2-[[3-bromo-6-(5-methyltetrazol-1-yl)pyrrolo[2,3-b]pyridin-1-yl]methoxy]ethyl-trimethyl-silane (850 mg, 2.08 mmol, 1 eq), BPD (790.93 mg, 3.11 mmol, 1.5 eq), Pd(dppf)Cl$_2$ (151.93 mg, 207.64 umol, 0.1 eq), KOAc (407.56 mg, 4.15 mmol, 2 eq) in dioxane (10 mL) was degassed and purged with N$_2$ for 3 times, and then the mixture was stirred at 100° C. for 2 h under N$_2$ atmosphere. It was cooled to the room temperature. The reaction mixture was diluted with H$_2$O (60 mL) and extracted with EtOAc (30 mL×3). The combined organic layers were washed with brine (50 mL), dried over Na$_2$SO$_4$, filtered and concentrated under reduced pressure to give a residue. It was purified by flash silica gel chromatography (ISCO®; 20 g SepaFlash® Silica Flash Column, Eluent of 0~8% Ethyl acetate/Petroleum ether gradient @ 75 mL/min) to afford the title compound (600 mg, 47% purity) as colorless oil.

(Note: The reaction was combined with another reaction in 90 mg scale for work up)

Step 5: Tert-butyl (3S)-3-[[4-[6-(5-methyltetrazol-1-yl)-1-(2-trimethylsilylethoxymethyl)pyrrolo[2,3-b]pyridin-3-yl]-5-(trifluoromethyl)pyrimidin-2-yl]amino]piperidine-1-carboxylate

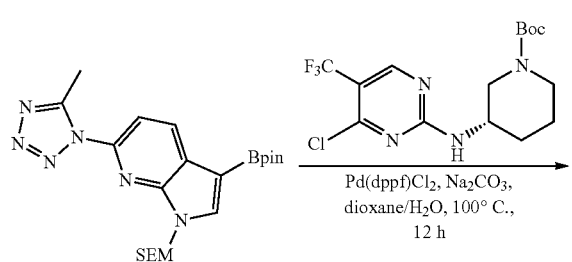

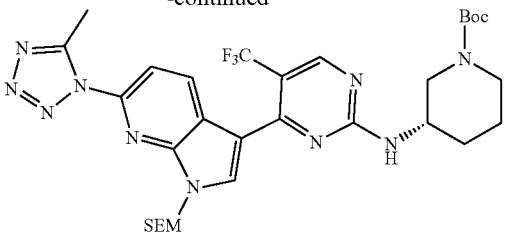

A mixture of trimethyl-[2-[[6-(5-methyltetrazol-1-yl)-3-(4,4,5,5-tetramethyl-1,3,2-dioxaborolan-2-yl)pyrrolo[2,3-b]pyridin-1-yl]methoxy]ethyl]silane (600 mg, 1.31 mmol, 1 eq), tert-butyl(3S)-3-[[4-chloro-5-(trifluoromethyl)pyrimidin-2-yl]amino]piperidine-1-carboxylate (300.35 mg, 788.75 umol, 0.6 eq), Pd(dppf)Cl$_2$ (96.19 mg, 131.46 umol, 0.1 eq), Na$_2$CO$_3$ (278.66 mg, 2.63 mmol, 2 eq) in dioxane (6 mL) and H$_2$O (1.2 mL) was degassed and purged with N$_2$ for 3 times, and then the mixture was stirred at 100° C. for 12 h under N$_2$ atmosphere. It was cooled to the room temperature. The reaction mixture was diluted with H$_2$O (60 mL) and extracted with EtOAc (30 mL×3). The combined organic layers were washed with brine (50 mL), dried over Na$_2$SO$_4$, filtered and concentrated under reduced pressure to give a residue. It was purified by flash silica gel chromatography (ISCO®; 12 g SepaFlash® Silica Flash Column, Eluent of 0~30% Ethyl acetate/Petroleum ether gradient @ 75 mL/min) to afford the title compound (200 mg, 296.39 umol, 22% yield) as a yellow oil.

Step 6: 4-[6-(5-methyltetrazol-1-yl)-1H-pyrrolo[2,3-b]pyridin-3-yl]-N-[(3S)-3-piperidyl]-5-(trifluoromethyl)pyrimidin-2-amine

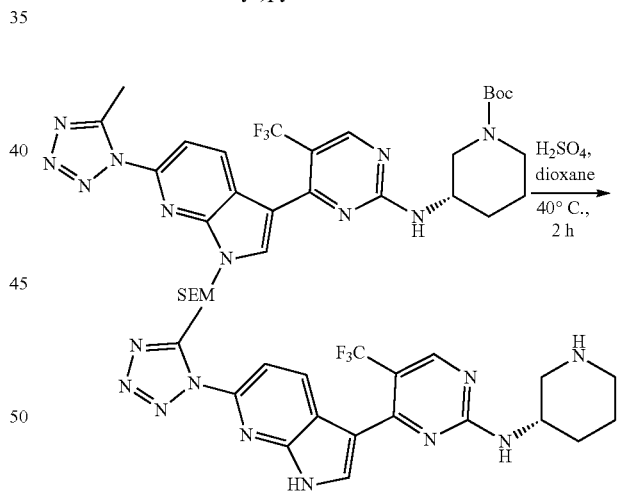

To a solution of tert-butyl (3S)-3-[[4-[6-(5-methyltetrazol-1-yl)-1-(2-trimethylsilylethoxy methyl)pyrrolo[2,3-b]pyridin-3-yl]-5-(trifluoromethyl)pyrimidin-2-yl]amino]piperidine-1-carboxylate (200 mg, 296.39 umol, 1 eq) in dioxane (2 mL) was added H$_2$SO$_4$ (296.63 mg, 2.96 mmol, 161.21 uL, 98% purity, 10 eq). The mixture was stirred at 40° C. for 2 h. It was diluted with H$_2$O (10 mL) and adjusted to pH=12 with aq. NaOH (4 N), then extracted with EtOAc (10 mL×3). The combined organic layers were washed with brine (10 mL), dried over Na$_2$SO$_4$, filtered and concentrated under reduced pressure to give a residue. The residue was purified by twice prep-HPLC (FA condition and neutral condition) to afford the title compound (4.3 mg, free) as a white solid. (Note: The reaction was combined with another reaction in 20 mg scale for purification and work up.)

Example 35. Synthesis of 4-[6-(3-methyl-1,2,4-thiadiazol-5-yl)-1H-pyrrolo[2,3-b]pyridin-3-yl]-N-[(3S)-3-piperidyl-5-(trifluoromethyl)pyrimidin-2-amine (Compound 142)

Step 1: 1H-pyrrolo[2,3-b]pyridine-6-carbothioamide

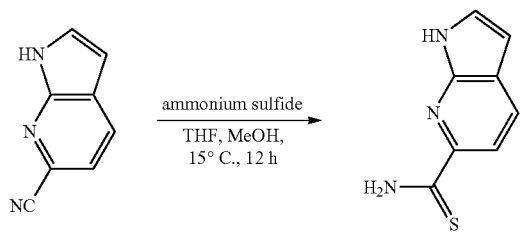 [SMILES: N#Cc1ccc2cc[nH]c2n1 ; NC(=S)c1ccc2cc[nH]c2n1]

To a solution of 1H-pyrrolo[2,3-b]pyridine-6-carbonitrile (2 g, 13.97 mmol, 1 eq) in MeOH (20 mL) and THF (10 mL) was added ammonium sulfide (1.71 g, 25.15 mmol, 1.72 mL, 1.8 eq) at 15° C. Then the solution was stirred at 15° C. for 12 h under $N_2$ atmosphere. The solution was quenched by addition of $H_2O$ (30 mL) at 15° C., and extracted with EtOAc (30 mL×2). The combined organic layers were washed with brine (20 mL×2), dried over anhydrous $Na_2SO_4$, filtered and concentrated under reduced pressure to give a residue. The residue was purified by column chromatography ($SiO_2$, PE/EtOAc=30/1 to 1/1) to afford the title compound (1 g, 5.64 mmol, 40.38% yield) as a yellow solid. (Note: The reaction was combined with another reaction (ET19050-19) in 1 g scale for purification and work up.)

Step 2: (NE)-N-[1-(dimethylamino)ethylidene]-1H-pyrrolo[2,3-b]pyridine-6-carbothioamide

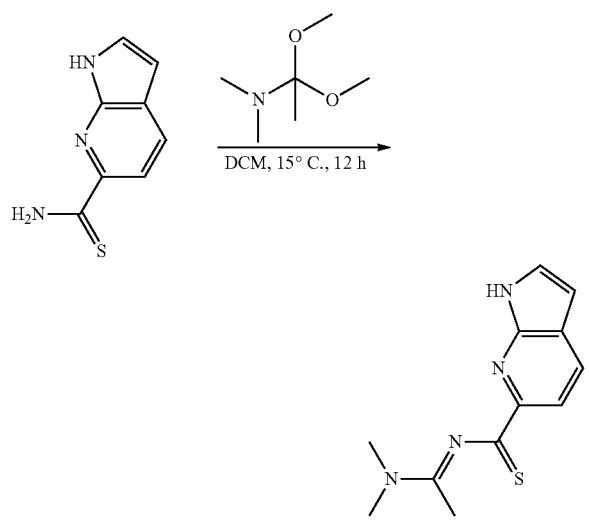

To a solution of 1H-pyrrolo[2,3-b]pyridine-6-carbothioamide (1 g, 5.64 mmol, 1 eq) in DCM (10 mL) was added 1, 1-dimethoxy-N, N-dimethyl-ethanamine (751.52 mg, 5.64 mmol, 824.94 uL, 1 eq) at 15° C. The solution was stirred at 15° C. for 12 h. It was concentrated under reduced pressure to afford the title compound (1.3 g, crude) as a yellow solid which was used into next step without further purification. (Note: The reaction was combined with another reaction in 1.2 g scale for work up.)

Step 3: 3-methyl-5-(1H-pyrrolo[2,3-b]pyridin-6-yl)-1,2,4-thiadiazole

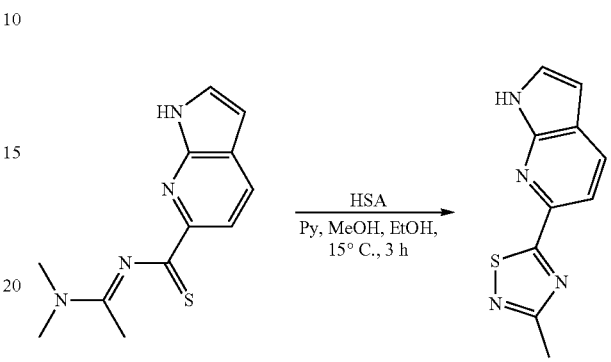

To a solution of (NE)-N-[1-(dimethylamino)ethylidene]-1H-pyrrolo[2,3-b]pyridine-6-carbo thioamide (1.3 g, 5.28 mmol, 1 eq) in EtOH (10 mL) was added a solution of Py (1 mL) and amino hydrogen sulfate (2.03 g, 17.96 mmol, 3.40 eq) in MeOH (10 mL). The mixture was stirred at 15° C. for 3 h under $N_2$ atmosphere. The reaction mixture was quenched by addition $H_2O$ (20 mL) at 15° C., and extracted with EtOAc (30 mL×2). The combined organic layers were washed with brine (20 mL×2), dried over $Na_2SO_4$, filtered and concentrated under reduced pressure to give a residue. It was purified by column chromatography ($SiO_2$, PE/EtOAc=30/1 to 1/1) to afford the title compound (1 g, 4.62 mmol, 87.62% yield) as a yellow solid. (Note: The reaction was combined with another reaction in 450 mg scale for purification and work up.)

Step 4: 5-(3-bromo-1H-pyrrolo[2,3-b]pyridin-6-yl)-3-methyl-1,2,4-thiadiazole

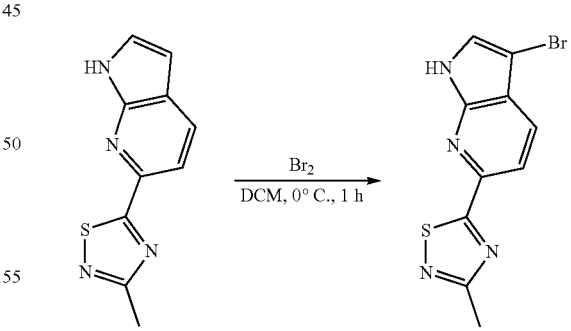

To a solution of 3-methyl-5-(1H-pyrrolo[2,3-b]pyridin-6-yl)-1,2,4-thiadiazole (1 g, 4.62 mmol, 1 eq) in DCM (10 mL) was added $Br_2$ (738.96 mg, 4.62 mmol, 238.37 uL, 1 eq) at 0° C. The mixture was degassed and purged with $N_2$ for 3 times and stirred at 0° C. for 1 h under $N_2$ atmosphere. The reaction was concentrated under reduced pressure to give a residue. It was triturated with MTBE (methyl tert-butyl ether) at 15° C. for 10 min to afford title compound (1.2 g, 2.03 mmol, 43.96% yield, 50% purity) as a yellow solid.

(Note: The reaction was combined with another reaction in 290 mg scale for purification and work up.)

Step 5: 2-[[3-bromo-6-(3-methyl-1,2,4-thiadiazol-5-yl)pyrrolo[2,3-b]pyridin-1-yl]methoxy]ethyl-trimethyl-silane

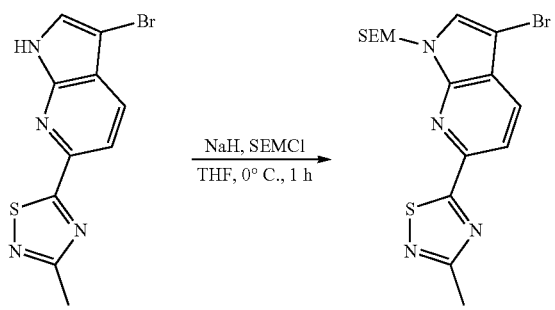

To a solution of 5-(3-bromo-1H-pyrrolo[2,3-b]pyridin-6-yl)-3-methyl-1,2,4-thiadiazole (1.2 g, 4.07 mmol, 1 eq) in THF (10 mL) was added NaH (325.22 mg, 8.13 mmol, 60% purity, 2 eq) and 2-(chloromethoxy)ethyl-trimethyl-silane (1.36 g, 8.13 mmol, 1.44 mL, 2 eq) at 0° C. Then the mixture was stirred at 0° C. for 1 h under $N_2$ atmosphere. The reaction mixture was quenched by addition of $H_2O$ (20 mL) at 15° C., and extracted with EtOAc (20 mL×2). The combined organic layers were washed with (20 mL×2), dried over $Na_2SO_4$, filtered and concentrated under reduced pressure to give a residue. The residue was purified by column chromatography ($SiO_2$, PE/EtOAc=30/1 to 1/1) to afford the title compound (1.1 g, 2.33 mmol, 57.24% yield, 90% purity) as a yellow solid.

Step 6: Trimethyl-[2-[[6-(3-methyl-1,2,4-thiadiazol-5-yl)-3-(4,4,5,5-tetramethyl-1,3,2-dioxaborolan-2-yl)pyrrolo[2,3-b]pyridin-1-yl]methoxy]ethyl]silane

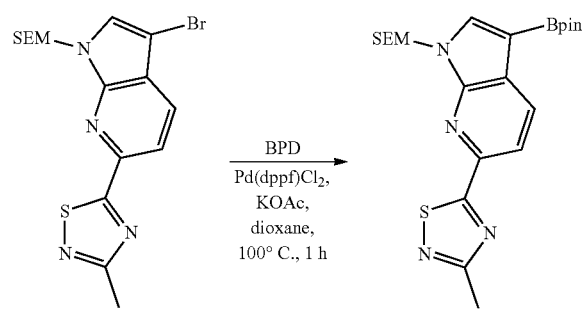

A mixture of 2-[[3-bromo-6-(3-methyl-1,2,4-thiadiazol-5-yl)pyrrolo[2, 3-b]pyridin-1-yl]m ethoxy]ethyl-trimethyl-silane (500 mg×2, 1.18 mmol, 1 eq), 4, 4, 5, 5-tetramethyl-2-(4, 4, 5, 5-tetramethyl-1, 3, 2-dioxaborolan-2-yl)-1, 3, 2-dioxaborolane (447.69 mg, 1.76 mmol, 1.5 eq), Pd(dppf)$Cl_2$ (86.00 mg, 117.53 umol, 0.1 eq), KOAc (230.70 mg, 2.35 mmol, 2 eq) in dioxane (8 mL) was degassed and purged with $N_2$ for 3 times, and then the mixture was stirred at 100° C. for 1 h under $N_2$ atmosphere. The reaction mixture was quenched by addition of $H_2O$ (10 mL) at 15° C., and extracted with EtOAc (20 mL×2). The combined organic layers were washed with brine (10 mL×2), dried over $Na_2SO_4$, filtered and concentrated under reduced pressure to give a residue. It was purified by column chromatography ($SiO_2$, PE/EtOAc=30/1 to 1/1) to afford the title compound (800 mg, 541.82 umol, 23.05% yield, 32% purity) as a black brown solid Step 7: Tert-butyl(3S)-3-[[4-[6-(3-methyl-1,2,4-thiadiazol-5-yl)-1-(2-trimethylsilylethoxymethyl)pyrrolo[2,3-b]pyridin-3-yl]-5-(trifluoromethyl)pyrimidin-2-yl]amino]piperidine-1-carboxylate

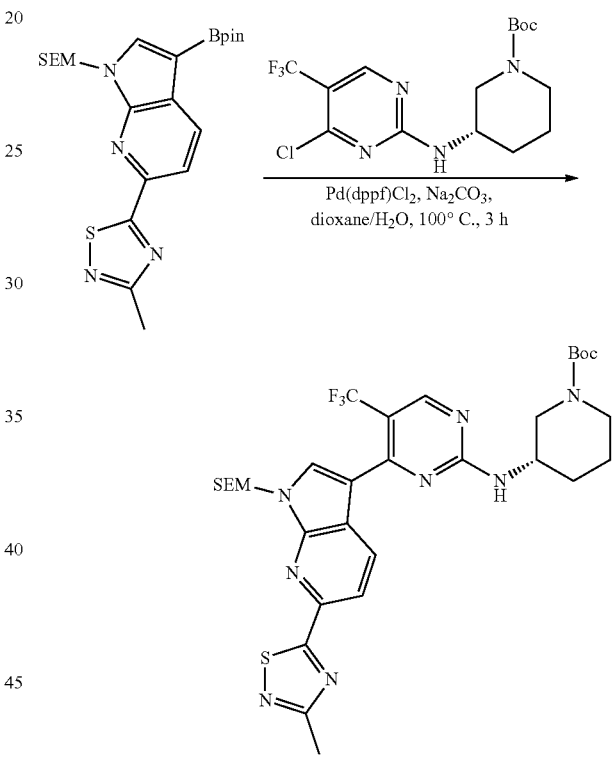

A mixture of trimethyl-[2-[[6-(3-methyl-1,2,4-thiadiazol-5-yl)-3-(4,4,5,5-tetramethyl-1,3,2-dioxaborolan-2-yl)pyrrolo[2,3-b]pyridin-1-yl]methoxy]ethyl]silane (800 mg, 1.69 mmol, 1 eq), tert-butyl(3S)-3-[[4-chloro-5-(trifluoromethyl)pyrimidin-2-yl]amino]piperidine-1-carboxylate (644.75 mg, 1.69 mmol, 1 eq), $Na_2CO_3$ (358.92 mg, 3.39 mmol, 2 eq), Pd(dppf)$Cl_2$ (123.89 mg, 169.32 umol, 0.1 eq) in dioxane (10 mL) and $H_2O$ (2 mL) was degassed and purged with $N_2$ for 3 times, and then the mixture was stirred at 100° C. for 3 h under $N_2$ atmosphere. The resulting mixture was quenched by addition $H_2O$ (10 mL) at 15° C. and extracted with EtOAc (20 mL×2). The combined organic layers were washed with brine (15 mL×2), dried over $Na_2SO_4$, filtered and concentrated under reduced pressure to give a residue. It was purified by column chromatography ($SiO_2$, PE/EtOAc=30/1 to 5/1) to afford the title compound (150 mg, 136.79 umol, 8.08% yield, 63% purity) as a brown solid.

Step 8: 4-[6-(3-methyl-1,2,4-thiadiazol-5-yl)-1H-pyrrolo[2,3-b]pyridin-3-yl]-N-[(3S)-3-piperidyl-5-(trifluoromethyl)pyrimidin-2-amine

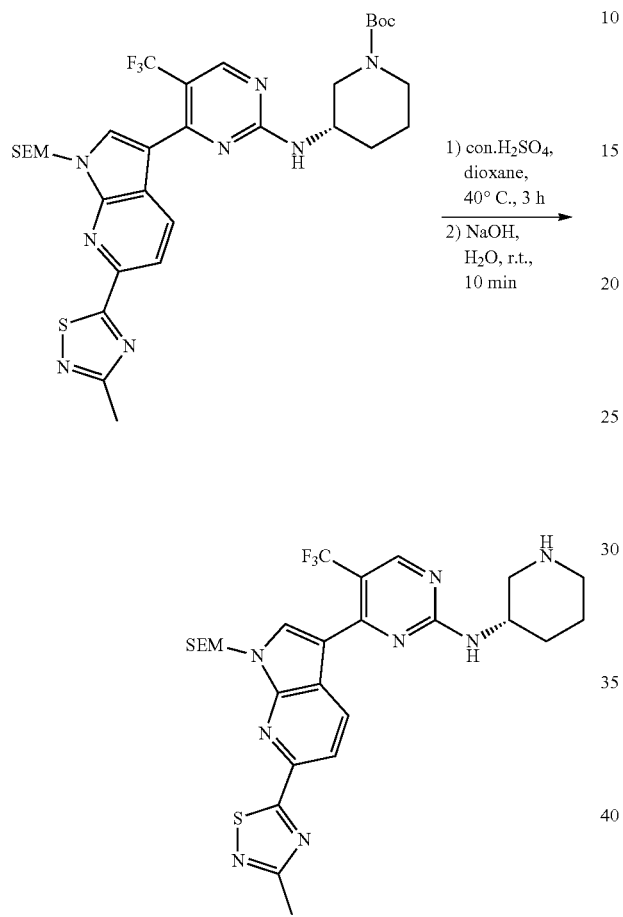

To a solution of tert-butyl (3S)-3-[[4-[6-(3-methyl-1,2,4-thiadiazol-5-yl)-1-(2-trimethylsilylethoxymethyl)pyrrolo[2,3-b]pyridin-3-yl]-5-(trifleoromethyl)pyrimidin-2-yl]amino]piperidin e-1-carboxylate (150 mg, 217.12 umol, 1 eq) in dioxane (1 mL) was added H$_2$SO$_4$ (217.30 mg, 2.17 mmol, 118.10 uL, 98% purity, 10 eq). The mixture was degassed and purged with N$_2$ for 3 times and stirred at 40° C. for 3 h under N$_2$ atmosphere. The reaction mixture was quenched by addition of H$_2$O (10 mL) at 15° C., and extracted with EtOAc (15 mL×2). The organic layer was concentrated to give crude residue, which was dissolved in H$_2$O (5 mL). NaOH was added to adjust pH to 12. The mixture was stirred for 10 min at 15° C. The stirred solution was extracted with EtOAc (10 mL×2). The combined organic layers were washed with brine (10 mL×2), dried over Na$_2$SO$_4$, filtered and concentrated under reduced pressure to give a residue. It was purified by prep-HPLC (HCl condition) to afford the title compound (6.7 mg, HCl salt 95% purity) as a yellow solid.

Example 36. Synthesis of (3R, 5S)—N-methyl-5-[[4-(6-thiazol-2-yl-1H-pyrrolo[2,3-b]pyridin-3-yl)-5-(trifluoromethyl)pyrimidin-2-yl]amino]piperidine-3-carboxamide (Compound 145)

Step 1: O1-tert-butyl O3-methyl-(3R,5S)-5-[[4-[1-(benzenesulfonyl)-6-thiazol-2-yl-pyrrolo[2,3-b]pyridin-3-yl]-5-(trifluoromethyl)pyrimidin-2-yl]amino]piperidine-1,3-dicarboxylate

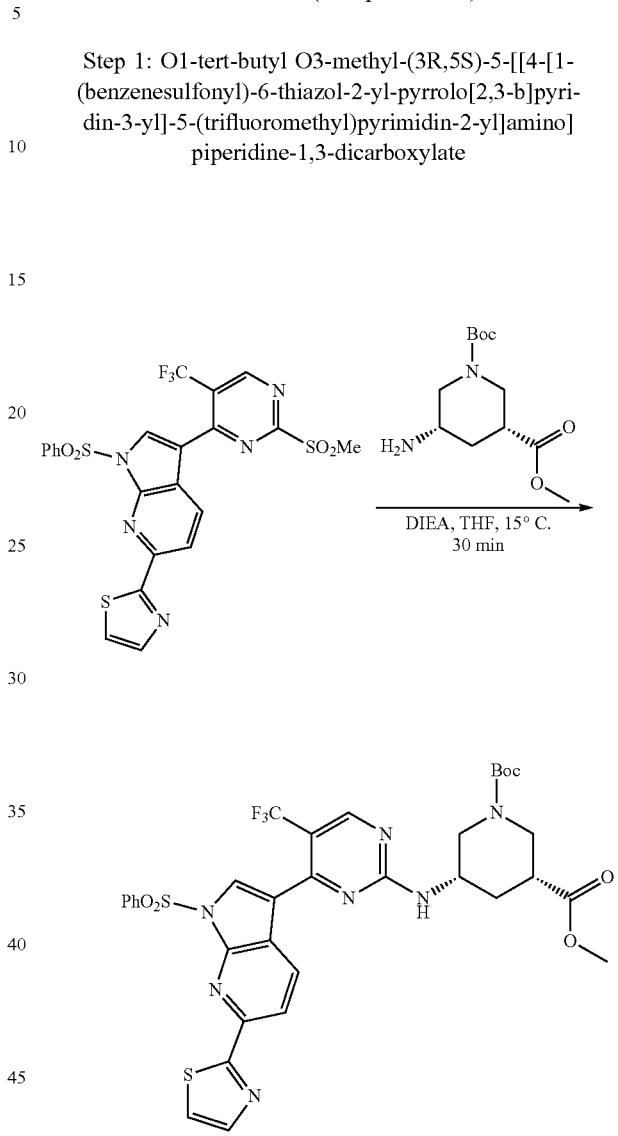

A mixture of 2-[1-(benzenesulfonyl)-3-[2-methylsulfonyl-5-(trifluoromethyl)pyrimidin-4-yl]pyrrolo[2,3-b]pyridin-6-yl]thiazole (0.28 g, 495.08 umol, 1 eq), 01-tert-butyl O3-methyl (3R)-5-aminopiperidine-1,3-dicarboxylate (191.83 mg, 742.62 umol, 1.5 eq) and DIEA (191.95 mg, 1.49 mmol, 258.70 uL, 3 eq) in THF (5 mL) was stirred at 15° C. for 30 min. The reaction mixture was diluted with H$_2$O (50 mL) and extracted with EtOAc (20 mL×3). The combined organic layers were washed with brine (100 mL×2), dried over Na$_2$SO$_4$, filtered and concentrated under reduced pressure to give a residue. It was purified by column chromatography (SiO$_2$, Petroleum ether/Ethyl acetate=10/1 to 1/1) to afford the title compound (260 mg) as a yellow solid.

(Note: The reaction was combined with another reaction in 20 mg scale for work up)

Step 2: (3R, 5S)-1-tert-butoxycarbonyl-5-[[4-(6-thiazol-2-yl-1H-pyrrolo[2,3-b]pyridin-3-yl)-5-(trifluoromethyl)pyrimidin-2-yl]amino]piperidine-3-carboxylic Acid

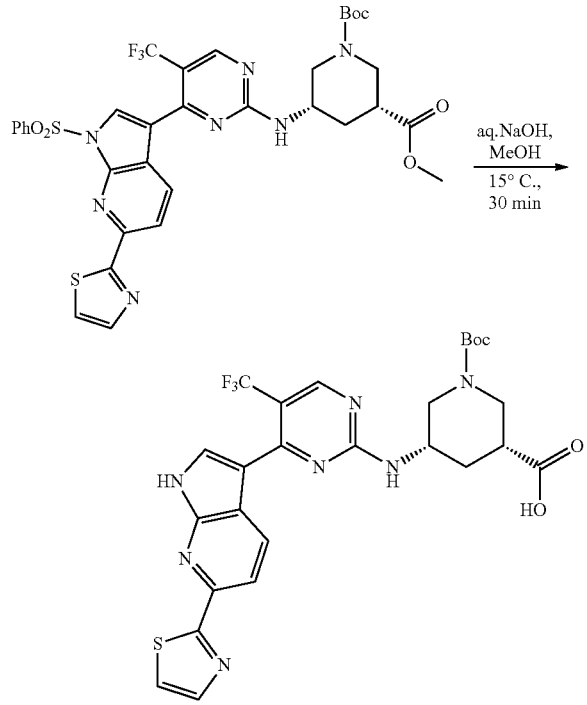

To a solution of O1-tert-butyl O3-methyl (3R,5S)-5-[[4-[1-(benzenesulfonyl)-6-thiazol-2-yl-pyrrolo[2,3-b]pyridin-3-yl]-5-(trifluoromethyl)pyrimidin-2-yl]amino]piperidine-1,3-dicarboxylate (240 mg, 322.68 umol, 1 eq) in MeOH (5 mL) was added NaOH (2 M, 1.61 mL, 10 eq). The mixture was stirred at 15° C. for 30 min. The reaction mixture was adjusted pH to 4 with aqueous HCl (0.5 M), and extracted with EtOAc (30 mL×3). The combined organic layers were washed with brine (90 mL×2), dried over Na$_2$SO$_4$, filtered and concentrated under reduced pressure to afford the title compound (170 mg) as a yellow solid.

(Note: The reaction was combined with another reaction in 20 mg scale for work up).

Step 3: Tert-butyl (3R, 5S)-3-(methylcarbamoyl)-5-[[4-(6-thiazol-2-yl-1H-pyrrolo[2,3-b]pyridin-3-yl)-5-(trifluoromethyl)pyrimidin-2-yl]amino]piperidine-1-carboxylate

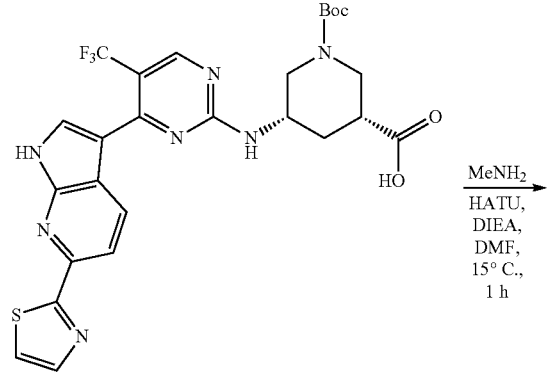

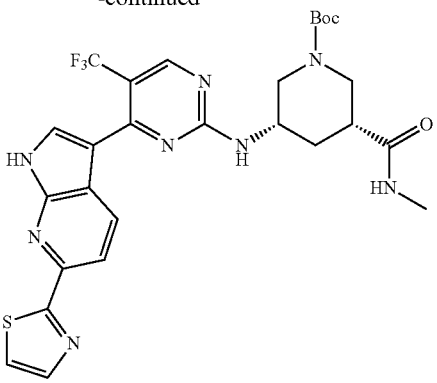

To a solution of (3R,5S)-1-tert-butoxycarbonyl-5-[[4-(6-thiazol-2-yl-1H-pyrrolo[2,3-b]pyridin-3-yl)-5-(trifluoromethyl)pyrimidin-2-yl]amino]piperidine-3-carboxylic acid (140 mg, 237.45 umol, 1 eq) in DMF (2 mL) was added HATU ((Dimethylamino)-N,N-dimethyl(3H-[1,2,3]triazolo[4,5-b]pyridin-3-yloxy)methaniminium hexafluorophosphate; 135.43 mg, 356.18 umol, 1.5 eq), DIEA (92.07 mg, 712.36 umol, 124.08 uL, 3 eq), methanamine (2 M, 356.18 uL, 3 eq). The mixture was stirred at 15° C. for 1 h. The reaction mixture was poured into saturated aqueous NaHCO$_3$ (20 mL), stirred for 5 min. Then, the solid was formed. It was filtered to afford the title compound (160 mg) as a yellow solid.

(Note: The reaction was combined with another reaction in 10 mg scale for work up)

Step 4: (3R, 5S)—N-methyl-5-[[4-(6-thiazol-2-yl-1H-pyrrolo[2,3-b pyridin-3-yl)-5-(trifluoromethyl)pyrimidin-2-yl]amino]piperidine-3-carboxamide

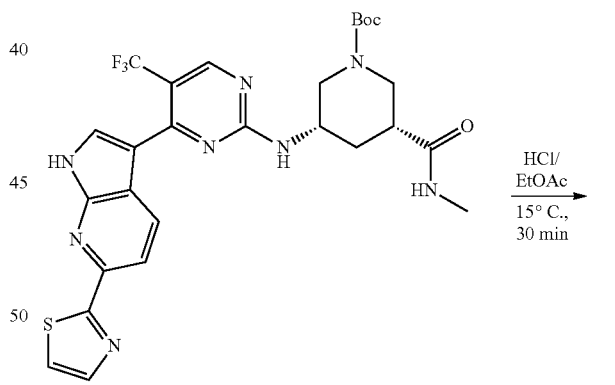

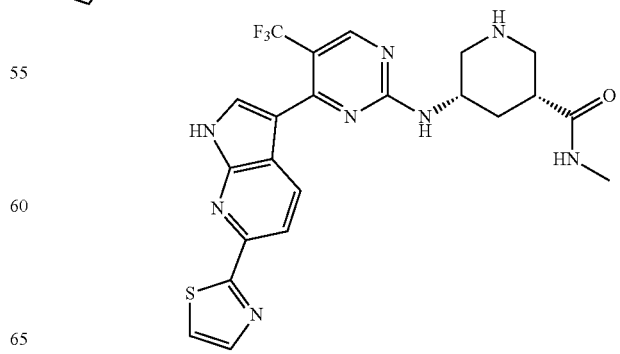

A mixture of tert-butyl (3R,5S)-3-(methylcarbamoyl)-5-[[4-(6-thiazol-2-yl-1H-pyrrolo[2,3-b]pyridin-3-yl)-5-(trifluoromethyl)pyrimidin-2-yl]amino]piperidine-1-carboxylate (150 mg, 248.91 umol, 1 eq) and HCl/EtOAc (4 M, 3 mL) was stirred at 15° C. for 30 min. The mixture was concentrated to give a residue. It was purified by prep-HPLC (neutral condition) to afford the title compound (19.4 mg) as a white solid. (Note: The reaction was combined with another reaction in 10 mg scale for purification).

Example 37. Synthesis of (3R, 5S)-5-[[4-[6-(3, 5-dimethylisoxazol-4-yl)-1H-pyrazolo[3,4-b]pyridin-3-yl]-5-(trifluoromethyl)pyrimidin-2-yl]amino]piperidin-3-ol (Compound 146)

Step 1: (3R, 5S)-1-benzyl-5-[[4-[6-(3, 5-dimethylisoxazol-4-yl)-1-tetrahydropyran-2-yl-pyrazolo[3,4-b]pyridin-3-yl]-5-(trifluoromethyl)pyrimidin-2-yl]amino]piperidin-3-ol

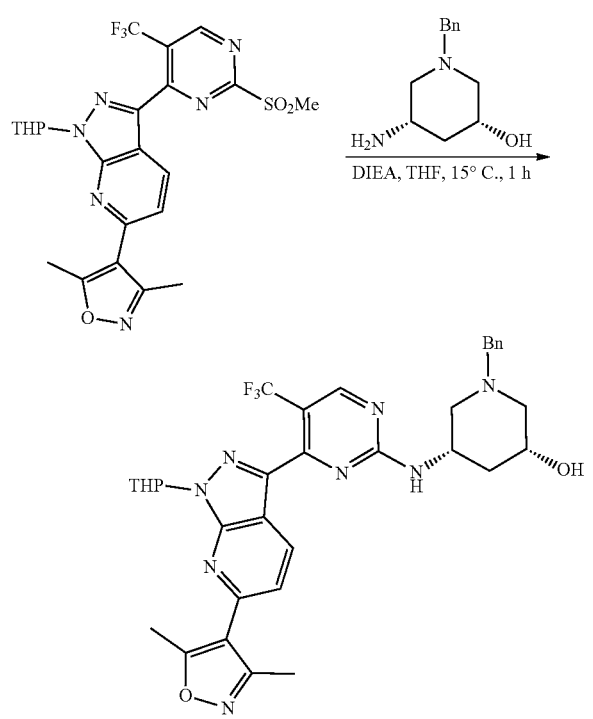

A mixture of 3,5-dimethyl-4-[3-[2-methylsulfonyl-5-(trifluoromethyl)pyrimidin-4-yl]-1-tetrahydropyran-2-yl-pyrazolo[3,4-b]pyridin-6-yl]isoxazole (0.25 g, 478.47 umol, 1 eq), (3R,5S)-5-amino-1-benzyl-piperidin-3-ol (98.70 mg, 478.47 umol, 1 eq), DIEA (185.51 mg, 1.44 mmol, 250.02 uL, 3 eq) in THF (5 mL) was stirred at 15° C. for 1 h. The mixture was poured into water (20 mL), and then extracted with EtOAc (10 mL×3). The combined organic layers were washed with brine (50 mL), dried over Na$_2$SO$_4$, filtered and concentrated under reduced pressure to give a residue. The residue was purified by column chromatography (SiO$_2$, Petroleum ether/Ethyl acetate=10/1 to 0/1) to afford the title compound (190 mg) as a yellow solid Step 2: Tert-butyl (3S, 5R)-3-[[4-[6-(3, 5-dimethylisoxazol-4-yl)-1-tetrahydropyran-2-yl-pyrazolo[3,4-b]pyridin-3-yl]-5-(trifluoromethyl)pyrimidin-2-yl]amino]-5-hydroxy-piperidine-1-carboxylate

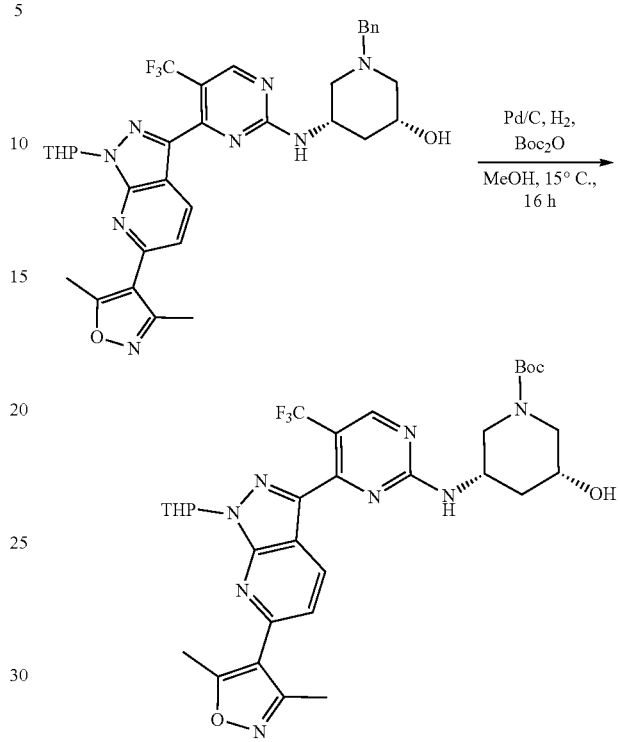

To a solution of (3R,5S)-1-benzyl-5-[[4-[6-(3, 5-dimethylisoxazol-4-yl)-1-tetrahydropyran-2-yl-pyrazolo[3,4-b]pyridin-3-yl]-5-(trifluoromethyl)pyrimidin-2-yl]amino]piperidin-3-ol (0.17 g, 262.07 umol, 1 eq) tert-butoxycarbonyl tert-butyl carbonate (171.59 mg, 786.22 umol, 180.62 uL, 3 eq) in MeOH (1 mL) was added Pd/C (10%, 0.2 g) under N$_2$. The suspension was degassed under vacuum and purged with H$_2$ several times. It was stirred at 15° C. for 16 h under H$_2$ atmosphere (15 psi). The reaction mixture was filtered and the filter was concentrated. The residue was purified by column chromatography (SiO$_2$, Petroleum ether/Ethyl acetate=10/1 to 0/1) to afford the title compound (90 mg) as a white solid. (Note: The reaction was combined with another reaction in 20 mg scale for work up.)

Step 3: (3R, 5S)-5-[[4-[6-(3,5-dimethylisoxazol-4-yl)-1H-pyrazolo[3,4-b]pyridin-3-yl]-5-(trifluoromethyl)pyrimidin-2-yl]amino]piperidin-3-ol

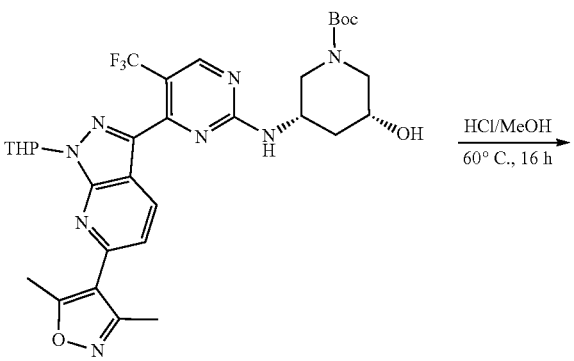

-continued

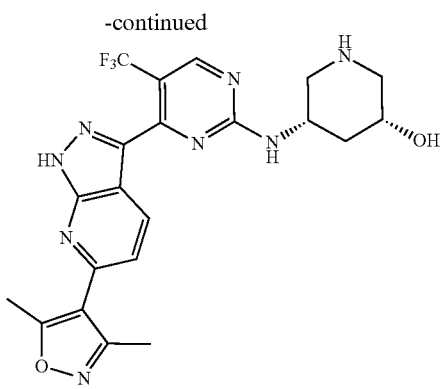

A mixture of tert-butyl (3S,5R)-3-[[4-[6-(3,5-dimethyl-isoxazol-4-yl)-1-tetrahydropyran-2-yl-pyrazolo[3,4-b]pyridin-3-yl]-5-(trifluoromethyl)pyrimidin-2-yl]amino]-5-hydroxy-piperidine-1-carboxylate (80 mg, 121.46 umol, 1 eq) in HCl/MeOH (4 M, 910.93 uL, 30 eq) was stirred at 60° C. for 16 h. It was concentrated and the residue was purified by prep-HPLC to afford the title compound (20 mg, 99.47% purity, FA) as a white solid. (Note: The reaction was combined with another reaction in 10 mg scale for work up.)

Example 38. Synthesis of (3R,5S)-5-[[4-[6-(3-methylisoxazol-4-yl)-1H-pyrrolo[2,3-b]pyridin-3-yl]-5-(trifluoromethyl)pyrimidin-2-yl]amino]piperidin-3-ol (Compound 148)

Step 1: 3-methyl-4-(1H-pyrrolo[2,3-b]pyridin-6-yl) isoxazole

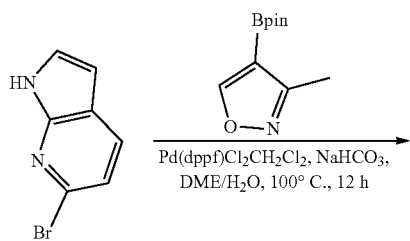

A mixture of 6-bromo-1H-pyrrolo[2,3-b]pyridine (1 g, 5.08 mmol, 1 eq), 3-methyl-4-(4,4,5,5-tetramethyl-1,3,2-dioxaborolan-2-yl)isoxazole (1.11 g, 5.33 mmol, 1.05 eq), Pd(dppf)Cl₂—CH₂Cl₂ (207.24 mg, 253.77 umol, 0.05 eq), NaHCO₃ (1.28 g, 15.23 mmol, 592.19 uL, 3 eq) in DME (10 mL) and H₂O (4 mL) was degassed and purged with N₂ for 3 times, and then the mixture was stirred at 100° C. for 12 h under N₂ atmosphere. It was cooled to the room temperature. The reaction mixture was diluted with H₂O (30 mL) and extracted with DCM (20 mL×3). The combined organic layers were washed with brine (20 mL), dried over Na₂SO₄, filtered and concentrated under reduced pressure to give a residue. The residue was purified by flash silica gel chromatography (ISCO®; 12 g SepaFlash® Silica Flash Column, Eluent of 0~15% Ethyl acetate/Petroleum ether gradient @ 50 mL/min) to afford the title compound (800 mg) as a yellow solid. (Note: The reaction was combined with another reaction (ET12872-179) in 50 mg scale for purification and work up.)

Step 2: 4-(3-bromo-1H-pyrrolo[2,3-b]pyridin-6-yl)-3-methyl-isoxazole

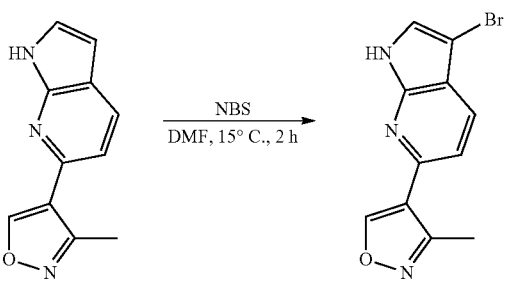 [SMILES: Cc1nocc1-c1ccc2cc[nH]c2n1 ; "NBS" ; Cc1nocc1-c1ccc2c(Br)c[nH]c2n1]

To a solution of 3-methyl-4-(1H-pyrrolo[2,3-b]pyridin-6-yl)isoxazole (720 mg, 3.61 mmol, 1 eq) in DMF (7 mL) was added NBS (771.93 mg, 4.34 mmol, 1.2 eq). The mixture was stirred at 15° C. for 2 h. The reaction mixture was diluted with H₂O (60 mL) and extracted with EtOAc (30 mL×3). The combined organic layers were washed with brine 50 (mL), dried over Na₂SO₄, filtered and concentrated under reduced pressure to give a residue. The residue was purified by flash silica gel chromatography (ISCO®; 12 g SepaFlash® Silica Flash Column, Eluent of 0~25% Ethyl acetate/Petroleum ether gradient @ 75 mL/min) to afford the title compound (600 mg, 2.16 mmol, 59.69% yield) as a colorless oil.

Step 3: 4-[1-(benzenesulfonyl)-3-bromo-pyrrolo[2,3-b]pyridin-6-yl]-3-methyl-isoxazole

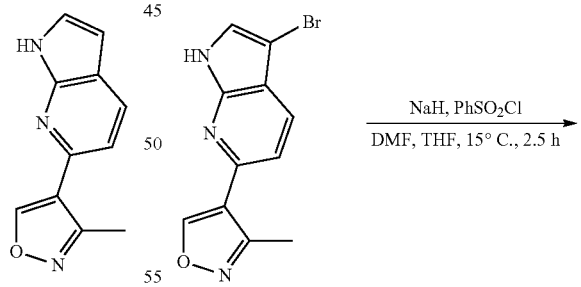

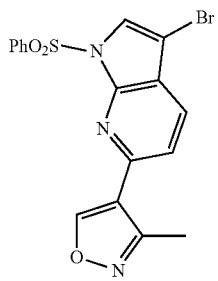

To a solution of 4-(3-bromo-1H-pyrrolo[2,3-b]pyridin-6-yl)-3-methyl-isoxazole (600 mg, 2.16 mmol, 1 eq) in DMF (5 mL) and THF (0.5 mL) was added NaH (129.44 mg, 3.24 mmol, 60% purity, 1.5 eq). The mixture was stirred at 15° C. for 10 min. Then benzenesulfonyl chloride (495.37 mg, 2.80 mmol, 358.96 uL, 1.3 eq) was added, the mixture was stirred at 15° C. for 2.3 h. The reaction mixture was diluted with H₂O (60 mL) and EtOAc (30 mL). Then it was filtered. The filtrate was partitioned and the water layer was extracted with EtOAc (30 mL×2). The filter cake and the combined organic layers were concentrated under reduced pressure to give a residue. The residue was diluted with MeOH (30 mL) and stirred for 20 min. The reaction mixture was filtered and the filter cake was dried in vacuum to afford the title compound (800 mg, 1.91 mmol, 88.65% yield) was obtained as a brown solid Step 4: 4-[1-(benzenesulfonyl)-3-(4,4,5,5-tetramethyl-1,3,2-dioxaborolan-2-yl)pyrrolo[2,3-b]pyridin-6-yl]-3-methyl-isoxazole

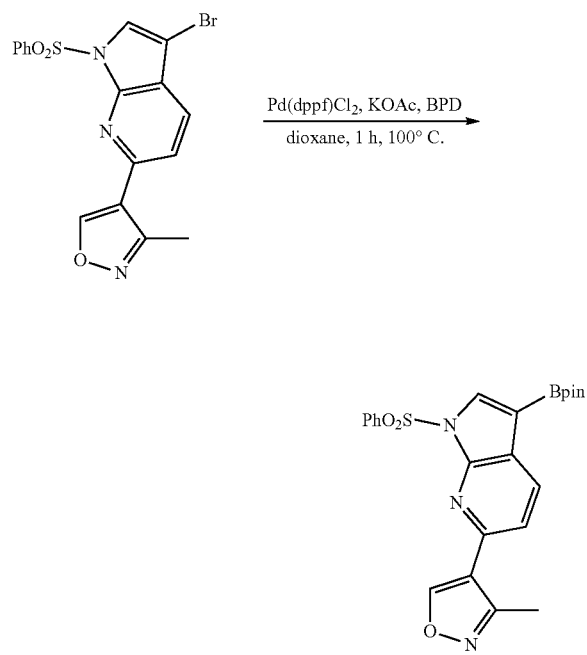

A mixture of 4-[1-(benzenesulfonyl)-3-bromo-pyrrolo[2,3-b]pyridin-6-yl]-3-methyl-isoxazole (670.00 mg, 1.60 mmol, 1 eq), 4,4,5,5-tetramethyl-2-(4,4,5,5-tetramethyl-1,3,2-dioxaborolan-2-yl)-1,3,2-dioxaborolane (610.16 mg, 2.40 mmol, 1.5 eq), Pd(dppf)Cl₂ (117.21 mg, 160.19 umol, 0.1 eq), KOAc (314.41 mg, 3.20 mmol, 2 eq) in dioxane (8 mL) was degassed and purged with N₂ for 3 times, and then the mixture was stirred at 100° C. for 1 h under N₂ atmosphere. It was cooled to the room temperature. The mixture was diluted with dioxane (30 mL) and filtered. The filtrate was concentrated under reduced pressure to afford the title compound (800 mg, crude) was obtained as a brown solid, and it was used into the next step without further purification.

Step 5: 4-[1-(benzenesulfonyl)-3-[2-methylsulfanyl-5-(trifluoromethyl)pyrimidin-4-yl]pyrrolo[2,3-b]pyridin-6-yl]-3-methyl-isoxazole

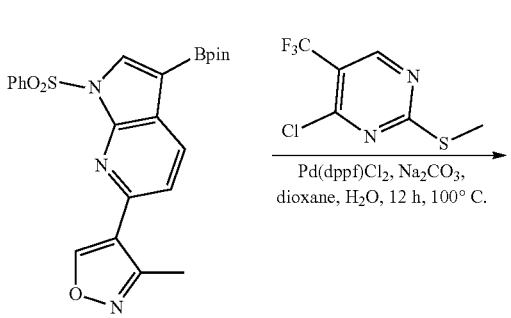

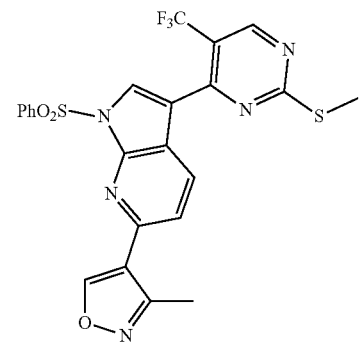

A mixture of 4-[1-(benzenesulfonyl)-3-(4,4,5,5-tetramethyl-1,3,2-dioxaborolan-2-yl)pyrrolo[2,3-b]pyridin-6-yl]-3-methyl-isoxazole (800 mg, 1.03 mmol, 1 eq), 4-chloro-2-methylsulfanyl-5-(trifluoromethyl)pyrimidine (235.83 mg, 1.03 mmol, 1 eq), Pd(dppf)Cl₂ (75.48 mg, 103.15 umol, 0.1 eq), Na₂CO₃ (218.66 mg, 2.06 mmol, 2 eq) in dioxane (10 mL) and H₂O (2 mL) was degassed and purged with N₂ for 3 times, and then the mixture was stirred at 100° C. for 12 hr under N₂ atmosphere. It was cooled to the room temperature. The reaction mixture was diluted with H₂O (60 mL) and extracted with EtOAc (30 mL×3). The combined organic layers were washed with brine (60 mL), dried over Na₂SO₄, filtered and concentrated under reduced pressure to give a residue. It was purified by flash silica gel chromatography (ISCO®; 20 g SepaFlash® Silica Flash Column, Eluent of 0~30% Ethyl acetate/Petroleum ether gradient @ 75 mL/min) to afford the title compound (200 mg, 150.51 umol, 14.59% yield, 40% purity) was obtained as a yellow solid. (Note: The reaction was combined with another reaction in 120 mg scale for purification and work up.)

Step 6: 4-[1-(benzenesulfonyl)-3-[2-methylsulfonyl-5-(trifluoromethyl)pyrimidin-4-yl]pyrrolo[2,3-b]pyridin-6-yl]-3-methyl-isoxazole

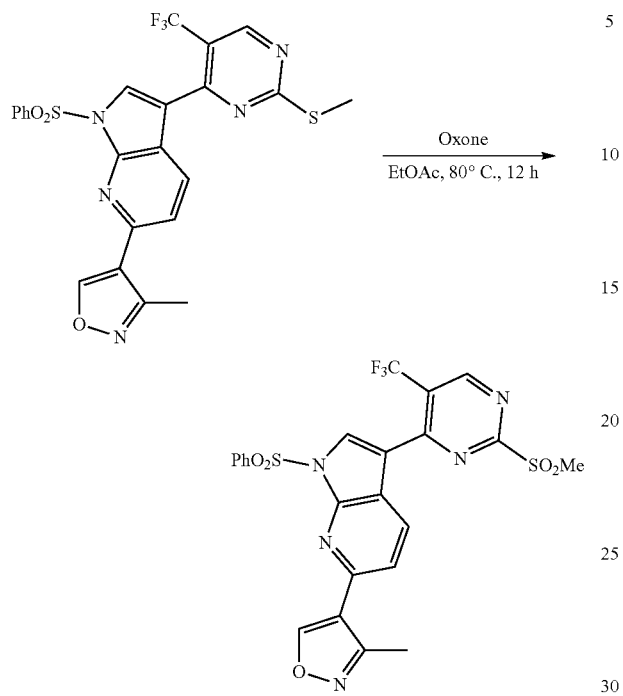

To a solution of 4-[1-(benzenesulfonyl)-3-[2-methylsulfanyl-5-(trifluoromethyl)pyrimidin-4-yl]pyrrolo[2,3-b]pyridin-6-yl]-3-methyl-isoxazole (180 mg, 338.65 umol, 1 eq) in EtOAc (10 mL) was added Oxone (1.04 g, 1.69 mmol, 5 eq). The mixture was stirred at 80° C. for 12 h. It was cooled to the room temperature. The reaction mixture was filtered and the filtrate was quenched by saturation Na₂SO₃ (30 mL). The water layer was extracted with EtOAc (20 mL×3). The combined organic layers were washed with brine (30 mL), dried over Na₂SO₄, filtrate and concentrated under reduced pressure to give a residue. The residue was purified by flash silica gel chromatography (ISCO®; 20 g SepaFlash® Silica Flash Column, Eluent of 0~50% Ethyl acetate/Petroleum ether gradient @ 75 mL/min) to afford the title compound (40 mg) as a white solid.

Step 7: (3R,5S)-5-[[4-[1-(benzenesulfonyl)-6-(3-methylisoxazol-4-yl)pyrrolo[2,3-b]pyridin-3-yl]-5-(trifluoromethyl)pyrimidin-2-yl]amino]-1-benzyl-piperidin-3-ol

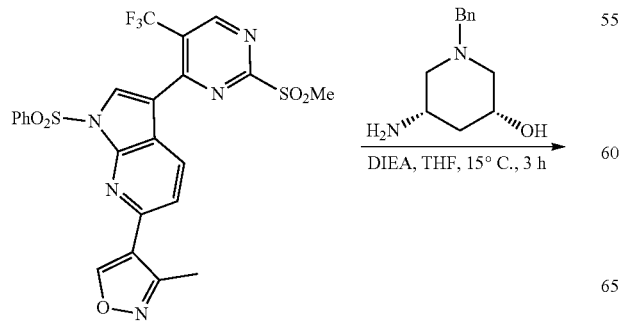

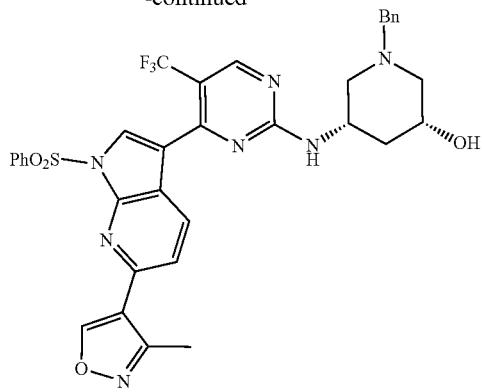

To a solution of 4-[1-(benzenesulfonyl)-3-[2-methylsulfonyl-5-(trifluoromethyl)pyrimidin-4-yl]pyrrolo[2,3-b]pyridin-6-yl]-3-methyl-isoxazole (35 mg, 62.11 umol, 1 eq) and DIPEA (40.14 mg, 310.54 umol, 54.09 uL, 5 eq) in THF (0.5 mL) was added (3R,5S)-5-amino-1-benzyl-piperidin-3-ol (12.81 mg, 62.11 umol, 1 eq). The mixture was stirred at 15° C. for 3 h. The reaction mixture was concentrated under reduced pressure to remove solvent. The residue was purified by flash silica gel chromatography (ISCO®; 4 g SepaFlash® Silica Flash Column, Eluent of 0~2% Dichloromethane/Methanol @ 50 mL/min) to afford the title compound (27 mg) was obtained as a white solid. (Note: The reaction was combined with another reaction in 5 mg scale for purification and work up.)

Step 8: Tert-butyl (3S,5R)-3-[[4-[1-(benzenesulfonyl)-6-(3-methylisoxazol-4-yl)pyrrolo[2,3-b]pyridine-3-yl]-5-(trifluoromethyl)pyrimidin-2-yl]amino]-5-hydroxy-piperidine-1-carboxylate

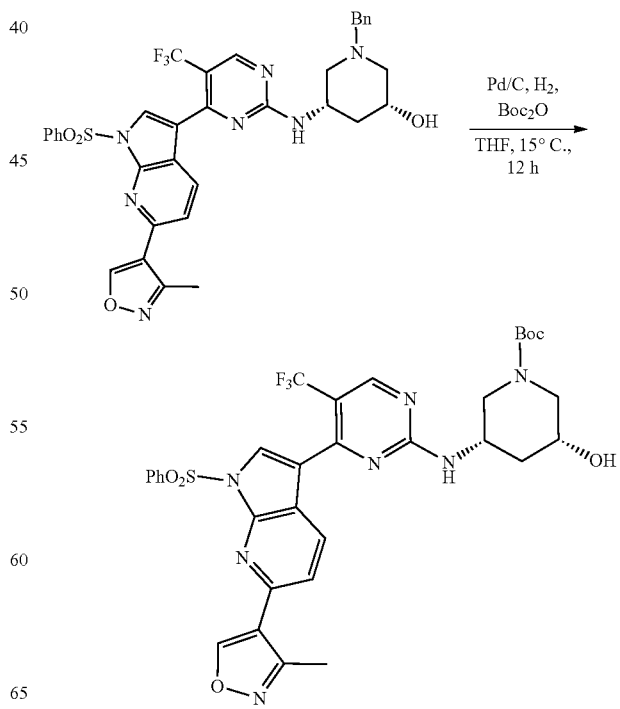

A mixture of (3R,5S)-5-[[4-[1-(benzenesulfonyl)-6-(3-methylisoxazol-4-yl)pyrrolo[2,3-b]pyridin-3-yl]-5-(trifluoromethyl)pyrimidin-2-yl]amino]-1-benzyl-piperidin-3-ol (22 mg, 31.90 umol, 1 eq), Boc₂O (10.44 mg, 47.85 umol, 10.99 uL, 1.5 eq), Pd/C (50 mg, 10% purity) in THF (0.5 mL) was degassed and purged with H2 for 3 times, and then the mixture was stirred at 15° C. for 12 h under H2 atmosphere (15 psi). The reaction mixture was filtered and concentrated under reduced pressure to afford the title compound (30 mg, crude) as yellow oil, and it was used into the next step without further purification.

Step 9: Tert-butyl (3R,5S)-3-hydroxy-5-[[4-[6-(3-methylisoxazol-4-yl)-1H-pyrrolo[2,3-b]pyridin-3-yl]-5-(trifluoromethyl)pyrimidin-2-yl]amino]piperidine-1-carboxylate

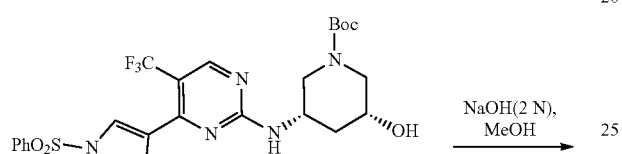

To a solution of tert-butyl (3S,5R)-3-[[4-[1-(benzenesulfonyl)-6-(3-methylisoxazol-4-yl) pyrrolo[2,3-b]pyridin-3-yl]-5-(trifluoromethyl)pyrimidin-2-yl]amino]-5-hydroxy-piperidine-1-carboxylate (30 mg, 42.88 umol, 1 eq) in MeOH (0.5 mL) was added NaOH (2 M, 0.4 mL). The mixture was stirred at 60° C. for 0.5 h. It was cooled to the room temperature. The reaction mixture was diluted with H₂O (10 mL) and extracted with EtOAc (10 mL×4). The combined organic layers were washed with brine (20 mL), dried over Na₂SO₄, filtered and concentrated under reduced pressure to give a residue. The residue was purified by flash silica gel chromatography (ISCO®; 4 g SepaFlash® Silica Flash Column, Eluent of 0~8% Dichloromethane/Methanol @ 50 mL/min) to afford the title compound (5 mg, 8.94 umol, 20.84% yield) as a white solid.

Step 10: (3R,5S)-5-[[4-[6-(3-methylisoxazol-4-yl)-1H-pyrrolo[2,3-b]pyridin-3-yl]-5-(trifluoromethyl)pyrimidin-2-yl]amino]piperidin-3-ol To a solution of tert-butyl (3R,5S)-3-hydroxy-5-[[4-[6-(3-methylisoxazol-4-yl)-1H-pyrrolo[2,3-b]pyridin-3-yl]-5-(trifluoromethyl)pyrimidin-2-yl]amino]piperidine-1-carboxylate (4 mg, 7.15 umol, 1 eq) in EtOAc (0.5 mL) was added HCl/EtOAc (4 M, 0.5 mL, 279.77 eq). The mixture was stirred at 15° C. for 0.5 h. The reaction mixture was concentrated under reduced pressure to remove solvent. The residue was purified by prep-HPLC to afford the title compound (FA, 2 mg, 94.37% purity) was obtained as a white solid. (Note: The reaction was combined with another reaction in 1 mg scale for purification and work up.)

Example 39. Synthesis of N-[(3S,6S)-6-methyl-3-piperidyl]-4-[6-(3-methyltriazol-4-yl)-1H-pyrrolo[2,3-b]pyridin-3-yl]-5-(trifluoromethyl)pyrimidin-2-amine (Compound 150)

Step 1: 1-(benzenesulfonyl)-6-bromo-pyrrolo[2,3-b]pyridine

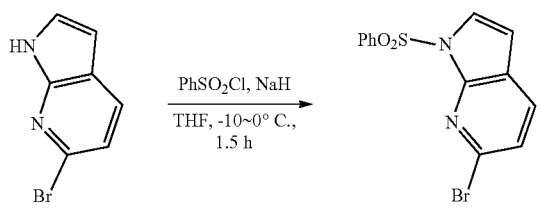

To a solution of 6-bromo-1H-pyrrolo[2,3-b]pyridine (2 g, 10.15 mmol, 1 eq) in THF (30 mL) was added NaH (608.98 mg, 15.23 mmol, 60% purity, 1.5 eq) at −10° C. The mixture was stirred at −10° C. to 0° C. for 0.5 h. Then benzenesulfonyl chloride (2.15 g, 12.18 mmol, 1.56 mL, 1.2 eq) was added to the above and the resulting mixture was stirred at 0° C. for 1 h. It was poured into water (50 mL). The aqueous phase was extracted with EtOAc (50 mL×3). The combined organic phase was washed with brine (50 mL×2), dried over anhydrous Na₂SO₄, filtered and concentrated in vacuum. The residue was washed with MeOH (8 mL), filtered and the filter cake was collected to afford the title compound (3.0 g, 7.83 mmol, 77.13% yield, 88% purity) as a white solid.

Step 2: 1-(benzenesulfonyl)-6-(3-methyltriazol-4-yl) pyrrolo[2,3-b]pyridine

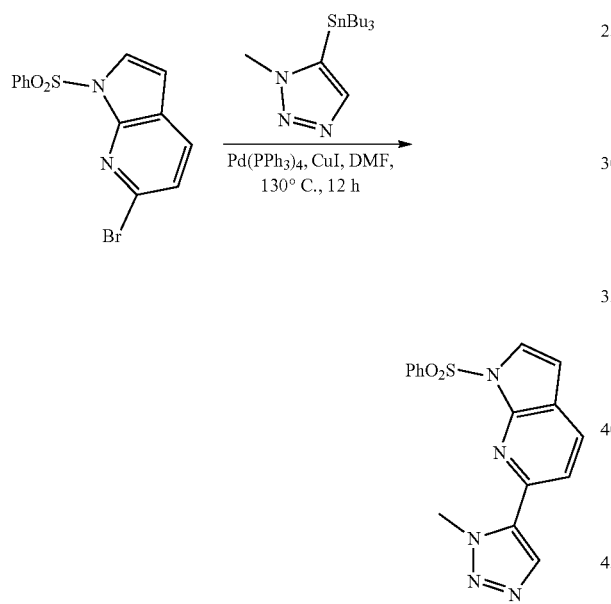

To a solution of 1-(benzenesulfonyl)-6-bromo-pyrrolo[2,3-b]pyridine (1.1 g, 3.26 mmol, 1 eq) and tributyl-(3-methyltriazol-4-yl) stannane (3.40 g, 4.57 mmol, 1.4 eq) in DMF (30 mL) was added Pd(PPh₃)₄ (376.97 mg, 326.22 umol, 0.1 eq) and CuI (62.13 mg, 326.22 umol, 0.1 eq). The mixture was stirred at 130° C. under N₂ for 12 h. The reaction mixture was cooled to r.t., and poured into water (50 mL). The aqueous phase was extracted with EtOAc (50 mL×3). The combined organic phase was washed with brine (100 mL×2), dried over anhydrous Na₂SO₄, filtered and concentrated in vacuum. The residue was purified by silica gel chromatography (100-200 mesh silica gel, Petroleum ether/EtOAc=5/1, 0/1) to afford 1 g product with 77% purity. Then the product was washed with MeOH (5 mL), filtered and the filter cake was collected to afford the title compound (0.9 g, 2.39 mmol, 73.16% yield, 90% purity) as a yellow solid.

Step 3: 6-(3-methyltriazol-4-yl)-1H-pyrrolo[2,3-b] pyridine

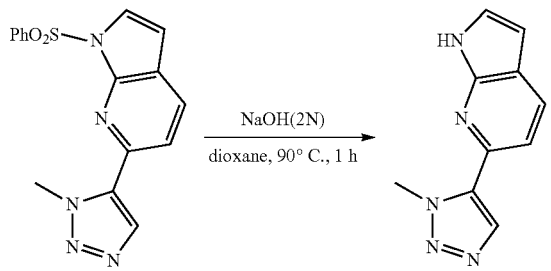

To a solution of 1-(benzenesulfonyl)-6-(3-methyltriazol-4-yl) pyrrolo[2,3-b]pyridine (0.7 g, 2.06 mmol, 1 eq) in dioxane (15 mL) was added NaOH (2 M, 5.16 mL, 5 eq). The mixture was stirred at 90° C. for 1 h. The mixture was diluted with water (10 mL), extracted with EtOAc (15 mL×3). The combined organic phase was washed with brine (10 mL×2), dried over anhydrous Na₂SO₄, filtered and concentrated in vacuum to afford the title compound (0.5 g, crude) as a yellow solid and used directly in next step.

Step 4: 3-bromo-6-(3-methyltriazol-4-yl)-1H-pyrrolo [2,3-b]pyridine

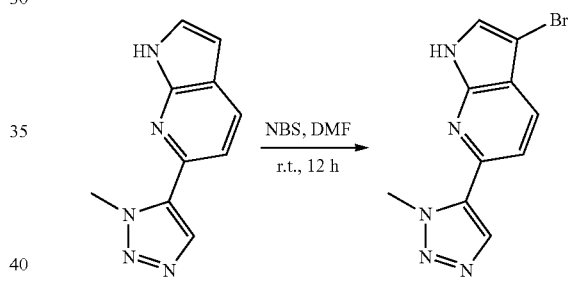

To a solution of 6-(3-methyltriazol-4-yl)-1H-pyrrolo[2,3-b]pyridine (0.5 g, 2.51 mmol, 1 eq) in DMF (10 mL) was added NBS (446.72 mg, 2.51 mmol, 1 eq). The mixture was stirred at 15° C. for 12 h. The residue was poured into water (100 mL) and stirred for 5 min. The solid was formed and filtered. The filter cake was collected to afford the title compound (0.7 g, crude) as a yellow solid which was used in next step directly.

Step 5: 1-(benzenesulfonyl)-3-bromo-6-(3-methyltriazol-4-yl) pyrrolo[2,3-b]pyridine

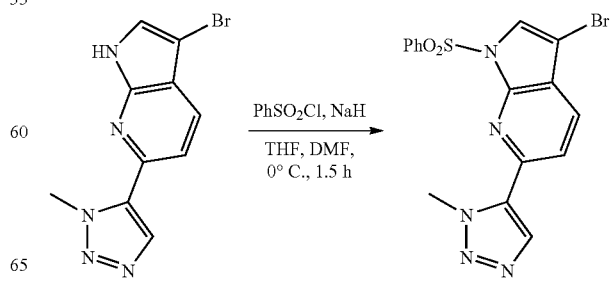

To a solution of 3-bromo-6-(3-methyltriazol-4-yl)-1H-pyrrolo[2,3-b]pyridine (0.65 g, 2.34 mmol, 1 eq) in DMF (9 mL)/THF (1 mL) was added NaH (140.22 mg, 3.51 mmol, 60% purity, 1.5 eq) at 0° C. After 0.5 h, benzenesulfonyl chloride (619.20 mg, 3.51 mmol, 448.70 uL, 1.5 eq) was added and the resulting mixture was stirred at 0° C. for 1 h. It was poured into water (100 mL) and stirred for 5 min. The mixture was filtered and the filter cake was collected. It was triturated with MeOH (5 mL) and filtered to give the crude product. It was purified by silica gel chromatography (PE:EtOAc=1:1-0:1) to afford the title compound (1 g, crude) as a pink solid.

Step 6: 1-(benzenesulfonyl)-6-(3-methyltriazol-4-yl)-3-(4,4,5,5-tetramethyl-1,3,2-dioxaborolan-2-yl) pyrrolo[2,3-b]pyridine

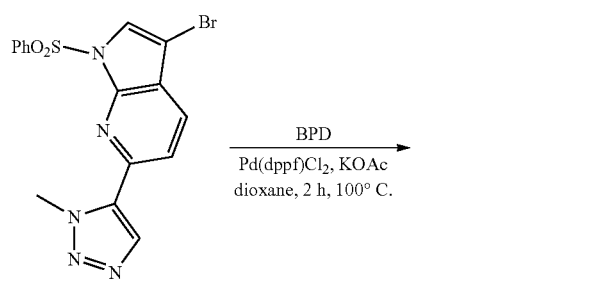

To a solution of 1-(benzenesulfonyl)-3-bromo-6-(3-methyltriazol-4-yl) pyrrolo[2,3-b]pyridine (0.7 g, 1.67 mmol, 1 eq), BPD (637.47 mg, 2.51 mmol, 1.5 eq) in dioxane (15 mL) was added KOAc (328.49 mg, 3.35 mmol, 2 eq) and Pd(dppf)Cl$_2$ (122.46 mg, 167.36 umol, 0.1 eq). The mixture was stirred at 100° C. under N$_2$ atmosphere for 2 h. It was cooled to r.t., and poured into water (30 mL). The aqueous phase was extracted with EtOAc (30 mL×3). The combined organic phase was washed with brine (30 mL×2), dried over anhydrous Na$_2$SO$_4$, filtered and concentrated in vacuum. The residue was purified by silica gel chromatography (100-200 mesh silica gel, PE/EtOAc=5/1, 1/1) to afford the title compound (0.4 g, batch 1) as a white solid. Batch 2: (0.2 g) was obtained as a yellow solid which contained some de-Br product.

Step 7: 1-(benzenesulfonyl)-3-[2-methylsulfanyl-5-(trifluoromethyl)pyrimidin-4-yl]-6-(3-methyltriazol-4-yl) pyrrolo[2,3-b]pyridine

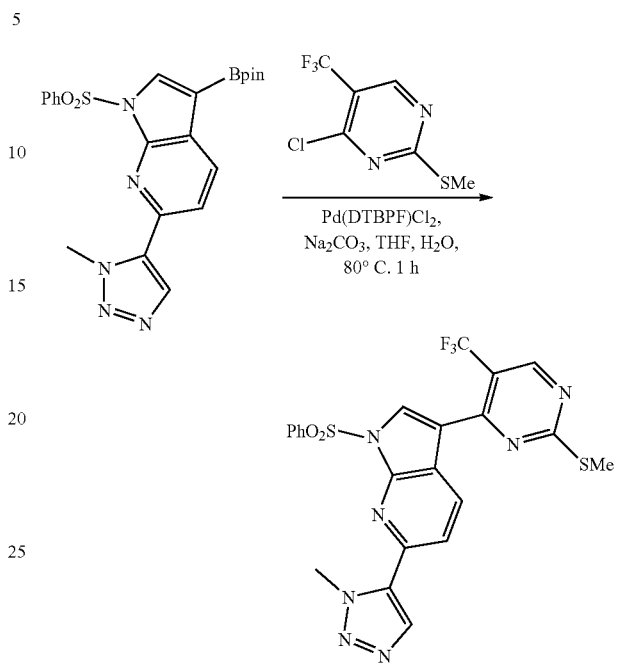

To a solution of 1-(benzenesulfonyl)-6-(3-methyltriazol-4-yl)-3-(4, 4, 5, 5-tetramethyl-1, 3, 2-dioxaborolan-2-yl) pyrrolo[2,3-b]pyridine (0.05 M, 25.79 mL, 1 eq), 4-chloro-2-methylsulfanyl-5-(trifluoromethyl)pyrimidine (294.79 mg, 1.29 mmol, 1 eq) in H$_2$O (2 mL)/THF (16 mL) was added Na$_2$CO$_3$ (273.32 mg, 2.58 mmol, 2 eq) and ditertbutyl(cyclopentyl)phosphane; dichloropalladium; iron (84.04 mg, 128.94 umol, 0.1 eq). The mixture was stirred at 80° C. under N$_2$ for 1 h. It was cooled to r.t. and poured into water (50 mL). The aqueous phase was extracted with ethyl acetate (50 mL×3). The combined organic phase was washed with brine (50 mL×2), dried over anhydrous Na$_2$SO$_4$, filtered and concentrated in vacuum. The residue was purified by silica gel chromatography (100-200 mesh silica gel, PE/EtOAc=10/1, 0/1, contained 10% DCM) to afford the title compound (0.43 g, 647.19 umol, 50.19% yield, 80% purity) as a yellow solid.

Step 8: 1-(benzenesulfonyl)-3-[2-methylsulfonyl-5-(trifluoromethyl)pyrimidin-4-yl]-6-(3-methyltriazol-4-yl) pyrrolo[2,3-b]pyridine

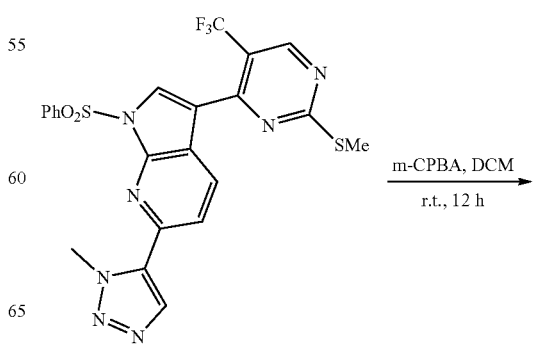

-continued

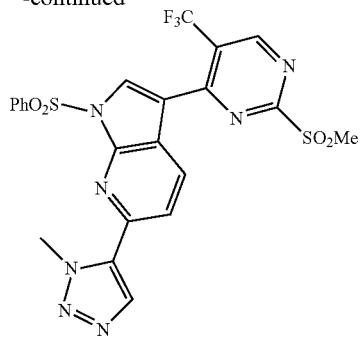

To a solution of 1-(benzenesulfonyl)-3-[2-methylsulfanyl-5-(trifluoromethyl)pyrimidin-4-yl]-6-(3-methyltriazol-4-yl) pyrrolo[2,3-b]pyridine (0.41 g, 771.35 umol, 1 eq) in DCM (20 mL) was added m-CPBA (391.50 mg, 1.93 mmol, 2.5 eq). The mixture was stirred at 15° C. for 12 h. The solution was quenched by sat.NaHCO$_3$ (20 mL) and sat.Na$_2$SO$_3$ (20 mL). The mixture was stirred for 5 min. The aqueous phase was extracted with DCM (30 mL×3). The combined organic phase dried over anhydrous Na$_2$SO$_4$, filtered and concentrated in vacuum. The residue was washed with a mixture of Petroleum ether/EtOAc=3/1 (5 mL), filtered and the filter cake was collected to afford the title compound (0.35 g, crude) as a yellow solid and used directly.

Step 9: Benzyl(2S,5S)-5-[[4-[1-(benzenesulfonyl)-6-(3-methyltriazol-4-yl)pyrrolo[2,3-b]pyridine-3-yl]-5-(trifluoromethyl)pyrimidin-2-yl]amino]-2-methyl-piperidine-1-carboxylate (product 1) and Benzyl (2R,5R)-5-[[4-[1-(benzenesulfonyl)-6-(3-methyltriazol-4-yl)pyrrolo[2,3-b]pyridin-3-yl]-5-(trifluoromethyl)pyrimidin-2-yl]amino]-2-methyl-piperidine-1-carboxylate (Product 2)

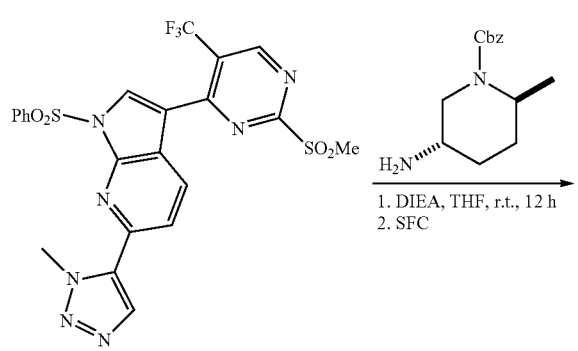

To a solution of 1-(benzenesulfonyl)-3-[2-methylsulfonyl-5-(trifluoromethyl)pyrimidin-4-yl]-6-(3-methyltriazol-4-yl) pyrrolo[2,3-b]pyridine (0.35 g, 621.08 umol, 1 eq) and benzyl 5-amino-2-methyl-piperidine-1-carboxylate (308.45 mg, 1.24 mmol, 2 eq) in THF (15 mL) was added DIEA (401.35 mg, 3.11 mmol, 540.91 uL, 5 eq). The mixture was stirred at 15° C. for 12 h. The resulting mixture was poured into water (30 mL). The aqueous phase was extracted with EtOAc (30 mL×2). The combined organic phase was washed with brine (30 mL×2), dried over anhydrous Na$_2$SO$_4$, filtered and concentrated in vacuum. The residue was purified by silica gel chromatography (100-200 mesh silica gel, Petroleum ether/EtOAc=10/1, 1/1) to afford a racemate product (150 mg). Then the product was separation by SFC (column: DAICEL CHIRALPAK AS-H (250 mm*30 mm, 5um); mobile phase: [0.1% NH3H$_2$O MeOH]; B %: 45%-45%, 5 min) to afford product 1 (peak 1: RT=1.71 min, 70 mg, 80.36 umol, 12.94% yield, 84% purity) as a yellow solid, and product 2 (peak 2: 50 mg, 64.23 umol, 10.34% yield, 94% purity) as a yellow solid.

Step 10: (2S,5S)-2-methyl-5-[[4-[6-(3-methyltriazol-4-yl)-1H-pyrrolo[2,3-b]pyridin-3-yl]-5-(trifluoromethyl)pyrimidin-2-yl]amino]piperidine-1-carboxylate

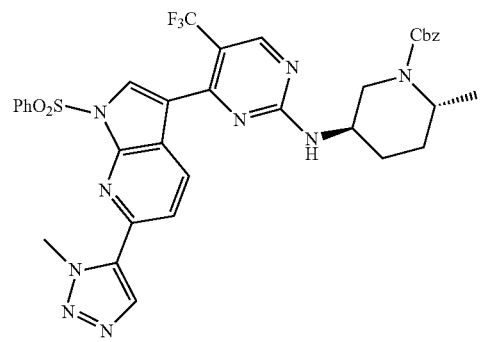

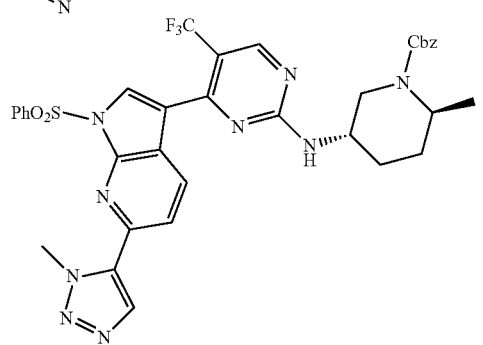

+

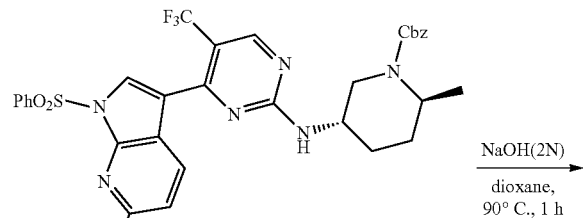

-continued

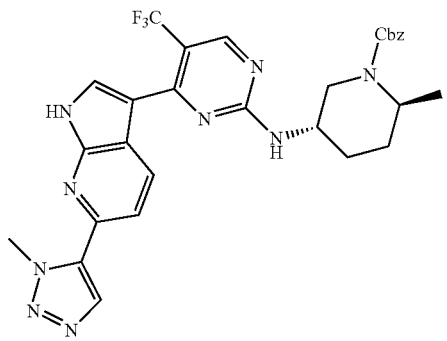

To a solution of benzyl (2S,5S)-5-[[4-[1-(benzenesulfonyl)-6-(3-methyltriazol-4-yl) pyrrolo[2,3-b]pyridin-3-yl]-5-(trifluoromethyl)pyrimidin-2-yl]amino]-2-methyl-piperidine-1-carboxylate (50 mg, 68.33 umol, 1 eq) in dioxane (4 mL) was added NaOH (2 M, 170.82 uL, 5 eq). The mixture was stirred at 90° C. for 1 h. It was cooled to 15° C. and poured into water (20 mL). The aqueous phase was extracted with EtOAc (20 mL×3). The combined organic phase was washed with brine (20 mL×2), dried over anhydrous Na$_2$SO$_4$, filtered and concentrated in vacuum to afford the title compound (50 mg, crude) as a yellow solid and used directly.

(Note: The reaction was combined with another batch in 20 mg scale for purification.)

Step 11: N-[(3S,6S)-6-methyl-3-piperidyl]-4-[6-(3-methyltriazol-4-yl)-1H-pyrrolo[2,3-b]pyridin-3-yl]-5-(trifluoromethyl)pyrimidin-2-amine

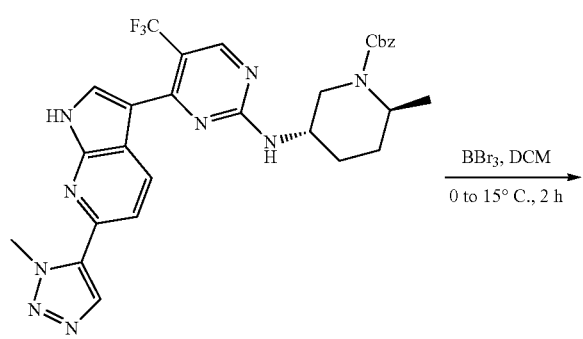

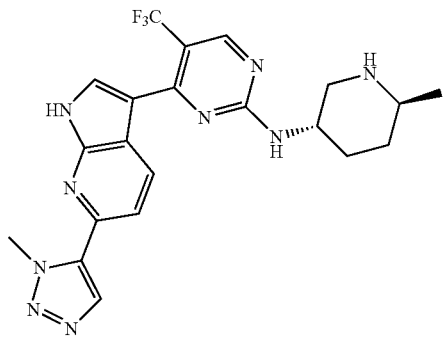

To a solution of benzyl (2S,5S)-2-methyl-5-[[4-[6-(3-methyltriazol-4-yl)-1H-pyrrolo[2,3-b]pyridin-3-yl]-5-(trifluoromethyl)pyrimidin-2-yl]amino]piperidine-1-carboxylate (50 mg, 84.52 umol, 1 eq) in DCM (5 mL) was added BBr$_3$ (105.87 mg, 422.59 umol, 40.72 uL, 5 eq). The mixture was stirred at 15° C. for 2 h. The mixture was concentrated in vacuum. The residue was washed with a mixture solution of Petroleum ether/EtOAc=3/1 (15 mL), filtered and the filter cake was collected. Then the filter cake was dissolved with MeOH (1 mL) and purified by prep-HPLC (HCl) to afford the title compound (20.6 mg, 99% purity, HCl) as a yellow solid. (Note: The reaction was combined with another batch in 20 mg scale for purification.)

Example 40. Synthesis of N-[(3R,6R)-6-methyl-3-piperidyl]-4-[6-(3-methyltriazol-4-yl)-1H-pyrrolo[2,3-b]pyridin-3-yl]-5-(trifluoromethyl)pyrimidin-2-amine (Compound 151)

Step 1: (2R,5R)-2-methyl-5-[[4-[6-(3-methyltriazol-4-yl)-1H-pyrrolo[2,3-b]pyridin-3-yl]-5-(trifluoromethyl)pyrimidin-2-yl]amino]piperidine-1-carboxylate

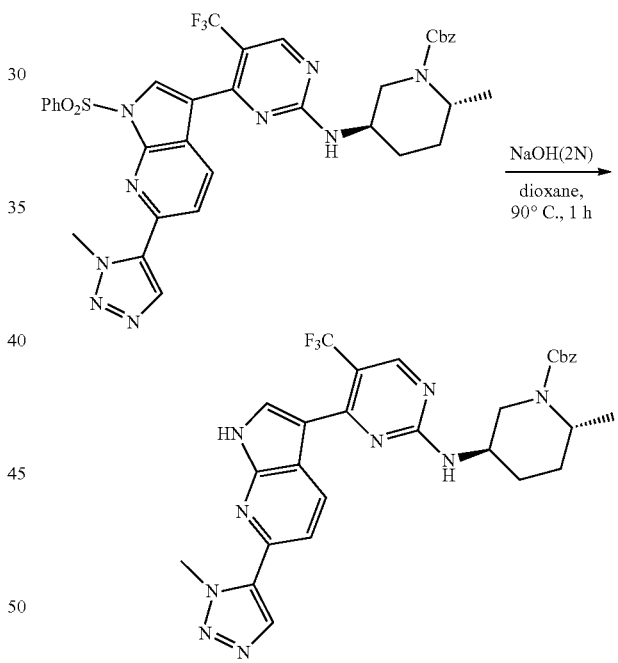

To a solution of benzyl (2R, 5R)-5-[[4-[1-(benzenesulfonyl)-6-(3-methyltriazol-4-yl) pyrrolo[2,3-b]pyridin-3-yl]-5-(trifluoromethyl)pyrimidin-2-yl]amino]-2-methyl-piperidine-1-carboxylate (50 mg, 68.33 umol, 1 eq) in dioxane (4 mL) was added NaOH (2 M, 170.82 uL, 5 eq). The mixture was stirred at 90° C. for 1 h. The reaction mixture was cooled to r.t. and poured into water (20 mL). The aqueous phase was extracted with EtOAc (20 mL×3). The combined organic phase was washed with brine (20 mL×2), dried over anhydrous Na$_2$SO$_4$, filtered and concentrated in vacuum to afford the title compound (50 mg, crude) as a yellow solid and used directly.

Step 2: N-[(3R, 6R)-6-methyl-3-piperidyl]-4-[6-(3-methyltriazol-4-yl)-1H-pyrrolo[2,3-b]pyridin-3-yl]-5-(trifluoromethyl)pyrimidin-2-amine

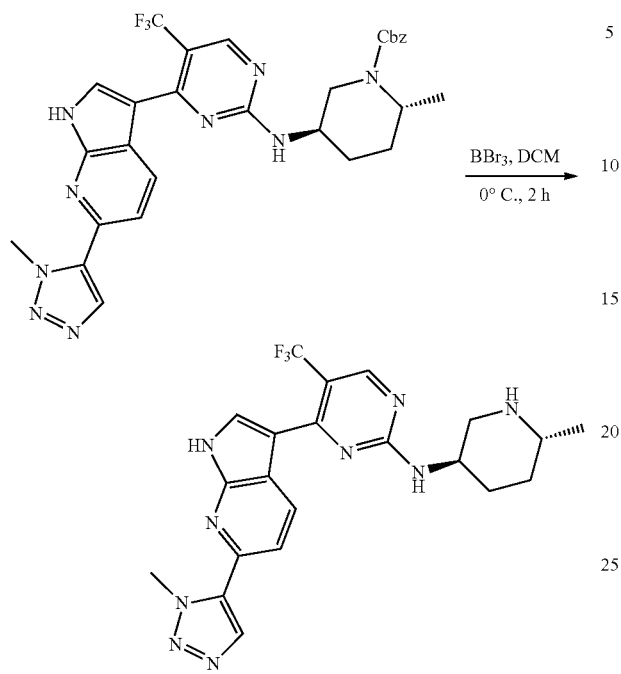

To a solution of benzyl (2R, 5R)-2-methyl-5-[[4-[6-(3-methyltriazol-4-yl)-1H-pyrrolo[2,3-b]pyridin-3-yl]-5-(trifluoromethyl)pyrimidin-2-yl]amino]piperidine-1-carboxylate (50 mg, 84.52 umol, 1 eq) in DCM (5 mL) was added BBr₃ (105.87 mg, 422.59 umol, 40.72 uL, 5 eq) at 0° C. The mixture was stirred at 0° C. for 2 h. The mixture was concentrated in vacuum. The residue was washed with a mixture solution of Petroleum ether/EtOAc=3/1 (15 mL), filtered and the filter cake was collected. Then the filter cake was dissolved with MeOH (1 mL) and purified by prep-HPLC (HCl) to afford the title compound (21 mg, 42.41 umol, 50.17% yield, 99.74% purity, HCl) as a yellow solid.

Example 41. Synthesis of 4-[6-(3,5-dimethylisoxazol-4-yl)-1H-pyrazolo[3,4-b]pyridin-3-yl]-N-[(3S, 6S)-6-methyl-3-piperidyl]-5-(trifluoromethyl)pyrimidin-2-amine (Compound 152)

Step 1: Benzyl(2S,5S)-5-[[4-[6-(3,5-dimethylisoxazol-4-yl)-1-tetrahydropyran-2-yl-pyrazolo[3,4-b]pyridin-3-yl]-5-(trifluoromethyl)pyrimidin-2-yl]amino]-2-methyl-piperidine-1-carboxylate

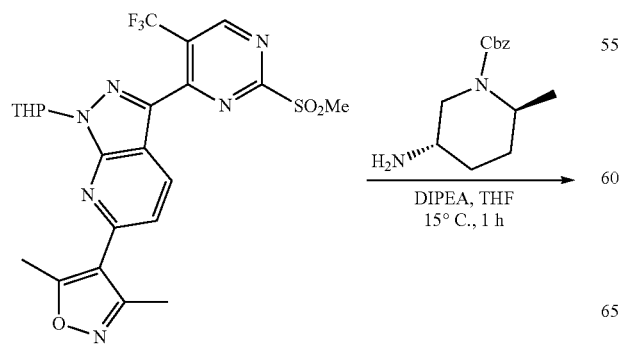

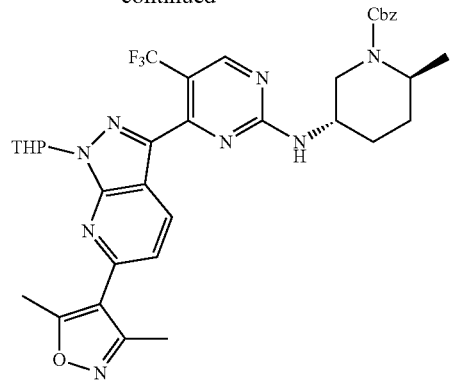

To a solution of 3,5-dimethyl-4-[3-[2-methylsulfonyl-5-(trifluoromethyl)pyrimidin-4-yl]-1-tetrahydropyran-2-yl-pyrazolo[3,4-b]pyridin-6-yl]isoxazole (178.85 mg, 342.30 umol, 1 eq) in THF (1 mL) was added DIPEA (132.72 mg, 1.03 mmol, 178.86 uL, 3 eq) and benzyl (2S,5S)-5-amino-2-methyl-piperidine-1-carboxylate (0.17 g, 684.60 umol, 2 eq). The mixture was stirred at 15° C. for 1 h. The reaction mixture concentrated under reduced pressure to give a residue. The residue was purified by column chromatography (SiO₂, Petroleum ether/EtOAc=2/1) to afford the title compound (150 mg) as a white solid.

Step 2: Benzyl(2S,5S)-5-[[4-[6-(3,5-dimethylisoxazol-4-yl)-1H-pyrazolo[3,4-b]pyridin-3-yl]-5-(trifluoromethyl)pyrimidin-2-yl]amino]-2-methyl-piperidine-1-carboxylate

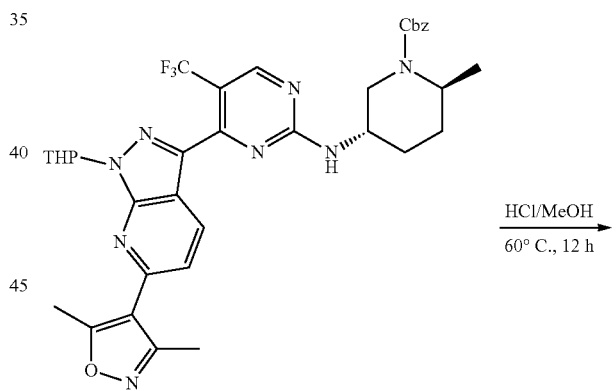

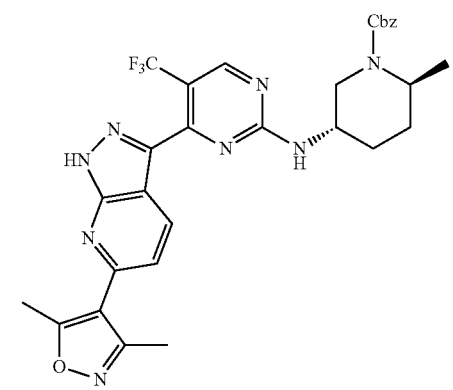

To a solution of benzyl(2S,5S)-5-[[4-[6-(3, 5-dimethyl-isoxazol-4-yl)-1-tetrahydropyran-2-yl-pyrazolo[3,4-b]pyridin-3-yl]-5-(trifluoromethyl)pyrimidin-2-yl]amino]-2-methyl-piperidine-1-carboxylate (0.15 g, 217.17 umol, 1 eq) in MeOH (2 mL) was added HCl/MeOH (4 M, 54.29 uL, 1.00 eq). The mixture was stirred at 60° C. for 12 h. The reaction mixture was concentrated under reduced pressure to afford the title compound (120 mg) as a yellow solid.

Step 3: 4-[6-(3,5-dimethylisoxazol-4-yl)-1H-pyrazolo[3,4-b]pyridin-3-yl]-N-[(3S,6S)-6-methyl-3-piperidyl]-5-(trifluoromethyl)pyrimidin-2-amine Example 42. Synthesis of 4-[6-(3,5-dimethylisoxazol-4-yl)-1H-pyrazolo[3,4-b]pyridin-3-yl]-N-[(3R, 6R)-6-methyl-3-piperidyl]-5-(trifluoromethyl)pyrimidin-2-amine (Compound 153)

Step 1: benzyl (2R,5R)-5-[[4-[6-(3,5-dimethylisoxazol-4-yl)-1-tetrahydropyran-2-yl-pyrazolo[3,4-b]pyridin-3-yl]-5-(trifluoromethyl)pyrimidin-2-yl]amino]-2-methyl-piperidine-1-carboxylate

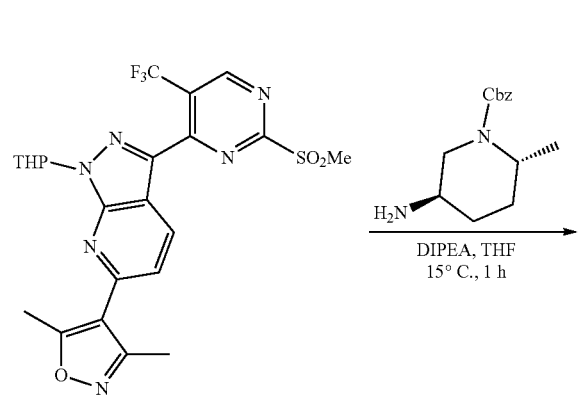

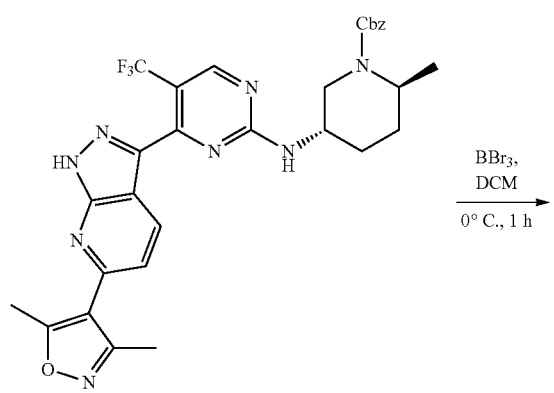

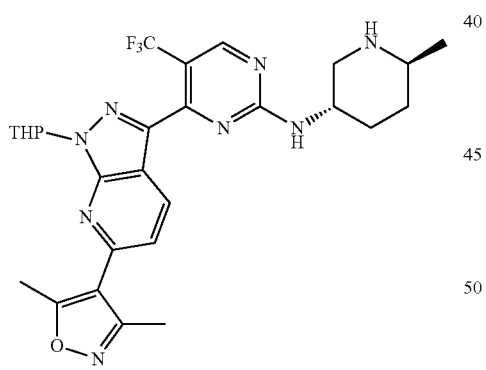

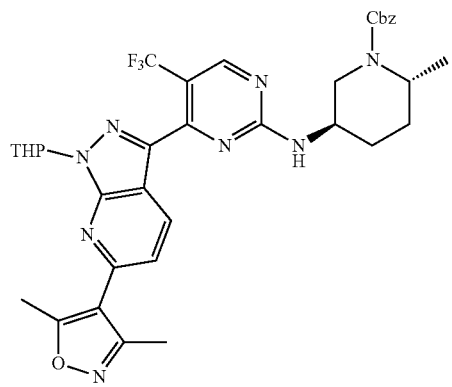

To a solution of benzyl (2S,5S)-5-[[4-[6-(3,5-dimethyl-isoxazol-4-yl)-1H-pyrazolo[3,4-b]pyridin-3-yl]-5-(trifluoromethyl)pyrimidin-2-yl]amino]-2-methyl-piperidine-1-carboxylate (0.1 g, 164.85 umol, 1 eq) in DCM (0.2 mL) was added BBr₃ (82.60 mg, 329.71 umol, 31.77 uL, 2 eq) at 0° C. The mixture was stirred at 0° C. for 1 h. The reaction mixture was concentrated. The residue was purified by prep-HPLC to afford the title compound (37.6 mg, HCl salt, 100% purity) as a yellow solid. (Note: The reaction was combined with another reaction in 20 mg scale for work-up and purification).

To a solution of 3,5-dimethyl-4-[3-[2-methylsulfonyl-5-(trifluoromethyl)pyrimidin-4-yl]-1-tetrahydropyran-2-yl-pyrazolo[3,4-b]pyridin-6-yl]isoxazole (157.81 mg, 302.03 umol, 1 eq) in THF (1 mL) was added DIPEA (117.10 mg, 906.09 umol, 157.82 uL, 3 eq) and benzyl (2R,5R)-5-amino-2-methyl-piperidine-1-carboxylate (0.15 g, 604.06 umol, 2 eq). The mixture was stirred at 15° C. for 1 h. The reaction mixture concentrated under reduced pressure to give a residue. The residue was purified by column chromatography (SiO₂, Petroleum ether/Ethyl acetate=2/1) to afford the title compound (140 mg) as a white solid.

Step 2: benzyl (2R,5R)-5-[[4-[6-(3,5-dimethylisoxazol-4-yl)-1H-pyrazolo[3,4-b]pyridin-3-yl]-5-(trifluoromethyl)pyrimidin-2-yl]amino]-2-methyl-piperidine-1-carboxylate

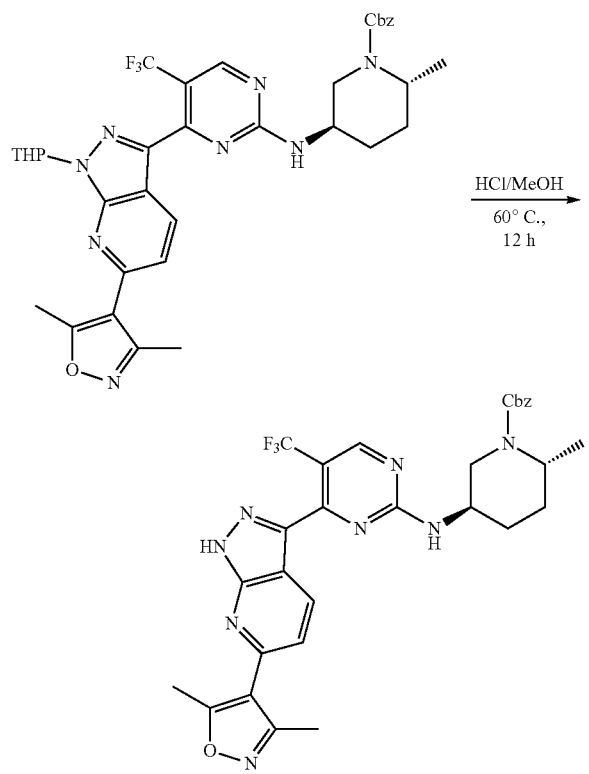

To a solution of benzyl (2R,5R)-5-[[4-[6-(3,5-dimethylisoxazol-4-yl)-1-tetrahydropyran-2-yl-pyrazolo[3,4-b]pyridin-3-yl]-5-(trifluoromethyl)pyrimidin-2-yl]amino]-2-methyl-piperidine-1-carboxylate (120.00 mg, 173.73 umol, 1 eq) in MeOH (0.2 mL) was added HCl/MeOH (4 M, 1 mL). The mixture was stirred at 60° C. for 12 h. It was concentrated under reduced pressure to afford the title compound (110 mg) as a yellow solid.

Step 3: 4-[6-(3,5-dimethylisoxazol-4-yl)-1H-pyrazolo[3,4-b]pyridin-3-yl]-N-[(3R,6R)-6-methyl-3-piperidyl]-5-(trifluoromethyl)pyrimidin-2-amine

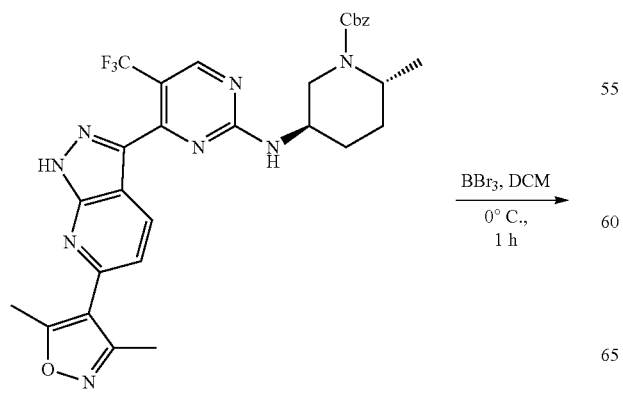

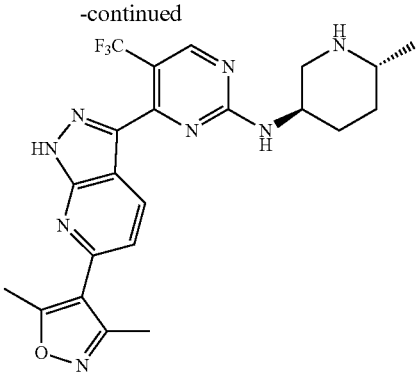

To a solution of benzyl (2R,5R)-5-[[4-[6-(3,5-dimethylisoxazol-4-yl)-1H-pyrazolo[3,4-b]pyridin-3-yl]-5-(trifluoromethyl)pyrimidin-2-yl]amino]-2-methyl-piperidine-1-carboxylate (0.09 g, 148.37 umol, 1 eq) in DCM (2 mL) was added BBr$_3$ (74.34 mg, 296.74 umol, 28.59 uL, 2 eq) at 0° C. The mixture was stirred at 0° C. for 1 h. The reaction mixture was concentrated under reduced pressure to give a residue. It was purified by prep-HPLC (HCl condition) to afford the title compound (21.7 mg) as a yellow solid.

(Note: The reaction was combined with another reaction in 20 mg scale for work-up and purification).

Example 43. Synthesis of N-[(3S,6S)-6-methyl-3-piperidyl]-4-[6-(5-methyl-1,3,4-thiadiazol-2-yl)-1H-pyrrolo[2,3-b]pyridin-3-yl]-5-(trifluoromethyl)pyrimidin-2-amine (Compound 154)

Step 1: Trimethyl-[2-[[3-[2-methylsulfanyl-5-(trifluoromethyl)pyrimidin-4-yl]-6-(5-methyl-1,3,4-thiadiazol-2-yl)pyrrolo[2,3-b]pyridin-1-yl]methoxy]ethyl]silane

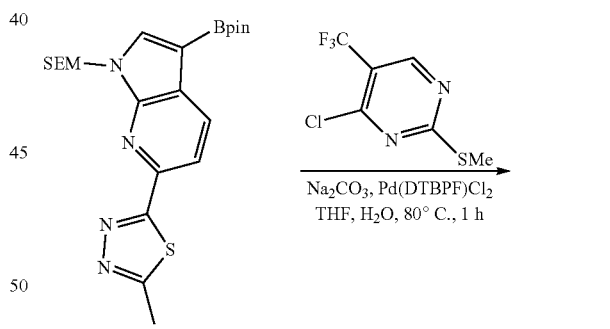

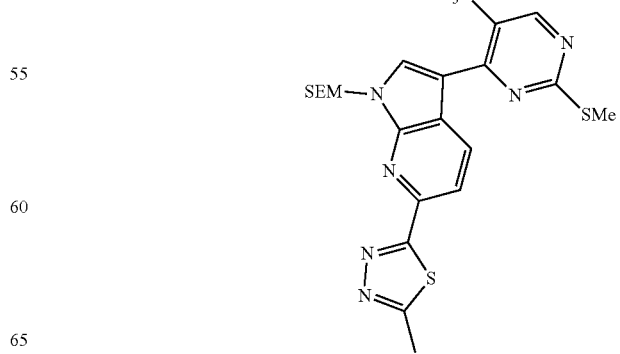

A mixture of trimethyl-[2-[[6-(5-methyl-1,3,4-thiadiazol-2-yl)-3-(4,4,5,5-tetramethyl-1,3,2-dioxaborolan-2-yl)pyrrolo[2,3-b]pyridin-1-yl]methoxy]ethyl]silane (0.05 M, 22.86 mL, 1 eq), 4-chloro-2-methylsulfanyl-5-(trifluoromethyl)pyrimidine (261.29 mg, 1.14 mmol, 1 eq), Na$_2$CO$_3$ (242.27 mg, 2.29 mmol, 2 eq) and ditert-butyl (cyclopentyl)phosphane:dichloropalladium:iron (74.49 mg, 114.29 umol, 0.1 eq) in THF (20 mL) and H$_2$O (2 mL) was degassed and purged with N$_2$ for 3 times, and then the mixture was stirred at 80° C. for 1 h under N$_2$ atmosphere. It was diluted by addition H$_2$O (100 mL), and extracted with EtOAc (50 mL×3), dried over Na$_2$SO$_4$, filtered and concentrated under reduced pressure to give a residue. The residue was purified by column chromatography (SiO$_2$, Petroleum ether/Ethyl acetate=10/1 to 5/1) to afford the title compound (150 mg) as a yellow solid. (Note: The reaction was combined with another reaction in 20 mg scale for purification.)

Step 2: Trimethyl-[2-[[3-[2-methylsulfonyl-5-(trifluoromethyl)pyrimidin-4-yl]-6-(5-methyl-1,3,4-thiadiazol-2-yl)pyrrolo[2,3-b]pyridin-1-yl]methoxy]ethyl]silane

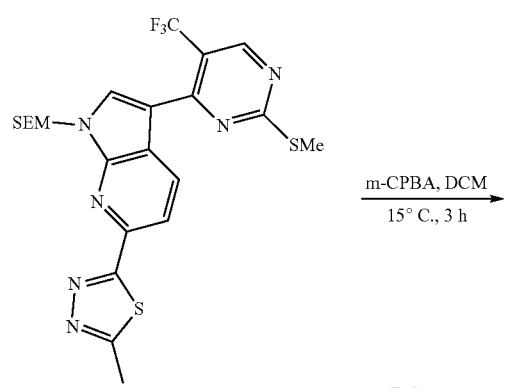

To a solution of trimethyl-[2-[[3-[2-methylsulfanyl-5-(trifluoromethyl)pyrimidin-4-yl]-6-(5-methyl-1,3,4-thiadiazol-2-yl)pyrrolo[2,3-b]pyridin-1-yl]methoxy]ethyl]silane (140 mg, 259.89 umol, 1 eq) in DCM (3 mL) was added m-CPBA (131.91 mg, 649.73 umol, 85% purity, 2.5 eq). The mixture was stirred at 15° C. for 3 h. The solution was washed with Sat.Na$_2$SO$_3$ (30 mL), Sat.NaHCO$_3$ (30 mL), brine (50 mL). The organic layers were dried over Na$_2$SO$_4$ and concentrated. The residue was washed with PE/EtOAc=5/1 (5 mL) and filtered to afford the title compound (120 mg) as a yellow solid. (Note: The reaction was combined with another reaction in 10 mg scale for purification.)

Step 3: Benzyl(2S,5S)-2-methyl-5-[[4-[6-(5-methyl-1,3,4-thiadiazol-2-yl)-1-(2-trimethylsilylethoxymethyl)pyrrolo[2,3-b]pyridin-3-yl]-5-(trifluoromethyl)pyrimidin2-yl]amino]piperidine-1-carboxylate

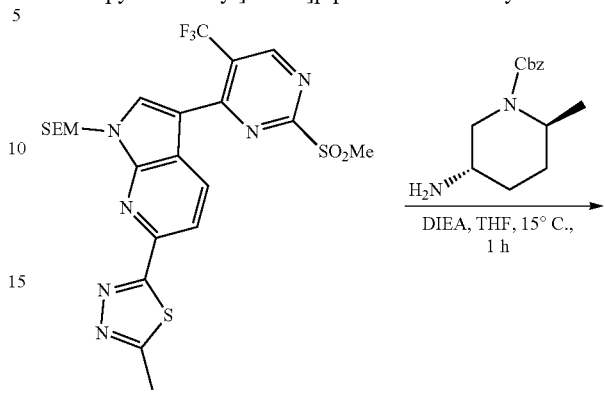

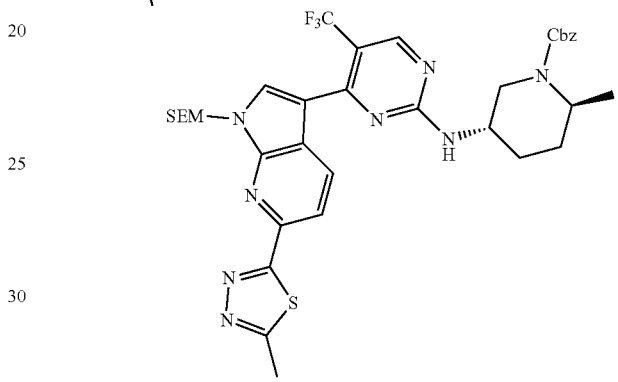

To a solution of trimethyl-[2-[[3-[2-methylsulfonyl-5-(trifluoromethyl)pyrimidin-4-yl]-6-(5-methyl-1,3,4-thiadiazol-2-yl)pyrrolo[2,3-b]pyridin-1-yl]methoxy]ethyl]silane (0.12 g, 210.27 umol, 1 eq) in THF (2 mL) was added DIEA (81.53 mg, 630.82 umol, 109.88 uL, 3 eq), benzyl (2S,5S)-5-amino-2-methyl-piperidine-1-carboxylate (104.43 mg, 420.55 umol, 2 eq). The mixture was stirred at 15° C. for 1 h. The resulting mixture was concentrated. The residue was purified by column chromatography (SiO$_2$, Petroleum ether/Ethyl acetate=10/1 to 2/1) to afford the title compound (0.09 g, 85.26 umol, 40.55% yield, 70% purity) as yellow oil.

Step 4: Benzyl (2S,5S)-2-methyl-5-[[4-[6-(5-methyl-1,3,4-thiadiazol-2-yl)-1H-pyrrolo[2,3-b]pyridin-3-yl]-5-(trifluoromethyl)pyrimidin-2-yl]amino]piperidine-1-carboxylate

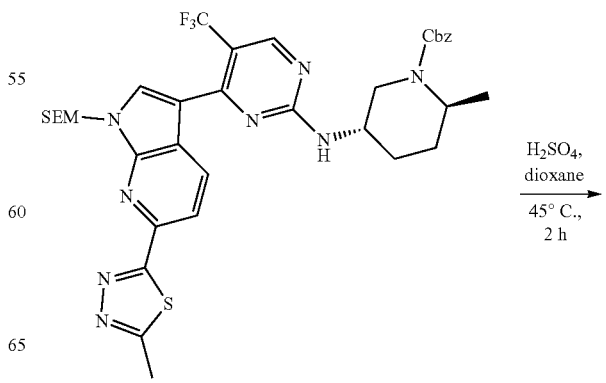

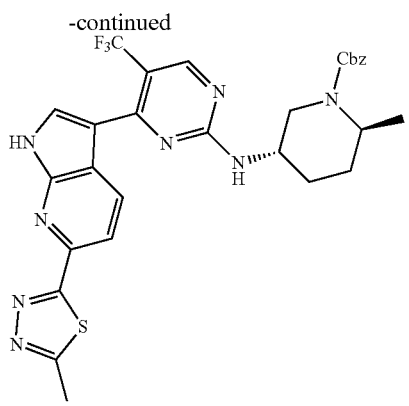

To a solution of benzyl (2S,5S)-2-methyl-5-[[4-[6-(5-methyl-1,3,4-thiadiazol-2-yl)-1-(2-trimethylsilylethoxymethyl)pyrrolo[2,3-b]pyridin-3-yl]-5-(trifluoromethyl)pyrimidin-2-yl]amino]piperidine-1-carboxylate (90 mg, 121.80 umol, 1 eq) in dioxane (3 mL) was added $H_2SO_4$ (1.19 g, 12.18 mmol, 649.26 uL, 100 eq). The mixture was stirred at 45° C. for 2 h. The mixture was adjusted pH to 8 with saturated aqueous NaOH, and extracted with EtOAc (50 mL×3), dried over $Na_2SO_4$, filtered and concentrated under reduced pressure to afford the title compound (0.12 g, crude) as a yellow solid.

Step 5: N-[(3S,6S)-6-methyl-3-piperidyl]-4-[6-(5-methyl-1, 3, 4-thiadiazol-2-yl)-1H-pyrrolo[2,3-b]pyridin-3-yl]-5-(trifluoromethyl)pyrimidin-2-amine

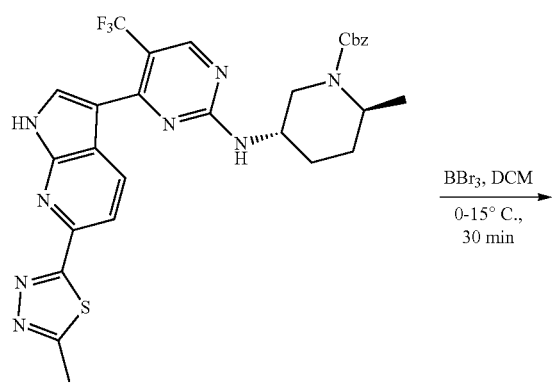

To a solution of benzyl(2S,5S)-2-methyl-5-[[4-[6-(5-methyl-1,3, 4-thiadiazol-2-yl)-1H-pyrrolo[2,3-b]pyridin-3-yl]-5-(trifluoromethyl)pyrimidin-2-yl]amino]piperidine-1-carboxylate (0.12 g, 197.16 umol, 1 eq) in DCM (3 mL) was added $BBr_3$ (148.18 mg, 591.49 umol, 56.99 uL, 3 eq). The mixture was stirred at 15° C. for 30 min. It was concentrated. The residue was triturated with PE/EtOAc=5/1 (5 mL) and filtered. The crude product was purified by prep-HPLC (HCl condition) to afford the title compound (19.5 mg, 38.16 umol, 19.36% yield, 100% purity, HCl) as a yellow solid.

Example 44. Synthesis of 4-[6-(5-methyl-1,3,4-thiadiazol-2-yl)-1H-pyrrolo[2,3-b]pyridin-3-yl]-N-[(3S)-3-piperidyl]-5-(trifluoromethyl)pyrimidin-2-amine (Compound 155)

Step 1: Trimethyl-[2-[[6-(5-methyl-1, 3, 4-thiadiazol-2-yl) pyrrolo[2,3-b]pyridin-1-yl]methoxy]ethyl] silane

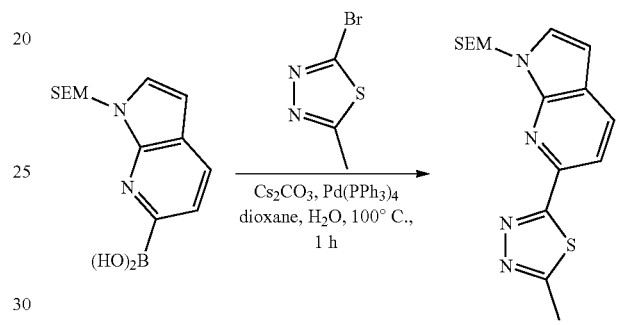

A mixture of [1-(2-trimethylsilylethoxymethyl)pyrrolo[2,3-b]pyridin-6-yl]boronic acid (4 g, 13.69 mmol, 1 eq), 2-bromo-5-methyl-1,3,4-thiadiazole (2.45 g, 13.69 mmol, 1 eq), $Cs_2CO_3$ (8.92 g, 27.38 mmol, 2 eq), $Pd(PPh_3)_4$ (1.58 g, 1.37 mmol, 0.1 eq) in dioxane (50 mL) and $H_2O$ (5 mL) was degassed and purged with $N_2$ for 3 times, and then the mixture was stirred at 100° C. for 1 h under $N_2$ atmosphere. The reaction mixture was diluted with $H_2O$ (300 mL) and extracted with EtOAc (100 mL×3). The combined organic layers were washed with brine (300 mL×2), dried over $Na_2SO_4$, filtered and concentrated under reduced pressure to give a residue. The residue was purified by column chromatography ($SiO_2$, Petroleum ether/Ethyl acetate=10/1 to 4/1) to afford the title compound (1.6 g, 4.39 mmol, 32.04% yield, 95% purity) as a yellow solid.

Step 2: 2-[[3-bromo-6-(5-methyl-1, 3, 4-thiadiazol-2-yl) pyrrolo[2,3-b]pyridin-1-yl]methoxy]ethyl-trimethyl-silane

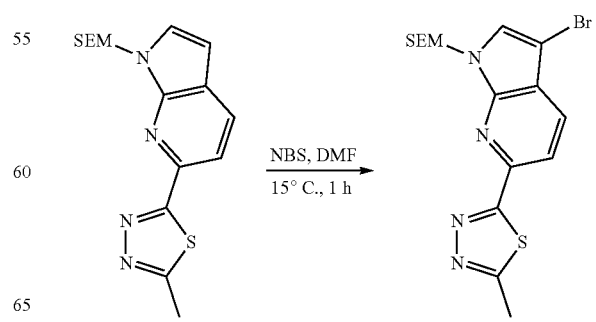

To a solution of trimethyl-[2-[[6-(5-methyl-1, 3, 4-thiadiazol-2-yl) pyrrolo[2,3-b]pyridin-1-yl]methoxy]ethyl]silane (1.6 g, 4.62 mmol, 1 eq) in DMF (20 mL) was added NBS (821.79 mg, 4.62 mmol, 1 eq). The mixture was stirred at 15° C. for 1 h. The resulting mixture was diluted with H₂O 200 mL and extracted with EtOAc (100 mL×3). The combined organic layers were washed with brine (300 mL×2), dried over Na₂SO₄, filtered and concentrated under reduced pressure to give a residue. The residue was purified by column chromatography (SiO₂, Petroleum ether/Ethyl acetate=10/1 to 5/1) to afford the title compound (1.6 g) as a yellow solid.

Step 3: Trimethyl-[2-[[6-(5-methyl-1,3,4-thiadiazol-2-yl)-3-(4,4,5,5-tetramethyl-1,3,2-dioxaborolan-2-yl)pyrrolo[2,3-b]pyridin-1-yl]methoxy]ethyl]silane

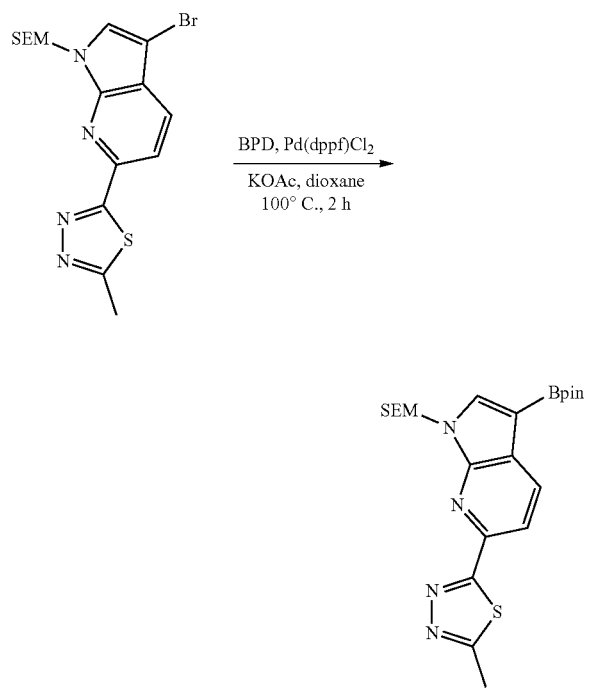

A mixture of 2-[[3-bromo-6-(5-methyl-1, 3, 4-thiadiazol-2-yl)pyrrolo[2,3-b]pyridin-1-yl]methoxy]ethyl-trimethyl-silane (1.6 g, 3.76 mmol, 1 eq), 4,4,5,5-tetramethyl-2-(4,4,5,5-tetramethyl-1,3,2-dioxaborolan-2-yl)-1,3,2-dioxaborolane (1.91 g, 7.52 mmol, 2 eq), AcOK (738.21 mg, 7.52 mmol, 2 eq) and Pd(dppf)Cl₂ (275.20 mg, 376.10 umol, 0.1 eq) in dioxane (30 mL) was degassed and purged with N₂ for 3 times, and then the mixture was stirred at 100° C. for 2 h under N₂ atmosphere. It was filtered and the filtrate was concentrated. The residue was purified by column chromatography (SiO₂, Petroleum ether/Ethyl acetate=10/1 to 4:1, plate 1) to give a residue (1.5 g). 200 mg of crude product was purified by prep-HPLC (TFA condition). Then the eluent was concentrated to give a residue to afford the title compound (100 mg, TFA) as yellow oil.

Step 4: Tert-butyl(3S)-3-[[4-[6-(5-methyl-1,3,4-thiadiazol-2-yl)-1-(2-trimethylsilylethoxymethyl)pyrrolo[2,3-b]pyridin-3-yl]-5-(trifluoromethyl)pyrimidin-2-yl]amino]piperidine-1-carboxylate

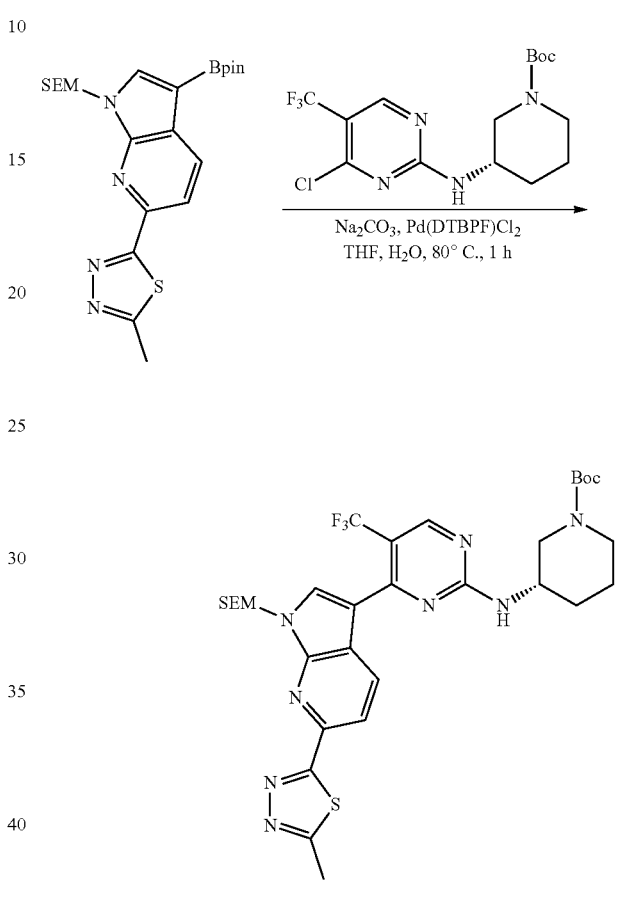

A mixture of trimethyl-[2-[[6-(5-methyl-1,3,4-thiadiazol-2-yl)-3-(4,4,5,5-tetramethyl-1,3,2-dioxaborolan-2-yl)pyrrolo[2,3-b]pyridin-1-yl]methoxy]ethyl]silane (0.05 M, 3.41 mL, 1 eq, TFA), tert-butyl (3S)-3-[[4-chloro-5-(trifluoromethyl)pyrimidin-2-yl]amino]piperidine-1-carboxylate (77.91 mg, 204.60 umol, 1.2 eq), Na₂CO₃ (36.14 mg, 341.00 umol, 2 eq) and ditert-butyl(cyclopentyl)phosphane; dichloropalladium; iron (11.11 mg, 17.05 umol, 0.1 eq) in THF (5 mL) and H₂O (0.5 mL) was degassed and purged with N₂ for 3 times, and then the mixture was stirred at 80° C. for 1 h under N₂ atmosphere. The reaction mixture was diluted with H₂O (50 mL) and extracted with EtOAc (20 mL×3). The combined organic layers were washed with brine (60 mL×2), dried over Na₂SO₄, filtered and concentrated under reduced pressure to give a residue.

The residue was purified by column chromatography (SiO₂, Petroleum ether/Ethyl acetate=10/1 to 1/1) to afford the title compound (0.11 g) as a white solid.

Step 5: 4-[6-(5-methyl-1,3,4-thiadiazol-2-yl)-1H-pyrrolo[2,3-b]pyridin-3-yl]-N-[(3S)-3-piperidyl]-5-(trifluoromethyl)pyrimidin-2-amine

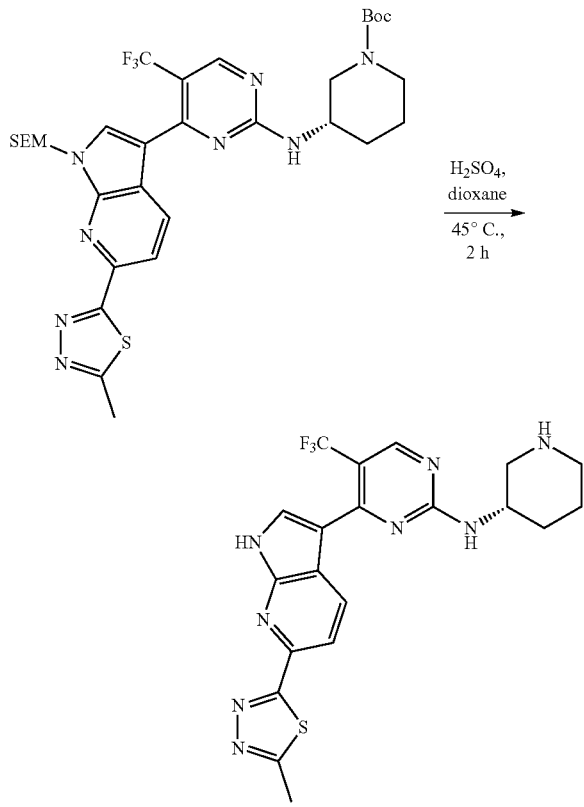

To a solution of tert-butyl(3S)-3-[[4-[6-(5-methyl-1,3,4-thiadiazol-2-yl)-1-(2-trimethylsilylethoxymethyl)pyrrolo[2,3-b]pyridin-3-yl]-5-(trifluoromethyl)pyrimidin-2-yl]amino]piperidine-1-carboxylate (0.11 g, 159.22 umol, 1 eq) in dioxane (3 mL) was added $H_2SO_4$ (1.56 g, 15.92 mmol, 848.73 uL, 100 eq). The solution was stirred at 45° C. for 2 h. The mixture was adjusted pH to 8 with saturated aqueous NaOH, and extracted with EtOAc (50 mL×3), dried over $Na_2SO_4$, filtered and concentrated under reduced pressure to give a residue. The residue was purified by prep-HPLC (HCl condition) to afford the title compound (17.4 mg, 34.89 umol, 21.91% yield, 99.65% purity, HCl) as a yellow solid.

Example 45. Synthesis of 4-[6-(3-methylisoxazol-4-yl)-1H-pyrrolo[2,3-b]pyridin-3-yl]-N-[(3S,6S)-6-methyl-3-piperidyl]-5-(trifluoromethyl)pyrimidin-2-amine (Compound 156)

Step 1: 4-[1-(benzenesulfonyl)-3-(4,4,5,5-tetramethyl-1,3,2-dioxaborolan-2-yl) pyrrolo[2,3-b]pyridin-6-yl]-3-methyl-isoxazole

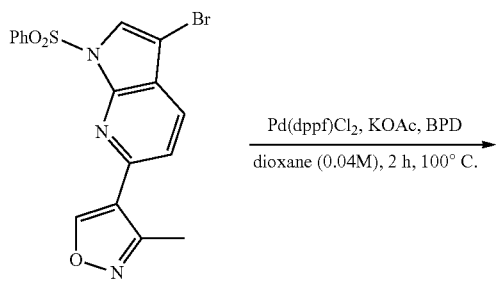

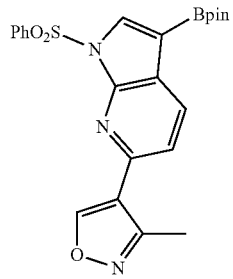

A mixture of 4-[1-(benzenesulfonyl)-3-bromo-pyrrolo[2,3-b]pyridin-6-yl]-3-methyl-isoxazole (1.5 g, 3.59 mmol, 1 eq), 4,4,5,5-tetramethyl-2-(4,4,5,5-tetramethyl-1,3,2-dioxaborolan-2-yl)-1,3,2-dioxaborolane (1.37 g, 5.38 mmol, 1.5 eq), Pd(dppf)Cl$_2$ (262.41 mg, 358.63 umol, 0.1 eq), KOAc (703.91 mg, 7.17 mmol, 2 eq) in dioxane (90 mL) was degassed and purged with N$_2$ for 3 times, and then the mixture was stirred at 100° C. for 2 h under N$_2$ atmosphere. It was cooled to the room temperature and concentrated under reduced pressure to remove solvent. The residue was purified by column chromatography (SiO$_2$, Petroleum ether/Ethyl acetate=20/1 to 5/1) to afford the title compound (1.2 g) was obtained as a white solid. (Note: The reaction was combined with another reaction in 200 mg scale for purification and work up.)

Step 2: 4-[1-(benzenesulfonyl)-3-[2-methylsulfanyl-5-(trifluoromethyl)pyrimidin-4-yl]pyrrolo[2,3-b]pyridin-6-yl]-3-methyl-isoxazol)

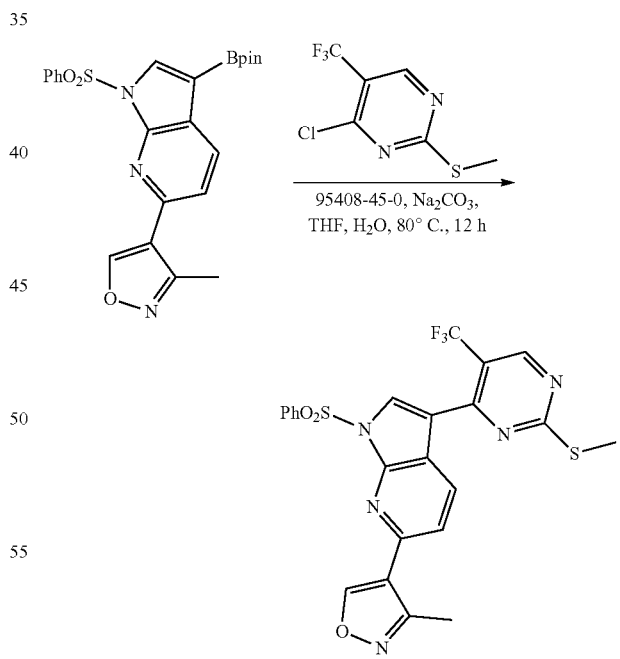

A mixture of 4-[1-(benzenesulfonyl)-3-(4,4,5,5-tetramethyl-1,3,2-dioxaborolan-2-yl) pyrrolo[2,3-b]pyridin-6-yl]-3-methyl-isoxazole (1.1 g, 2.36 mmol, 1 eq), 4-chloro-2-methylsulfanyl-5-(trifluoromethyl)pyrimidine (540.45 mg, 2.36 mmol, 1 eq), ditert-butyl(cyclopentyl) phosphane; dichloropalladium; iron (154.07 mg, 236.39 umol, 0.1 eq), Na$_2$CO$_3$ (501.10 mg, 4.73 mmol, 2 eq) in THF (40 mL) and H₂O (4 mL) was degassed and purged with N₂ for 3 times, and then the mixture was stirred at 80° C. for 12 h under N₂ atmosphere. It was cooled to the room temperature and diluted with H₂O (60 mL) and extracted with EtOAc (30 mL×3). The combined organic layers were washed with brine (60 mL), dried over Na₂SO₄, filtered and concentrated under reduced pressure to give a residue. The residue was purified by flash silica gel chromatography (ISCO®; 20 g SepaFlash® Silica Flash Column, Eluent of 0~30% Ethyl acetate/Petroleum ether gradient @ 75 mL/min) to afford the title compound (800 mg, crude) as a yellow solid.

Step 3: 4-[1-(benzenesulfonyl)-3-[2-methylsulfonyl-5-(trifluoromethyl)pyrimidin-4-yl]pyrrolo[2,3-b]pyridin-6-yl]-3-methyl-isoxazole

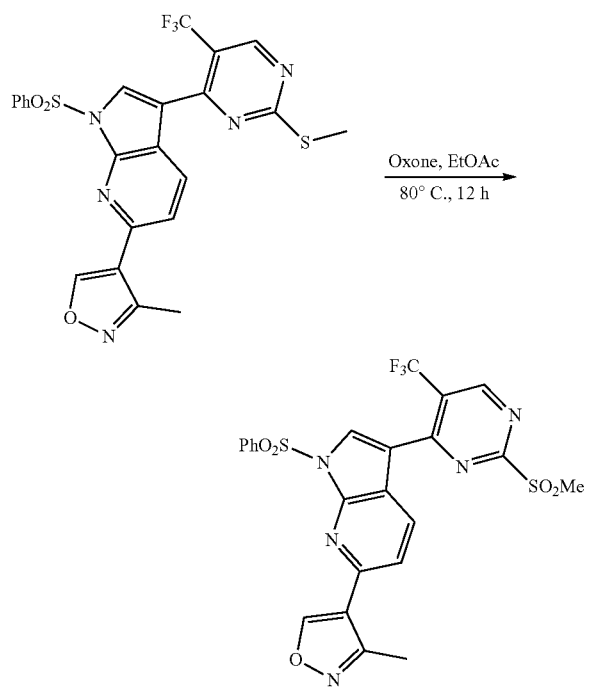

To a solution of 4-[1-(benzenesulfonyl)-3-[2-methylsulfanyl-5-(trifluoromethyl)pyrimidin-4-yl]pyrrolo[2,3-b]pyridin-6-yl]-3-methyl-isoxazole (800 mg, 1.51 mmol, 1 eq) in EtOAc (40 mL) was added Oxone (4.63 g, 7.53 mmol, 5 eq). The mixture was stirred at 80° C. for 12 h. The reaction mixture was filtered and the filtrate was quenched by saturation Na₂SO₃ (60 mL). The water layer was extracted with EtOAc (30 mL×3). The combined organic layers were washed with brine (50 mL), dried over Na₂SO₄, filtrate and concentrated. The residue was purified by flash silica gel chromatography (ISCO®; 20 g SepaFlash® Silica Flash Column, Eluent of 0~50% Ethyl acetate/Petroleum ether gradient @ 75 mL/min) to afford the title compound (380 mg, 674.32 umol, 44.80% yield) as a pink solid.

Step 4: Benzyl(2S,5S)-5-[[4-[1-(benzenesulfonyl)-6-(3-methylisoxazol-4-yl)pyrrolo[2,3-b]pyridin-3-yl]-5-(trifluoromethyl)pyrimidin-2-yl]amino]-2-methyl-piperidine-1-carboxylate

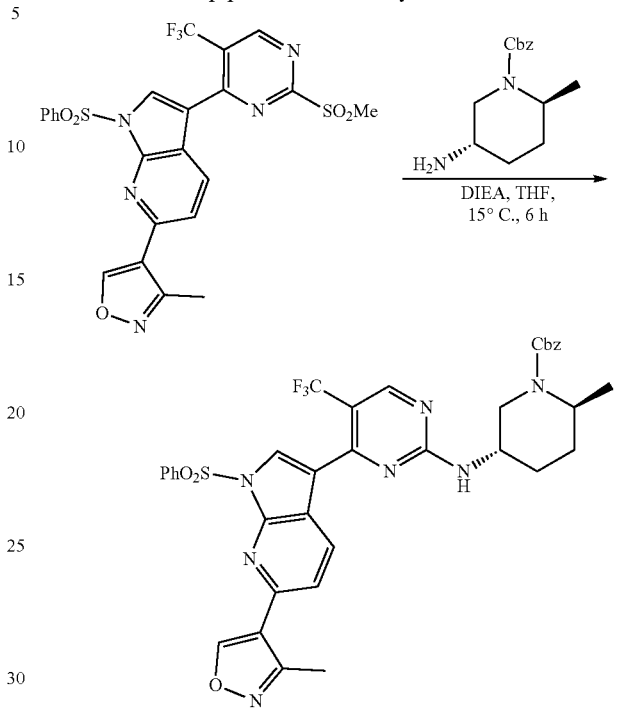

To a solution of 4-[1-(benzenesulfonyl)-3-[2-methylsulfonyl-5-(trifluoromethyl)pyrimidin-4-yl]pyrrolo[2,3-b]pyridin-6-yl]-3-methyl-isoxazole (170 mg, 301.67 umol, 1 eq) and benzyl (2S,5S)-5-amino-2-methyl-piperidine-1-carboxylate (74.91 mg, 301.67 umol, 1 eq) in THF (2 mL) was added DIPEA (194.94 mg, 1.51 mmol, 262.72 uL, 5 eq). The mixture was stirred at 15° C. for 6 h. It was concentrated under reduced pressure to remove solvent. The residue was purified by flash silica gel chromatography (ISCO®; 4 g SepaFlash® Silica Flash Column, Eluent of 0~25% Ethyl acetate/Petroleum ether gradient @ 50 mL/min) to afford the title compound (100 mg) as a yellow solid. (Note: The reaction was combined with another reaction in 20 mg scale for purification and work up.)

Step 5: Benzyl(2S,5S)-2-methyl-5-[[4-[6-(3-methyl-isoxazol-4-yl)-1H-pyrrolo[2,3-b]pyridin-3-yl]-5-(trifluoromethyl)pyrimidin-2-yl]amino]piperidine-1-carboxylate

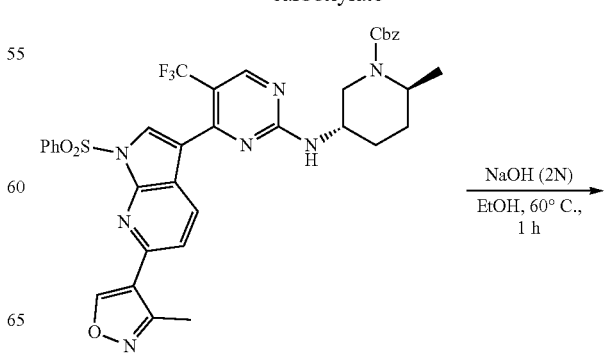

-continued

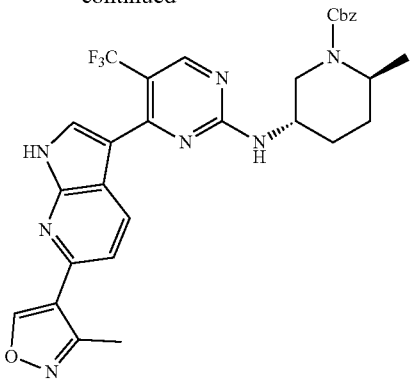

To a solution of benzyl(2S,5S)-5-[[4-[1-(benzenesulfonyl)-6-(3-methylisoxazol-4-yl) pyrrolo[2,3-b]pyridin-3-yl]-5-(trifluoromethyl)pyrimidin-2-yl]amino]-2-methyl-piperidine-1-carboxylate (90 mg, 122.99 umol, 1 eq) in EtOH (3 mL) was added NaOH (2 M, 2.5 mL). The mixture was stirred at 60° C. for 1 h. The reaction mixture was diluted with $H_2O$ (10 mL) and extracted with EtOAc (10 mL×3). The combined organic layers were washed with brine (10 mL), dried over $Na_2SO_4$, filtered and concentrated under reduced pressure to afford the title compound (80 mg) as a yellow solid, and it was used into the next step without further purification. (Note: The reaction was combined with another reaction in 10 mg scale for purification and work up.)

Step 6: 4-[6-(3-methylisoxazol-4-yl)-1H-pyrrolo[2,3-b]pyridin-3-yl]-N-[(3S,6S)-6-methyl-3-piperidyl] 5-(trifluoromethyl)pyrimidin-2-amine

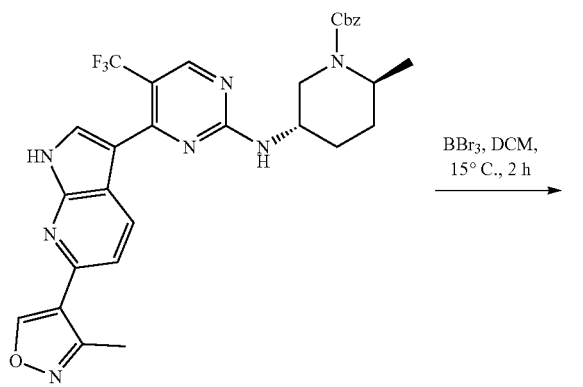

To a solution of benzyl(2S,5S)-2-methyl-5-[[4-[6-(3-methylisoxazol-4-yl)-1H-pyrrolo[2,3-b]pyridin-3-yl]-5-(trifluoromethyl)pyrimidin-2-yl]amino]piperidine-1-carboxylate (70 mg, 118.33 umol, 1 eq) in DCM (7 mL) was added $BBr_3$ (148.22 mg, 591.63 umol, 57.01 uL, 5 eq). The mixture was stirred at 15° C. for 2 h. The reaction mixture was quenched by saturation $NaHCO_3$ solution (1.5 mL), and then concentrated under reduced pressure to give a residue. The residue was diluted with $H_2O$ (1.5 mL) and DMF (1.5 mL), then adjusted to pH=4 with HCl (2 N). The residue was purified by prep-HPLC (FA condition) to afford the title compound (FA, 22.2 mg, 98.26% purity) as a white solid.

Example 46. Synthesis of 4-[6-(3-methylisoxazol-4-yl)-1H-pyrrolo[2,3-b]pyridin-3-yl]-N-[(3R,6R)-6-methyl-3-piperidyl]-5-(trifluoromethyl)pyrimidin-2-amine (Compound 157)

Step 1: Benzyl (2R,5R)-5-[[4-[1-(benzenesulfonyl)-6-(3-methylisoxazol-4-yl)pyrrolo[2,3-b]pyridin-3-yl]-5-(trifluoromethyl)pyrimidin-2-yl]amino]-2-methyl-piperidine-1-carboxylate

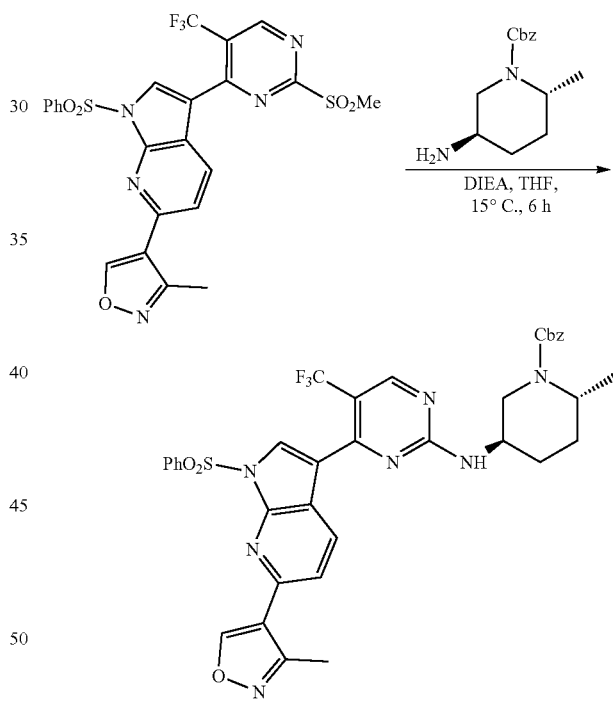

To a solution of 4-[1-(benzenesulfonyl)-3-[2-methylsulfonyl-5-(trifluoromethyl)pyrimidin-4-yl]pyrrolo[2,3-b]pyridin-6-yl]-3-methyl-isoxazole (170 mg, 301.67 umol, 1 eq) and benzyl (2R,5R)-5-amino-2-methyl-piperidine-1-carboxylate (74.91 mg, 301.67 umol, 1 eq) in THF (2 mL) was added DIPEA (194.94 mg, 1.51 mmol, 262.72 uL, 5 eq). The mixture was stirred at 15° C. for 6 h. The solution was concentrated under reduced pressure to remove solvent. The residue was purified by flash silica gel chromatography (ISCO®; 4 g SepaFlash® Silica Flash Column, Eluent of 0~25% EtOAc/PE @ 50 mL/min) to afford the title compound (120 mg) as a yellow solid. (Note: The reaction was combined with another reaction in 20 mg scale for work up)

Step 2: Benzyl (2R,5R)-2-methyl-5-[[4-[6-(3-meth-ylisoxazol-4-yl)-1H-pyrrolo[2,3-b]pyridin-3-yl]-5-(trifluoromethyl)pyrimidin-2-yl]amino]piperidine-1-carboxylate

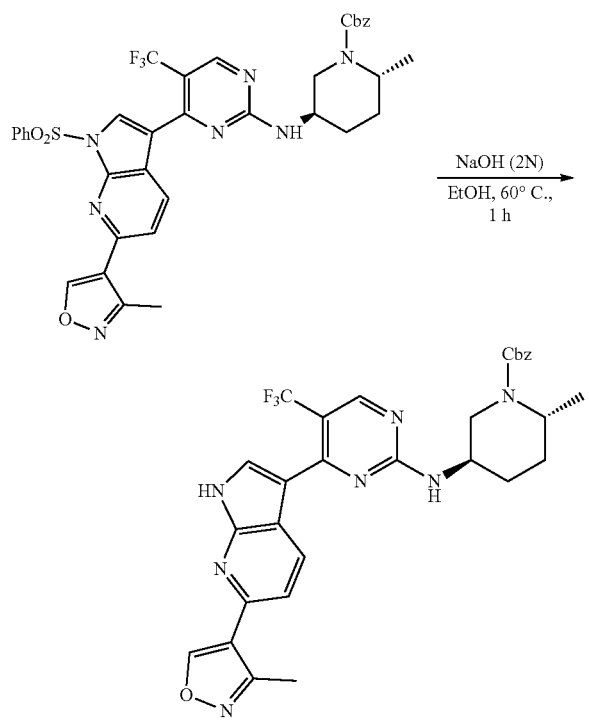

To a solution of benzyl (2R,5R)-5-[[4-[1-(benzenesulfo-nyl)-6-(3-methylisoxazol-4-yl)pyrrolo[2,3-b]pyridin-3-yl]-5-(trifluoromethyl)pyrimidin-2-yl]amino]-2-methyl-piperidine-1-carboxylate (110.15 mg, 150.53 umol, 1 eq) in EtOH (3 mL) was added NaOH (2 M, 2.5 mL). The mixture was stirred at 60° C. for 1 h. The reaction mixture was diluted with H₂O 10 mL and extracted with EtOAc (10 mL×3). The combined organic layers were washed with brine (10 mL), dried over Na₂SO₄, filtered and concentrated under reduced pressure to afford the title (100 mg) as a yellow solid which was used into the next step without further purification.

Step 3: 4-[6-(3-methylisoxazol-4-yl)-1H-pyrrolo[2,3-b]pyridin-3-yl]-N-[(3R,6R)-6-methyl-3-piperidyl]-5-(trifluoromethyl)pyrimidin-2-amine

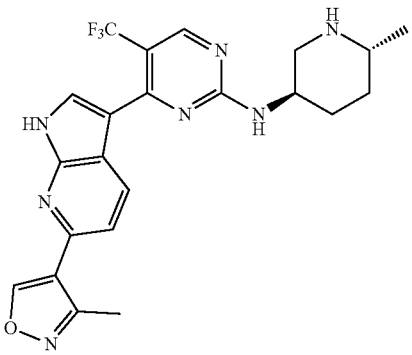

To a solution of benzyl (2R,5R)-2-methyl-5-[[4-[6-(3-methylisoxazol-4-yl)-1H-pyrrolo[2,3-b]pyridin-3-yl]-5-(tri-fluoromethyl)pyrimidin-2-yl]amino]piperidine-1-carboxy-late (90 mg, 152.13 umol, 1 eq) in DCM (9 mL) was added BBr₃ (190.56 mg, 760.67 umol, 73.29 uL, 5 eq). The mixture was stirred at 15° C. for 2 h. The reaction mixture was quenched by saturation NaHCO₃ (1.5 mL), and then concentrated under reduced pressure to give a residue. The residue was diluted with H₂O (1.5 mL) and DMF (1.5 mL), then adjusted to pH=4 with HCl (2 N). The residue was purified by prep-HPLC (FA condition) to afford the title compound (FA, 20.3 mg) as a white solid.

Example 47. Synthesis of N-[(3R,6R)-6-methyl-3-piperidyl]-4-[6-(5-methyl-1,3,4-thiadiazol-2-yl)-1H-pyrrolo[2,3-b]pyridin-3-yl]-5-(trifluoromethyl)py-rimidin-2-amine (Compound 158)

Step 1: Benzyl (2R, 5R)-2-methyl-5-[[4-[6-(5-methyl-1,3,4-thiadiazol-2-yl)-1-(2-trimethylsily-lethoxymethyl)pyrrolo[2,3-b]pyridin-3-yl]-5-(trifluo-romethyl)pyrimidin-2-yl]amino]piperidine-1-carboxylate

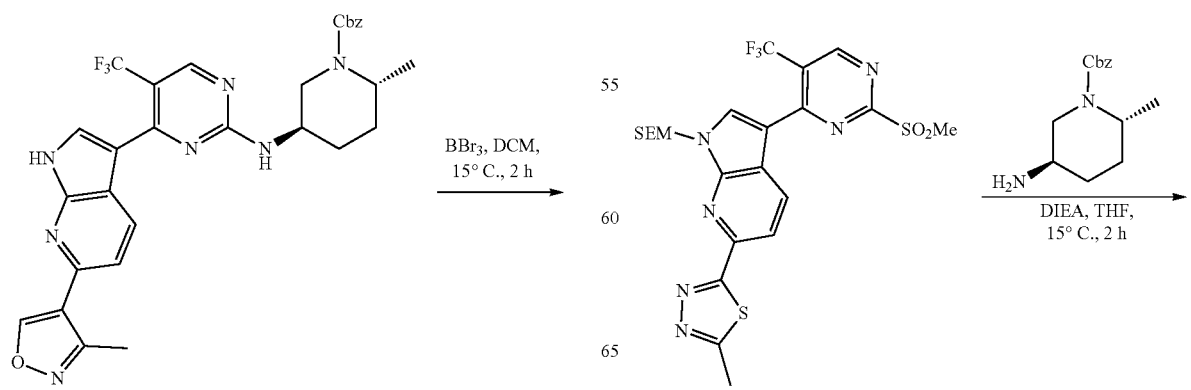

171
-continued

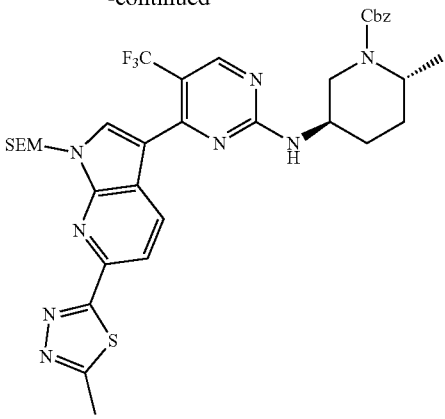

To a solution of trimethyl-[2-[[3-[2-methylsulfonyl-5-(trifluoromethyl)pyrimidin-4-yl]-6-(5-methyl-1,3,4-thiadiazol-2-yl)pyrrolo[2,3-b]pyridin-1-yl]methoxy]ethyl]silane (0.2 g, 350.46 umol, 1 eq) in THF (2 mL) was added DIEA (135.88 mg, 1.05 mmol, 183.13 uL, 3 eq), benzyl (2R,5R)-5-amino-2-methyl-piperidine-1-carboxylate (149.68 mg, 602.79 umol, 1.72 eq). The mixture was stirred at 15° C. for 2 h. The reaction mixture was concentrated to give a residue. The residue was purified by column chromatography (SiO$_2$, PE/EtOAc=10/1 to 2/1) to afford the title compound (250 mg) as yellow oil.

Step 2: N-[(3R,6R)-6-methyl-3-piperidyl]-4-[6-(5-methyl-1,3,4-thiadiazol-2-yl)-1H-pyrrolo[2,3-b]pyridin-3-yl]-5-(trifluoromethyl)pyrimidin-2-amine

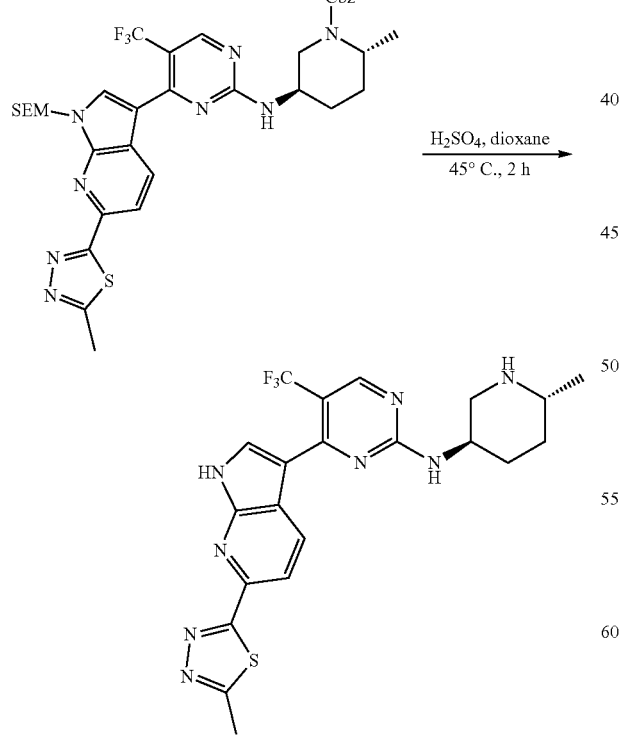

To a solution of benzyl (2R,5R)-2-methyl-5-[[4-[6-(5-methyl-1,3,4-thiadiazol-2-yl)-1-(2-trimethylsilylethoxymethyl)pyrrolo[2,3-b]pyridin-3-yl]-5-(trifluoromethyl)pyrimidin-2-yl]amino]piperidine-1-carboxylate (0.25 g, 338.34 umol, 1 eq) in dioxane (5 mL) was added H$_2$SO$_4$ (3.32 g, 33.83 mmol, 1.80 mL, 100 eq). The mixture was stirred at 45° C. for 2 h. The mixture was adjusted pH to 8 with saturated aqueous NaOH, and extracted with EtOAc (50 mL×3), dried over Na$_2$SO$_4$, filtered and concentrated under reduced pressure to give a residue. It was purified by prep-HPLC (HCl condition) to afford the title compound (27.8 mg, 51.69 umol, 15.28% yield, 95% purity, HCl) as a yellow solid.

Example 48. Synthesis of N-[(3R,6R)-6-methyl-3-piperidyl]-4-[6-(3-methyl-1,2,4-thiadiazol-5-yl)-1H-pyrrolo[2,3-b]pyridin-3-yl]-5-(trifluoromethyl)pyrimidin-2-amine (Compound 159)

Step 1: Trimethyl-[2-[[6-(3-methyl-1,2,4-thiadiazol-5-yl)pyrrolo[2,3-b]pyridin-1-yl]methoxy]ethyl]silane

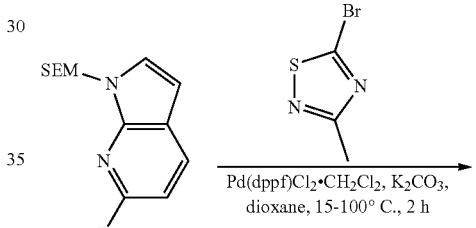

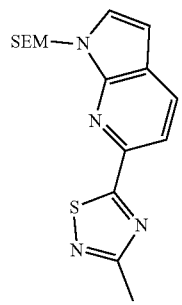

To a solution of [1-(2-trimethylsilylethoxymethyl)pyrrolo[2,3-b]pyridin-6-yl]boronic acid (3.92 g, 13.40 mmol, 1.6 eq), 5-bromo-3-methyl-1,2,4-thiadiazole (1.5 g, 8.38 mmol, 1 eq) in dioxane (40 mL) was added K$_2$CO$_3$ (2.89 g, 20.95 mmol, 2.5 eq) and Pd(dppf)Cl$_2$.CH$_2$Cl$_2$ (684.19 mg, 837.81 umol, 0.1 eq) at 15° C., the reaction mixture was degassed and purged with N$_2$ for 3 times and stirred at 100° C. for 2 h. The resulting solution was filtered and concentrated to give a residue. The residue was purified by silica gel column (PE/EtOAc=100/1 to 25/1) to afford the title compound (1.1 g, 3.17 mmol, 37.89% yield) as a colorless oil.

Step 2: 2-[[3-bromo-6-(3-methyl-1,2,4-thiadiazol-5-yl)pyrrolo[2,3-b]pyridin-1-yl]methoxy]ethyl-trimethyl-silane

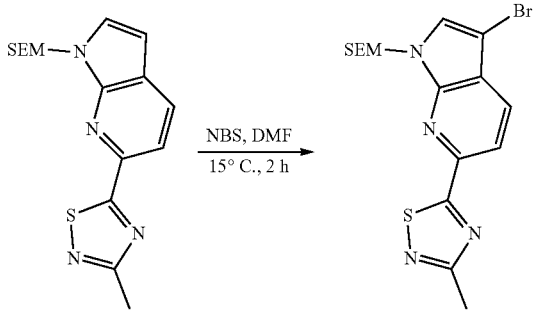 [SMILES: Cc1nsc(-c2ccc3ccn(COCC[Si](C)(C)C)c3n2)n1 ; Cc1nsc(-c2ccc3c(Br)cn(COCC[Si](C)(C)C)c3n2)n1]

To a stirred solution of trimethyl-[2-[[6-(3-methyl-1,2,4-thiadiazol-5-yl)pyrrolo[2,3-b]pyridin-1-yl]methoxy]ethyl]silane (1.1 g, 3.17 mmol, 1 eq) in DMF (30 mL) was added NBS (553.69 mg, 3.11 mmol, 0.98 eq), the reaction mixture was stirred at 15° C. for 2 h. Then it was diluted with EtOAc (80 mL), washed with sub-saturated brine (50 mL×3) and saturated brine (50 mL). The organic layer was dried over $Na_2SO_4$ and concentrated to give a residue. It was purified by silica gel column (PE/EtOAc=50/1 to 20/1) to afford the title compound (1.15 g, 2.70 mmol, 85.16% yield) as a white solid.

Step 3: Trimethyl-[2-[[6-(3-methyl-1,2,4-thiadiazol-5-yl)-3-(4,4,5,5-tetramethyl-1,3,2-dioxaborolan-2-yl)pyrrolo[2,3-b]pyridin-1-yl]methoxy]ethyl]silane

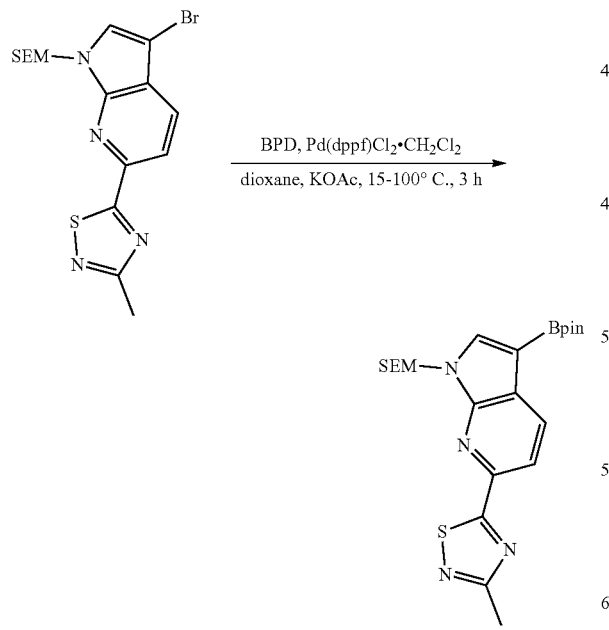

To a solution of 2-[[3-bromo-6-(3-methyl-1,2,4-thiadiazol-5-yl)pyrrolo[2,3-b]pyridin-1-yl]methoxy]ethyl-trimethyl-silane (1 g, 2.35 mmol, 1 eq) and 4,4,4',4',5,5,5',5'-octamethyl-2,2'-bi(1,3,2-dioxaborolane) (895.38 mg, 3.53 mmol, 1.5 eq) in dioxane (20 mL) was added KOAc (461.39 mg, 4.70 mmol, 2 eq) and Pd(dppf)Cl$_2$·CH$_2$Cl$_2$ (191.96 mg, 235.06 umol, 0.1 eq) at 15° C., the reaction mixture was degassed and purged with N$_2$ for 3 times and stirred at 100° C. for 3 h. The final reaction mixture was filtered and concentrated to give a residue. The residue was purified by silica gel column (PE/EtOAc=50/1) to afford the title compound (1.05 g, not pure) as a yellow solid. (Note: The reaction was combined with another reaction in 200 mg scale for work up.)

Step 4: Trimethyl-[2-[[3-[2-methylsulfanyl-5-(trifluoromethyl)pyrimidin-4-yl]-6-(3-methyl-1,2,4-thiadiazol-5-yl)pyrrolo[2,3-b]pyridin-1-yl]methoxy]ethyl]silane

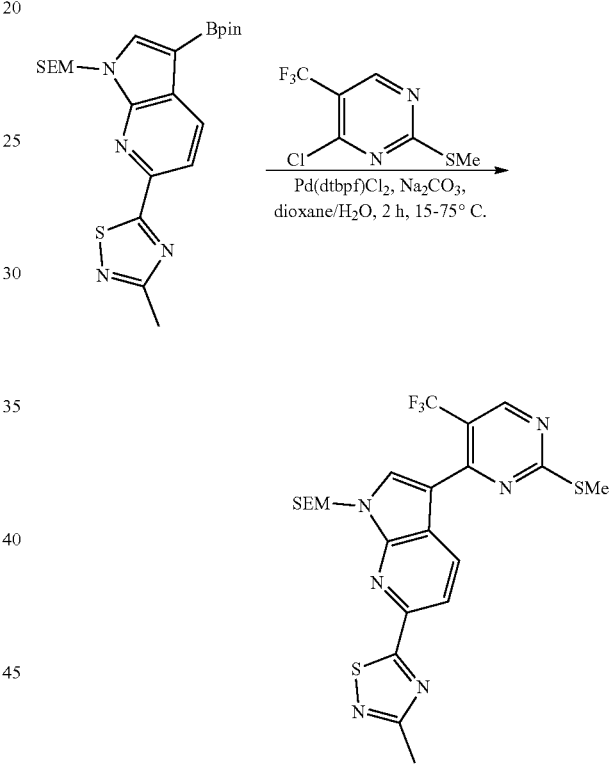

To a solution of trimethyl-[2-[[6-(3-methyl-1,2,4-thiadiazol-5-yl)-3-(4,4,5,5-tetramethyl-1,3,2-dioxaborolan-2-yl)pyrrolo[2,3-b]pyridin-1-yl]methoxy]ethyl]silane (929.99 mg, 1.97 mmol, 1 eq) and 4-chloro-2-methylsulfanyl-5-(trifluoromethyl)pyrimidine (0.45 g, 1.97 mmol, 1 eq) in H$_2$O (2.5 mL) and THF (12.5 mL) was added Na$_2$CO$_3$ (417.24 mg, 3.94 mmol, 2 eq) and ditert-butyl(cyclopentyl)phosphane; dichloropalladium; iron (128.28 mg, 196.83 umol, 0.1 eq) at 15° C., the reaction mixture was degassed and purged with N$_2$ for 3 times, and stirred at 75° C. for 2 h. The mixture was diluted with EtOAc (50 mL), washed with H$_2$O (20 mL). The organic layer was dried over Na$_2$SO$_4$ and concentrated to give a residue. It was purified by silica gel column (PE/EtOAc=50/1 to 10/1) to afford the title compound (550 mg) as a white solid. (Note: The reaction was combined with another reaction in 100 mg scale for work up.)

Step 5: Trimethyl-[2-[[3-[2-methylsulfonyl-5-(trifluoromethyl)pyrimidin-4-yl]-6-(3-methyl-1,2,4-thiadiazol-5-yl)pyrrolo[2,3-b]pyridin-1-yl]methoxy]ethyl]silane

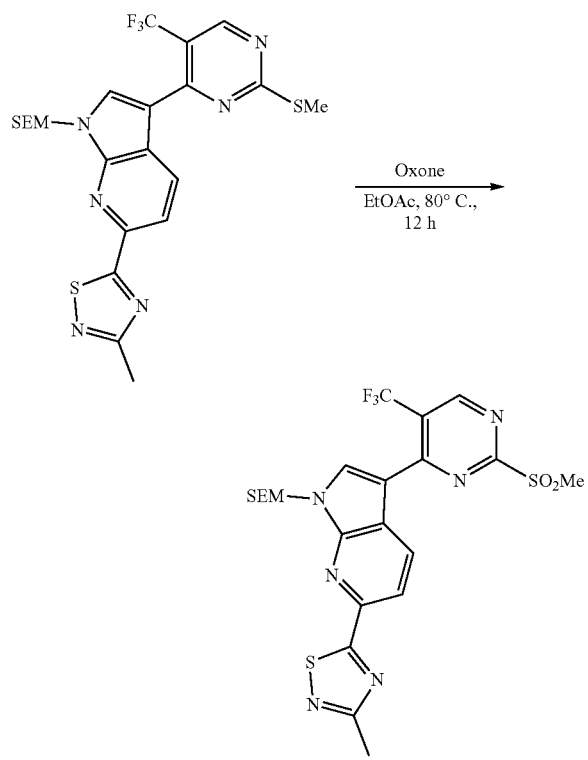

A mixture of trimethyl-[2-[[3-[2-methylsulfanyl-5-(trifluoromethyl)pyrimidin-4-yl]-6-(3-methyl-1,2,4-thiadiazol-5-yl)pyrrolo[2,3-b]pyridin-1-yl]methoxy]ethyl]silane (0.5 g, 928.19 umol, 1 eq) and Oxone (2.85 g, 4.64 mmol, 5 eq) in EtOAc (20 mL) was stirred at 80° C. for 12 h. It was filtered and washed with EtOAc (30 mL). The organic layer was washed with aq.Na₂SO₃ (10 mL×3), dried over Na₂SO₄ and concentrated to give a residue. The residue was purified by silica gel column (PE/EtOAc=15/1 to 5/1) to afford the title compound (120 mg) as a yellow solid.

(Note: The reaction was combined with another reaction in 50 mg scale for work up)

Step 6: Benzyl (2R,5R)-2-methyl-5-[[4-[6-(3-methyl-1,2,4-thiadiazol-5-yl)-1-(2-trimethylsilylethoxy methyl)pyrrolo[2,3-b]pyridin-3-yl]-5-(trifluoromethyl)pyrimidin-2-yl]amino]piperidine-1-carboxylate

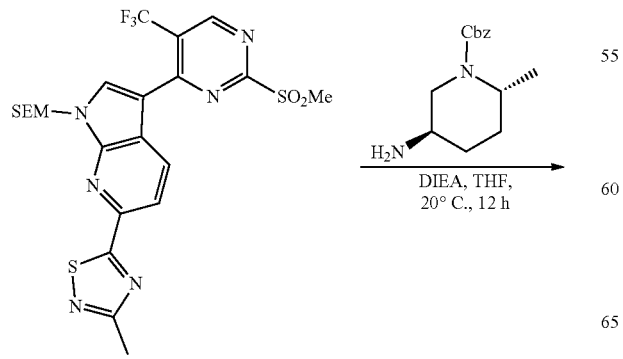

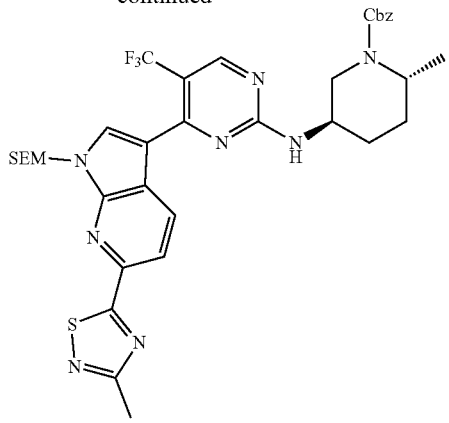

To a solution of trimethyl-[2-[[3-[2-methylsulfonyl-5-(trifluoromethyl)pyrimidin-4-yl]-6-(3-methyl-1,2,4-thiadiazol-5-yl)pyrrolo[2,3-b]pyridin-1-yl]methoxy]ethyl]silane (0.1 g, 175.23 umol, 1 eq) and benzyl (2R,5R)-5-amino-2-methylpiperidine-1-carboxylate (43.51 mg, 175.23 umol, 1 eq) in THF (2.5 mL) was added DIEA (113.24 mg, 876.14 umol, 152.61 uL, 5 eq), the reaction mixture was stirred at 20° C. for 12 h. The final reaction mixture was concentrated to give a residue. The residue was purified by silica gel column (PE/EtOAc=20/1 to 5/1) to afford the title compound (90 mg) as a yellow solid. (Note: The reaction was combined with another reaction in 20 mg scale for work up.)

Step 7: Benzyl (2S,5S)-2-methyl-5-[[4-[6-(3-methyl-1,2,4-thiadiazol-5-yl)-1H-pyrrolo[2,3-b]pyridin-3-yl]-5-(trifluoromethyl)pyrimidin-2-yl]amino]piperidine-1-carboxylate

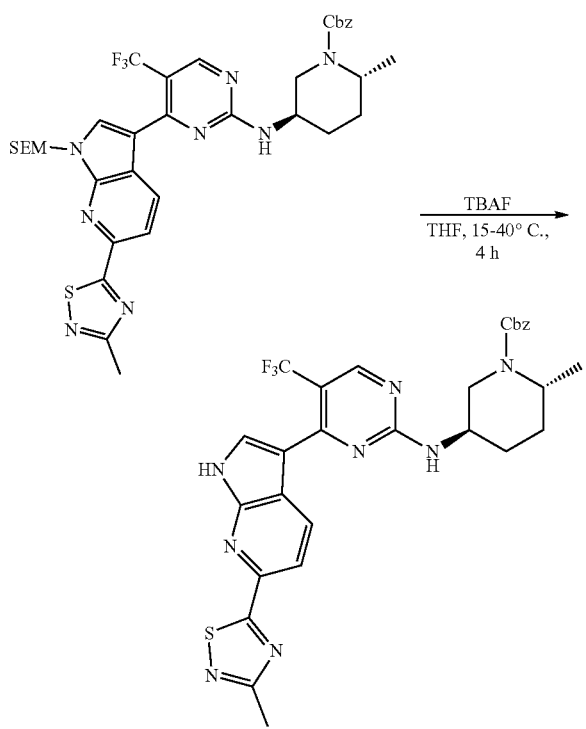

To a solution of benzyl (2S,5S)-2-methyl-5-[[4-[6-(3-methyl-1,2,4-thiadiazol-5-yl)-1-(2-tri methylsilylethoxymethyl)pyrrolo[2,3-b]pyridin-3-yl]-5-(trifluoromethyl)pyrimidin-2-yl]amino]piperidine-1-carboxylate (0.085 g, 115.04 umol, 1 eq) in THF (2 mL) was added TBAF (1 M, 1.73 mL, 15 eq) at 15° C., the reaction mixture was stirred at 40° C. for 4 h. It was partitioned between aq.NaHCO₃ (15 mL) and EtOAc (25 mL). The organic layer was washed with aq.NaHCO₃ (15 mL×3), dried over Na₂SO₄ and concentrated to give a residue. The residue was purified by silica gel column (PE/EtOAc=20/1 to 5/1) to afford the title compound (75 mg) of as a yellow solid. (Note: The reaction was combined with another reaction in 5 mg scale for work up.)

Step 8: N-[(3R,6R)-6-methyl-3-piperidyl]-4-[6-(3-methyl-1,2,4-thiadiazol-5-yl)-1H-pyrrolo[2,3-b]pyridin-3-yl]-5-(trifluoromethyl)pyrimidin-2-amine

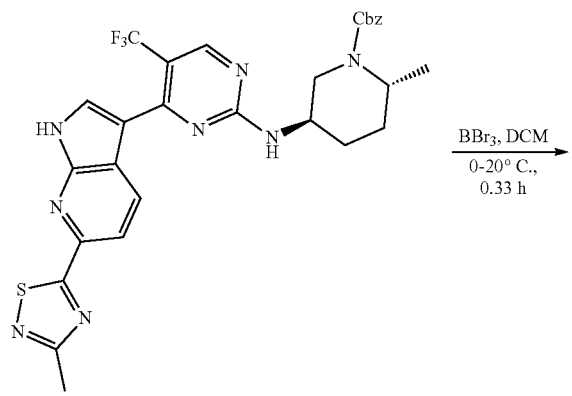

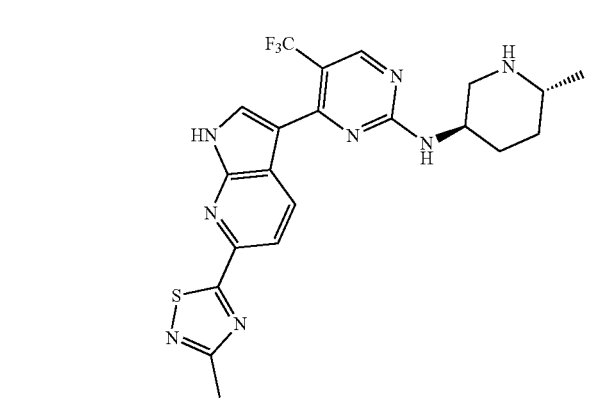

To a solution of benzyl (2R,5R)-2-methyl-5-[[4-[6-(3-methyl-1,2,4-thiadiazol-5-yl)-1H-pyrrolo[2,3-b]pyridin-3-yl]-5-(trifluoromethyl)pyrimidin-2-yl]amino]piperidine-1-carboxylate (68 mg, 111.73 umol, 1 eq) in DCM (3 mL) was added BBr₃ (139.95 mg, 558.63 umol, 53.83 uL, 5 eq) at 0° C., the reaction mixture was stirred at 20° C. for 0.33 h. The resulting solution was quenched with H₂O (0.2 mL), basified to pH=7 with NaHCO₃ and concentrated. The residue was purified by HCl prep-HPLC to afford the title compound (14.3 mg, 94.3% purity) as a white solid.

Example 49. Synthesis of 4-[6-(4-methyloxazol-5-yl)-1H-pyrrolo[2,3-b]pyridin-3-yl]-N-[(3S)-3-piperidyl]-5-(trifluoromethyl)pyrimidin-2-amine (Compound 161)

Step 1: 2-[(6-bromopyrrolo[2,3-b]pyridin-1-yl)methoxy]ethyl-trimethyl-silane

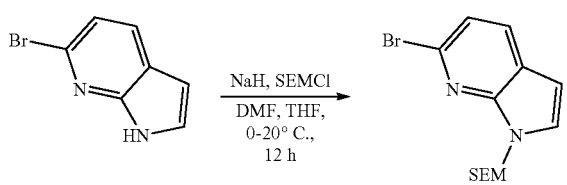 [SMILES: Brc1ccc2cc[nH]c2n1 ; C[Si](C)(C)CCOCn1ccc2ccc(Br)nc21]

To a solution of 6-bromo-1H-pyrrolo[2,3-b]pyridine (2 g, 10.15 mmol, 1 eq) in DMF (18 mL) and THF (2 mL) was added NaH (609.04 mg, 15.23 mmol, 60% purity, 1.5 eq) at 0° C. The mixture was stirred at 0° C. for 0.5 h. Then the 2-(chloromethoxy) ethyl-trimethyl-silane (2.03 g, 12.18 mmol, 2.16 mL, 1.2 eq) was added. The resulting mixture was stirred at 15° C. for another 11.5 h. The solution was poured into H₂O (100 mL), extracted by EtOAc (50 mL×3). The combined organic layers were washed by brine (100 mL×2), dried over Na₂SO₄, filtered and concentrated under reduced pressure to afford the title compound (3.3 g, crude) as yellow oil, which was used into the next step without further purification.

Step 2: 1-(benzenesulfonyl)-3-bromo-pyrrolo[2,3-b]pyridine-6-carbonitrile

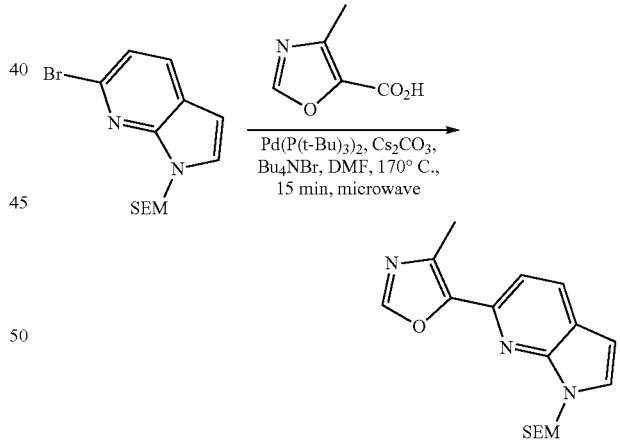

2-[(6-bromopyrrolo[2,3-b]pyridin-1-yl) methoxy]ethyl-trimethyl-silane (0.3 g, 916.61 umol, 1 eq), 4-methyloxazole-5-carboxylic acid (233.00 mg, 1.83 mmol, 2 eq) and palladium; tritert-butylphosphane (23.42 mg, 45.83 umol, 0.05 eq), tetrabutylammonium; chloride; hydrate (271.26 mg, 916.61 umol, 1 eq), Cs₂CO₃ (447.98 mg, 1.37 mmol, 1.5 eq) were taken up into a microwave tube in DMF (9 mL). The sealed tube was heated at 170° C. for 15 min under microwave. The reaction mixture was poured into H₂O (100 mL) and extracted with EtOAc (50 mL×3). The combined organic layers were washed with brine (150 mL×2), dried over Na₂SO₄, filtered and concentrated under reduced pressure to give a residue. The residue was purified by column chromatography (SiO₂, PE/EtOAc=10/1 to 2/1) to afford the title compound (0.35 g, 1.06 mmol, 23.18% yield, 5 batches in parallel) as yellow oil.

Step 3: 2-[[3-bromo-6-(4-methyloxazol-5-yl) pyrrolo[2,3-b]pyridin-1-yl]methoxy]ethyl-trimethylsilane

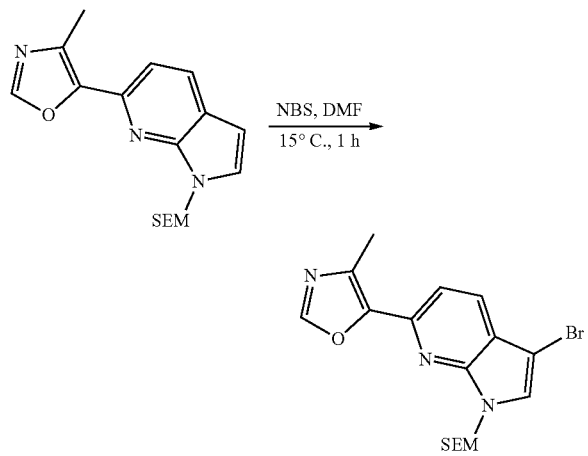

To a solution of trimethyl-[2-[[6-(4-methyloxazol-5-yl) pyrrolo[2,3-b]pyridin-1-yl]methoxy]ethyl]silane (0.25 g, 758.80 umol, 1 eq) in DCM (3 mL) was added NBS (81.03 mg, 455.28 umol, 0.6 eq). The mixture was stirred at 15° C. for 1 h. The solution was poured into H₂O (20 mL) and extracted with DCM (10 mL×3). The combined organic layers were washed with brine (30 mL×2), dried over Na₂SO₄, filtered and concentrated under reduced pressure to give a residue. The residue was purified by column chromatography (SiO₂, PE/EtOAc=10/1 to 3/1) to afford the title compound (250 mg) as yellow solid.

Step 4: trimethyl-[2-[[6-(4-methyloxazol-5-yl)-3-(4, 4, 5, 5-tetramethyl-1, 3, 2-dioxaborolan-2-yl) pyrrolo[2,3-b]pyridin-1-yl]methoxy]ethyl]silane

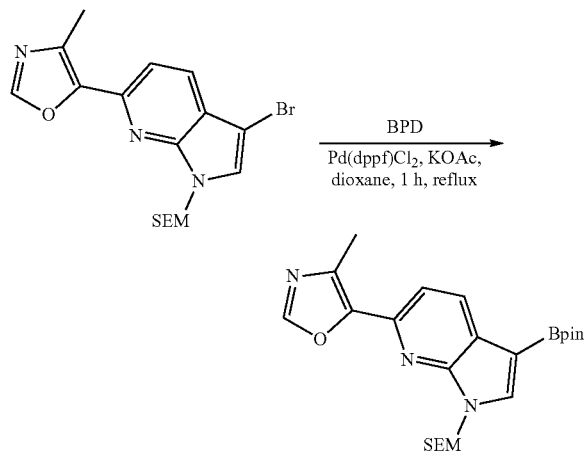

To a solution of 2-[[3-bromo-6-(4-methyloxazol-5-yl) pyrrolo[2,3-b]pyridin-1-yl]methoxy]ethyl-trimethyl-silane (0.16 g, 391.81 umol, 1 eq) in dioxane (3.5 mL) was added BPD (149.24 mg, 587.71 umol, 1.5 eq), KOAc (76.91 mg, 783.61 umol, 2 eq) and Pd(dppf)Cl₂ (28.67 mg, 39.18 umol, 0.1 eq). The mixture was stirred at 100° C. for 1 h under N₂. It was concentrated under reduced pressure to give a residue. It was purified by column chromatography (SiO₂, PE/EtOAc=10/1 to 1/1) to afford the title compound (0.2 g) as yellow oil.

Step 5: Tert-butyl (3S)-3-[[4-[6-(4-methyloxazol-5-yl)-1-(2-trimethylsilylethoxymethyl)pyrrolo[2,3-b]pyridin-3-yl]-5-(trifluoromethyl)pyrimidin-2-yl]amino]piperidine-1-carboxylate

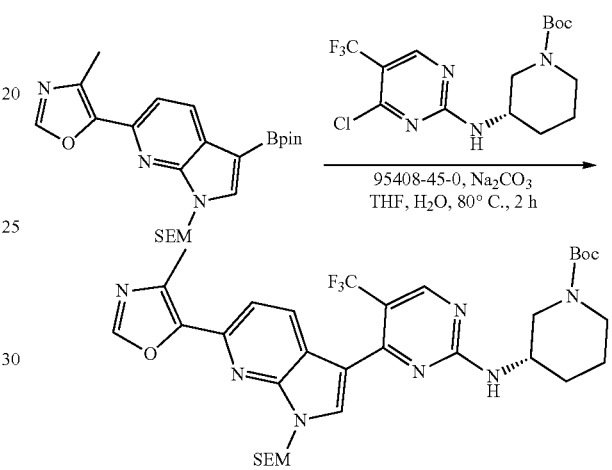

To a solution of trimethyl-[2-[[6-(4-methyloxazol-5-yl)-3-(4, 4, 5, 5-tetramethyl-1, 3, 2-dioxaborolan-2-yl) pyrrolo[2,3-b]pyridin-1-yl]methoxy]ethyl]silane (0.2 g, 439.15 umol, 1 eq) in THF (6 mL) and H₂O (1 mL) was added tert-butyl (3S)-3-[[4-chloro-5-(trifluoromethyl)pyrimidin-2-yl]amino]piperidine-1-carboxylate (167.22 mg, 439.15 umol, 1 eq), ditert-butyl(cyclopentyl) phosphane:dichloropalladium:iron (28.62 mg, 43.91 umol, 0.1 eq) and Na₂CO₃ (93.09 mg, 878.29 umol, 2 eq). The mixture was stirred at 80° C. for 2 h under N₂. The solution was concentrated under reduced pressure to give a residue. The residue was purified by column chromatography (SiO₂, PE/EtOAc=10/1 to 1/1) to afford the title compound (70 mg, 68% purity) as a white solid. (Note: The reaction mixture was combined with another batch in 20 mg scale for worked up and purification.)

Step 6: 4-[6-(4-methyloxazol-5-yl)-1H-pyrrolo[2,3-b]pyridin-3-yl]-N-[(3S)-3-piperidyl]-5-(trifluoromethyl)pyrimidin-2-amine

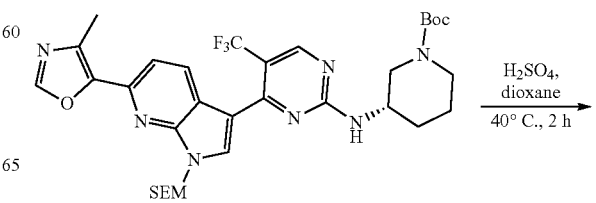

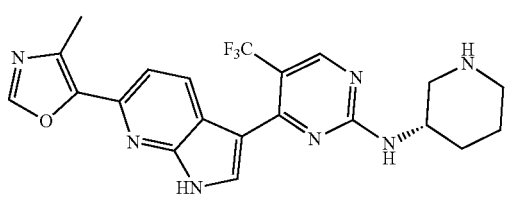

To a solution of tert-butyl (3S)-3-[[4-[6-(4-methyloxazol-5-yl)-1-(2-trimethylsilylethoxymethyl)pyrrolo[2,3-b]pyridin-3-yl]-5-(trifluoromethyl)pyrimidin-2-yl]amino]piperidine-1-carboxylate (0.06 g, 89.05 umol, 1 eq) in dioxane (1 mL) was added $H_2SO_4$ (87.34 mg, 890.47 umol, 47.47 uL, 10 eq). The mixture was stirred at 40° C. for 2 h. It was diluted with $H_2O$ (10 mL) and adjusted pH to 12 with NaOH. Then the solution was extracted with EtOAc (10 mL×3). The combined organic layers were washed with brine (30 mL), dried over $Na_2SO_4$, filtered and concentrated under reduced pressure to give a residue. It was purified by prep-HPLC (FA condition) to afford the title compound (5.5 mg, FA salt, 100% purity) as a white solid. (Note: The reaction mixture was combined with another batch in 10 mg scale for work-up and purification.)

Example 50. Synthesis of 4-[6-(5-methyl-1,2,4-oxadiazol-3-yl)-1H-pyrrolo[2,3-b]pyridin-3-yl]-N-[(3S,6S)-6-methyl-3-piperidyl]-5-(trifluoromethyl)pyrimidin-2-amine (Compound 162)

Step 1: 1H-pyrrolo[2,3-b]pyridine-6-carbonitrile

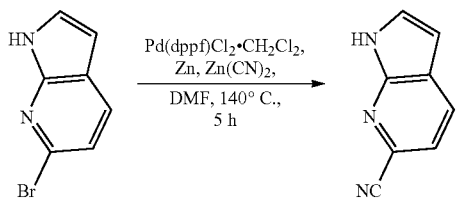 [SMILES: Brc1ccc2cc[nH]c2n1 ; N#Cc1ccc2cc[nH]c2n1]

A mixture of 6-bromo-1H-pyrrolo[2,3-b]pyridine (10 g, 50.75 mmol, 1 eq), Zn (331.88 mg, 5.08 mmol, 0.1 eq), $Zn(CN)_2$ (4.17 g, 35.53 mmol, 2.26 mL, 0.7 eq) and $Pd(dppf)Cl_2 \cdot CH_2Cl_2$ (2.07 g, 2.54 mmol, 0.05 eq) in DMF (100 mL) was degassed and purged with $N_2$ for 3 times, and then the mixture was stirred at 140° C. for 5 h under $N_2$ atmosphere. It was diluted with water (500 mL) and EtOAc (300 mL), and then filtered to remove the solid, the solid was washed with EtOAc (200 mL×2). The combined organic layers were washed with brine (500 mL), dried over $Na_2SO_4$, filtered and concentrated under reduced pressure to give a residue. The residue was purified by column chromatography (SiO$_2$, PE/EtOAc=5/1 to 2/1) to afford the title compound (5.3 g, 89% purity) as a green solid.

Step 2: 3-bromo-1H-pyrrolo[2,3-b]pyridine-6-carbonitrile

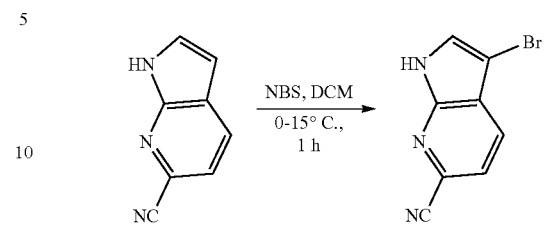

To a solution of 1H-pyrrolo[2,3-b]pyridine-6-carbonitrile (4 g, 25.15 mmol, 1 eq) in DCM (40 mL) was added NBS (5.37 g, 30.18 mmol, 1.2 eq) at 0° C. The mixture was stirred at 15° C. for 1 h. It was concentrated and the residue was washed with PE (500 mL) and the solid was filtered to afford the title compound (5 g, crude) as a yellow solid.

Step 3: 1-(benzenesulfonyl)-3-bromo-pyrrolo[2,3-b]pyridine-6-carbonitrile

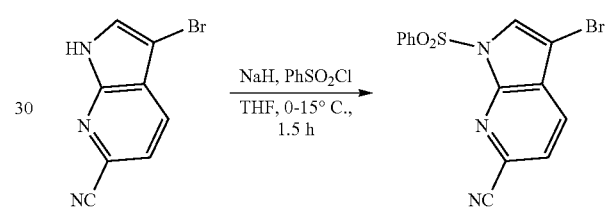

To a solution of 3-bromo-1H-pyrrolo[2,3-b]pyridine-6-carbonitrile (5 g, 22.52 mmol, 1 eq) in THF (50 mL) was added NaH (900.65 mg, 22.52 mmol, 60% purity, 1 eq) at 0° C. The mixture was stirred at 0° C. for 0.5 h. And then benzenesulfonyl chloride (5.17 g, 29.27 mmol, 3.75 mL, 1.3 eq) was added into the mixture was stirred at 15° C. for 1 h. It was quenched by addition water (200 mL) at 15° C., and then extracted with EtOAc (100 mL×2). The combined organic layers were washed with brine (200 mL), dried over $Na_2SO_4$, filtered and concentrated under reduced pressure to give a residue. The residue was purified by column chromatography (SiO$_2$, Petroleum ether/Ethyl acetate=7/1 to 2/1) to afford a crude product (4.5 g). Then it was triturated with EtOAc (5 mL) and PE (50 mL), the solid was filtered and dried to afford the title compound (4 g, 95% purity) as a white solid.

Step 4: 1-(benzenesulfonyl)-3-(4, 4, 5, 5-tetramethyl-1, 3, 2-dioxaborolan-2-yl) pyrrolo[2,3-b]pyridine-6-carbonitrile

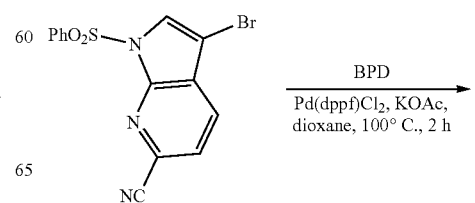

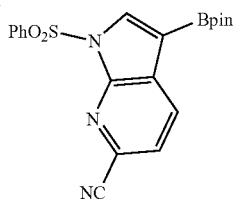

A mixture of 1-(benzenesulfonyl)-3-bromo-pyrrolo[2,3-b]pyridine-6-carbonitrile (4 g, 11.04 mmol, 1 eq), BPD (4.21 g, 16.57 mmol, 1.5 eq), KOAc (2.17 g, 22.09 mmol, 2 eq), Pd(dppf)Cl$_2$ (1.21 g, 1.66 mmol, 0.15 eq) in dioxane (40 mL) was degassed and purged with N$_2$ for 5 times, and then the mixture was stirred at 100° C. for 2 h under N$_2$ atmosphere. It was filtered, and washed by EtOAc (200 mL×3). The combined organic layers were washed with brine (300 mL×2), dried over Na$_2$SO$_4$, filtered and concentrated under reduced pressure to give a residue. The residue was combined with the solid and purified by column chromatography (SiO$_2$, Petroleum ether/Ethyl acetate=6/1 to 3/1) to afford the title compound (4 g, 85% purity) as an orange solid.

Step 5: 1-(benzenesulfonyl)-3-[2-methylsulfanyl-5-(trifluoromethyl)pyrimidin-4-yl]pyrrolo[2,3-b]pyridine-6-carbonitrile

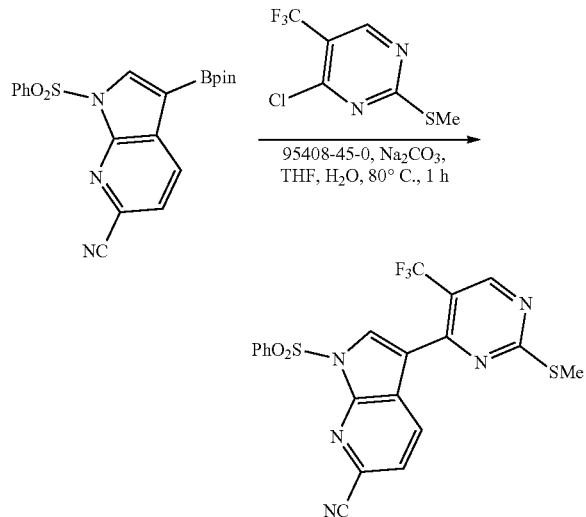

A mixture of 1-(benzenesulfonyl)-3-(4, 4, 5, 5-tetramethyl-1, 3, 2-dioxaborolan-2-yl) pyrrolo[2,3-b]pyridine-6-carbonitrile (2 g, 4.89 mmol, 1 eq), 4-chloro-2-methylsulfanyl-5-(trifluoromethyl)pyrimidine (1.68 g, 7.33 mmol, 1.5 eq), ditert-butyl (cyclopentyl) phosphane:dichloropalladium:iron (318.50 mg, 488.68 umol, 0.1 eq), Na$_2$CO$_3$ (1.04 g, 9.77 mmol, 2 eq) in THF (60 mL) and H$_2$O (6 mL) was degassed and purged with N$_2$ for 5 times, and then the mixture was stirred at 80° C. for 1 h under N$_2$ atmosphere. It was filtered to remove the solid, and washed with EtOAc (250 mL×2). The filtrate was washed with brine (500 mL), dried over Na$_2$SO$_4$, filtered and concentrated under reduced pressure to give a residue. The residue was purified by column chromatography (SiO$_2$, PE/EtOAc=6/1 to 2/1) to afford the title compound (0.8 g) as a white solid. (Note: The reaction was combined with another reaction in 100 mg scale for work-up.)

Step 6: 1-(benzenesulfonyl)-3-[2-methylsulfonyl-5-(trifluoromethyl)pyrimidin-4-yl]pyrrolo[2,3-b]pyridine-6-carbonitrile

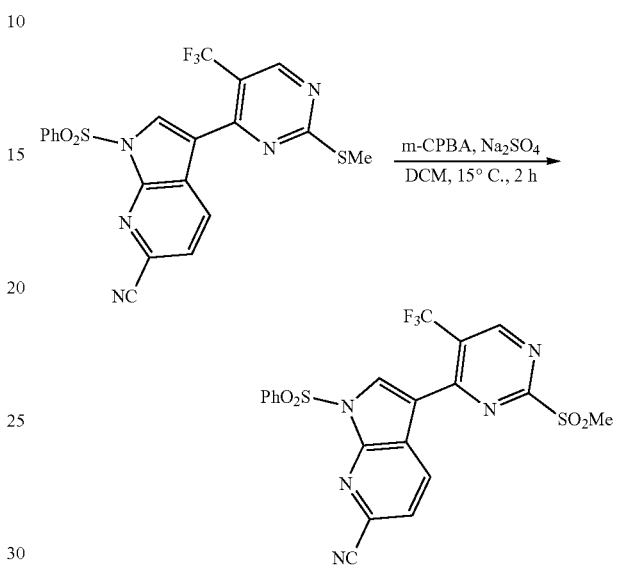

To a solution of 1-(benzenesulfonyl)-3-[2-methylsulfanyl-5-(trifluoromethyl)pyrimidin-4-yl]pyrrolo[2,3-b]pyridine-6-carbonitrile (0.06 g, 115.05 umol, 1 eq, FA) in DCM (4 mL) was added m-CPBA (51.39 mg, 253.12 umol, 85% purity, 2.2 eq) and Na$_2$SO$_4$ (18.23 mg, 128.38 umol, 13.02 uL, 1.12 eq). The mixture was stirred at 15° C. for 2 h. The reaction mixture was poured into the saturated Na$_2$SO$_3$ and NaHCO$_3$ solution (200 mL), then extracted with DCM (100 mL×3), the combined organic layers were washed with brine (300 mL), dried over Na$_2$SO$_4$, filtered and concentrated under reduced pressure to afford the title compound (900 mg, crude) as a white solid which was used directly into the next step without purification. (Note: The reaction was combined with another reaction in 800 mg scale for work-up.)

Step 7: Benzyl (2S,5S)-5-[[4-[1-(benzenesulfonyl)-6-cyano-pyrrolo[2,3-b]pyridin-3-yl]-5-(trifluoromethyl)pyrimidin-2-yl]amino]-2-methyl-piperidine-1-carboxylate

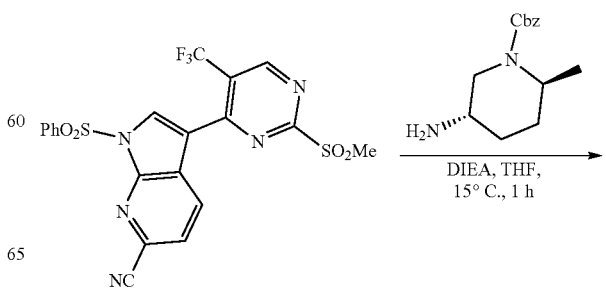

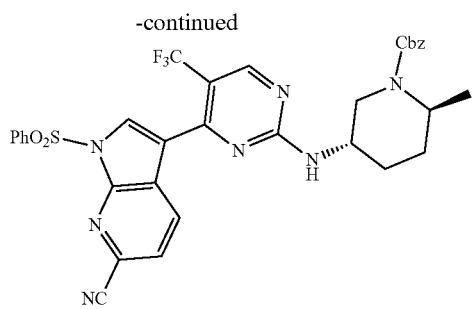

To a solution of 1-(benzenesulfonyl)-3-[2-methylsulfonyl-5-(trifluoromethyl)pyrimidin-4-yl]pyrrolo[2,3-b]pyridine-6-carbonitrile (0.42 g, 827.64 umol, 1 eq) in THF (4.6 mL) was added DIPEA (213.93 mg, 1.66 mmol, 288.31 uL, 2 eq) and benzyl (2S,5S)-5-amino-2-methyl-piperidine-1-carboxylate (246.62 mg, 993.17 umol, 1.2 eq). The mixture was stirred at 15° C. for 1 h. It was concentrated under reduced pressure to remove solvent. The residue was diluted with water (20 mL) and extracted with EtOAc (20 mL×2). The combined organic layers were washed with brine (40 mL), dried over $Na_2SO_4$, filtered and concentrated under reduced pressure to give a residue. The residue was purified by column chromatography ($SiO_2$, PE/EtOAc=4/1 to 2/1) to afford the title compound (300 mg, 80% purity) as a white solid. (Note: The reaction was combined with another reaction in 40 mg scale for work-up.)

Step 8: Benzyl (2S,5S)-5-[[4-[1-(benzenesulfonyl)-6-[(E)-N'-hydroxycarbamimidoyl]pyrrolo[2,3-b]pyridin-3-yl]-5-(trifluoromethyl)pyrimidin-2-yl]amino]-2-methyl-piperidine-1-carboxylate

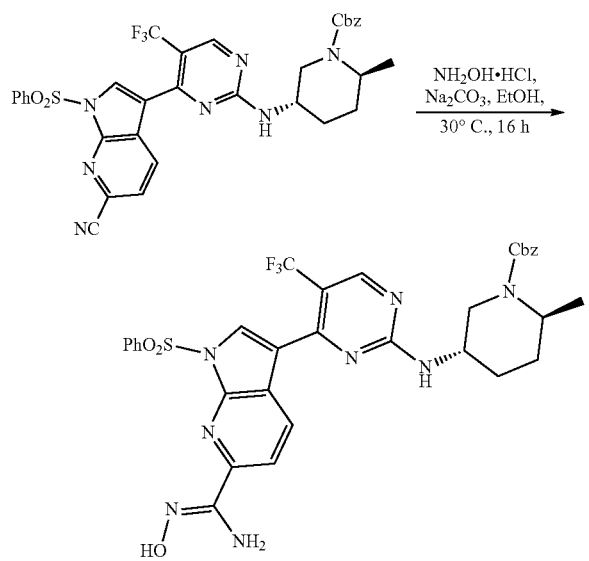

To a solution of benzyl (2S,5S)-5-[[4-[1-(benzenesulfonyl)-6-cyano-pyrrolo[2,3-b]pyridin-3-yl]-5-(trifluoromethyl)pyrimidin-2-yl]amino]-2-methyl-piperidine-1-carboxylate (300.00 mg, 444.00 umol, 1 eq) in EtOH (20 mL) was added hydroxylamine; hydrochloride (308.54 mg, 4.44 mmol, 10 eq) and $Na_2CO_3$ (564.71 mg, 5.33 mmol, 12 eq). The mixture was stirred at 30° C. for 16 h. It was filtered, and the filtrate was concentrated under reduced pressure to afford the title compound (400 mg, crude) as a white solid which was used directly into the next step without purification.

Step 9: Benzyl (2S,5S)-5-[[4-[1-(benzenesulfonyl)-6-(5-methyl-1,2,4-oxadiazol-3-yl) pyrrolo[2,3-b]pyridin-3-yl]-5-(trifluoromethyl)pyrimidin-2-yl]amino]-2-methyl-piperidine-1-carboxylate

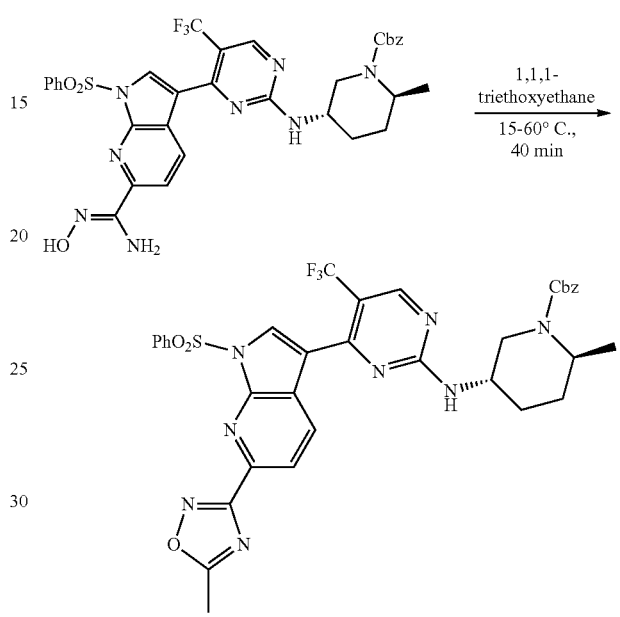

Benzyl (2S,5S)-5-[[4-[1-(benzenesulfonyl)-6-[(E)-N'-hydroxycarbamimidoyl]pyrrolo[2,3-b]pyridin-3-yl]-5-(trifluoromethyl)pyrimidin-2-yl]amino]-2-methyl-piperidine-1-carboxylate (0.36 g, 507.97 umol, 1 eq) in 1, 1, 1-triethoxyethane (0.4 mL) was added TFA (2.90 mg, 25.40 umol, 1.88 uL, 0.05 eq). The mixture was stirred at 15° C. for 10 min. Then the mixture was stirred at 60° C. for 30 min. The solution was concentrated under reduced pressure to give a residue. The residue was purified by column chromatography ($SiO_2$, PE/EtOAc=2/1) to afford the title compound (220 mg, 96% purity) as a white solid.

Step 10: Benzyl (2S,5S)-2-methyl-5-[[4-[6-(5-methyl-1,2,4-oxadiazol-3-yl)-1H-pyrrolo[2,3-b]pyridin-3-yl]-5-(trifluoromethyl)pyrimidin-2-yl]amino] piperidine-1-carboxylate

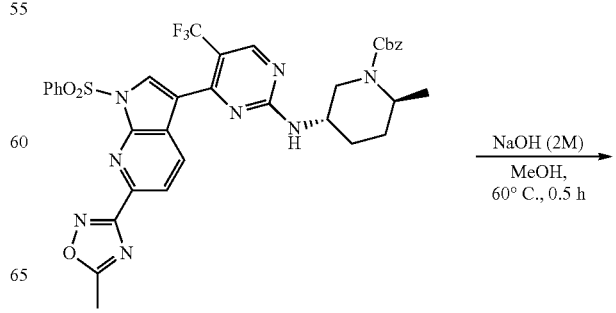

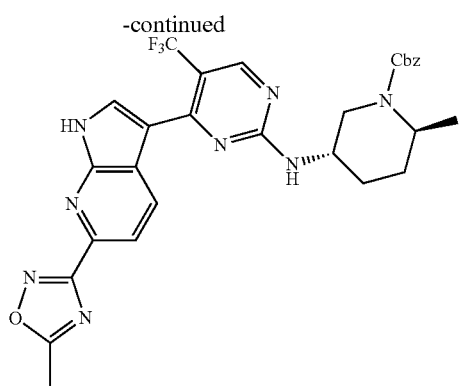

To a solution of benzyl (2S,5S)-5-[[4-[1-(benzenesulfonyl)-6-(5-methyl-1,2,4-oxadiazol-3-yl) pyrrolo[2,3-b]pyridin-3-yl]-5-(trifluoromethyl)pyrimidin-2-yl]amino]-2-methyl-piperidine-1-carboxylate (0.2 g, 272.95 umol, 1 eq) in MeOH (24 mL) was added NaOH (2 M, 4.09 mL, 30 eq). The mixture was stirred at 60° C. for 0.5 h. The reaction mixture was concentrated under reduced pressure to remove solvent. It was diluted with water 30 mL, adjusted pH to 7 by added HCl (1 M), and then extracted with EtOAc (30 mL). The organic layers were washed with brine (30 mL), dried over $Na_2SO_4$, filtered and concentrated under reduced pressure to afford the title compound (180 mg, crude) as a white solid. The crude product was used directly into the next step without purification. (Note: The reaction was combined with another reaction in 20 mg scale for work-up.)

Step 11: 4-[6-(5-methyl-1,2,4-oxadiazol-3-yl)-1H-pyrrolo[2,3-b]pyridin-3-yl]-N-[(3S,6S)-6-methyl-3-piperidyl]-5-(trifluoromethyl)pyrimidin-2-amine

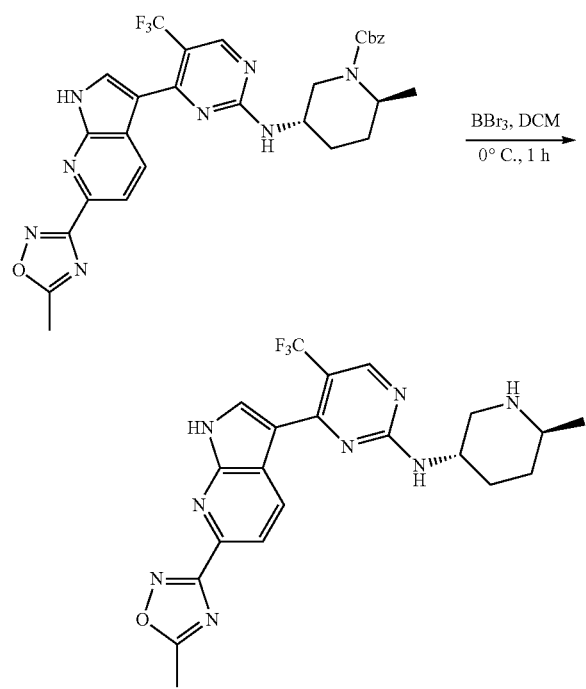

To a solution of benzyl (2S,5S)-2-methyl-5-[[4-[6-(5-methyl-1,2,4-oxadiazol-3-yl)-1H-pyrrolo[2,3-b]pyridin-3-yl]-5-(trifluoromethyl)pyrimidin-2-yl]amino]piperidine-1-carboxylate (160 mg, 270.01 umol, 1 eq) in DCM (3.2 mL) was added $BBr_3$ (676.43 mg, 2.70 mmol, 260.17 uL, 10 eq) at 0° C., and then the mixture was stirred at this temperature for 1 h. It was concentrated under reduced pressure to give a residue, and then it was washed with PE (160 mL) and collected the cake. The crude product was purified by prep-HPLC (FA condition) to afford the title compound (26.7 mg, FA, 100% purity, 100% ee value) as a white solid. (Note: The reaction was combined with another reaction in 20 mg scale for work-up.)

Example 51. Synthesis of 4-[6-(5-methyl-1,2,4-oxadiazol-3-yl)-1H-pyrrolo[2,3-b]pyridin-3-yl]-N-[(3R, 6R)-6-methyl-3-piperidyl]-5-(trifluoromethyl)pyrimidin-2-amine (Compound 163)

Step 1: Benzyl (2R, 5R)-5-[[4-[1-(benzenesulfonyl)-6-cyano-pyrrolo[2,3-b]pyridin-3-yl]-5-(trifluoromethyl)pyrimidin-2-yl]amino]-2-methyl-piperidine-1-carboxylate

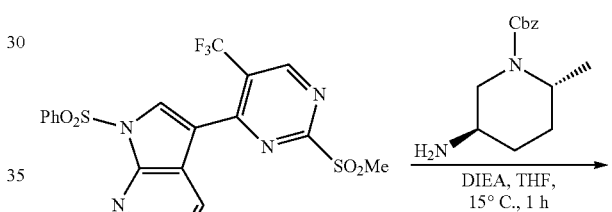

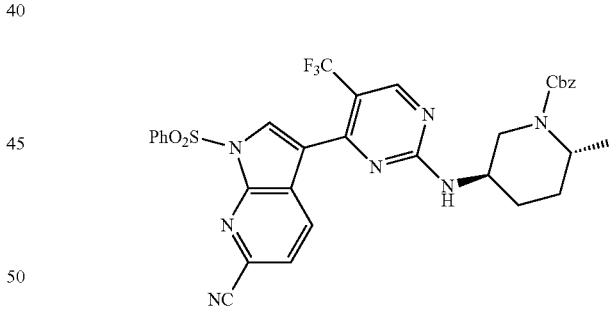

To a solution of 1-(benzenesulfonyl)-3-[2-methylsulfonyl-5-(trifluoromethyl)pyrimidin-4-yl]pyrrolo[2,3-b]pyridine-6-carbonitrile (400 mg, 788.23 umol, 1 eq) in THF (4 mL) was added DIPEA (203.75 mg, 1.58 mmol, 274.59 uL, 2 eq) and benzyl (2R, 5R)-5-amino-2-methyl-piperidine-1-carboxylate (234.88 mg, 945.88 umol, 1.2 eq). The mixture was stirred at 15° C. for 1 h. It was concentrated under reduced pressure to remove solvent. The residue was diluted with water 20 mL and extracted with EtOAc (20 mL×2). The combined organic layers were washed with brine (40 mL), dried over $Na_2SO_4$, filtered and concentrated under reduced pressure to give a residue. It was purified by column chromatography ($SiO_2$, PE/EtOAc=4/1 to 2/1) to afford the title compound (350 mg, 70% purity) as a white solid.

Step 2: Benzyl (2R, 5R)-5-[[4-[1-(benzenesulfonyl)-6-[(E)-N'-hydroxycarbamimidoyl]pyrrolo[2,3-b]pyridin-3-yl]-5-(trifluoromethyl)pyrimidin-2-yl]amino]-2-methyl-piperidine-1-carboxylate

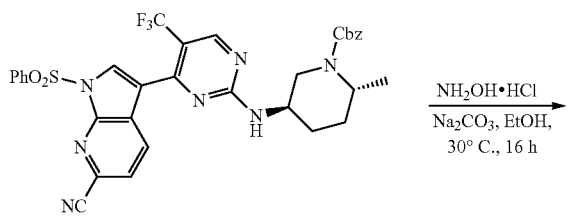

To a solution of benzyl (2R,5R)-5-[[4-[1-(benzenesulfonyl)-6-cyano-pyrrolo[2,3-b]pyridin-3-yl]-5-(trifluoromethyl)pyrimidin-2-yl]amino]-2-methyl-piperidine-1-carboxylate (350.00 mg, 518.00 umol, 1 eq) in EtOH (23 mL) was added hydroxylamine; hydrochloride (359.96 mg, 5.18 mmol, 10 eq) and Na$_2$CO$_3$ (658.82 mg, 6.22 mmol, 12 eq). The mixture was stirred at 30° C. for 16 h. It was filtered, and the filtrate was concentrated under reduced pressure to afford the title compound (400 mg, crude) as a white solid which was used directly into the next step without purification.

Step 3: Benzyl (2R, 5R)-5-[[4-[1-(benzenesulfonyl)-6-(5-methyl-1,2,4-oxadiazol-3-yl) pyrrolo[2,3-b]pyridin-3-yl]-5-(trifluoromethyl)pyrimidin-2-yl]amino]-2-methyl-piperidine-1-carboxylate To a solution of benzyl (2R, 5R)-5-[[4-[1-(benzenesulfonyl)-6-[(E)-N'-hydroxycarbamimidoyl]pyrrolo[2,3-b]pyridin-3-yl]-5-(trifluoromethyl)pyrimidin-2-yl]amino]-2-methyl-piperidine-1-carboxylate (400.00 mg, 564.41 umol, 1 eq) in AcOH (4 mL) was added Ac$_2$O (69.14 mg, 677.29 umol, 63.44 uL, 1.2 eq). The mixture was stirred at 90° C. for 16 h. It was residue was diluted with water 30 mL. The solid was formed and filtered to collect the cake. The crude product was purified by column chromatography (SiO$_2$, Petroleum ether/Ethyl acetate=5/1 to 3/1) to afford the title compound (180 mg, 94% purity) as a white solid.

Step 4: Benzyl (2R, 5R)-2-methyl-5-[[4-[6-(5-methyl-1,2,4-oxadiazol-3-yl)-1H-pyrrolo[2,3-b]pyridin-3-yl]-5-(trifluoromethyl)pyrimidin-2-yl]amino] piperidine-1-carboxylate To a solution of benzyl (2R, 5R)-5-[[4-[1-(benzenesulfonyl)-6-(5-methyl-1,2,4-oxadiazol-3-yl) pyrrolo[2,3-b]pyridin-3-yl]-5-(trifluoromethyl)pyrimidin-2-yl]amino]-2-methyl-piperidine-1-carboxylate (0.1 g, 136.48 umol, 1 eq) in MeOH (12 mL) was added NaOH (2 M, 2.05 mL, 30 eq).

The mixture was stirred at 60° C. for 0.5 h. It was concentrated under reduced pressure to remove solvent. The residue was diluted with water 30 mL, adjusted pH to 7 by added HCl (1 M), and then extracted with EtOAc (30 mL). The organic layers were washed with brine (30 mL), dried over Na$_2$SO$_4$, filtered and concentrated under reduced pressure to afford the title compound (110 mg, crude) as a white solid. The crude product was used directly into the next step without purification. (Note: The reaction was combined with another reaction in 20 mg scale for work-up and purification.)

Step 5: 4-[6-(5-methyl-1,2,4-oxadiazol-3-yl)-1H-pyrrolo[2,3-b]pyridin-3-yl]-N-[(3R, 6R)-6-methyl-3-piperidyl]-5-(trifluoromethyl)pyrimidin-2-amine

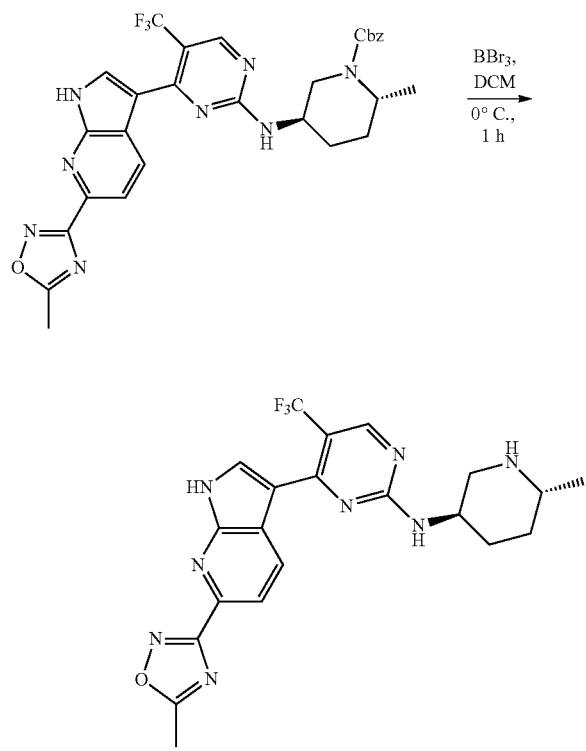

To a solution of benzyl (2R, 5R)-2-methyl-5-[[4-[6-(5-methyl-1,2,4-oxadiazol-3-yl)-1H-pyrrolo[2,3-b]pyridin-3-yl]-5-(trifluoromethyl)pyrimidin-2-yl]amino]piperidine-1-carboxylate (80 mg, 135.01 umol, 1 eq) in DCM (1.6 mL) was added BBr$_3$ (338.22 mg, 1.35 mmol, 130.08 uL, 10 eq) at 0° C., and then the mixture was stirred at this temperature for 1 h. The reaction mixture was concentrated under reduced pressure to give a residue, and then the residue was triturated with PE (60 mL), filtered and dried. The crude product was purified by prep-HPLC (FA condition) to afford the title compound (17.3 mg, FA, 100% purity, 100% ee value) as a white solid. (Note: The reaction mixture was combined with another batch in 15 mg scale for worked up and purification.)

Example 52. Synthesis of N-[(3R, 6R)-6-methyl-3-piperidyl]-4-[6-(1-methyltetrazol-5-yl)-1H-pyrrolo[2,3-b]pyridin-3-yl]-5-(trifluoromethyl)pyrimidin-2-amine (Compound 164)

Step 1: Benzyl (2R, 5R)-2-methyl-5-[[4-[6-(1-methyltetrazol-5-yl)-1-(2-trimethylsilylethoxymethyl)pyrrolo[2,3-b]pyridin-3-yl]-5-(trifluoromethyl)pyrimidin-2-yl]amino]piperidine-1-carboxylate

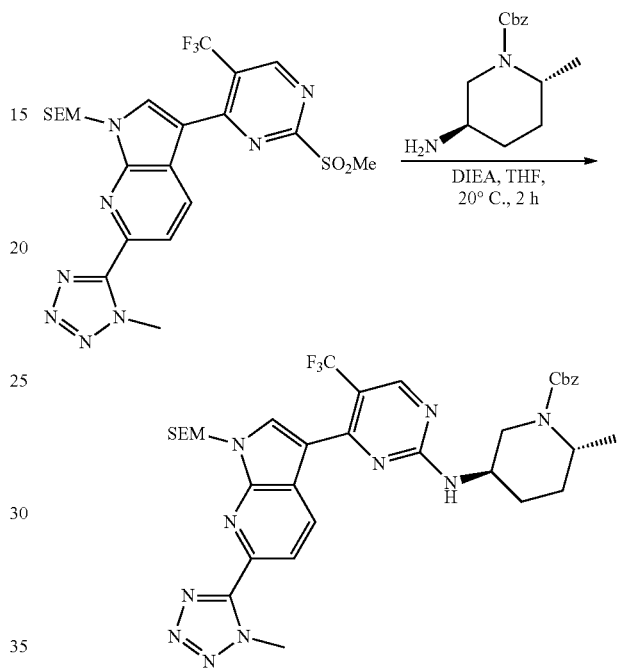

To a solution of trimethyl-[2-[[3-[2-methylsulfonyl-5-(trifluoromethyl)pyrimidin-4-yl]-6-(1-methyltetrazol-5-yl) pyrrolo[2,3-b]pyridin-1-yl]methoxy]ethyl]silane (0.27 g, 486.82 umol, 1 eq), benzyl (2R, 5R)-5-amino-2-methyl-piperidine-1-carboxylate (181.33 mg, 730.23 umol, 1.5 eq) in THF (5 mL) was added DIEA (188.75 mg, 1.46 mmol, 254.38 uL, 3 eq). The mixture was stirred at 20° C. for 2 h. The reaction mixture was concentrated to give a residue. It was purified by column chromatography (SiO$_2$, PE/EtOAc=10/1 to 2/1) to afford the title compound (0.22 g, 295.23 umol, 60.64% yield, 97% purity) as a yellow solid.

Step 2: N-[(3R, 6R)-6-methyl-3-piperidyl]-4-[6-(1-methyltetrazol-5-yl)-1H-pyrrolo[2,3-b]pyridin-3-yl]-5-(trifluoromethyl)pyrimidin-2-amine

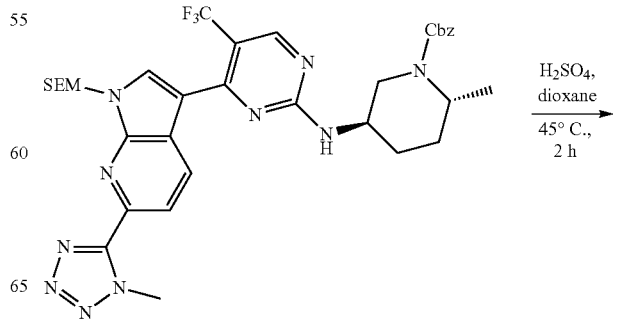

-continued

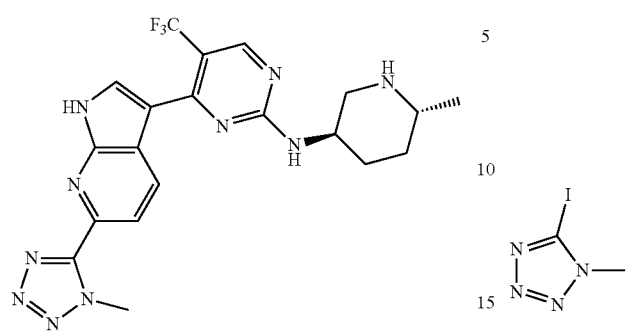

To a solution of benzyl (2R, 5R)-2-methyl-5-[[4-[6-(1-methyltetrazol-5-yl)-1-(2-trimethylsilylethoxymethyl)pyrrolo[2,3-b]pyridin-3-yl]-5-(trifluoromethyl)pyrimidin-2-yl]amino]piperidine-1-carboxylate (0.22 g, 304.36 umol, 1 eq) in dioxane (5 mL) was added H₂SO₄ (4.48 g, 45.65 mmol, 2.43 mL, 150 eq). The mixture was stirred at 45° C. for 2 h. The mixture was adjusted pH to 8 with saturated aqueous NaOH, and extracted with EtOAc (50 mL×3), dried over Na₂SO₄, filtered and concentrated under reduced pressure to give a residue. It was purified by prep-HPLC (FA condition) to afford the title compound (31.4 mg, 56.64 umol, 18.61% yield, 91% purity, FA) as a white solid.

Example 53. Synthesis of N-[(3S,6S)-6-methyl-3-piperidyl]-4-[6-(1-methyltetrazol-5-yl)-1H-pyrrolo[2,3-b]pyridin-3-yl]-5-(trifluoromethyl)pyrimidin-2-amine (Compound 165)

Step 1: 5-iodo-1-methyl-tetrazole

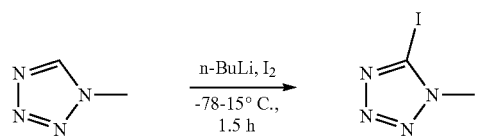

To a solution of 1-methyltetrazole (3 g, 35.68 mmol, 1 eq) in THF (90 mL) was added dropwise n-BuLi (2.5 M, 18.55 mL, 1.3 eq) at −78° C. under N₂ atmosphere. After addition, the mixture was stirred at this temperature for 30 min, and then molecular iodine (9.06 g, 35.68 mmol, 7.19 mL, 1 eq) was added at −78° C. The resulting mixture was stirred at 15° C. for 1 h. The mixture was diluted with H₂O (200 mL) and extracted with EtOAc (100 mL×3). The combined organic layers were washed with brine (300 mL×2), dried over Na₂SO₄ filtered and concentrated under reduced pressure to afford the title compound (3 g, crude) as brown oil.

Step 2: Trimethyl-[2-[[6-(1-methyltetrazol-5-yl)pyrrolo[2,3-b]pyridin-1-yl]methoxy]ethyl]silane

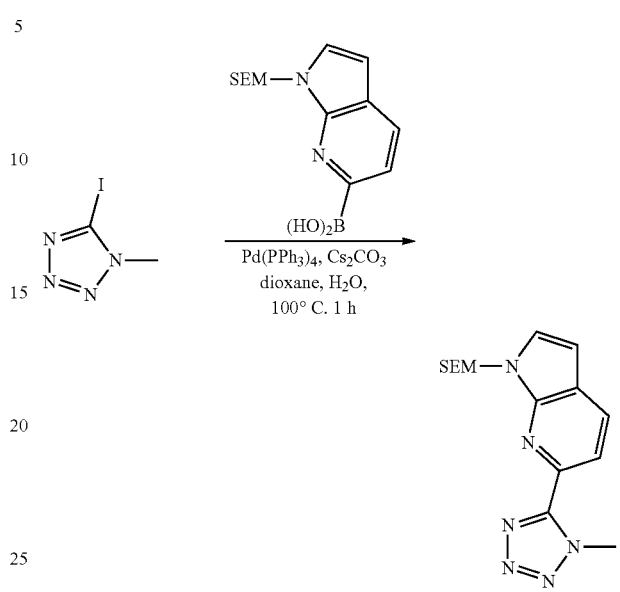

A mixture of [1-(2-trimethylsilylethoxymethyl)pyrrolo[2,3-b]pyridin-6-yl]boronic acid (3.96 g, 13.55 mmol, 1 eq), 5-iodo-1-methyl-tetrazole (3.7 g, 17.62 mmol, 1.3 eq), Cs₂CO₃ (8.83 g, 27.11 mmol, 2 eq), Pd(PPh₃)₄ (1.57 g, 1.36 mmol, 0.1 eq) in dioxane (70 mL) and H₂O (7 mL) was degassed and purged with N₂ for 3 times, and then the mixture was stirred at 100° C. for 1 h under N₂ atmosphere. It was diluted with H₂O 300 mL and extracted with EtOAc (100 mL×3). The combined organic layers were washed with brine (300 mL×2), dried over Na₂SO₄, filtered and concentrated under reduced pressure to give a residue that was purified by column chromatography (SiO₂, PE/EtOAc=10/1 to 4/1) to afford the title compound (2 g) as a yellow solid. (Note: The reaction was combined with another reaction in 500 mg scale for work up.)

Step 3: 2-[[3-bromo-6-(1-methyltetrazol-5-yl) pyrrolo[2,3-b]pyridin-1-yl]methoxy]ethyl-trimethyl-silane

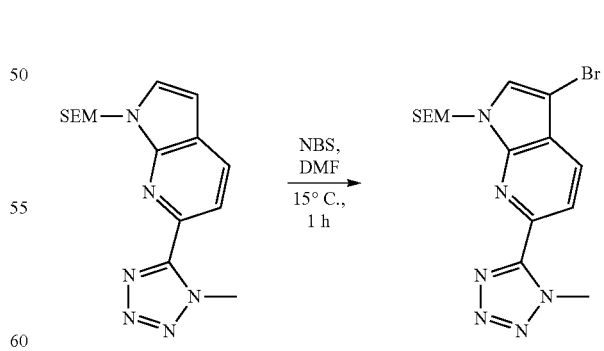

To a solution of trimethyl-[2-[[6-(1-methyltetrazol-5-yl)pyrrolo[2,3-b]pyridin-1-yl]methoxy]ethyl]silane (1.7 g, 5.14 mmol, 1 eq) in DMF (40 mL) was added NBS (915.59 mg, 5.14 mmol, 1 eq). The mixture was stirred at 15° C. for 1 h. The mixture was diluted with H₂O 200 mL and extracted with EtOAc (100 mL×3). The combined organic layers were washed with brine (300 mL×2), dried over Na₂SO₄, filtered and concentrated under reduced pressure to give a residue. It was washed with MTBE (8 mL) and filtered to afford the title compound (1.9 g) as a red solid. (Note: The reaction was combined with another reaction in 300 mg scale for work up.)

Step 4: Trimethyl-[2-[[6-(1-methyltetrazol-5-yl)-3-(4, 4, 5, 5-tetramethyl-1, 3, 2-dioxaborolan-2-yl) pyrrolo[2,3-b]pyridin-1-yl]methoxy]ethyl]silane

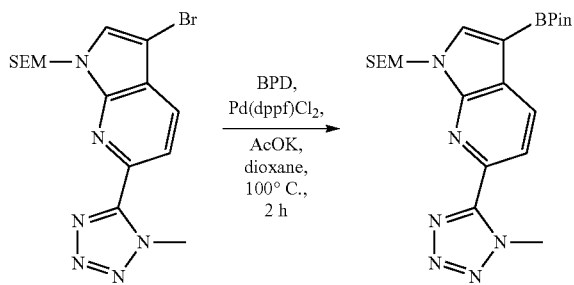

A mixture of 2-[[3-bromo-6-(1-methyltetrazol-5-yl) pyrrolo[2,3-b]pyridin-1-yl]methoxy]ethyl-trimethyl-silane (1.8 g, 4.40 mmol, 1 eq), 4, 4, 5, 5-tetramethyl-2-(4, 4, 5, 5-tetramethyl-1, 3, 2-dioxaborolan-2-yl)-1, 3, 2-dioxaborolane (2.23 g, 8.79 mmol, 2 eq), AcOK (863.07 mg, 8.79 mmol, 2 eq) and Pd(dppf)Cl₂ (321.74 mg, 439.72 umol, 0.1 eq) in dioxane (40 mL) was degassed and purged with N₂ for 3 times, and then the mixture was stirred at 100° C. for 2 h under N₂ atmosphere. The solution was filtered and the filtrate was concentrated to give a residue. It was purified by column chromatography (SiO₂, PE/EtOAc=10/1 to 5/1) to give a residue. Then the residue was purified by reverse column. The eluent solution was adjusted pH to 8 with NaHCO₃ and extracted with EtOAc (60 mL×3), The combined organic layers were washed with brine (200 mL×2), dried over Na₂SO₄, filtered and concentrated under reduced pressure to afford the title compound (700 mg) as a white solid.

Step 5: Trimethyl-[2-[[3-[2-methylsulfanyl-5-(trifluoromethyl)pyrimidin-4-yl]-6-(1-methyltetrazol-5-yl) pyrrolo[2,3-b]pyridin-1-yl]methoxy]ethyl]silane

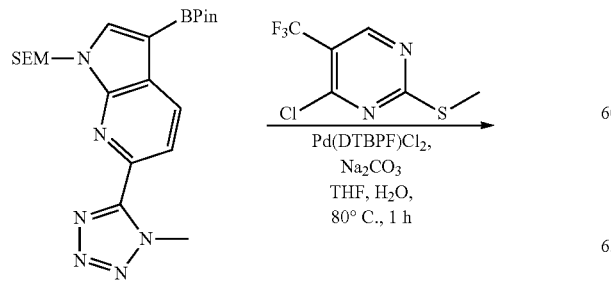

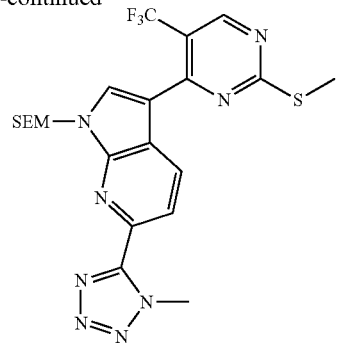

A mixture of trimethyl-[2-[[6-(1-methyltetrazol-5-yl)-3-(4, 4, 5, 5-tetramethyl-1, 3, 2-dioxaborolan-2-yl) pyrrolo[2, 3-b]pyridin-1-yl]methoxy]ethyl]silane (0.05 M, 28.48 mL, 1 eq), 4-chloro-2-methylsulfanyl-5-(trifluoromethyl)pyrimidine (488.38 mg, 2.14 mmol, 1.5 eq), Na₂CO₃ (301.89 mg, 2.85 mmol, 2 eq) and ditert-butyl (cyclopentyl) phosphane: dichloropalladium:iron (92.82 mg, 142.41 umol, 0.1 eq) in THF (30 mL) and H₂O (3 mL) was degassed and purged with N₂ for 3 times, and then the mixture was stirred at 80° C. for 1 h under N₂ atmosphere. It was diluted with H₂O 80 mL and extracted with EtOAc (30 mL×3). The combined organic layers were washed with brine (60 mL×2), dried over Na₂SO₄, filtered and concentrated under reduced pressure to give a residue. The residue was purified by column chromatography (SiO₂, PE/EtOAc=10/1 to 5/1) to afford the title compound (660 mg) as yellow oil. (Note: The reaction was combined with another reaction in 50 mg scale for work up.)

Step 6: Trimethyl-[2-[[3-[2-methylsulfonyl-5-(trifluoromethyl)pyrimidin-4-yl]-6-(1-methyltetrazol-5-yl) pyrrolo[2,3-b]pyridin-1-yl]methoxy]ethyl]silane

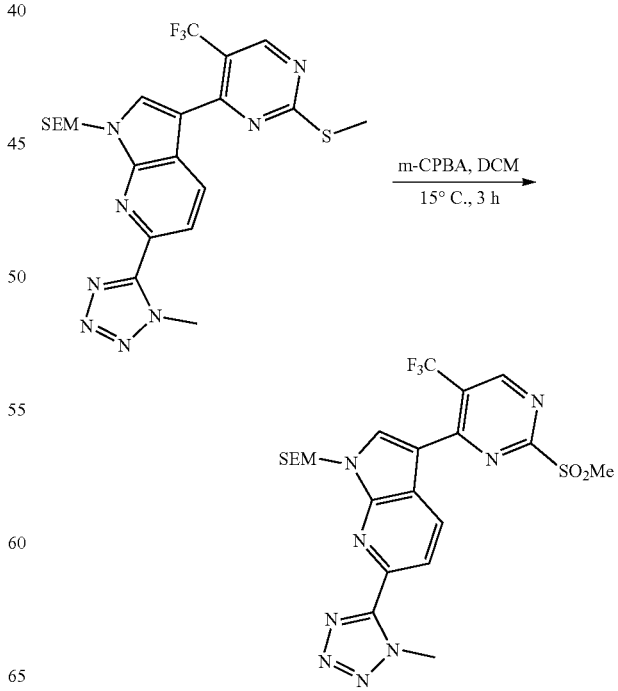

To a solution of trimethyl-[2-[[3-[2-methylsulfanyl-5-(trifluoromethyl)pyrimidin-4-yl]-6-(1-methyltetrazol-5-yl) pyrrolo[2,3-b]pyridin-1-yl]methoxy]ethyl]silane (0.66 g, 1.26 mmol, 1 eq) in DCM (10 mL) was added m-CPBA (640.98 mg, 3.16 mmol, 85% purity, 2.5 eq). The mixture was stirred at 15° C. for 3 h. The mixture was washed with Sat.Na$_2$SO$_3$ (30 mL), Sat.NaHCO$_3$ (30 mL), brine (50 mL). The organic layers were dried over Na$_2$SO$_4$ and concentrated to give a residue. The residue was washed with PE/EtOAc=5/1 (8 mL) and filtered to afford the title compound (0.54 g, crude) as a yellow solid.

Step 7: Benzyl (2S,5S)-2-methyl-5-[[4-[6-(1-methyltetrazol-5-yl)-1-(2-trimethylsilylethoxymethyl) pyrrolo[2,3-b]pyridin-3-yl]-5-(trifluoromethyl)pyrimidin-2-yl]amino]piperidine-1-carboxylate

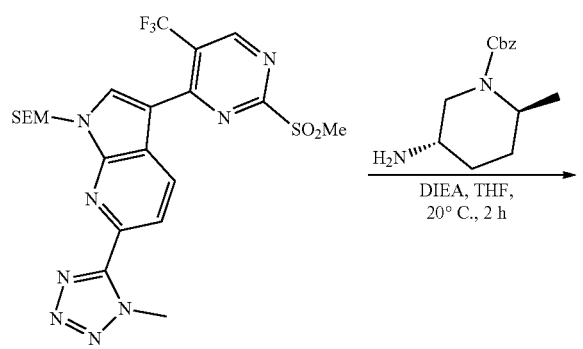

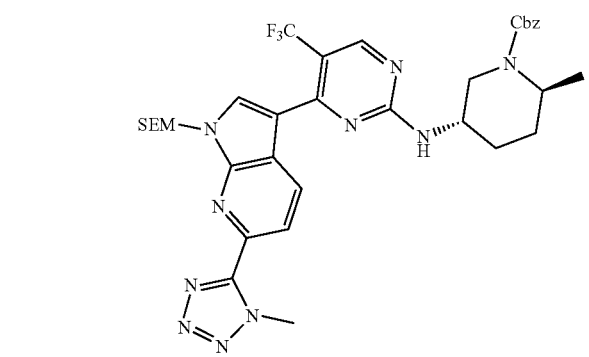

To a solution of trimethyl-[2-[[3-[2-methylsulfonyl-5-(trifluoromethyl)pyrimidin-4-yl]-6-(1-methyltetrazol-5-yl) pyrrolo[2,3-b]pyridin-1-yl]methoxy]ethyl]silane (0.27 g, 486.82 umol, 1 eq), benzyl (2S,5S)-5-amino-2-methyl-piperidine-1-carboxylate (145.06 mg, 584.18 umol, 1.2 eq) in THF (5 mL) was added DIEA (188.75 mg, 1.46 mmol, 254.38 uL, 3 eq). The mixture was stirred at 20° C. for 2 h. The resulting solution was concentrated to give a residue. It was purified by column chromatography (SiO$_2$, PE/EtOAc=10/1 to 2/1) to afford the title compound (0.26 g, 348.90 umol, 71.67% yield, 97% purity) as a yellow solid.

Step 8: N-[(3S,6S)-6-methyl-3-piperidyl]-4-[6-(1-methyltetrazol-5-yl)-1H-pyrrolo[2,3-b]pyridin-3-yl]-5-(trifluoromethyl)pyrimidin-2-amine

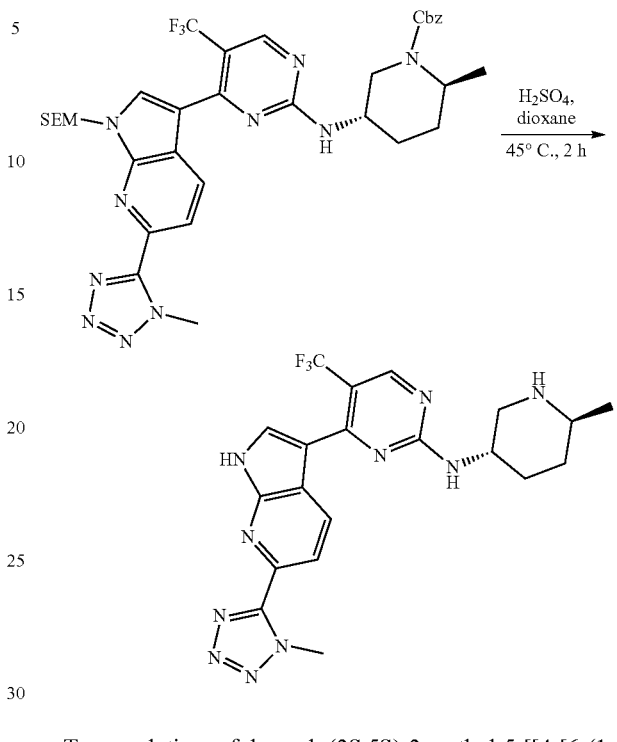

To a solution of benzyl (2S,5S)-2-methyl-5-[[4-[6-(1-methyltetrazol-5-yl)-1-(2-trimethylsilylethoxymethyl)pyrrolo[2,3-b]pyridin-3-yl]-5-(trifluoromethyl)pyrimidin-2-yl]amino]piperidine-1-carboxylate (0.25 g, 345.86 umol, 1 eq) in dioxane (5 mL) was added H$_2$SO$_4$ (5.09 g, 51.88 mmol, 2.77 mL, 150 eq). The mixture was stirred at 45° C. for 2 h. The solution was adjusted pH to 8 with saturated aqueous NaOH, and extracted with EtOAc (50 mL×3), dried over Na$_2$SO$_4$, filtered and concentrated under reduced pressure to give a residue. The residue was purified by prep-HPLC (FA condition) to afford the title compound (30.9 mg, FA) as a white solid. (Note: The reaction was combined with another reaction in 10 mg scale for purification).

Example 54. Synthesis of 4-[6-(5-methyl-1,2,4-oxadiazol-3-yl)-1H-pyrazolo[3,4-b]pyridin-3-yl]-N-[(3S,6S)-6-methyl-3-piperidyl]-5-(trifluoromethyl) pyrimidin-2-amine (Compound 167)

Step 1: Benzyl (2S,5S)-5-[[4-(6-cyano-1-tetrahydropyran-2-yl-pyrazolo[3,4-b]pyridin-3-yl)-5-(trifluoromethyl)pyrimidin-2-yl]amino]-2-methyl-piperidine-1-carboxylate

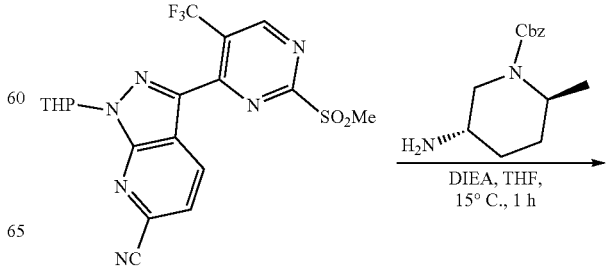

-continued

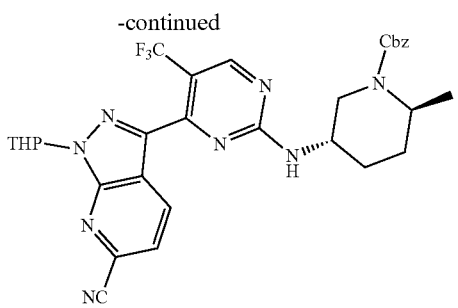

To a solution of 3-[2-methylsulfonyl-5-(trifluoromethyl)pyrimidin-4-yl]-1-tetrahydropyran-2-yl-pyrazolo[3,4-b]pyridine-6-carbonitrile (150 mg, 331.56 umol, 1 eq) in THF (2 mL) was added benzyl (2S,5S)-5-amino-2-methyl-piperidine-1-carboxylate (98.80 mg, 397.87 umol, 1.2 eq) and DIEA (428.52 mg, 3.32 mmol, 577.51 uL, 10 eq). The mixture was stirred at 15° C. for 1 h. It was poured into water (5 mL) and extracted with EtOAc (10 mL×3). The combined organic layer was washed with brine (10 mL×3) and sat. NaHCO₃ (20 mL), dried over Na₂SO₄, filtered. The filtrate was concentrated under reduced pressure to give a residue. The residue was purified by MPLC (SiO₂, PE/EtOAc=3/1 to 1/1) to afford the title compound (85 mg, crude) as white solid.

Step 2: Benzyl (2S,5S)-5-[[4-[6-[(Z)—N'-hydroxycarbamimidoyl]-1-tetrahydropyran-2-yl-pyrazolo[3,4-b]pyridin-3-yl]-5-(trifluoromethyl)pyrimidin-2-yl]amino]-2-methyl-piperidine-1-carboxylate

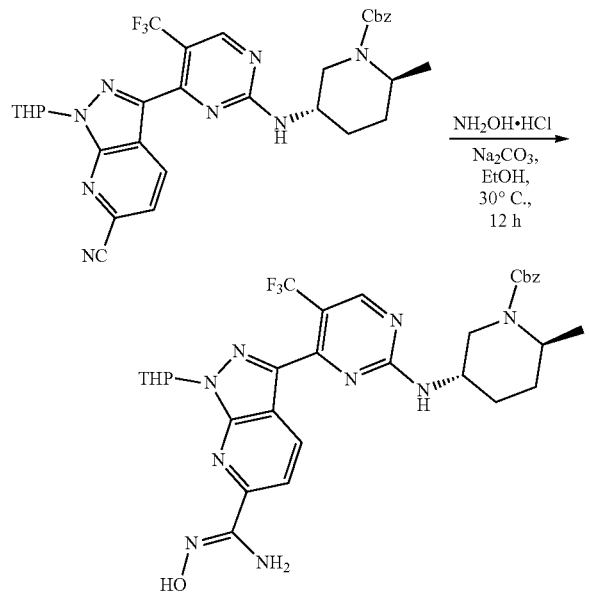

To a mixture of benzyl (2S,5S)-5-[[4-(6-cyano-1-tetrahydropyran-2-yl-pyrazolo[3,4-b]pyridin-3-yl)-5-(trifluoromethyl)pyrimidin-2-yl]amino]-2-methyl-piperidine-1-carboxylate (85.00 mg, 136.96 umol, 1 eq) in EtOH (2 mL) was added Na₂CO₃ (174.19 mg, 1.64 mmol, 12 eq) and NH₂OH·HCl (95.17 mg, 1.37 mmol, 10 eq). The mixture was stirred at 30° C. for 12 h. It was filtered and concentrated under reduced pressure to afford the title compound (100 mg, crude) as yellow solid which was used next step without further purification. (Note: The reaction was combined with another reaction in 200 mg scale for work up.)

Step 3: Benzyl (2S,5S)-2-methyl-5-[[4-[6-(5-methyl-1,2,4-oxadiazol-3-yl)-1-tetrahydropyran-2-yl-pyrazolo[3,4-b]pyridin-3-yl]-5-(trifluoromethyl)pyrimidin-2-yl]amino]piperidine-1-carboxylate

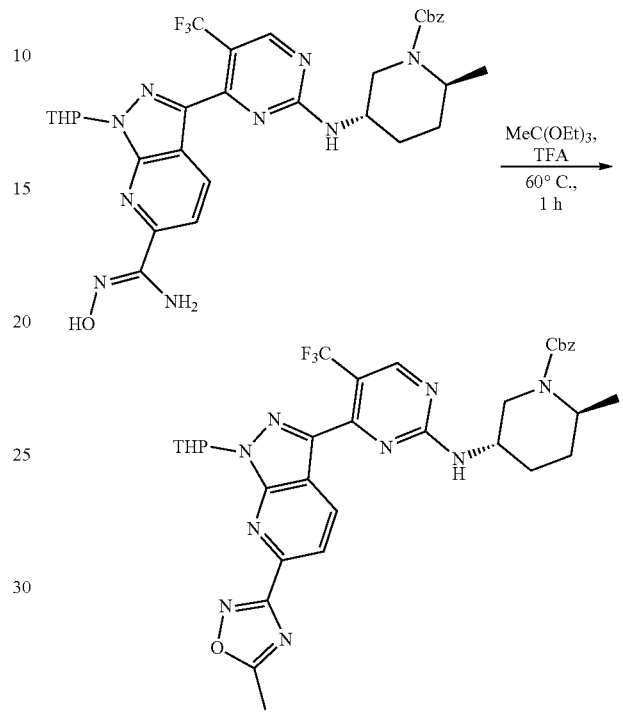

To a solution of benzyl (2S,5S)-5-[[4-[6-[(Z)—N'-hydroxycarbamimidoyl]-1-tetrahydropyran-2-yl-pyrazolo[3,4-b]pyridin-3-yl]-5-(trifluoromethyl)pyrimidin-2-yl]amino]-2-methyl-piperidine-1-carboxylate (100 mg, 152.99 umol, 1 eq) in 1,1,1-triethoxyethane (885.00 mg, 5.46 mmol, 1 mL, 35.66 eq) was added TFA (3.49 mg, 30.60 umol, 2.27 uL, 0.2 eq) at 15° C. The mixture was stirred at 15° C. for 10 min, then the mixture was stirred at 60° C. for 50 min. The mixture was concentrated to obtain the residue. It was purified by MPLC (SiO₂, PE/EtOAc=5/1 to 1/1) to afford the title compound (50 mg, 67.51 umol, 44.13% yield, 91.5% purity) as brown solid.

Step 4: Benzyl (2S,5S)-2-methyl-5-[[4-[6-(5-methyl-1,2,4-oxadiazol-3-yl)-1H-pyrazolo[3,4-b]pyridin-3-yl]-5-(trifluoromethyl)pyrimidin-2-yl]amino]piperidine-1-carboxylate

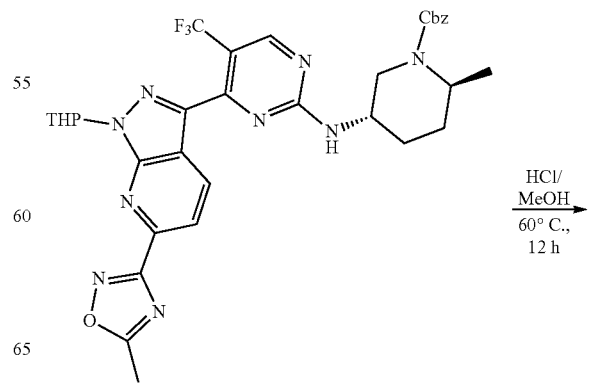

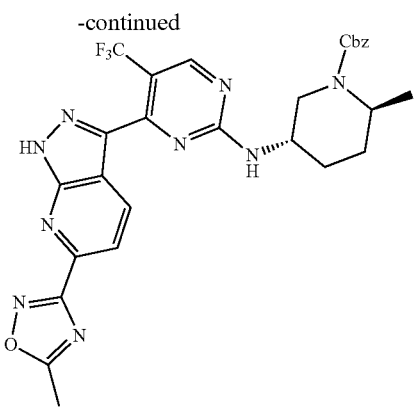

To a solution of benzyl (2S,5S)-2-methyl-5-[[4-[6-(5-methyl-1,2,4-oxadiazol-3-yl)-1-tetrahydropyran-2-yl-pyrazolo[3,4-b]pyridin-3-yl]-5-(trifluoromethyl)pyrimidin-2-yl]amino]piperidine-1-carboxylate (50.00 mg, 73.78 umol, 1 eq) in HCl/MeOH (2 mL) was stirred at 60° C. for 12 h. The reaction mixture was concentrated under reduced pressure to afford the title compound (50 mg, crude) as yellow solid.

Step 5: 4-[6-(5-methyl-1,2,4-oxadiazol-3-yl)-1H-pyrazolo[3,4-b]pyridin-3-yl]-N-[(3S,6S)-6-methyl-3-piperidyl]-5-(trifluoromethyl)pyrimidin-2-amine

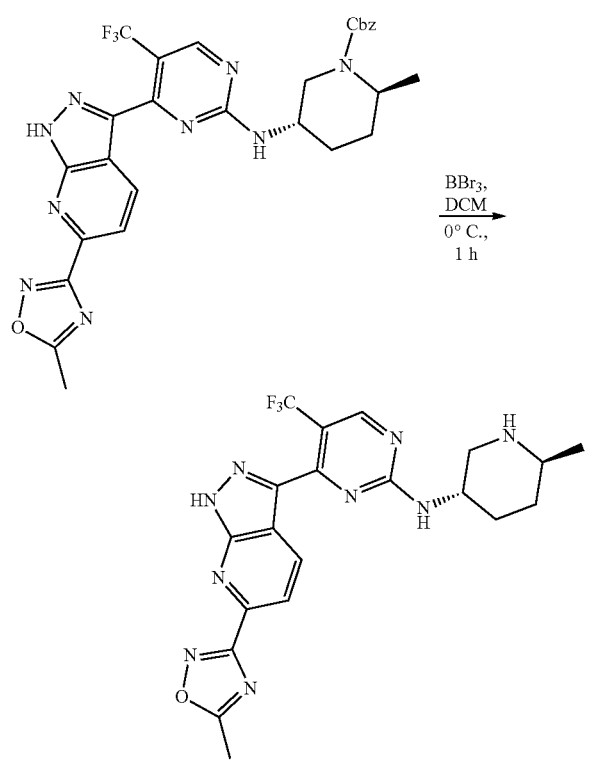

To a solution of benzyl (2S,5S)-2-methyl-5-[[4-[6-(5-methyl-1,2,4-oxadiazol-3-yl)-1H-pyrazolo[3,4-b]pyridin-3-yl]-5-(trifluoromethyl)pyrimidin-2-yl]amino]piperidine-1-carboxylate (50.00 mg, 84.24 umol, 1 eq) in DCM (2 mL) was added BBr₃ (105.52 mg, 421.19 umol, 40.58 uL, 5 eq) at 0° C. The mixture was stirred at 0° C. for 1 h. The reaction mixture was concentrated under reduced pressure to give a residue. It was purified by prep-HPLC (HCl condition) to afford the title compound (12.7 mg, 23.76 umol, 28.21% yield, 92.78% purity, HCl) as white solid.

Example 55. Synthesis of 4-[6-(5-methyl-1,2,4-oxadiazol-3-yl)-1H-pyrazolo[3,4-b]pyridin-3-yl]-N-[(3S)-3-piperidyl]-5-(trifluoromethyl)pyrimidin-2-amine (Compound 168)

Step 1: Tert-butyl (3S)-3-[[4-(6-cyano-1-tetrahydropyran-2-yl-pyrazolo[3,4-b]pyridin-3-yl)-5-(trifluoromethyl)pyrimidin-2-yl]amino]piperidine-1-carboxylate

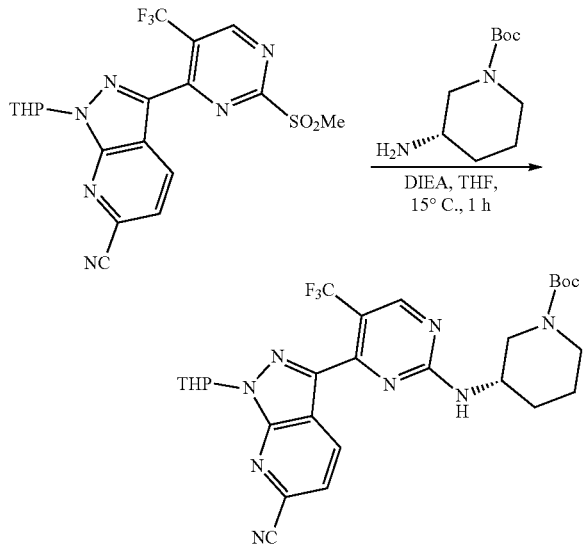

To a solution of 3-[2-methylsulfonyl-5-(trifluoromethyl)pyrimidin-4-yl]-1-tetrahydropyran-2-yl-pyrazolo[3,4-b]pyridine-6-carbonitrile (160 mg, 353.66 umol, 1 eq) in THF (1.6 mL) was added tert-butyl (3S)-3-aminopiperidine-1-carboxylate (77.91 mg, 389.03 umol, 1.1 eq), DIEA (228.54 mg, 1.77 mmol, 308.01 uL, 5 eq) at 15° C. The mixture was stirred at 15° C. for 1 h. It was poured into water (10 mL) and extracted with EtOAc (10 mL×3). The combined organic layer was washed with brine (10 mL×3), dried over Na₂SO₄, filtered. The filtrate was concentrated under reduced pressure to give a residue. It was purified by MPLC (SiO₂, PE/EtOAc=3/1 to 1/1) to afford the title compound (200 mg) as yellow solid.

Step 2: Tert-butyl (3S)-3-[[4-[6-[(Z)—N'-hydroxycarbamimidoyl]-1-tetrahydropyran-2-yl-pyrazolo[3,4-b]pyridin-3-yl]-5-(trifluoromethyl)pyrimidin-2-yl]amino]piperidine-1-carboxylate

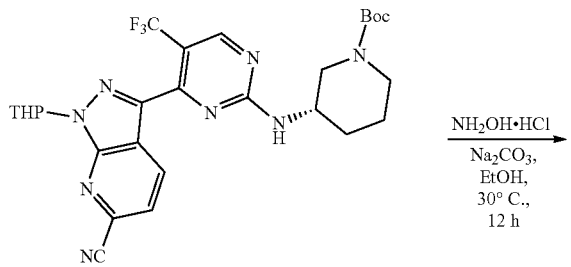

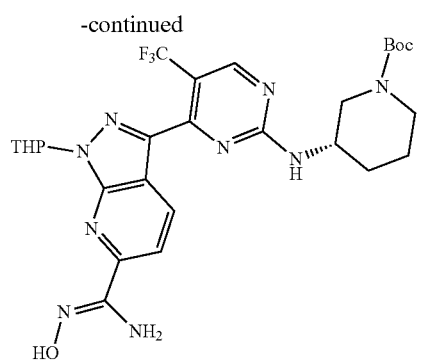

To a solution of tert-butyl (3S)-3-[[4-(6-cyano-1-tetrahydropyran-2-yl-pyrazolo[3,4-b]pyridin-3-yl)-5-(trifluoromethyl)pyrimidin-2-yl]amino]piperidine-1-carboxylate (200 mg, 349.30 umol, 1 eq) in EtOH (5 mL) was added NH₂OH.HCl (242.73 mg, 3.49 mmol, 10 eq) and Na₂CO₃ (444.26 mg, 4.19 mmol, 12 eq). The mixture was stirred at 30° C. for 12 h. It was filtered and concentrated under reduced pressure to afford the title compound (200 mg, crude) as yellow solid which was used next step directly. (Note: The reaction was combined with another reaction in 200 mg scale for work up.)

Step 3: Tert-butyl (3S)-3-[[4-[6-(5-methyl-1,2,4-oxadiazol-3-yl)-1-tetrahydropyran-2-yl-pyrazolo[3,4-b]pyridin-3-yl]-5-(trifluoromethyl)pyrimidin-2-yl]amino]piperidine-1-carboxylate

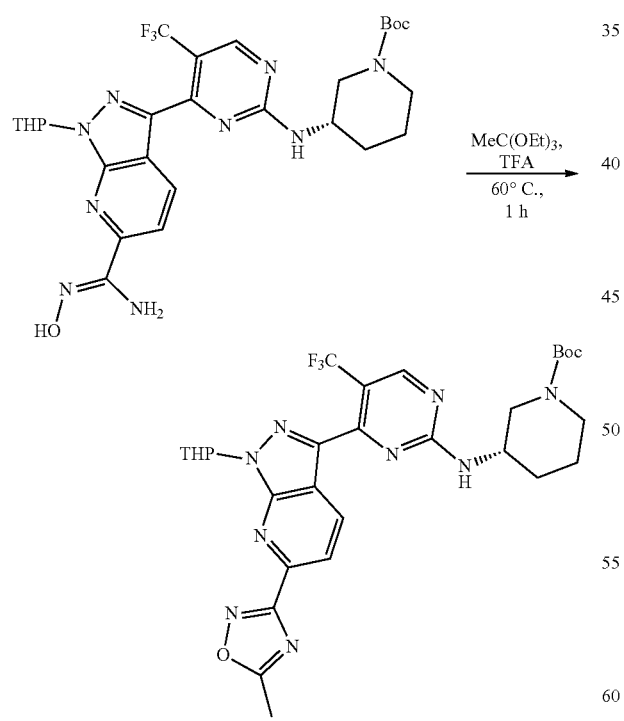

To a mixture of tert-butyl (3S)-3-[[4-[6-[(Z)—N'-hydroxycarbamimidoyl]-1-tetrahydropyran-2-yl-pyrazolo[3,4-b]pyridin-3-yl]-5-(trifluoromethyl)pyrimidin-2-yl]amino]piperidine-1-carboxylate (180 mg, 297.22 umol, 1 eq) and 1,1,1-triethoxyethane (964.36 mg, 5.94 mmol, 1.09 mL, 20 eq) was added TFA (3.39 mg, 29.72 umol, 2.20 uL, 0.1 eq). The mixture was stirred at 15° C. for 10 min, and then the mixture was stirred at 60° C. for 50 min. It was concentrated. The residue was purified by MPLC (SiO₂, PE/EtOAc=4/1 to 1/1) to afford the title compound (100 mg, 93.7% purity) as white solid.

Step 4: 4-[6-(5-methyl-1,2,4-oxadiazol-3-yl)-1H-pyrazolo[3,4-b]pyridin-3-yl]-N-[(3S)-3-piperidyl]-5-(trifluoromethyl)pyrimidin-2-amine

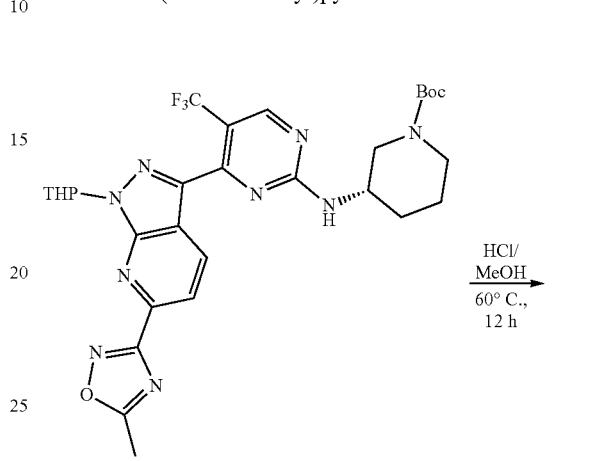

A solution of tert-butyl (3S)-3-[[4-[6-(5-methyl-1,2,4-oxadiazol-3-yl)-1-tetrahydropyran-2-yl-pyrazolo[3,4-b]pyridin-3-yl]-5-(trifluoromethyl)pyrimidin-2-yl]amino]piperidine-1-carboxylate (100 mg, 158.82 umol, 1 eq) in HCl/MeOH (3 mL) was stirred at 60° C. for 12 h. It was concentrated under reduced pressure to give a residue. It was purified by prep-HPLC (HCl condition) to afford the title compound (42 mg, 86.40 umol, 54.40% yield, 99.13% purity, HCl) as white solid.

Example 56. Synthesis of 4-(6-(3,5-dimethylisoxazol-4-yl)-5-fluoro-1H-indol-3-yl)-N—((S)-piperidin-3-yl)-5-(trifluoromethyl)pyrimidin-2-amine (Compound 134)

Step 1: 6-bromo-3-(2-chloro-5-(trifluoromethyl)pyrimidin-4-yl)-5-fluoro-1H-indole

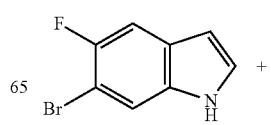

205

-continued

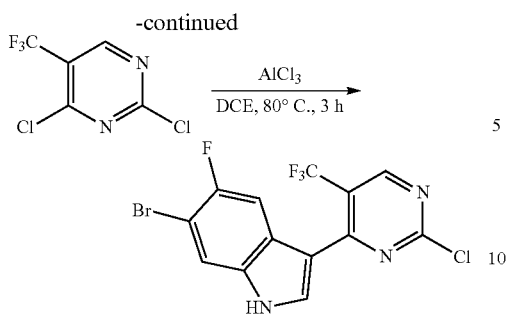

To a and rt solution of 2,4-dichloro-5-trifluoromethylpyrimidine (945 uL, 7.01 mmol) in anh. (anhydrous) DCE (3 mL) under nitrogen, was added aluminum trichloride (472 mg, 3.51 mmol), and the resulting mixture was stirred at 80° C. for 30 min. After this time, the reaction mixture was cooled to RT, and 6-bromo-5-fluoro indole (500 mg, 2.34 mmol) was added. The resulting mixture was stirred at 80° C. for 3 h, where the solution became reddish overtime. The mixture was then poured into crushed ice and EtOAc. Layers were separated, and organic layer was then dried over anh. $Na_2SO_4$, filtered, and concentrated under reduced pressure. The residue was purified by reverse phase chromatography (C18, ACN in aq. 10 mM ammonium formate, pH 3.8, 45 to 85% gradient) to afford the title compound (431 mg, 1.09 mmol, 47% yield) as a beige solid.

Step 2: (S)-tert-butyl 3-((4-(6-bromo-5-fluoro-1H-indol-3-yl)-5-(trifluoromethyl)pyrimidin-2-yl)amino)piperidine-1-carboxylate

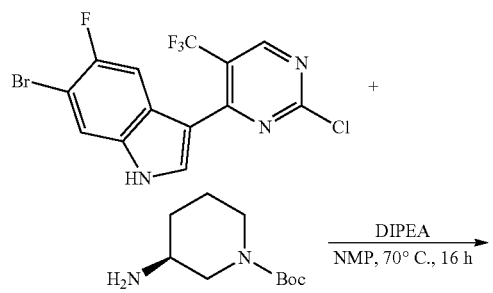

206

-continued

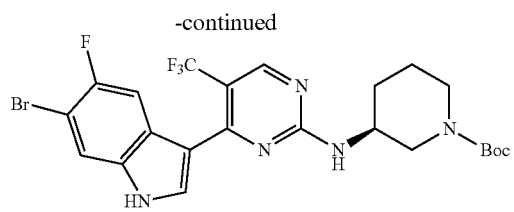

To a solution of 6-bromo-3-(2-chloro-5-(trifluoromethyl)pyrimidin-4-yl)-5-fluoro-1H-indole (410 mg, 1.04 mmol) and (S)-tert-butyl 3-aminopiperidine-1-carboxylate (234 mg, 1.14 mmol) in anh. NMP (2.1 mL), was added DIPEA (0.55 mL, 3.12 mmol). The reaction mixture was stirred at 70° C. for 16 h. The mixture was then diluted with EtOAc, washed with brine (2×20 mL), dried over anh. $Na_2SO_4$, filtered, and concentrated under reduced pressure. The residue was purified by column chromatography on silica gel (EtOAc in hexanes, 0 to 100% gradient) to afford the title compound (355 mg, 0.635 mmol, 61% yield) as a pale yellow oil that crystallized overtime.

Step 3: (3S)-tert-butyl 3-((4-(6-(3,5-dimethylisoxazol-4-yl)-5-fluoro-1H-indol-3-yl)-5-(trifluoromethyl)pyrimidin-2-yl)amino)piperidine-1-carboxylate

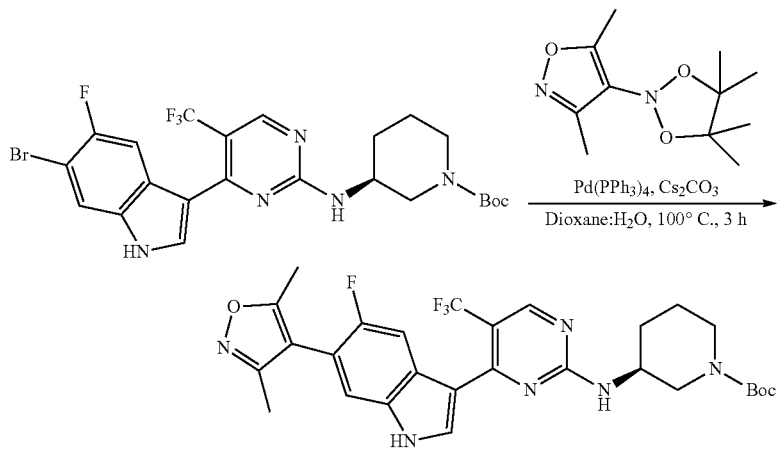

(S)-tert-Butyl 3-((4-(6-bromo-5-fluoro-1H-indol-3-yl)-5-(trifluoromethyl)pyrimidin-2-yl)amino)piperidine-1-carboxylate (100 mg, 0.179 mmol) and 3,5-dimethyl-4-(4,4,5,5-tetramethyl-1,3,2-dioxaborolan-2-yl)isoxazole (80 mg, 0.358 mmol) were dissolved in a previously degassed mixture of dioxane (3.0 mL) and water (1.5 mL). Cesium carbonate (118 mg, 0.358 mmol) and Pd(PPh$_3$)$_4$ (21 mg, 0.018 mmol) were then added to the reaction mixture subsequently. The resulting mixture was stirred at 100° C. for 3 h. After full conversion of starting material, the mixture was cooled to RT, diluted with water, and extracted with EtOAc (3×20 mL). Organic layers were combined, dried over anh. $Na_2SO_4$, filtered, and concentrated under reduced pressure. The residue was purified by column chromatography on silica gel (EtOAc in Hexanes, 0 to 100% gradient) to provide the title compound (88 mg, 0.153 mmol, 86% yield) as a pale yellow oil.

Step 4: 4-(6-(3,5-dimethylisoxazol-4-yl)-5-fluoro-1H-indol-3-yl)-N—((S)-piperidin-3-yl)-5-(trifluoromethyl)pyrimidin-2-amine

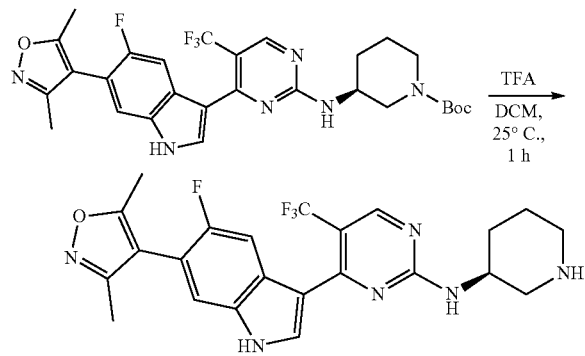

To a solution of (3S)-tert-butyl 3-((4-(6-(3,5-dimethylisoxazol-4-yl)-5-fluoro-1H-indol-3-yl)-5-(trifluoromethyl)pyrimidin-2-yl)amino)piperidine-1-carboxylate (88 mg, 0.153 mmol) in DCM (2.25 mL), was added TFA (0.6 mL, 7.67 mmol). After 1 h of stirring at RT, the reaction mixture was concentrated to dryness in vacuo. The crude was then re-dissolved in MeTHF and washed twice with aq. sat. NaHCO₃. Organic layer was concentrated, and the obtained residue was purified by reverse phase chromatography (C18, ACN in aq. 10 mM ammonium formate, pH 3.8, 0 to 55% gradient) to afford the title compound (29.6 mg, 0.062 mmol, 41% yield) as a white solid after lyophilization.

Example 57. Synthesis of (3S)-tert-butyl 3-((4-(6-(3,5-dimethylisoxazol-4-yl)-5-fluoro-1H-pyrrolo[2,3-b]pyridin-3-yl)-5-(trifluoromethyl)pyrimidin-2-yl)amino)piperidine-1-carboxylate (Compound 138)

Step 1: 4-(5-fluoro-1H-pyrrolo[2,3-b]pyridin-6-yl)-3,5-dimethylisoxazole

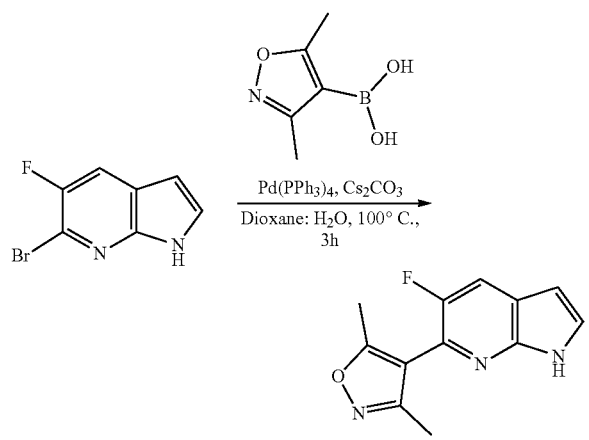

6-Bromo-5-fluoro-1H-pyrrolo[2,3-b]pyridine (592 mg, 2.67 mmol) and 3,5-dimethylisoxazol-4-yl-4-boronic acid (792 mg, 5.34 mmol) were dissolved in degassed 2:1 mixture of dioxane and water (30/15 mL). Cesium carbonate (1.75 g, 5.34 mmol) was added, and the mixture was degassed for 5 min. Pd(Ph₃)₄ (312 mg, 267 umol) was then added, and the reaction mixture was stirred at 100° C. for 3 h. The mixture was cooled to RT and diluted with water, the crude product was extracted from aq. phase with MeTHF (3 times). Organics were combined, dried over anh. Na₂SO₄, filtered, and concentrated in vacuo. The residue was purified by silica gel column chromatography (EtOAc in hexanes, 0 to 100% gradient) to afford the title compound (500 mg, 2.16 mmol, 81% yield) as a yellowish solid.

Step 2: 4-(3-bromo-5-fluoro-1H-pyrrolo[2,3-b]pyridin-6-yl)-3,5-dimethylisoxazole

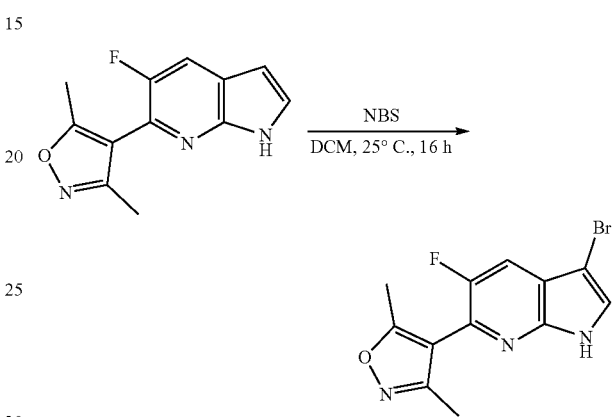

To a solution of 4-(5-fluoro-1H-pyrrolo[2,3-b]pyridin-6-yl)-3,5-dimethylisoxazole (500 mg, 2.16 mmol) in DCM (22 mL), was added NBS (388 mg, 2.16 mmol), and the reaction mixture was stirred at RT for 16 h. The mixture was quenched by the addition of Na₂S₂O₃ (aq. sat.) and stirred vigorously for 30 min. DCM was concentrated, and the crude product was extracted from aq. phase with EtOAc (3×30 mL). The combined organic phase was again washed with aq. sat. NaS₂O₃ (20 mL), water (2×10 mL), brine (2×20 mL), then dried over anh. Na₂SO₄, filtered, and concentrated in vacuo to afford the title compound as an orange-brown solid (666 mg, 2.15 mmol, quant. yield), which was used in the next step without further purification.

Step 3: 4-(3-bromo-5-fluoro-1-(phenylsulfonyl)-1H-pyrrolo[2,3-b]pyridin-6-yl)-3,5-dimethylisoxazole

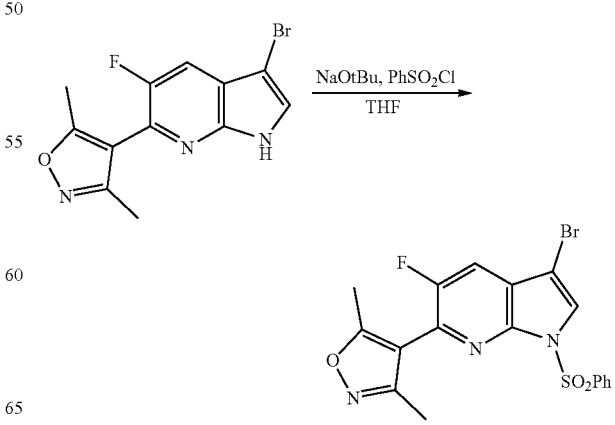

A solution of 4-(3-bromo-5-fluoro-1H-pyrrolo[2,3-b]pyridin-6-yl)-3,5-dimethylisoxazole (666 mg, 2.15 mmol) in THF (21.5 mL) was cooled to 0° C. and then treated with sodium tert-butoxide (248 mg, 2.58 mmol). After stirring for 30 min at this temperature, benzenesulfonyl chloride (303 uL, 2.25 mmol) was added, and the reaction mixture was stirred at RT until full conversion. The mixture was poured into water (50 mL), and then THF was concentrated under reduced pressure. The formed solid was filtered, washed with water, and dried in vacuo to afford the title compound as a tan solid (919 mg, 2.04 mmol, 95% yield), which was used in the next step without further purification.

Step 4: 4-(5-fluoro-1-(phenylsulfonyl)-3-(4,4,5,5-tetramethyl-1,3,2-dioxaborolan-2-yl)-1H-pyrrolo[2,3-b]pyridin-6-yl)-3,5-dimethylisoxazole

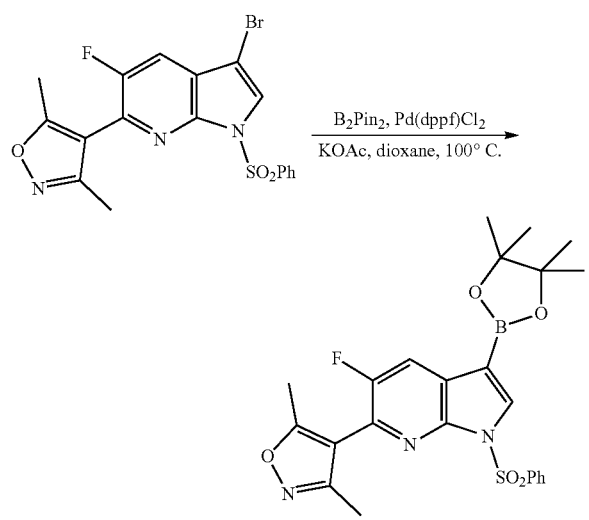

A mixture of 4-(3-bromo-5-fluoro-1-(phenylsulfonyl)-1H-pyrrolo[2,3-b]pyridin-6-yl)-3,5-dimethylisoxazole (455 mg, 1.01 mmol), potassium acetate (501 mg, 5.05 mmol) and B₂Pin₂ (bis(pinacolato)diboron; 655 mg, 2.53 mmol) in dioxane (10 mL) was degassed for 30 min by bubbling with nitrogen. Pd(dppf)Cl₂ (37.5 mg, 50.5 umol) was then added, and the reaction mixture was stirred in a sealed vial at 100° C. until full conversion (30 min). The mixture was cooled to RT, diluted with EtOAc, and filtered through Celite pad. The organic phase was washed with water (2×10 mL), brine (2×10 mL), dried over anh. Na₂SO₄, and concentrated in vacuo to afford the title compound as a yellowish oil (503 mg, 1.01 mmol, quant. yield), which was used in the next step without further purification.

Step 5: (3S)-tert-butyl 3-((4-(6-(3,5-dimethylisoxazol-4-yl)-5-fluoro-1-(phenylsulfonyl)-1H-pyrrolo[2,3-b]pyridin-3-yl)-5-(trifluoromethyl)pyrimidin-2-yl)amino)piperidine-1-carboxylate

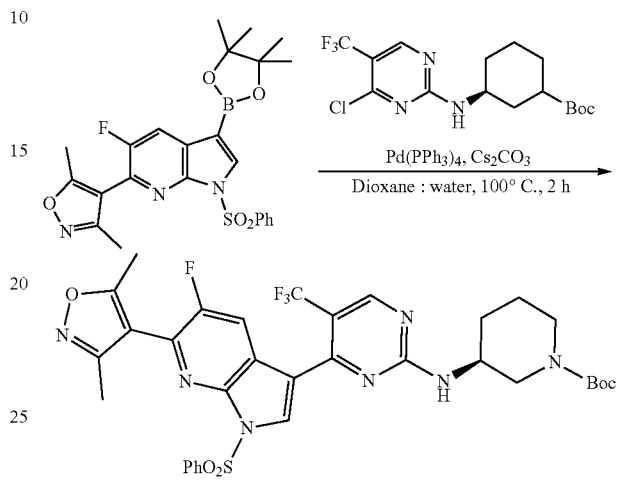

A solution of 4-(5-fluoro-1-(phenylsulfonyl)-3-(4,4,5,5-tetramethyl-1,3,2-dioxaborolan-2-yl)-1H-pyrrolo[2,3-b]pyridin-6-yl)-3,5-dimethylisoxazole (503 mg, 1.01 mmol), (S)-tert-butyl 3-((4-chloro-5-(trifluoromethyl)pyrimidin-2-yl)amino)piperidine-1-carboxylate [prepared as in PCT/US2014/015256] (424 mg, 1.11 mmol) and cesium carbonate (664 mg, 2.02 mmol) in dioxane and water (20 mL/10 mL) was degassed for 30 min by bubbling with nitrogen. Pd(PPh₃)₄ (119 mg, 0.101 mmol) was then added, and the reaction mixture was stirred at 100° C. for 2 h. The mixture was cooled to RT and concentrated under reduced pressure to remove dioxane. After re-dissolving in EtOAc (30 mL) and water (15 mL), the aqueous layer was extracted with EtOAc (2×15 mL). The collected organic phase was washed with water (2×15 mL), brine (2×15 mL), dried over anh. Na₂SO₄, filtered, and concentrated. The residue was purified by flash silica gel column chromatography (EtOAc in hexanes, 0 to 100% gradient) to provide the title compound (410 mg, 0.573 mmol, 57% yield) as a pale yellow solid.

Step 6: (3S)-tert-butyl 3-((4-(6-(3,5-dimethylisoxazol-4-yl)-5-fluoro-1H-pyrrolo[2,3-b]pyridin-3-yl)-5-(trifluoromethyl)pyrimidin-2-yl)amino)piperidine-1-carboxylate

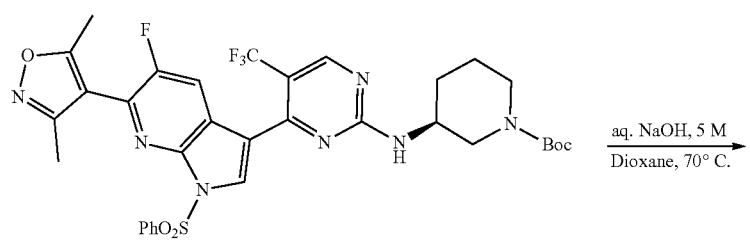

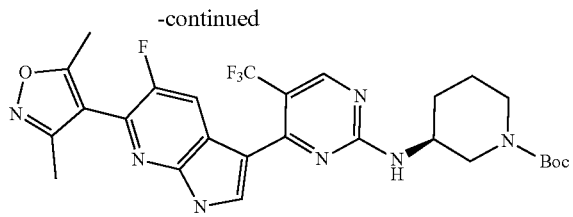

To a solution of (3S)-tert-butyl 3-((4-(6-(3,5-dimethyl-isoxazol-4-yl)-5-fluoro-1-(phenylsulfonyl)-1H-pyrrolo[2,3-b]pyridin-3-yl)-5-(trifluoromethyl)pyrimidin-2-yl)amino)piperidine-1-carboxylate (410 mg, 0.573 mmol) in dioxane (5 mL), was added aq. 5 M solution of sodium hydroxide (2.29 mL, 11.5 mmol), and the reaction mixture was stirred at 70° C. until full conversion (30 min). Cooled to RT, the mixture was concentrated, then re-dissolved in MeTHF, and water (20 mL) was added. The mixture was acidified to pH 3 with aq. 1 M HCl, then aq. layer was extracted with MeTHF (2×15 mL). The combined organic phase was washed with water (2×15 mL), brine (2×15 mL), dried over anh. Na$_2$SO$_4$, filtered, and concentrated in vacuo to afford the title compound (319 mg, 0.554 mmol, 97% yield) as a pale yellow solid, which was used in the next step without further purification.

Example 58. Synthesis of (S)-tert-butyl 3-((4-(6-(3,5-dimethylisothiazol-4-yl)-1H-pyrrolo[2,3-b]pyridin-3-yl)-5-(trifluoromethyl)pyrimidin-2-yl)amino)piperidine-1-carboxylate (Compound 166)

Step 1: (S)-3-(2-((1-(tert-butoxycarbonyl)piperidin-3-yl)amino)-5-(trifluoromethyl)pyrimidin-4-yl)-1H-pyrrolo[2,3-b]pyridine 7-oxide To a suspension of (S)-tert-butyl 3-((4-(1H-pyrrolo[2,3-b]pyridin-3-yl)-5-(trifluoromethyl)pyrimidin-2-yl)amino)piperidine-1-carboxylate [prepared from 1-(phenylsulfonyl)-3-(4,4,5,5-tetramethyl-1,3,2-dioxaborolan-2-yl)-1H-pyrrolo[2,3-b]pyridine and (S)-tert-butyl 3-((4-chloro-5-(trifluoromethyl)pyrimidin-2-yl)amino)piperidine-1-carboxylate as in Example 57] (3.20 g, 6.92 mmol) in DCM (68 mL) at 0° C., was added m-CPBA, 77%, portion wise (4.65 g, 20.76 mmol, 3 eq in total) over 16 h, stirring the reaction mixture at RT and monitoring conversion by LCMS. Then, water (50 mL) was added, and the crude product was extracted with DCM (2×100 mL). The combined organic phase was washed with sat. aq. NaHCO$_3$ (50 mL), brine (2×50 mL), dried over anh. Na$_2$SO$_4$, filtered, and concentrated in vacuo. The residue was purified by reverse phase column chromatography (C18, ACN in aq. 10 mM ammonium formate, pH 3.8, 0 to 100% gradient) to afford the title compound (1.2 g, 2.5 mmol, 36% yield) as a red solid.

Step 2: (S)-Methyl 3-(2-((1-(tert-butoxycarbonyl)piperidin-3-yl)amino)-5-(trifluoromethyl)pyrimidin-4-yl)-6-chloro-1H-pyrrolo[2,3-b]pyridine-1-carboxylate To a suspension of (S)-3-(2-((1-(tert-butoxycarbonyl)piperidin-3-yl)amino)-5-(trifluoromethyl)pyrimidin-4-yl)-1H-pyrrolo[2,3-b]pyridine 7-oxide (1.09 g, 2.27 mmol) in THF (12 mL), was added HMDS (1,1,1,3,3,3-Hexamethyldisilazane; 517 uL, 2.50 mmol), and the mixture was stirred under nitrogen at 0° C. Then, methyl chloroformate (443 uL, 5.68 mmol) was added, and the reaction mixture was stirred at RT until full conversion (4 h). The mixture was diluted with EtOAc, washed with aq. sat. NaHCO$_3$, water and brine, then dried over anh. Na$_2$SO$_4$, filtered, and concentrated under reduced pressure. The residue was purified by flash column silica gel chromatography (EtOAc in hexanes, 0 to 100% gradient) to provide the title compound (567 mg, 1.02 mmol, 45% yield) as a yellow foam.

Step 3: (S)-tert-butyl 3-((4-(6-chloro-1H-pyrrolo[2,3-b]pyridin-3-yl)-5-(trifluoromethyl)pyrimidin-2-yl)amino)piperidine-1-carboxylate

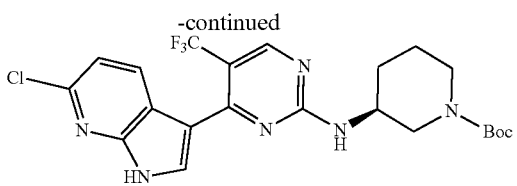

(S)-Methyl 3-(2-((1-(tert-butoxycarbonyl)piperidin-3-yl)amino)-5-(trifluoromethyl)pyrimidin-4-yl)-6-chloro-1H-pyrrolo[2,3-b]pyridine-1-carboxylate (567 mg, 1.02 mmol) was dissolved in THF (5 mL), and 2 M aq. sodium hydroxide (1 mL, 2.04 mmol) was added. The reaction mixture was stirred at RT until full conversion (1 h). The mixture was then diluted with MeTHF and water, and the organic layer was separated. The organic phase was dried over anh. Na₂SO₄, filtered, and concentrated in vacuo to afford the title compound (507 mg, quant. yield), which was used in the next step without further purification.

Step 4: (S)-(3-(2-((1-(tert-butoxycarbonyl)piperidin-3-yl)amino)-5-(trifluoromethyl)pyrimidin-4-yl)-1H-pyrrolo[2,3-b]pyridin-6-yl)boronic Acid

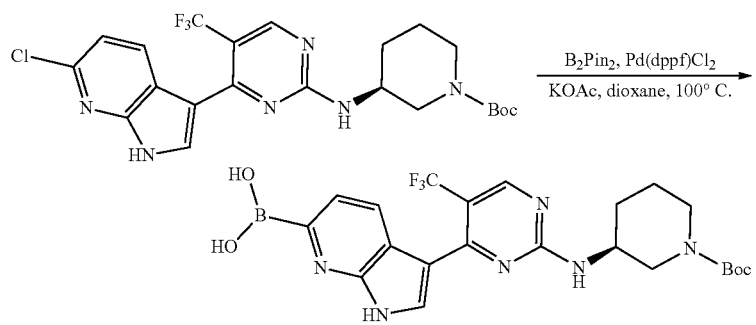

A flask was charged with (S)-tert-butyl 3-((4-(6-chloro-1H-pyrrolo[2,3-b]pyridin-3-yl)-5-(trifluoromethyl)pyrimidin-2-yl)amino)piperidine-1-carboxylate (507 mg, 1.02 mmol), bis(pinacolato)diboron (317 mg, 1.22 mmol), potassium acetate (506 mg, 5.10 mmol), and degassed dioxane (13 mL). The mixture was degassed for another 5 min, and then Pd(dppf)Cl₂×DCM complex (85 mg, 102 umol) was added. The reaction mixture was stirred at 100° C. for 16 h. The reaction mixture was cooled to RT, diluted with EtOAc, and filtered through Celite pad. The organic phase was washed with water and brine, dried over anh. Na₂SO₄, and concentrated in vacuo. The obtained dark-brown crude was triturated with the mixture of hexane/ether to afford the title compound as a grey solid, which was used in the next step without further purification.

Step 5: (S)-tert-butyl 3-((4-(6-(3,5-dimethylisothiazol-4-yl)-1H-pyrrolo[2,3-b]pyridin-3-yl)-5-(trifluoromethyl)pyrimidin-2-yl)amino)piperidine-1-carboxylate

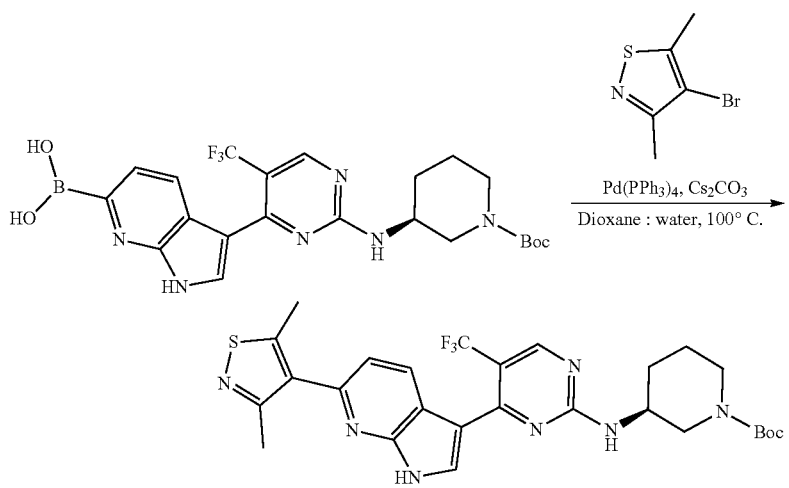

(S)-(3-(2-((1-(tert-butoxycarbonyl)piperidin-3-yl) amino)-5-(trifluoromethyl)pyrimidin-4-yl)-1H-pyrrolo[2,3-b]pyridin-6-yl)boronic acid (crude from the previous step, 1.02 mmol) and 4-bromo-3,5-dimethylisothiazole (274 mg, 1.43 mmol) were dissolved in degassed 2:1 mixture of dioxane and water (14/7 mL). Cesium carbonate (669 mg, 2.04 mmol) was added, and after degassing for 5 min, Pd(PPh$_3$)$_4$ (120 mg, 102 umol) was added. The reaction mixture was stirred at 100° C. for 1 h. Reaction mixture was cooled to RT and diluted with water, the product was extracted 2 times with EtOAc. Organics were combined, dried over anh. Na$_2$SO$_4$, filtered, and concentrated. Residue was purified by reverse phase chromatography (C18, ACN in aq. 10 mM ammonium formate, pH 3.8, 0 to 100% gradient) to provide the title compound (132 mg, 0.23 mmol, 22% yield over 2 steps) as a brown foam.

Example 59. Synthesis of (S)—N-(6,6-dimethylpiperidin-3-yl)-4-(6-(3-methylisoxazol-4-yl)-1H-pyrazolo[3,4-b]pyridin-3-yl)-5-(trifluoromethyl)pyrimidin-2-amine (Compound 160)

Step 1: 3-methyl-4-(1H-pyrazolo[3,4-b]pyridin-6-yl) isoxazole

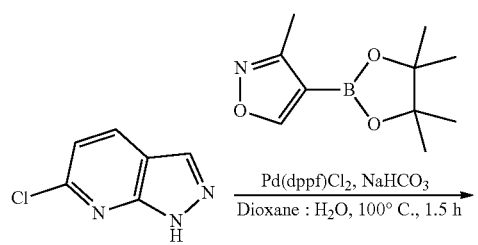

A mixture of 6-chloro-1H-pyrazolo[3,4-b]pyridine (565 mg, 3.68 mmol), 3-methyl-4-(4,4,5,5-tetramethyl-1,3,2-dioxaborolan-2-yl)isoxazole (1.10 g, 5.15 mmol), Pd(dppf)Cl$_2$ (150 mg, 184 umol), sodium bicarbonate (927 mg, 11.0 mmol) in dioxane (10 mL) and water (3 mL) was degassed with nitrogen (5 min), and then the reaction mixture was stirred at 100° C. for 1.5 h. The mixture was cooled down to RT, diluted with ethyl acetate (20 mL) and filtered through Celite pad. The organic phase was dried over anh. Na$_2$SO$_4$, filtered, concentrated, and the crude material was triturated in 20% DCM/Hexanes to afford the title compound (620 mg, 3.10 mmol, 84% yield) as a pale brown solid, which was used in the next step without further purification.

Step 2: 4-(3-iodo-1H-pyrazolo[3,4-b]pyridin-6-yl)-3-methylisoxazole

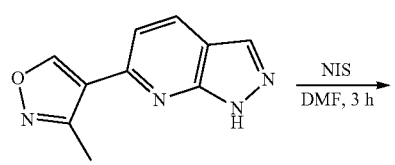

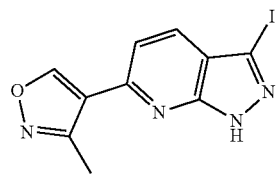

To a solution of 3-methyl-4-(1H-pyrazolo[3,4-b]pyridin-6-yl)isoxazole (500 mg, 2.50 mmol) in DMF (5 mL), was added N-iodosuccinimide (710 mg, 3.00 mmol), and the resulting mixture was stirred at RT for 3 h. The reaction mixture was then quenched with 10% aqueous sodium thiosulfate (25 mL), and the resulting suspension was stirred for 10 minutes. The suspension was then filtered to afford the title compound (757 mg, 2.32 mmol, 93% yield) as a brown solid, which was used in the next step without further purification.

Step 3: 4-(3-iodo-1-(tetrahydro-2H-pyran-2-yl)-1H-pyrazolo[3,4-b]pyridin-6-yl)-3-methylisoxazole

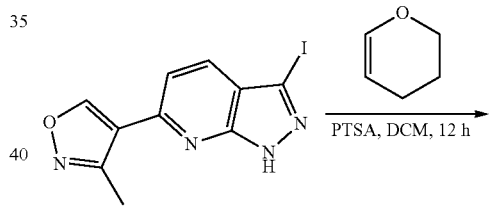

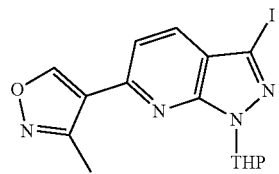

To a solution of 4-(3-iodo-1H-pyrazolo[3,4-b]pyridin-6-yl)-3-methylisoxazole (757 mg, 2.32 mmol) in DCM (10 mL), was added 3,4-dihydro-2H-pyran (240 uL, 2.55 mmol) followed by p-toluenesulfonic acid monohydrate (44.8 mg, 232 umol), and the solution was stirred at RT for 12 h. The reaction mixture was then diluted with ethyl acetate (20 mL), and the organic phase was washed with aq. sat. sodium bicarbonate (2×10 mL). The organic phase was dried over anh. Na$_2$SO$_4$, filtered, and concentrated under reduced pressure to afford the title compound (952 mg, 2.32 mmol, quant. yield), which was used in the next step without further purification.

Step 4: 3-methyl-4-(3-(2-(methylthio)-5-(trifluoromethyl)pyrimidin-4-yl)-1-(tetrahydro-2H-pyran-2-yl)-1H-pyrazolo[3,4-b]pyridin-6-yl)isoxazole

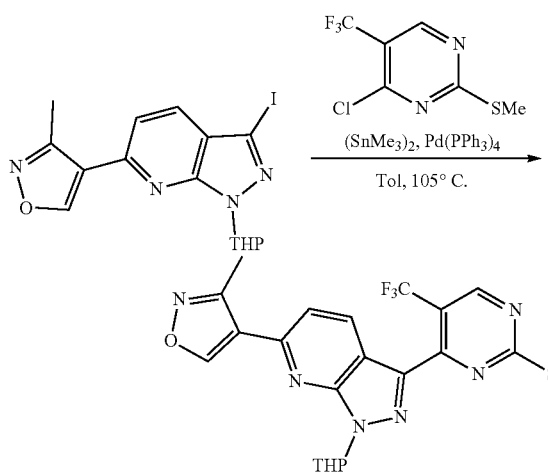

To a mixture of 4-(3-iodo-1-(tetrahydro-2H-pyran-2-yl)-1H-pyrazolo[3,4-b]pyridin-6-yl)-3-methylisoxazole (952 mg, 2.32 mmol), 4-chloro-2-(methylthio)-5-(trifluoromethyl)pyrimidine (637 mg, 2.78 mmol), and hexamethylditin (486 uL, 2.32 mmol) in toluene (13 mL), purged with nitrogen (5 min), was added Pd(PPh₃)₄ (268 mg, 232 umol), and the reaction mixture was stirred at 105° C. until full conversion (24 h). The reaction mixture was poured into a freshly prepared solution of aqueous potassium fluoride (1.0 g in 50 mL), and stirred for 30 min. The resulting mixture was filtered on Celite pad, and the filtrate was extracted with ethyl acetate (3×30 mL). The organic layers were combined, washed with brine (30 mL), dried over anh. Na₂SO₄, filtered, and concentrated under reduced pressure. The residue was purified by silica gel column chromatography (EtOAc in hexanes, 10 to 70% gradient) to afford the title compound (529 mg, 1.11 mmol, 48% yield).

Step 5: 3-methyl-4-(3-(2-(methylsulfonyl)-5-(trifluoromethyl)pyrimidin-4-yl)-1-(tetrahydro-2H-pyran-2-yl)-1H-pyrazolo[3,4-b]pyridin-6-yl)isoxazole

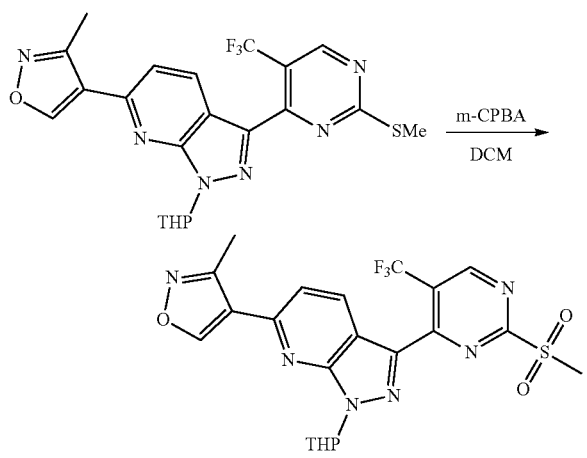

To a solution of 3-methyl-4-(3-(2-(methylthio)-5-(trifluoromethyl)pyrimidin-4-yl)-1-(tetrahydro-2H-pyran-2-yl)-1H-pyrazolo[3,4-b]pyridin-6-yl)isoxazole (500 mg, 1.05 mmol) in DCM (19 mL), was added m-CPBA (495 mg, 2.15 mmol), and the reaction mixture was stirred at RT, monitoring the conversion by LCMS. After 2.5 h with the conversion of 47%, another 0.7 eq of m-CPBA were added, and the reaction mixture was stirred at RT for 1 h. The reaction was then quenched with 10% aq. sodium thiosulfate (10 mL) and sat. aq. NaHCO₃ (10 mL). The resulting mixture was stirred for 15 minutes, then diluted with EtOAc (100 mL). The biphasic mixture was separated, and the organic phase was washed with sat. aq. NaHCO₃ (2×10 mL). The organic phase was dried over anh. Na₂SO₄, filtered, and concentrated under reduced pressure to afford the title compound (534 mg, quant. yield), which was used in the next step without further purification.

Step 6: N—((S)-6,6-dimethylpiperidin-3-yl)-4-(6-(3-methylisoxazol-4-yl)-1-(tetrahydro-2H-pyran-2-yl)-1H-pyrazolo[3,4-b]pyridin-3-yl)-5-(trifluoromethyl)pyrimidin-2-amine

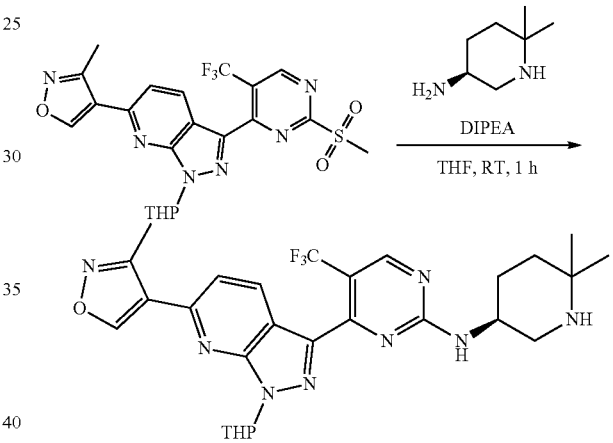

To a solution of 3-methyl-4-(3-(2-(methylsulfonyl)-5-(trifluoromethyl)pyrimidin-4-yl)-1-(tetrahydro-2H-pyran-2-yl)-1H-pyrazolo[3,4-b]pyridin-6-yl)isoxazole (534 mg, 1.05 mmol) in THF (6.4 mL), was added (S)-6,6-dimethylpiperidin-3-amine (202 mg, 1.58 mmol) followed by DIPEA (554 uL, 3.15 mmol), and the reaction mixture was stirred at RT for 1 h. The mixture was concentrated under reduced pressure, and the residue was purified by reverse phase chromatography (C18, ACN in aq. 10 mM ammonium bicarbonate buffer, pH 10, 0 to 100% gradient) to afford the title compound (143 mg, 0.26 mmol, 24% yield over two steps).

Step 7: (S)—N-(6,6-dimethylpiperidin-3-yl)-4-(6-(3-methylisoxazol-4-yl)-1H-pyrazolo[3,4-b]pyridin-3-yl)-5-(trifluoromethyl)pyrimidin-2-amine

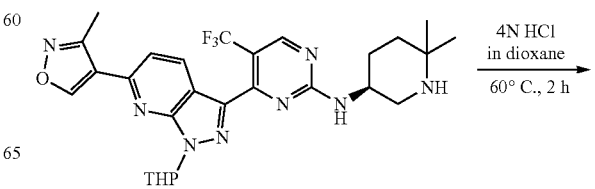

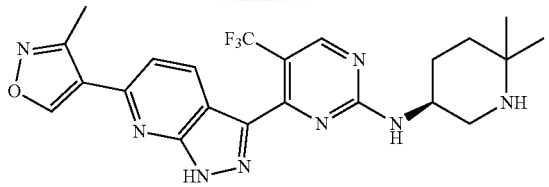

N—((S)-6,6-dimethylpiperidin-3-yl)-4-(6-(3-methyl-isoxazol-4-yl)-1-(tetrahydro-2H-pyran-2-yl)-1H-pyrazolo[3,4-b]pyridin-3-yl)-5-(trifluoromethyl)pyrimidin-2-amine (111 mg, 0.20 mmol) was dissolved in 4 N HCl in dioxane (2 mL), and the mixture was stirred at 60° C. for 2 h. The solution was then concentrated under reduced pressure, and the residue was purified by reverse phase chromatography (C18, ACN in aq. 0.1% formic acid buffer, 10 to 50% gradient) to afford the title compound (47 mg, 0.10 mmol, 50% yield) as a white HCl salt after lyophilization.

Example 60. 3-methyl-4-(3-(2-(methylthio)-5-(trifluoromethyl)pyrimidin-4-yl)-1-(phenylsulfonyl)-1H-pyrrolo[2,3-b]pyridin-6-yl)isoxazole (Compound 147)

Step 1: 4-(3-iodo-1H-pyrrolo[2,3-b]pyridin-6-yl)-3-methylisoxazole

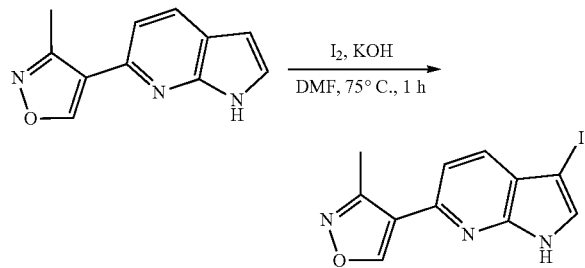

To a solution of 3-methyl-4-(1H-pyrrolo[2,3-b]pyridin-6-yl)isoxazole [prepared from 3-methyl-4-(4,4,5,5-tetramethyl-1,3,2-dioxaborolan-2-yl)isoxazole and 6-bromo-1H-pyrrolo[2,3-b]pyridine as in Example 59] (550 mg, 2.76 mmol) in DMF (2 mL), iodine (702 mg, 2.76 mmol) and KOH (94 mg, 5.52 mmol) were added in one portion. The reaction mixture was stirred at 75° C. for 1 h. The mixture was then cooled down to RT and quenched by addition of 10% HCl until pH was neutral, followed by the addition of aq. sat. sodium sulfite (3 mL) at 15° C. The resulting mixture was poured into water (20 mL), and the obtained solid was filtered to afford the title compound (847 mg, 2.60 mmol, 94% yield) as a pale orange solid, which was used in the next step without further purification.

Step 2: 4-(3-iodo-1-(phenylsulfonyl)-1H-pyrrolo[2,3-b]pyridin-6-yl)-3-methylisoxazole

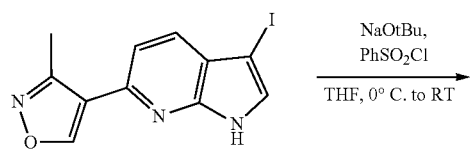

4-(3-Iodo-1H-pyrrolo[2,3-b]pyridin-6-yl)-3-methylisoxazole (847 mg, 2.60 mmol) was dissolved in THF (10 mL), and the resulting solution was cooled to 0° C. To the mixture, was added sodium tert-butoxide (325 mg, 3.38 mmol) portion wise, and the mixture was stirred for 10 min. Benzenesulfonyl chloride (332 uL, 2.60 mmol) was then added dropwise, and the reaction mixture was allowed to reach RT and stirred for 1 h. The reaction was diluted with water (60 mL), and the resulting suspension was filtered and washed with water (15 mL) to afford the title compound (1.12 g, 2.42 mmol, 93% yield) as a pale orange solid, which was used in the next step without further purification.

Step 3: 3-methyl-4-(3-(2-(methylthio)-5-(trifluoromethyl)pyrimidin-4-yl)-1-(phenylsulfonyl)-1H-pyrrolo[2,3-b]pyridin-6-yl)isoxazole

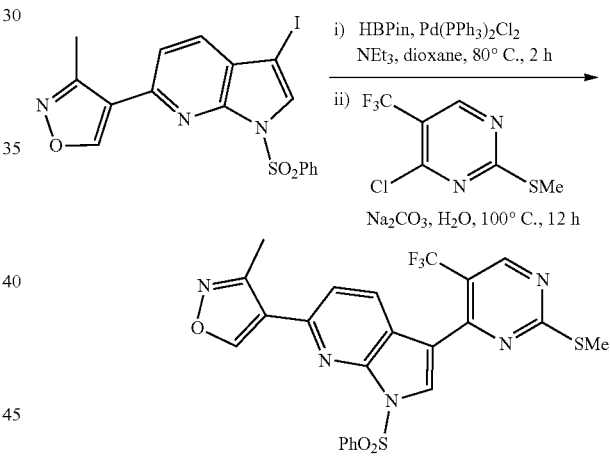

To a degassed mixture of 4-(3-iodo-1-(phenylsulfonyl)-1H-pyrrolo[2,3-b]pyridin-6-yl)-3-methylisoxazole (1.28 g, 2.75 mmol) and dichlorobis(triphenylphosphine)palladium (II) (96.5 mg, 138 umol) in dioxane (25.6 mL), was added triethylamine (2.30 mL, 16.5 mmol) followed by HBPin (4,4,5,5-Tetramethyl-1,3,2-dioxaborolane; 599 uL, 4.13 mmol). The resulting yellow suspension was stirred at 80° C. in a sealed vessel for 2 h. The reaction mixture was then cooled down to RT, and 4-chloro-2-(methylthio)-5-(trifluoromethyl)pyrimidine (629 uL, 2.75 mmol) and degassed water (600 uL) were added followed by the sodium carbonate (874 mg, 8.25 mmol). The resulting mixture was stirred at 100° C. for 12 h. The mixture was then cooled down to RT, diluted with EtOAc (25 mL), filtered on Celite pad, and concentrated under reduced pressure. The crude solid was triturated with 50% MTBE in hexanes, and the suspension was filtered to afford the title compound (510 mg, 0.96 mmol, 35% yield) as a pale beige solid, which was used in the next step without further purification.

221

Example 61. (3S,4S)-tert-butyl 3-((4-(6-(3,5-dimethylisoxazol-4-yl)-1-(phenylsulfonyl)-1H-pyrrolo[2,3-b]pyridin-3-yl)-5-(trifluoromethyl)pyrimidin-2-yl)amino)-4-methylpiperidine-1-carboxylate (Compound 143)

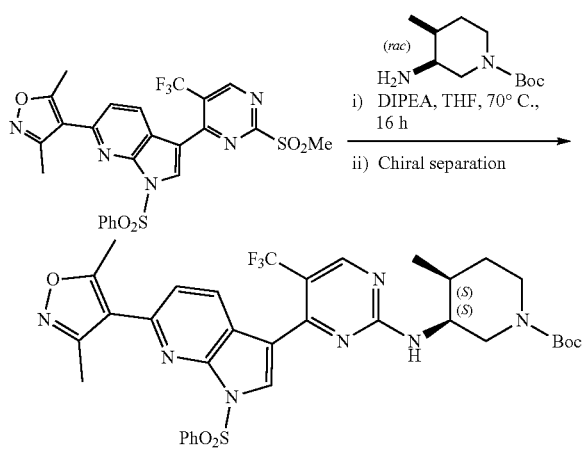

To a solution of 3,5-dimethyl-4-(3-(2-(methylsulfonyl)-5-(trifluoromethyl)pyrimidin-4-yl)-1-(phenylsulfonyl)-1H-pyrrolo[2,3-b]pyridin-6-yl)isoxazole [prepared from (3,5-dimethylisoxazol-4-yl)boronic acid and 6-bromo-1H-pyrrolo[2,3-b]pyridine, following Examples 59 and 60] (220 mg, 0.38 mmol) and racemic cis tert-butyl 3-amino-4-methylpiperidine-1-carboxylate (122 mg, 0.57 mmol) in anh. THF (3.8 mL), was added anh. DIPEA (200 uL, 1.14 mmol) at RT. The reaction mixture was stirred at 70° C. for 16 h. The mixture was diluted with EtOAc, washed with brine, dried over anh. Na₂SO₄, filtered, and concentrated under reduced pressure. The residue was purified by column silica gel chromatography (EtOAc in hexanes, 0 to 100% gradient) to provide the racemic product (137 mg, 0.19 mmol, 51% yield) as a pale yellow solid. The racemic compound was then separated by chiral HPLC using a ChiralPak IA column and 6:6:88 mixture of MeOH/DCM/Hexanes for elution. Two enantiomers were obtained: Peak 1 (tentatively assigned as (3R,4R), 36 mg) and Peak 2 (tentatively assigned as (3S,4S), 31 mg).

Example 62. (3S,4S)-tert-butyl 3-((4-(6-(3,5-dimethylisoxazol-4-yl)-1H-indol-3-yl)-5-(trifluoromethyl)pyrimidin-2-yl)amino)-4-methylpiperidine-1-carboxylate (Compound 135)

Step 1: racemic cis tert-butyl 3-((4-(6-bromo-1-(phenylsulfonyl)-1H-indol-3-yl)-5-(trifluoromethyl)pyrimidin-2-yl)amino)-4-methylpiperidine-1-carboxylate

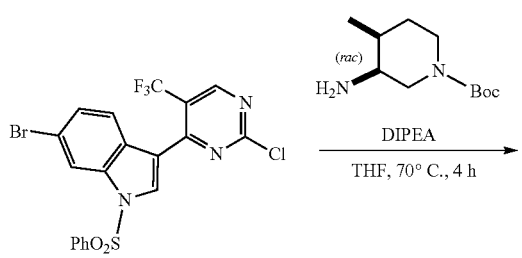

222

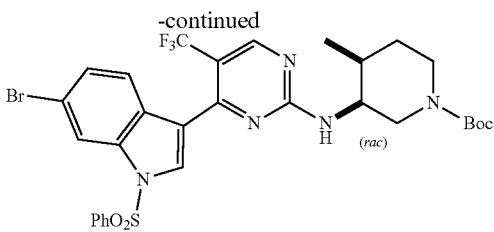

6-Bromo-3-(2-chloro-5-(trifluoromethyl)pyrimidin-4-yl)-1-(phenylsulfonyl)-1H-indole [prepared from 6-bromo-1H-indole and 2,4-dichloro-5-(trifluoromethyl)pyrimidine as in Example 56 and then protected as in Example 57] (360 mg, 0.70 mmol), racemic cis tert-butyl 3-amino-4-methylpiperidine-1-carboxylate (180 mg, 0.84 mmol) and DIPEA (183 uL, 1.05 mmol) were dissolved in anh. THF (7 mL). The reaction mixture was stirred at 70° C. until full conversion (4 h). The mixture was then diluted with EtOAc, washed with sat. aq. NaHCO₃, water, and brine. Organic phase was dried over anh. Na₂SO₄, filtered, and concentrated in vacuo. The residue was purified by normal phase silica gel chromatography (EtOAc in DCM, 0 to 100% gradient) to afford the title compound (473 mg, 0.68 mmol, 97% yield) as an off-white solid.

Step 2: (3S,4S)-tert-butyl 3-((4-(6-(3,5-dimethylisoxazol-4-yl)-1H-indol-3-yl)-5-(trifluoromethyl)pyrimidin-2-yl)amino)-4-methylpiperidine-1-carboxylate

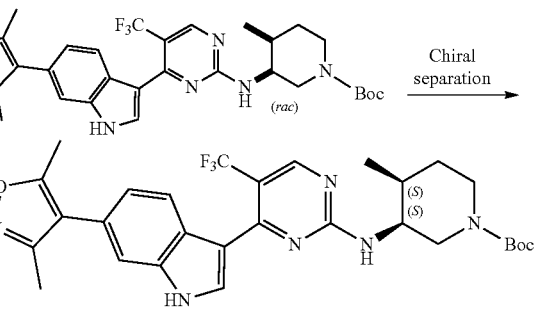

Racemic cis tert-butyl 3-((4-(6-(3,5-dimethylisoxazol-4-yl)-1H-indol-3-yl)-5-(trifluoromethyl)pyrimidin-2-yl)amino)-4-methylpiperidine-1-carboxylate (292 mg, yellow solid) was separated by Chiral SFC using ChiralPak IC column, 10×250 mm 5 um, 10% MeOH, 10 mL/min, 150 bar, column T: 40° C., run time (min): 27. Two enantiomers were obtained: Peak 1 (tentatively assigned as (3S,4S), 43 mg, white solid, ee=99.7%) and Peak 2 (tentatively assigned as (3R,4R), 38 mg, white solid, ee=99.15%).

The table of FIG. 3 provides additional details of the synthesis of certain compounds of the invention, as well as their NMR (nuclear magnetic resonance) and MS (mass spectroscopy) values.

Example 63. Inhibition of CDK Kinase Activity

Compounds described herein were assayed for inhibition of CDK7, CDK9, CDK12, and CDK2 activity at Biortus Biosciences (Jiangyin, Jiangsu Province, P.R. of China) using kinase assays for each CDK developed with a Caliper/LabChip EZ Reader (Perkin Elmer, Waltham, Mass.). These assays measure the amount of phosphorylated peptide substrate produced as a fraction of the total peptide following an incubation period at 27° C. with the following components: test compounds (variable concentrations from 10 μM down to 0.508 nM in a series of 3-fold serial dilutions), active CDK kinase protein (with the indicated cyclin, listed below for each CDK), ATP (2 mM), and substrate peptide (listed below) in the buffer 2-(N-morpholino)ethanesulfonate (MES buffer, 20 mM), pH 6.75, 0.01% (v/v) Tween 20 detergent, 0.05 mg/mL bovine serum albumin (BSA).

Specifically, the CDK7 inhibition assay used CDK7/Cyclin H/MAT1 complex (6 nM) and "5-FAM-CDK7tide" peptide substrate (2 μM, synthesized fluorophore-labeled peptide with the following sequence: 5-FAM-YSPTSPSYS-PTSPSYSPTSPSKKKK (SEQ ID NO:1), where "5-FAM" means 5-carboxyfluorescein) with 6 mM $MgCl_2$ in the buffer composition listed above. Furthermore, the CDK9 inhibition assay used CDK9/Cyclin T1 complex (8 nM) and "5-FAM-CDK9tide" peptide substrate (2 μM, synthesized fluorophore-labeled peptide with the following sequence: 5-FAM-GSRTPMY-$NH_2$ (SEQ ID NO:2) where 5-FAM is defined above and $NH_2$ signifies a C-terminal amide) with 10 mM $MgCl_2$ in the buffer composition listed above. The CDK12 inhibition assay used CDK12 (aa686-1082)/Cyclin K complex (50 nM) and "5-FAM-CDK9tide" (2 μM) as defined above, with 2 mM $MgCl_2$ in the buffer composition above. Additionally, the CDK2 inhibition assay used CDK2/Cyclin E1 complex (0.5 nM) and "5-FAM-CDK7tide" (2 μM; defined above) with 2 mM $MgCl_2$ in the buffer composition above.

The incubation period at 27° C. for each CDK inhibition assay was chosen such that the fraction of phosphorylated peptide product produced in each assay, relative to the total peptide concentration, was approximately 20% (±5%) for the uninhibited kinase (35 min. for CDK7, 35 min. for CDK2, 3 hr. for CDK12, 15 min. for CDK9). In cases where the compound titrations were tested and resulted in inhibition of peptide product formation, these data were fit to produce best-fit $IC_{50}$ values. The results of these assays are shown below in Table 1 where "A" represents a calculated $IC_{50}$ of less than 30 nM; "B" represents a calculated $IC_{50}$ of between 30 nM and less than 100 nM; "C" represents a calculated $IC_{50}$ of between 100 nM and less than 500 nM; "D" represents a calculated $IC_{50}$ of greater than or equal to 500 nM, and "NT" represents that the specified compound was not tested in the specified assay.

The inhibitory activity of selected compounds against CDK2, CDK7, CDK9, and CDK12 was found to be as follows:

| Compound | CDK12 | CDK2 | CDK7 | CDK9 |
|---|---|---|---|---|
| 100 | D | D | A | D |
| 101 | C | D | A | D |
| 102 | D | D | A | D |
| 103 | C | D | A | D |
| 104 | D | D | A | D |
| 105 | D | D | A | D |
| 106 | D | D | A | D |
| 107 | D | D | A | D |
| 108 | D | D | A | D |
| 109 | D | D | A | D |
| 110 | D | D | A | D |
| 111 | D | D | A | D |
| 112 | D | D | A | D |
| 113 | D | D | A | D |
| 114 | D | D | A | D |
| 115 | C | C | A | D |
| 116 | D | D | A | D |
| 117 | D | D | A | D |
| 118 | D | D | A | D |
| 119 | D | D | A | D |
| 120 | D | D | A | D |
| 121 | D | D | A | D |
| 122 | D | D | A | D |
| 123 | D | D | A | D |
| 124 | D | D | A | D |
| 125 | D | D | A | D |
| 126 | D | D | A | D |
| 127 | D | D | A | D |
| 128 | D | D | A | D |
| 129 | D | D | A | D |
| 130 | D | D | A | D |
| 131 | D | D | A | D |
| 132 | D | D | A | D |
| 133 | D | D | A | D |
| 134 | D | D | A | D |
| 135 | D | D | B | D |
| 136 | D | D | A | D |
| 137 | D | D | A | D |
| 138 | D | D | A | D |
| 139 | D | D | A | D |
| 140 | D | D | A | D |
| 141 | D | D | A | D |
| 142 | D | D | A | D |
| 143 | D | D | A | D |
| 144 | D | D | A | D |
| 145 | D | D | A | D |
| 146 | D | D | A | D |
| 147 | D | D | A | D |
| 148 | D | D | A | D |
| 149 | D | D | A | D |
| 150 | D | D | A | D |
| 151 | D | D | A | D |
| 152 | D | D | A | D |
| 153 | D | D | A | D |
| 154 | D | D | A | D |
| 155 | D | D | A | D |
| 156 | D | D | A | D |
| 157 | D | D | A | D |
| 158 | D | D | A | D |
| 159 | D | D | A | D |
| 160 | D | D | A | D |
| 161 | D | D | A | D |
| 162 | D | D | A | D |
| 163 | D | D | A | D |
| 164 | D | D | A | D |
| 165 | D | D | B | D |
| 166 | D | D | A | D |
| 167 | D | D | A | D |
| 168 | D | D | A | D |

Example 64. Inhibition of Cell Proliferation

HCC70 and MB453 cells are cell lines derived from human triple negative breast cancer COV318 and COV504 cells are cell lines derived from human ovarian cancer. Representative compounds of the invention were tested at different concentrations (from 4 μM to 126.4 pM; 0.5 log serial dilutions) for their ability to inhibit the proliferation of each of these cell lines. Known CDK inhibitors dinaciclib or N-((1S,3R)-3-((5-chloro-4-(1H-indol-3-yl) pyrimidin-2-yl) amino)cyclohexyl)-5-((E)-4-(dimethylamino)but-2-enamido)picolinamide and triptolide were used as positive controls. Cells were seeded at approximately 2,000 cells/well and grown in ATCC-formulated RPMI-1640 Medium (ATCC 30-2001)+10% FBS. The cells were cultured at 37° C. in a humidified chamber in the presence of 5% $CO_2$. Proliferation assays were conducted over a 72-hour time period. CyQUANT® Direct Cell Proliferation Assay (Life Technologies, Chicago, Ill. USA) was used to assess the anti-proliferative effects of the compounds following manufacturer's directions and utilizing the reagents supplied with the CyQUANT® Direct Cell kit. The results of the assay are shown below in Table 2 where "A" represents a calculated $IC_{50}$ of less than 100 nM; "B" represents a calculated $IC_{50}$ of between 100 nM and less than 500 nM; "C" represents a calculated $IC_{50}$ of between 500 nM and less than 1 µM; "D" represents a calculated $IC_{50}$ of greater than 1 µM. Cell proliferation inhibition activity of selected compounds against HCC70, MB453, COV318 and COV504 cells was found to be as follows:

| Compound | HCC70 | COV318 | COV504 | MB453 |
|---|---|---|---|---|
| 100 | A | B | A | A |
| 101 | A | A | A | A |
| 102 | A | B | A | A |
| 103 | B | B | A | A |
| 104 | A | B | A | A |
| 105 | A | C | B | B |
| 106 | A | B | A | A |
| 107 | B | B | B | B |
| 108 | A | A | A | A |
| 109 | B | A | A | B |
| 110 | A | B | A | A |
| 111 | B | B | A | B |
| 112 | B | D | B | B |
| 113 | C | D | C | B |
| 114 | A | A | A | A |
| 115 | A | A | A | A |
| 116 | A | A | A | A |
| 117 | B | C | A | A |
| 118 | A | B | A | A |
| 119 | A | D | A | A |
| 120 | B | C | B | A |
| 121 | B | B | A | A |
| 122 | B | D | A | A |
| 123 | B | B | A | A |
| 124 | A | A | A | A |
| 125 | B | B | A | A |
| 126 | A | B | A | A |
| 127 | D | B | A | A |
| 128 | A | B | A | A |
| 129 | A | A | A | A |
| 130 | B | B | B | B |
| 131 | B | B | A | A |
| 132 | A | A | A | A |
| 133 | A | B | A | A |
| 134 | A | A | A | A |
| 135 | B | D | A | A |
| 136 | A | D | A | A |
| 137 | A | A | A | A |
| 138 | A | A | A | A |
| 139 | A | D | A | A |
| 140 | D | D | B | C |
| 141 | B | B | A | B |
| 142 | A | C | A | A |
| 143 | A | D | A | A |
| 144 | A | D | A | A |
| 145 | B | D | B | B |
| 146 | C | D | B | B |
| 147 | A | D | A | A |
| 148 | D | D | C | B |
| 149 | A | A | A | A |
| 150 | B | B | A | A |
| 151 | D | D | D | C |
| 152 | D | D | C | B |
| 153 | A | A | A | A |
| 154 | B | D | B | D |
| 155 | A | A | A | A |
| 156 | C | D | B | B |
| 157 | A | A | A | A |
| 158 | A | B | A | A |
| 159 | A | D | A | A |
| 160 | D | D | B | B |
| 161 | A | B | A | A |
| 162 | B | D | A | C |
| 163 | A | D | A | A |
| 164 | B | C | A | A |
| 165 | D | D | C | C |
| 166 | A | A | A | A |
| 167 | A | B | A | B |
| 168 | A | A | A | A |

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context (for example, where it is evident from the context that "A or B" can mean only "A" or, alternatively, only "B"). The invention includes embodiments in which exactly one member of the group is present in, employed in, or otherwise relevant to a given product or process as well as embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists every possible subgroup of the elements is also disclosed, and any element(s) can be removed from the group. In general, where the invention, or aspects or embodiments of the invention, is/are referred to as comprising or including particular elements and/or features, other aspects or embodiments of the invention consist of, or consist essentially of, such elements and/or features. For practicality and simplicity, not all of those aspects or embodiments have been specifically set forth in haec verba herein but are nevertheless within the scope of the present invention. Where ranges are given, endpoints are included. Furthermore, unless otherwise indicated or otherwise evident from the context, values that are expressed as ranges can assume any specific value or sub-range within the stated ranges in different embodiments of the invention, to the tenth of the unit of the lower limit of the range, and any value may be as stated or "about" the stated value.

One of ordinary skill in the art will recognize or be able to ascertain using no more than routine experimentation, many equivalents to the specific embodiments of the compositions and methods described and claimed herein. Such equivalents are intended to be encompassed by the following claims.

What is claimed is:
1. A compound of Formula (I):
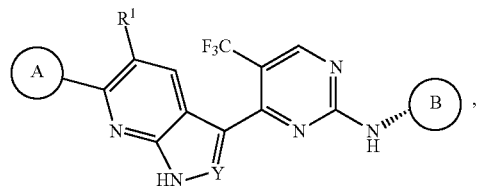
or a pharmaceutically acceptable salt, stereoisomer, or isotopic form thereof, wherein:
ring A is
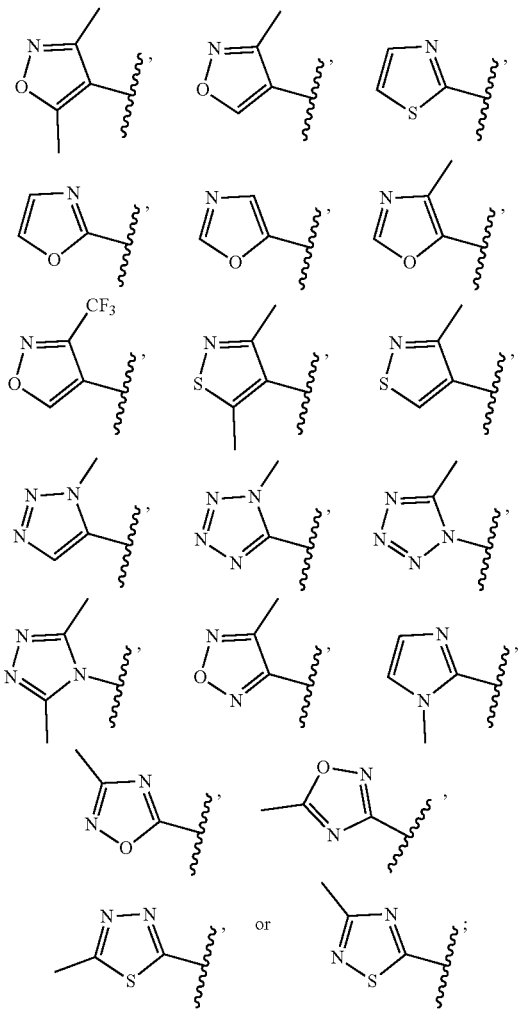
ring B is
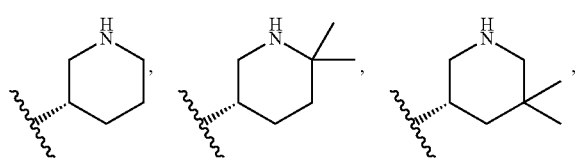
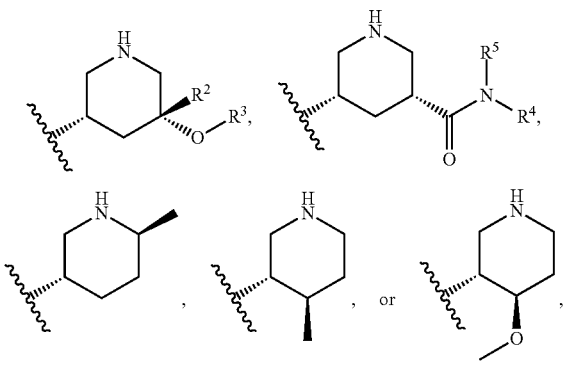
wherein each of $R^2$, $R^3$, $R^4$ and $R^5$ are, independently, hydrogen or —$CH_3$;
X and Y are, independently, N or CH;
$R^1$ is hydrogen or fluoro; and
the compound is other than:
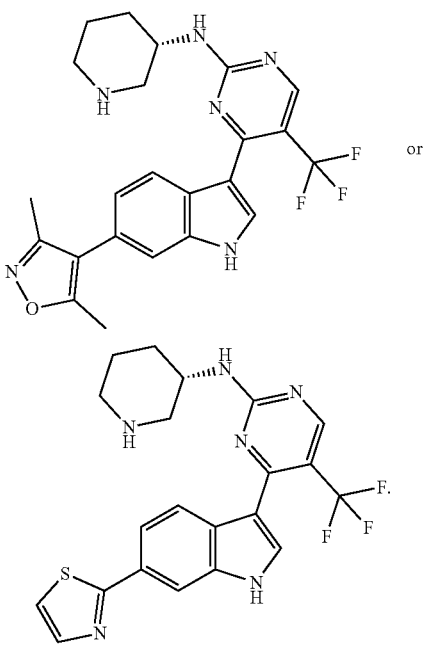
2. The compound of claim 1, wherein ring A is
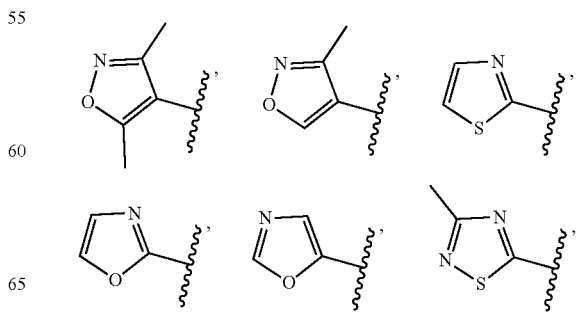

-continued

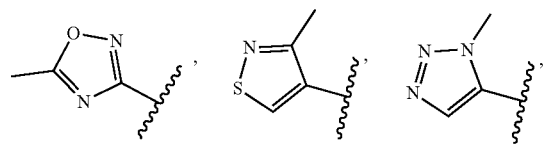

3. The compound of claim 1, wherein ring B is

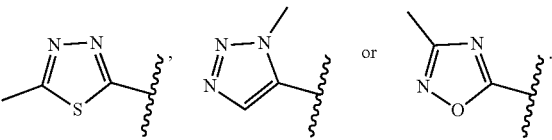

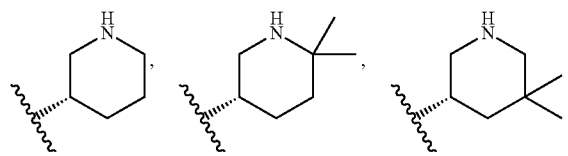

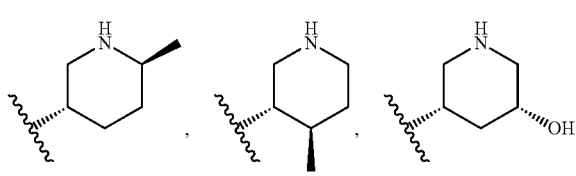

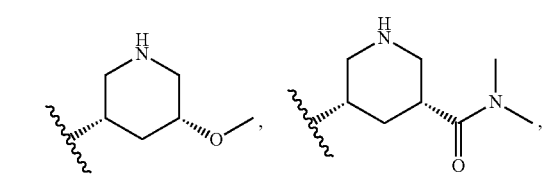

4. The compound of claim 3, wherein ring B is

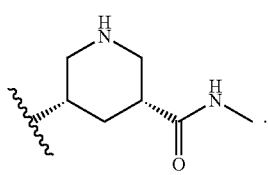 [SMILES: *[C@@H]1CNC[C@H](C(=O)NC)C1]

5. The compound of claim 1, wherein X is CH and Y is CH.

6. The compound of claim 1, wherein X is N.

7. A compound of Formula II:

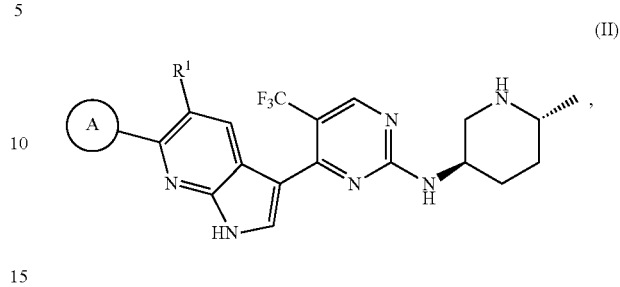

(II)

or a pharmaceutically acceptable salt, stereoisomer, or isotopic form thereof, wherein:

ring A is

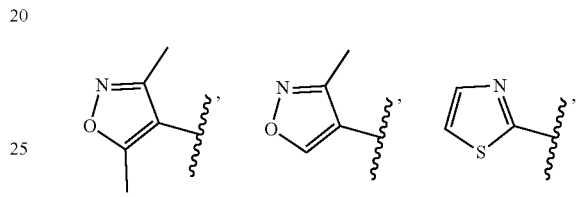

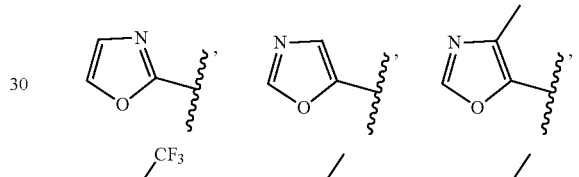

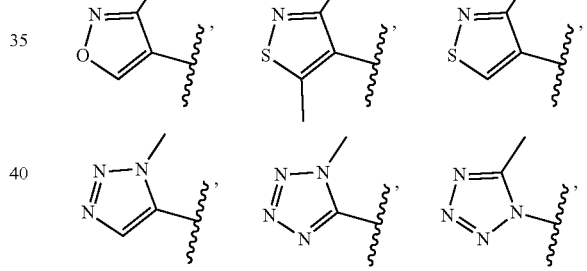

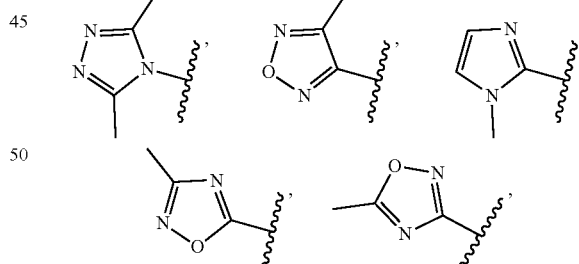

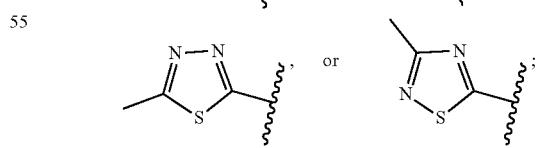

and $R^1$ is hydrogen or fluoro.

8. A compound selected from any one of the compounds set forth below or a pharmaceutically acceptable salt, stereoisomer, or isotopic form thereof:

Compound 100
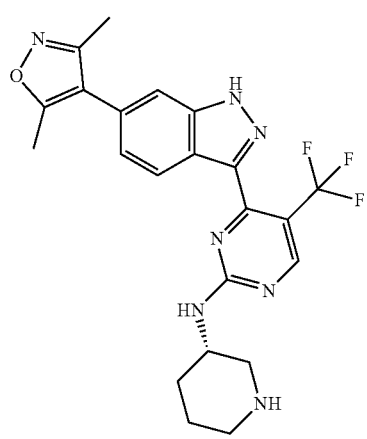
Compound 103
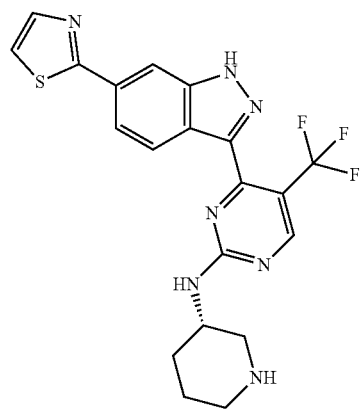
Compound 101
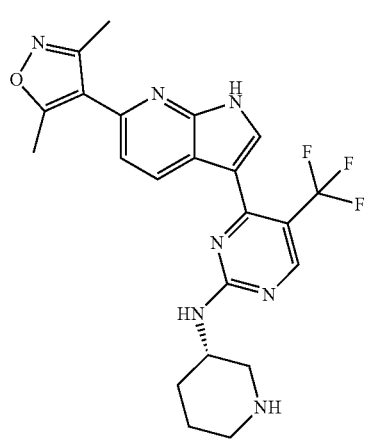
Compound 104
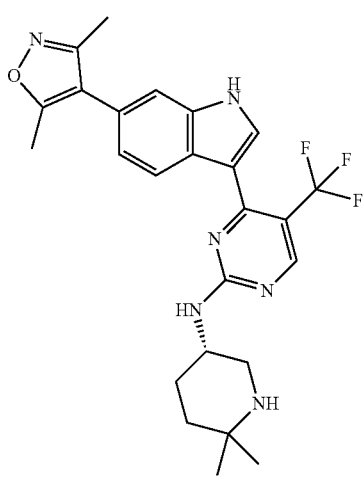
Compound 102
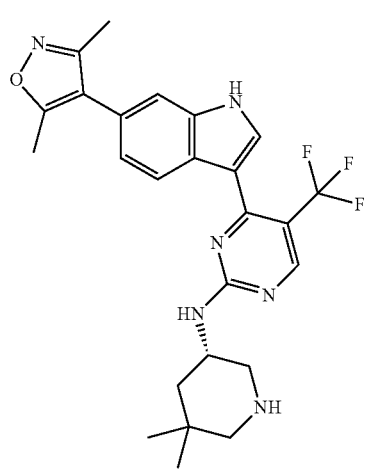
Compound 105
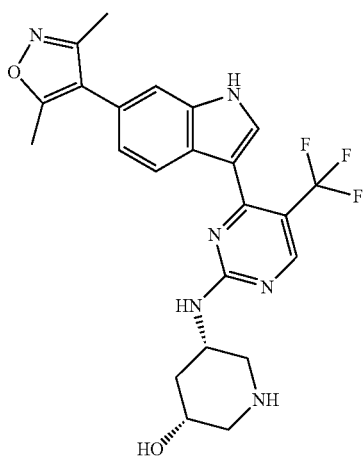

Compound 106
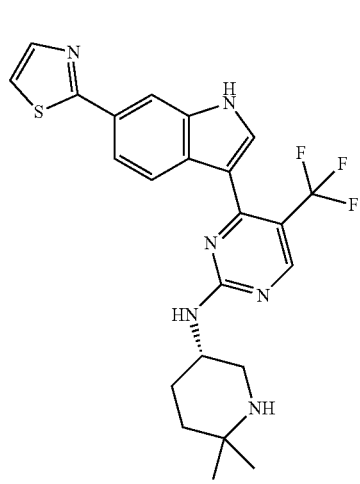
Compound 107
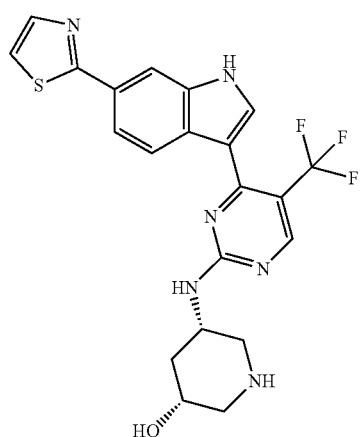
Compound 108
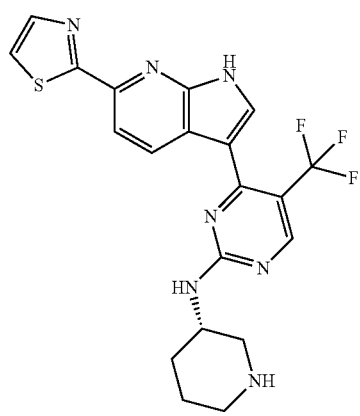
Compound 109
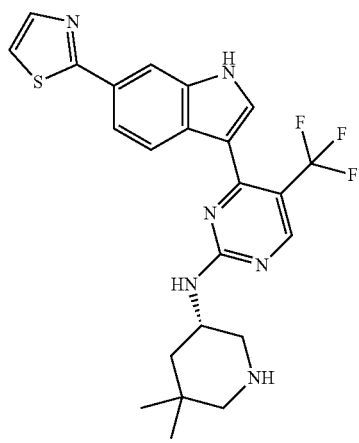
Compound 110
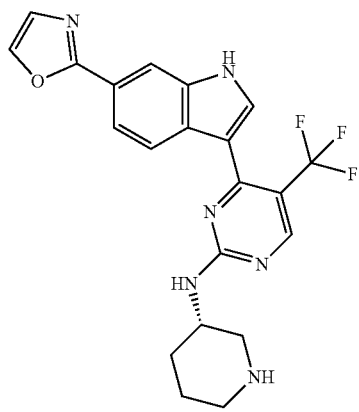
Compound 111
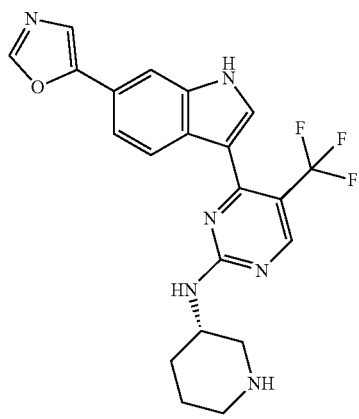

Compound 112
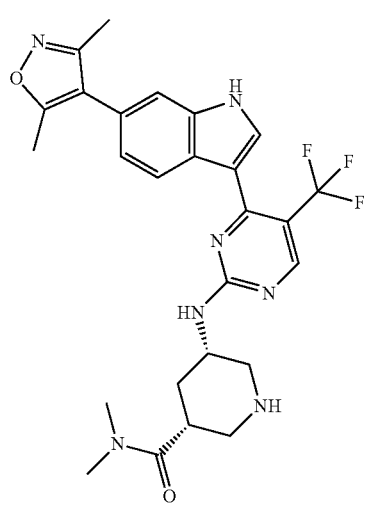
Compound 115
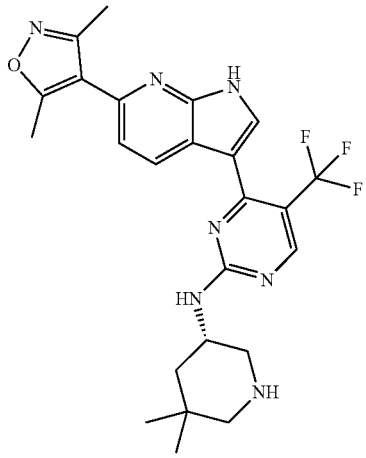
Compound 113
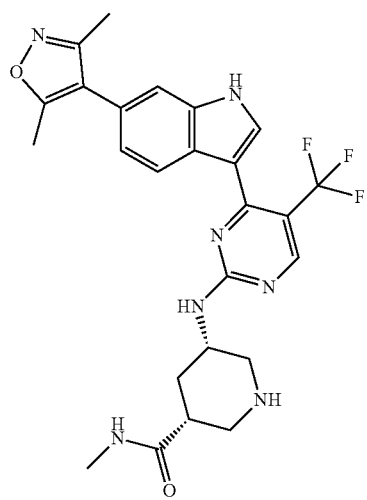
Compound 116
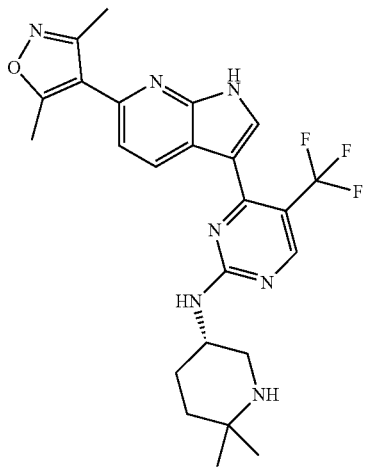
Compound 114
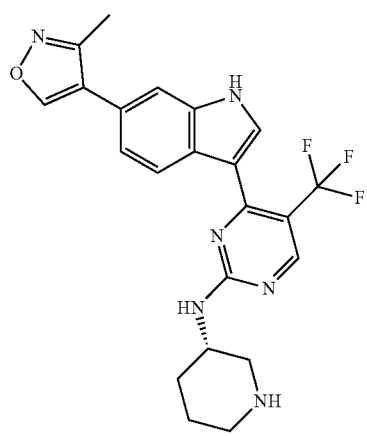
Compound 117
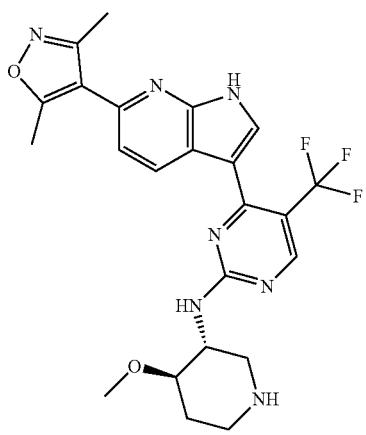

Compound 118
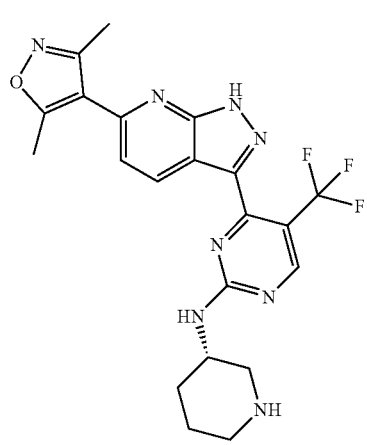
Compound 119
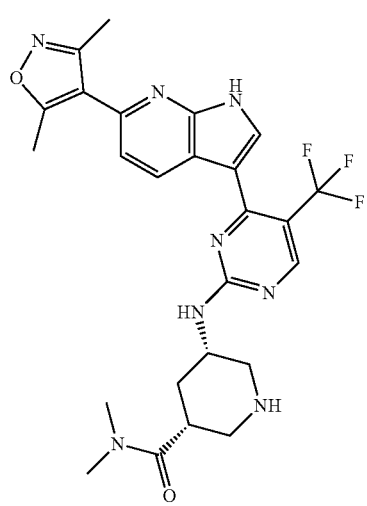
Compound 120
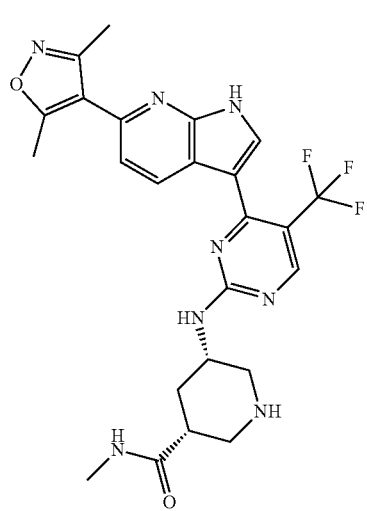
Compound 121
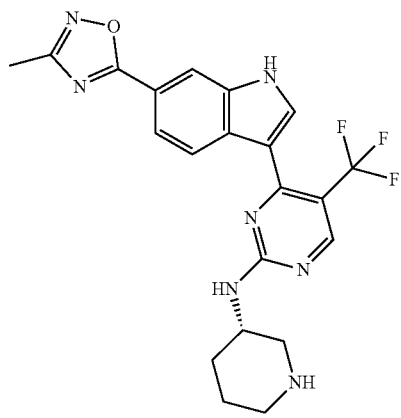
Compound 122
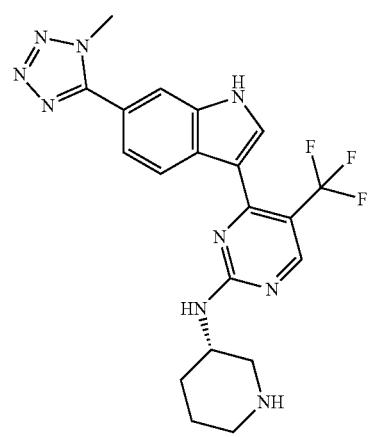
Compound 123
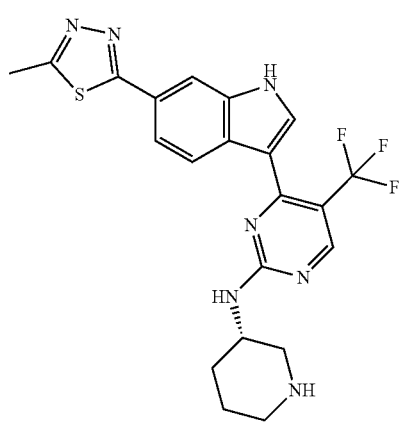

Compound 124
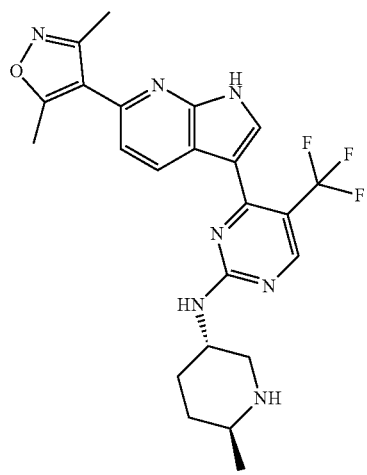
Compound 127
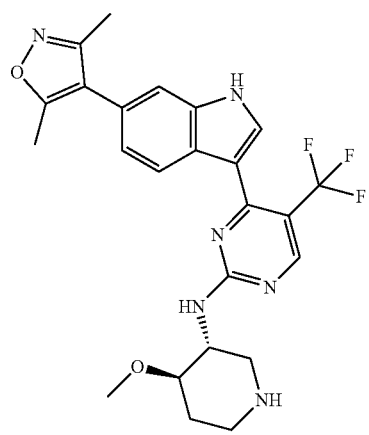
Compound 125
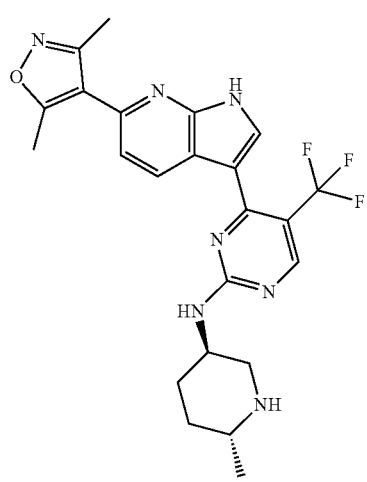
Compound 128
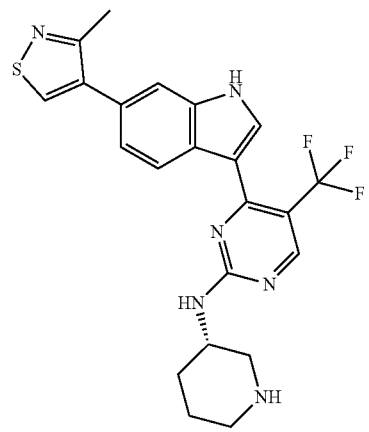
Compound 126
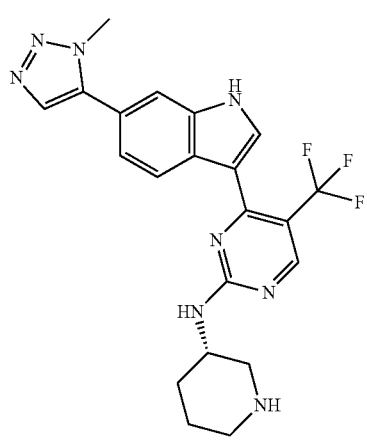
Compound 129
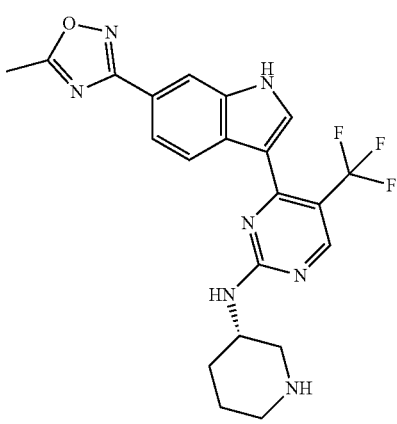

Compound 130
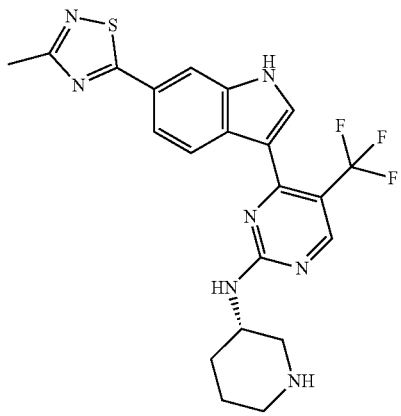
Compound 131
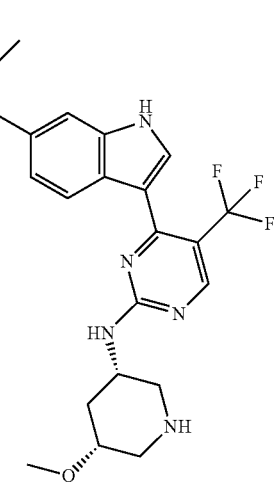
Compound 132
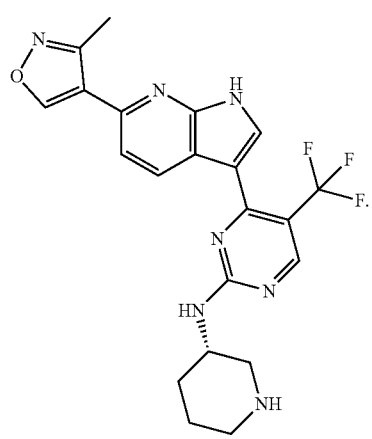
Compound 133
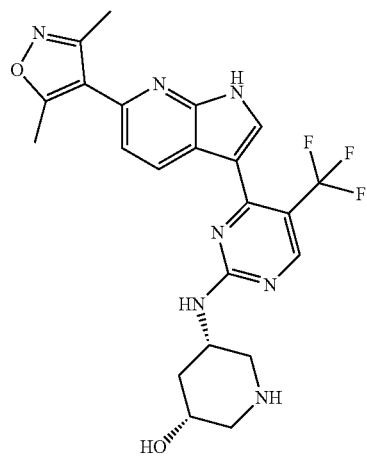
Compound 134
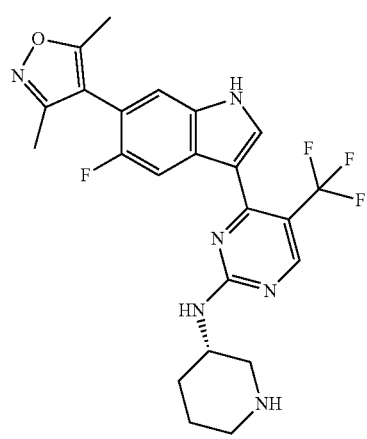
Compound 135
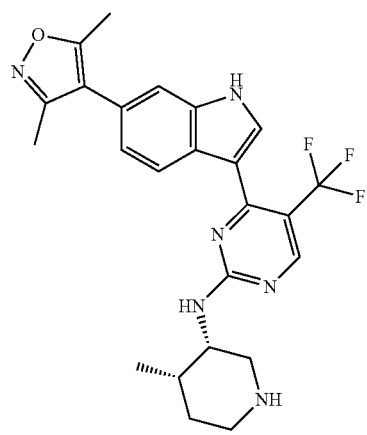
9. A compound selected from any one of the compounds set forth below or a pharmaceutically acceptable salt, stereoisomer, or isotopic form thereof:

Compound 136
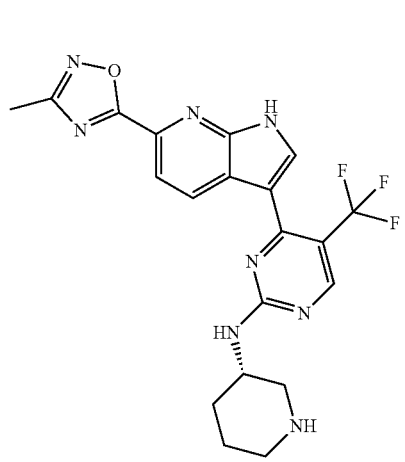
Compound 139
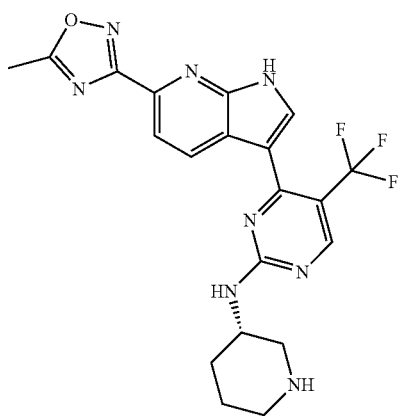
Compound 137
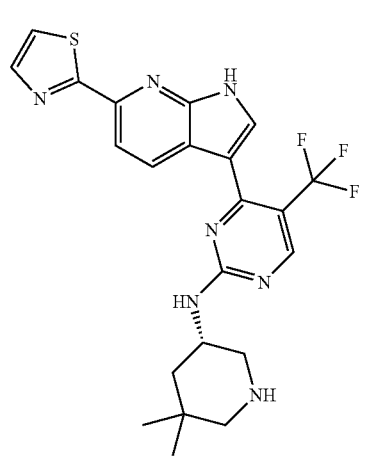
Compound 140
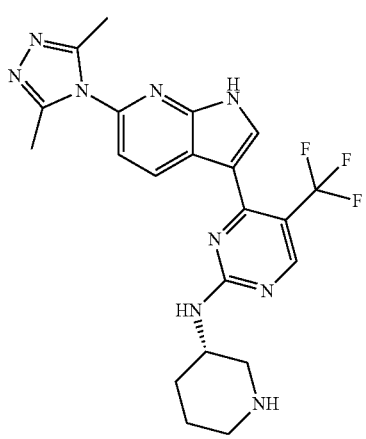
Compound 138
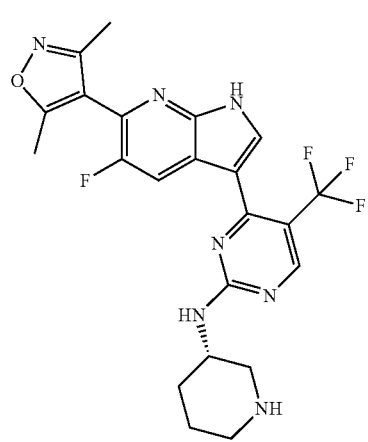
Compound 141
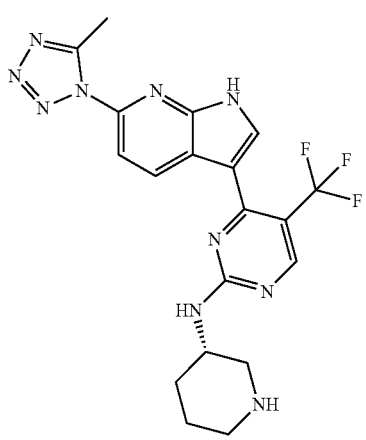

245
-continued
Compound 142
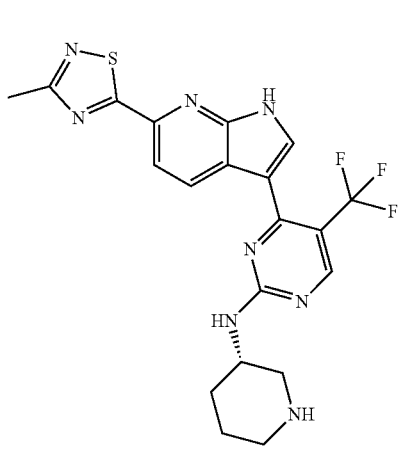
Compound 143
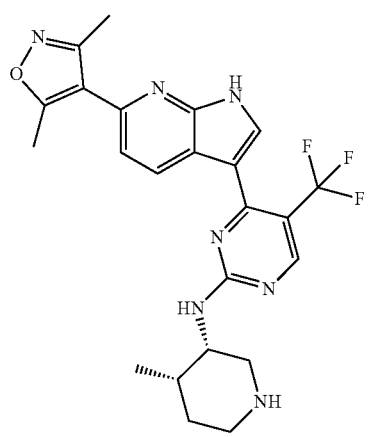
Compound 144
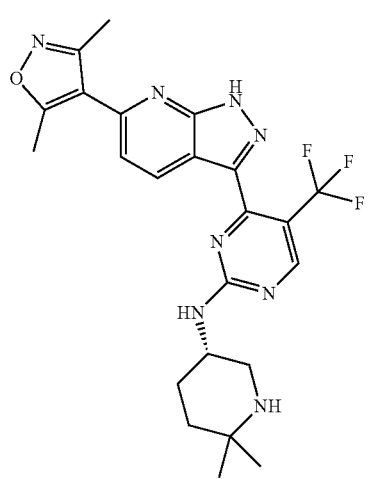
246
-continued
Compound 145
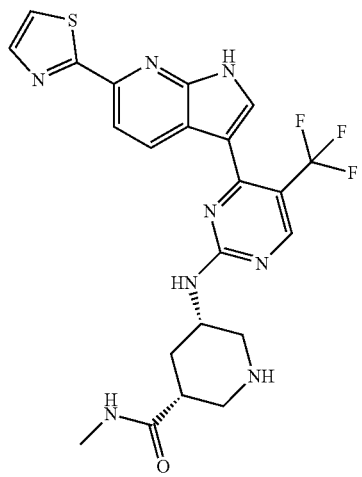
Compound 146
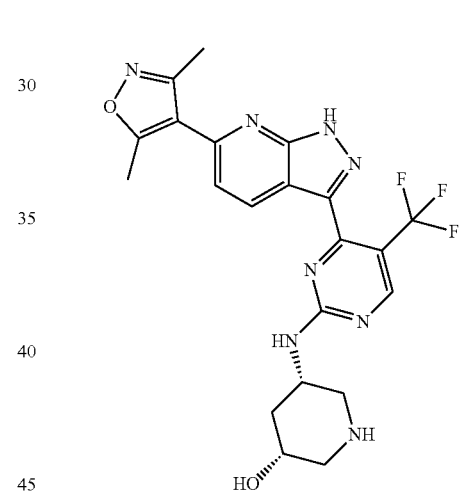
Compound 147
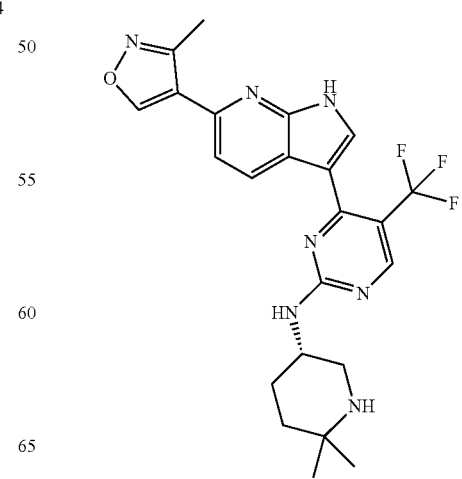

Compound 148
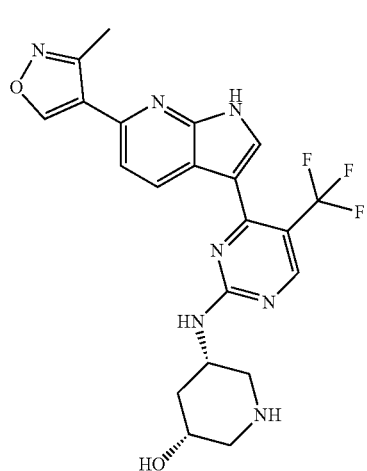
Compound 151
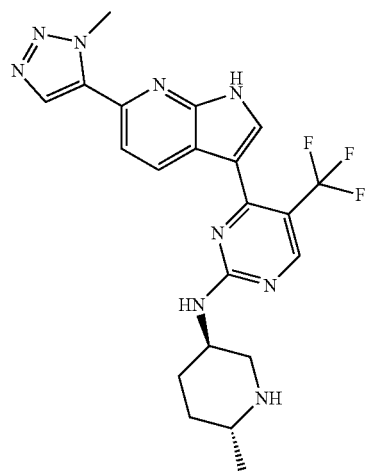
Compound 149
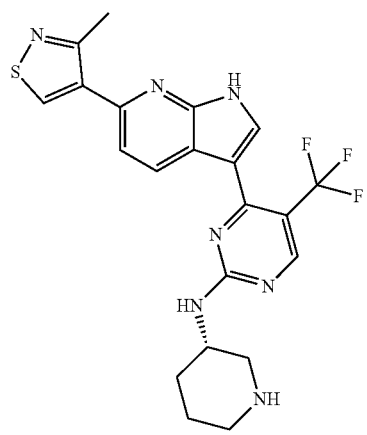
Compound 152
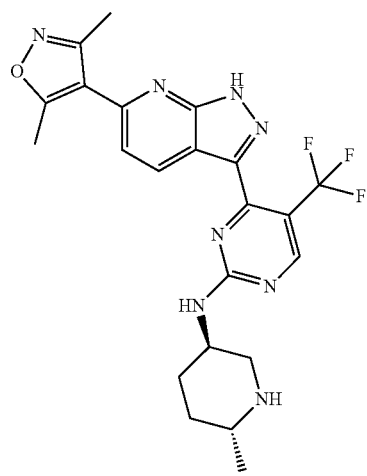
Compound 150
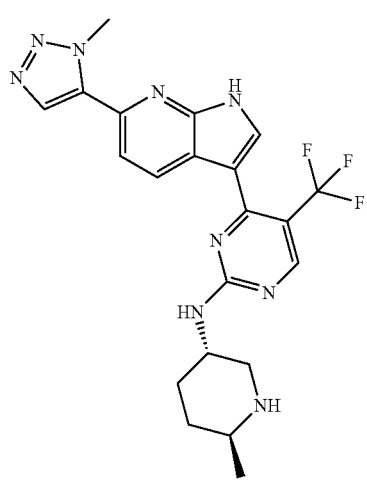
Compound 153
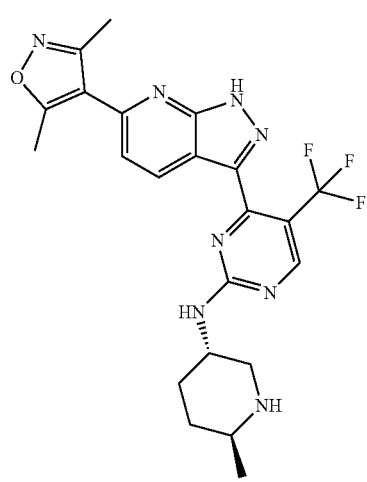

-continued
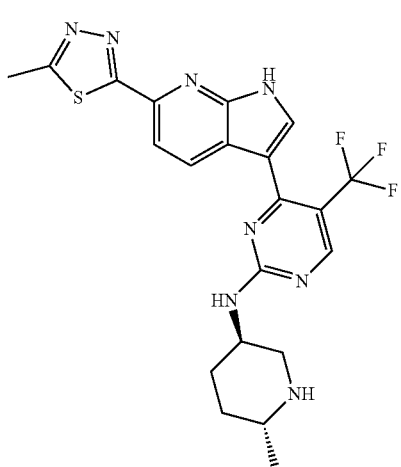
Compound 154
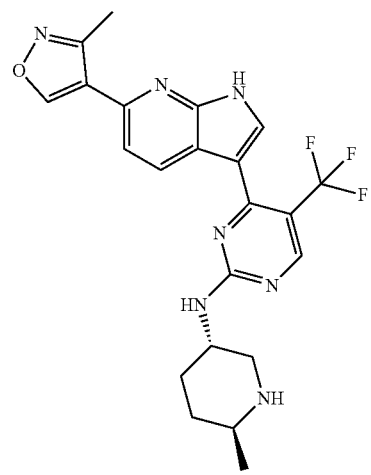
Compound 157
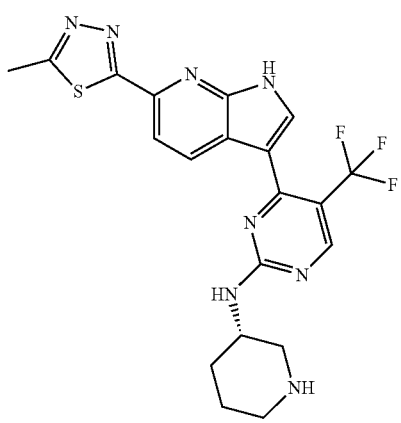
Compound 155
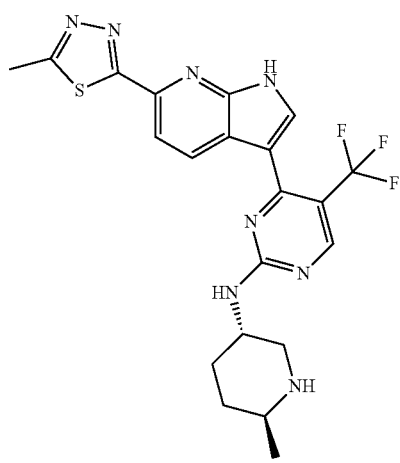
Compound 158
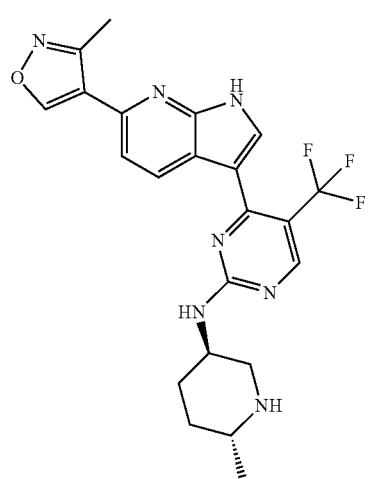
Compound 156
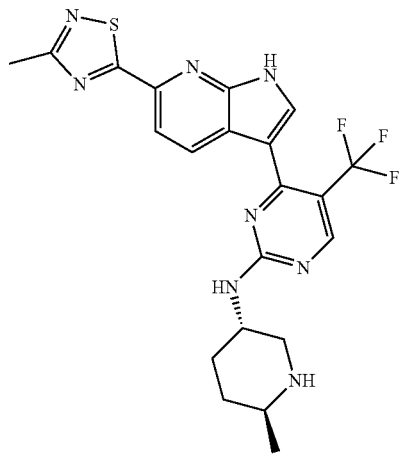
Compound 159

-continued
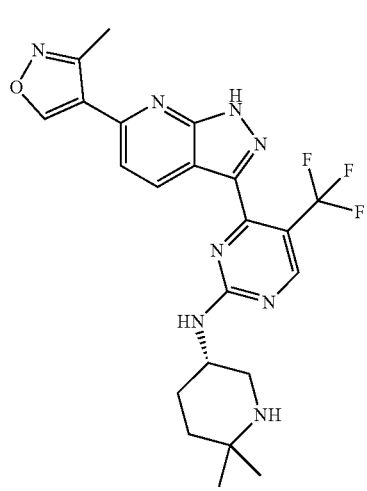
Compound 160
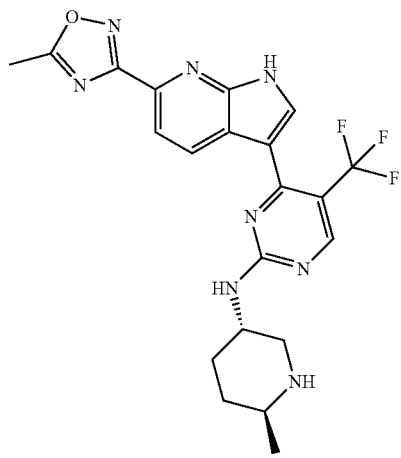
Compound 163
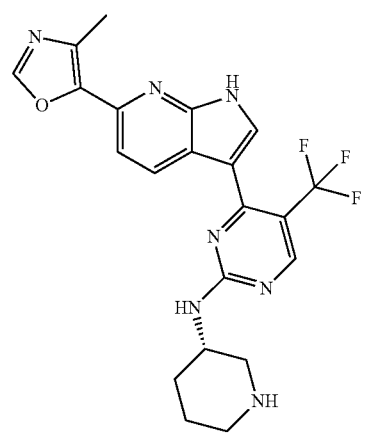
Compound 161
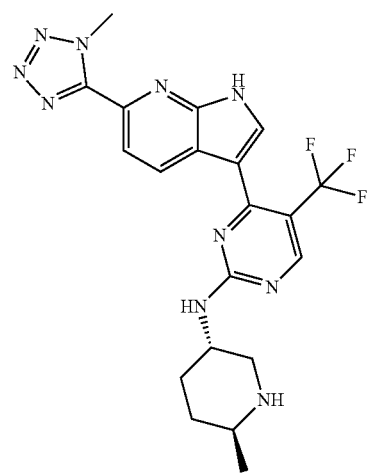
Compound 164
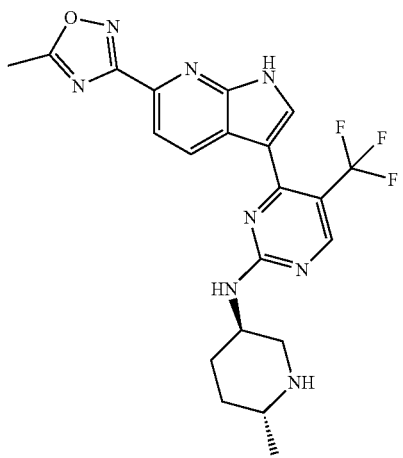
Compound 162
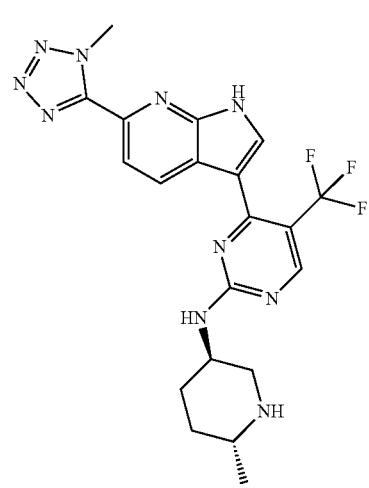
Compound 165

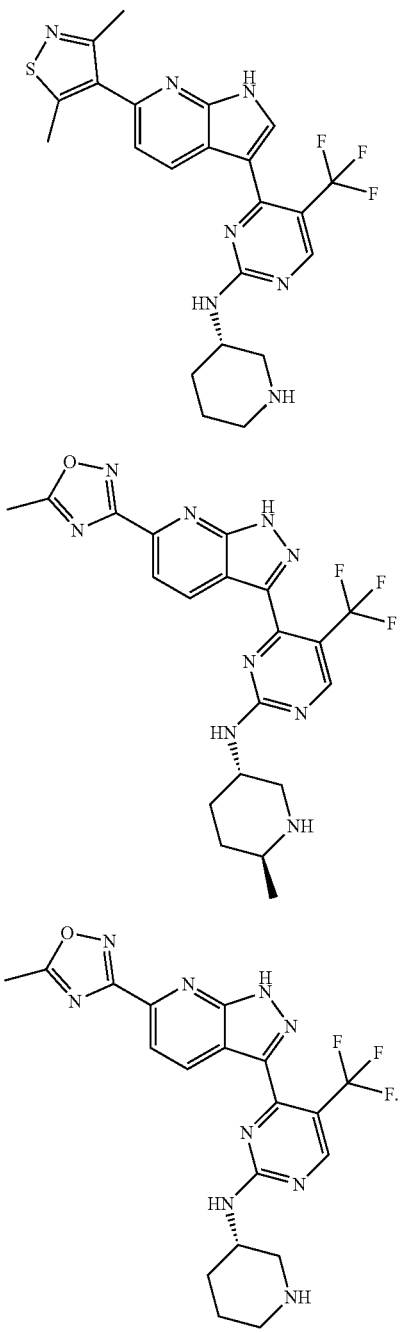

Compound 166

Compound 167

Compound 168

10. A pharmaceutical composition comprising a compound of claim 1 or the pharmaceutically acceptable salt, stereoisomer, or isotopic form thereof; and a pharmaceutically acceptable excipient.

11. A method of treating a patient suffering from a disease associated with aberrant activity of CDK7, the method comprising a step of administering to the patient a therapeutically effective amount of the compound of claim 1 or the pharmaceutically acceptable salt, stereoisomer, or isotopic form thereof, optionally within a pharmaceutical composition.

12. The method of claim 11, wherein the disease is a proliferative disease, an infectious disease, or a disease caused by or associated with expanded repeats of simple nucleotide tracts.

13. The method of claim 12, wherein the proliferative disease is a cancer.

14. The method of claim 13, wherein the cancer is a blood cancer, a bone cancer, a brain cancer, a breast cancer, a lung cancer, melanoma, or an ovarian cancer.

15. The method of claim 11, further comprising a step of administering to the patient one or more second agents, wherein the second agent is an anti-proliferative agent, an anti-cancer agent, an immunosuppressant agent, or a pain-relieving agent.

16. A pharmaceutical composition comprising a compound of claim 7 or the pharmaceutically acceptable salt, stereoisomer, or isotopic form thereof; and a pharmaceutically acceptable excipient.

17. A method of treating a patient suffering from a disease associated with aberrant activity of CDK7, the method comprising a step of administering to the patient a therapeutically effective amount of the compound of claim 7 or the pharmaceutically acceptable salt, stereoisomer, or isotopic form thereof, optionally within a pharmaceutical composition.

18. The method of claim 17, wherein the disease is a proliferative disease, an infectious disease, or a disease caused by or associated with expanded repeats of simple nucleotide tracts.

19. The method of claim 18, wherein the proliferative disease is a cancer.

20. The method of claim 17, further comprising a step of administering to the patient one or more second agents, wherein the second agent is an anti-proliferative agent, an anti-cancer agent, an immunosuppressant agent, or a pain-relieving agent.

* * * * *

UNITED STATES PATENT AND TRADEMARK OFFICE
CERTIFICATE OF CORRECTION

PATENT NO. : 11,311,542 B2
APPLICATION NO. : 16/962808
DATED : April 26, 2022
INVENTOR(S) : Jason J. Marineau et al.

Page 1 of 1

It is certified that error appears in the above-identified patent and that said Letters Patent is hereby corrected as shown below:

In the Claims

At Column 227, Lines 5-13, replace:

"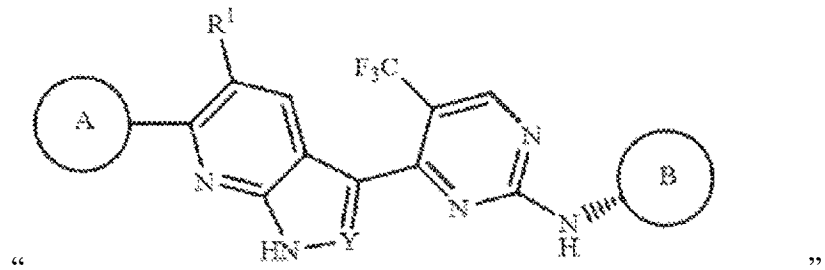"

With:

--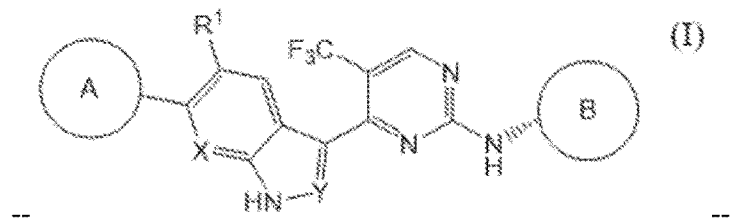--

Signed and Sealed this
Sixth Day of September, 2022

Katherine Kelly Vidal
*Director of the United States Patent and Trademark Office*